US007807879B2

(12) United States Patent
Schmülling et al.

(10) Patent No.: US 7,807,879 B2
(45) Date of Patent: Oct. 5, 2010

(54) METHOD FOR MODIFYING PLANT MORPHOLOGY, BIOCHEMISTRY AND PHYSIOLOGY

(76) Inventors: Thomas Schmülling, Preussenallee 30, D-14052 Berlin (DE); Tomás Werner, Gustav-Müller-Str.3, D-10829 Berlin (DE)

( * ) Notice: Subject to any disclaimer, the term of this patent is extended or adjusted under 35 U.S.C. 154(b) by 299 days.

(21) Appl. No.: 11/801,018

(22) Filed: May 8, 2007

(65) Prior Publication Data
US 2008/0222755 A1    Sep. 11, 2008

Related U.S. Application Data

(60) Division of application No. 10/014,101, filed on Dec. 10, 2001, now Pat. No. 7,259,296, which is a continuation-in-part of application No. PCT/EP01/06833, filed on Jun. 18, 2001.

(60) Provisional application No. 60/258,415, filed on Dec. 27, 2000.

(30) Foreign Application Priority Data

Jun. 16, 2000  (EP) ................................ 00870132
Mar. 16, 2001  (EP) ................................ 01870053

(51) Int. Cl.
C12N 15/82    (2006.01)
A01H 5/00     (2006.01)
A01H 5/10     (2006.01)

(52) U.S. Cl. .................. 800/298; 800/278; 800/290; 800/287

(58) Field of Classification Search .................. None
See application file for complete search history.

(56) References Cited

FOREIGN PATENT DOCUMENTS

WO    WO 99/06571    *    2/1999

OTHER PUBLICATIONS

Kaminek et al (1990, Plant Physiol. 93:1530-1538).*
Hare et al (1994, Physiologia Plantarum 91:128-136).*
Abstract: S.D. Rounsley, et al., (Jan. 1, 1998) XP002151606, Database Accession No. ID/AC=022213.
Abstract: M. Bevan, et al., (May 1, 2000) "Cytokinin oxidase-like protein", XP-002151607, Database Accession No. ID/AC=Q9SU77.
Abstract: X. Lin, et al., (May 1, 1999) "*Arabidopsis thaliana* chromosome II BAC F3P11 genomic sequence, Putative Cytokinin Oxidase", XP-002151608, Database Accession No. ID/AC=Q9ZUP1.
Abstract: Zhang, N., et al., (1999) "Initiation an elongation of lateral roots in *Lactuca sativa*", XP002151609, Database Accession No. AN=PREV199900326622, *International J. of Plant Sciences*, vol. 160(3), pp. 511-519.
Abstract: Y. Koda, et al., (1989) "Cytokinin production by tomato root. Identification of a major cytokinin produced by the root and environmental factors affecting the production", XP002151610, Database Accession No. AN=PREV198988038194, *J. of the Faculty of Agriculture Hokkaido University*, vol. 64 (1), pp. 10-20.
Abstract: M. Frank, et al., (1999) "TSD genes negatively regulate merismetic activity in *Arabidopsis*", XP002151616, Database Accession No. AN=PREV200000242628, *Biologia Plantarum* (Prague), vol. 42 (Suppl.), p. S47.
Doerner, et al., (Apr. 11, 1996) "Control of root growth and development by cyclin expression", *Nature*, vol. 380, pp. 520-523.
Faiss, et al., (1997) "Conditional transgenic expression of the ipt gene indicates a function for cytokinins in paracrine signaling in whole tobacco plants", *The Plant Journal*, 12(2), pp. 401-415.
Houba-Herin, et al., (1999) "Cytokinin oxidase from *Zea mays*: purification, cDNA cloning and expression in moss protoplasts", *The Plant Journal*, 17(6), pp. 615-626.
Klee, et al., (1995) "Transgenic plants in hormone biology", *Plant Hormones: Physiology, Biochemistry and Molecular Biology*, ed. Davies, P.J. (Klower, Dordrdrocht, the Netherlands), pp. 340-353.
Mok, M.C. (1994) "Cytokinins and Plant Development" in *Cytokines: Chemistry, Activity, and Function*Chapter 12, eds. Mok, D.W.S. & Mok, M.C., CRC Press, Inc., pp. 155-166.
Morris, et al.(1999) "Isolation of a Gene Encoding a Glycosylated Cytokinin Oxidase from Maize", *Biochemical and Biophysical Research Communications*, 255:328-333.
Motyka, et al., (1996) "Changes in Cytokinin Content and Cytokinin Oxidase Activity in Response to Derepression of ipt Gene Transcription in Transgenic Tobacco Calli and Plants", *Plant Physiol*, 112: 1035-1043.
Rinaldi, et al., (Aug. 1999) "Cytokinin oxidase strikes again", *Trends in Plant Sci*, Elsevier Science, vol. 4, No. 8, p. 300.
Schmulling, et al., (1999) "Recent advances in cytokinin research: Receptor candidates, primary response genes, mutants and transgenic plants", *Advances in Regulation of Plant Growth and Development* pp. 85-96.
Werner, et al., (Aug. 28, 2001) "Regulation of plant growth by cytokinin", *PNAS* vol. 98, No. 18, pp. 10487-10492.
Hare et al (1994) *Physiologia Plantarum* 91:128-136.
Bowie et al. (1990) *Science* 247:1306-1310.
McConnell et al. (2001) *Nature* 411 (6838):709-713.

(Continued)

*Primary Examiner*—Stuart F. Baum
(74) *Attorney, Agent, or Firm*—Ann R. Pokalsky, Esq.; Dilworth & Barrese, LLP

(57) ABSTRACT

The present invention provides nucleotide sequences and corresponding amino acid sequences for plant cytokinin oxidase proteins. In addition, vectors, host cells, and transgenic plants comprising such sequences as well as methods for stimulating root growth and/or enhancing the formation of lateral or adventitious roots and/or altering root geotropism using such sequences are provided by the present invention. Also provided by the present invention are methods for altering various plant phenotypes including delaying onset to flowering, increasing leaf thickness, reducing vessel size, inducing parthenocarpy, increasing branching, increasing seed size and/or weight, embryo size and/or weight, and cotyledon size and/or weight using cytokinin oxidase proteins and/or nucleic acid molecules encoding cytokinin oxidase.

8 Claims, 16 Drawing Sheets

OTHER PUBLICATIONS

Fourgoux-Nicol (1999) *Plant Molecular Biology* 40:857-872.
Kaminek et al (1990) *Plant Physiol* 93: 1530-1538.
Lin et al. (Jan. 1999) NCBI Accession No. AC005917.
Werner et al. (Aug. 28, 2001) *Proc. Nat. Acad. Sci.* 98(18):10487-10492.
Werner et al. (Nov. 2003) *The Plant Cell* 15:2532-2550.
Deaton (1999) Proceedings of Genetic and Evolutionary Computation Conference, vol. 2, AAAI, Morgan Kaufmann, San Francisco, 1999 Orlando, Florida Jul. 1999.

* cited by examiner

FIGURE 2

SEQUENCE LISTING

<160> NUMBER OF SEQ ID NOS: 42

<210> SEQ ID NO 1
<211> LENGTH: 2236
<212> TYPE: DNA
<213> ORGANISM: Arabidopsis thaliana

<400> SEQUENCE: 1

| | |
|---|---|
| atgggattga cctcatcctt acggttccat agacaaaaca acaagacttt cctcggaatc | 60 |
| ttcatgatct tagttctaag ctgtatacca ggtagaacca atctttgttc caatcattct | 120 |
| gttagtaccc caaaagaatt accttcttca aatccttcag atattcgttc ctcattagtt | 180 |
| tcactagatt tggagggtta tataagcttc gacgatgtcc acaatgtggc caaggacttt | 240 |
| ggcaacagat accagttacc acctttggca attctacatc aaggtcagt ttttgatatt | 300 |
| tcatcgatga tgaagcatat agtacatctg gctccacct caaatcttac agtagcagct | 360 |
| agaggccatg gtcactcgct tcaaggacaa gctctagctc atcaaggtgt tgtcatcaaa | 420 |
| atggagtcac ttcgaagtcc tgatatcagg atttataagg ggaagcaacc atatgttgat | 480 |
| gtctcaggtg gtgaaatatg ataaacatt ctacgcgaga ctctaaaata cggtctttca | 540 |
| ccaaagtcct ggacagacta ccttcatttg accgttggag gtacactatc taatgctgga | 600 |
| atcagcggtc aagcattcaa gcatggaccc caaatcaaca acgtctacca gctagagatt | 660 |
| gttacaggta tttcattcat gctttatctc tgcggtagtc tcaaaaaaat atgcacctgt | 720 |
| aaagaatatc catctcttca tgagcaaaaa cactgacgac tttaaataat ttttgactat | 780 |
| aaaacaagag tgcataggca caaatgtgaa atatgcaaca cacaattgta acttgcacca | 840 |
| agaaaaaagt tataaaaaca aacaactgat aagcaatata tttccaatat ttaatcaggg | 900 |
| aaaggagaag tcgtaacctg ttctgagaag cggaattctg aacttttctt cagtgttctt | 960 |
| ggcgggcttg gacagtttgg cataatcacc cgggcacgga tctctcttga ccagcaccg | 1020 |
| catatggtaa agttctatct tgaacaaagt tcaaacaata tacgctatga ttctaagaac | 1080 |
| cactttcctg acacagtcaa ataacttta ataggttaaa tggatcaggg tactctactc | 1140 |
| tgactttcct gcattttcaa gggaccaaga atatctgatt tcgaaggaga aaacttttga | 1200 |
| ttacgttgaa ggatttgtga taatcaatag aacagacctt ctcaataatt ggcgatcgtc | 1260 |
| attcagtccc aacgattcca cacaggcaag cagattcaag tcagatggga aaactctta | 1320 |
| ttgcctagaa gtggtcaaat atttcaaccc agaagaagct agctctatgg atcaggtaag | 1380 |
| atgtgaaagc aatatataac tagacttagt ttccacagag agctccaaat caaccgttgg | 1440 |
| ctactagcct actaacataa tgaatggttg ccgtgcagga aactggcaag ttactttcag | 1500 |
| agttaaatta tattccatcc actttgtttt catctgaagt gccatatatc gagtttctgg | 1560 |
| atcgcgtgca tatcgcagag agaaaactaa gagcaaaggg tttatgggag ttccacatc | 1620 |
| cctggctgaa tctcctgatt cctaagagca gcatatacca atttgctaca gaagttttca | 1680 |
| acaacattct cacaagcaac aacaacggtc ctatccttat ttatccagtc aatcaatcca | 1740 |
| agtaagtgag caaaatgcca aaagcaaatg cgtccagtga ttctgaaaca taaattacta | 1800 |
| accatatcca acatttgtg gtttcaggtg aagaaacat acatctttga taactccaaa | 1860 |
| tgaagatata ttctatctcg tagcctttct cccctctgca gtgccaaatt cctcagggaa | 1920 |
| aaacgatcta gagtaccttt tgaaacaaaa ccaaagagtt atgaacttct gcgcagcagc | 1980 |
| aaacctcaac gtgaagcagt atttgcccca ttatgaaact caaaaagagt ggaaatcaca | 2040 |

```
cttggcaaa agatgggaaa catttgcaca gaggaaacaa gcctacgacc ctctagcgat   2100
tctagcacct ggccaaagaa tattccaaaa gacaacagga aaattatctc ccatccaact   2160
cgcaaagtca aaggcaacag gaagtcctca aggtaccat tacgcatcaa tactgccgaa    2220
acctagaact gtataa                                                    2236
```

<210> SEQ ID NO 2
<211> LENGTH: 575
<212> TYPE: PRT
<213> ORGANISM: Arabidopsis thaliana

<400> SEQUENCE: 2

```
Met Gly Leu Thr Ser Ser Leu Arg Phe His Arg Gln Asn Asn Lys Thr
 1               5                  10                  15

Phe Leu Gly Ile Phe Met Ile Leu Val Leu Ser Cys Ile Pro Gly Arg
            20                  25                  30

Thr Asn Leu Cys Ser Asn His Ser Val Ser Thr Pro Lys Glu Leu Pro
        35                  40                  45

Ser Ser Asn Pro Ser Asp Ile Arg Ser Ser Leu Val Ser Leu Asp Leu
    50                  55                  60

Glu Gly Tyr Ile Ser Phe Asp Asp Val His Asn Val Ala Lys Asp Phe
65                  70                  75                  80

Gly Asn Arg Tyr Gln Leu Pro Pro Leu Ala Ile Leu His Pro Arg Ser
                85                  90                  95

Val Phe Asp Ile Ser Ser Met Met Lys His Ile Val His Leu Gly Ser
            100                 105                 110

Thr Ser Asn Leu Thr Val Ala Ala Arg Gly His Gly His Ser Leu Gln
        115                 120                 125

Gly Gln Ala Leu Ala His Gln Gly Val Val Ile Lys Met Glu Ser Leu
    130                 135                 140

Arg Ser Pro Asp Ile Arg Ile Tyr Lys Gly Lys Gln Pro Tyr Val Asp
145                 150                 155                 160

Val Ser Gly Gly Glu Ile Trp Ile Asn Ile Leu Arg Glu Thr Leu Lys
                165                 170                 175

Tyr Gly Leu Ser Pro Lys Ser Trp Thr Asp Tyr Leu His Leu Thr Val
            180                 185                 190

Gly Gly Thr Leu Ser Asn Ala Gly Ile Ser Gly Gln Ala Phe Lys His
        195                 200                 205

Gly Pro Gln Ile Asn Asn Val Tyr Gln Leu Glu Ile Val Thr Gly Lys
    210                 215                 220

Gly Glu Val Val Thr Cys Ser Glu Lys Arg Asn Ser Glu Leu Phe Phe
225                 230                 235                 240

Ser Val Leu Gly Gly Leu Gly Gln Phe Gly Ile Ile Thr Arg Ala Arg
                245                 250                 255

Ile Ser Leu Glu Pro Ala Pro His Met Val Lys Trp Ile Arg Val Leu
            260                 265                 270

Tyr Ser Asp Phe Ser Ala Phe Ser Arg Asp Gln Glu Tyr Leu Ile Ser
        275                 280                 285

Lys Glu Lys Thr Phe Asp Tyr Val Glu Gly Phe Val Ile Ile Asn Arg
    290                 295                 300

Thr Asp Leu Leu Asn Asn Trp Arg Ser Ser Phe Ser Pro Asn Asp Ser
305                 310                 315                 320

Thr Gln Ala Ser Arg Phe Lys Ser Asp Gly Lys Thr Leu Tyr Cys Leu
                325                 330                 335
```

| | | | | | | | | | | | | |
|---|---|---|---|---|---|---|---|---|---|---|---|---|
| Glu | Val | Val | Lys | Tyr | Phe | Asn | Pro | Glu | Glu | Ala | Ser | Ser | Met | Asp | Gln |
| | | 340 | | | | 345 | | | | 350 | | |

Glu Thr Gly Lys Leu Leu Ser Glu Leu Asn Tyr Ile Pro Ser Thr Leu
              355                 360                 365

Phe Ser Ser Glu Val Pro Tyr Ile Glu Phe Leu Asp Arg Val His Ile
          370                 375                 380

Ala Glu Arg Lys Leu Arg Ala Lys Gly Leu Trp Glu Val Pro His Pro
385                 390                 395                 400

Trp Leu Asn Leu Leu Ile Pro Lys Ser Ser Ile Tyr Gln Phe Ala Thr
              405                 410                 415

Glu Val Phe Asn Asn Ile Leu Thr Ser Asn Asn Gly Pro Ile Leu
              420                 425                 430

Ile Tyr Pro Val Asn Gln Ser Lys Trp Lys His Thr Ser Leu Ile
              435                 440                 445

Thr Pro Asn Glu Asp Ile Phe Tyr Leu Val Ala Phe Leu Pro Ser Ala
          450                 455                 460

Val Pro Asn Ser Ser Gly Lys Asn Asp Leu Glu Tyr Leu Leu Lys Gln
465                 470                 475                 480

Asn Gln Arg Val Met Asn Phe Cys Ala Ala Ala Asn Leu Asn Val Lys
                485                 490                 495

Gln Tyr Leu Pro His Tyr Glu Thr Gln Lys Glu Trp Lys Ser His Phe
              500                 505                 510

Gly Lys Arg Trp Glu Thr Phe Ala Gln Arg Lys Gln Ala Tyr Asp Pro
              515                 520                 525

Leu Ala Ile Leu Ala Pro Gly Gln Arg Ile Phe Gln Lys Thr Thr Gly
          530                 535                 540

Lys Leu Ser Pro Ile Gln Leu Ala Lys Ser Lys Ala Thr Gly Ser Pro
545                 550                 555                 560

Gln Arg Tyr His Tyr Ala Ser Ile Leu Pro Lys Pro Arg Thr Val
              565                 570                 575

<210> SEQ ID NO 3
<211> LENGTH: 2991
<212> TYPE: DNA
<213> ORGANISM: Arabidopsis thaliana

<400> SEQUENCE: 3

```
atggctaatc ttcgtttaat gatcacttta atcacggttt taatgatcac caaatcatca      60
aacggtatta aaattgattt acctaaatcc cttaacctca ccctctctac cgatccttcc     120
atcatctccg cagcctctca tgacttcgga aacataacca ccgtgacccc cggcggcgta     180
atctgccct  cctccaccgc tgatatctct cgtctcctcc aatacgccgc aaacggaaaa     240
agtacattcc aagtagcggc tcgtggccaa ggccactcct taaacggcca agcctcggtc     300
tccggcggag taatcgtcaa catgacgtgt atcactgacg tggtggtttc aaaagacaag     360
aagtacgctg acgtggcggc cgggacgtta tgggtggatg tgcttaagaa gacggcggag     420
aaagggggtgt cgccggtttc ttggacggat tatttgcata taaccgtcgg aggaacgttg     480
tcgaatggtg gaattggtgg tcaagtgttt cgaaacggtc ctcttgttag taacgtcctt     540
gaattggacg ttattactgg tacgcatctt ctaaactttg atgtacatac aacaacaaaa     600
actgttttg  ttttatagta ttttcatt   tttgtaccat aggttttatg ttttatagtt     660
gtgctaaact tcttgcacca cacgtaagtc ttcgaaacac aaaatgcgta acgcatctat     720
atgttttttg tacatattga atgttgttca tgagaaataa agtaattaca tatcacaca      780
```

-continued

```
tttattgtcg tacatatata aataattaaa gacaaatttt cacaattggt agcgtgttaa    840
tttgggattt ttgtaatgta catgcatgac gcatgcatat ggagcttttc ggttttctta    900
gatttgtgta gtatttcaaa tatatcattt attttctttc gaataaagag gtggtatatt    960
tttaaaatag caacatttca gaattttttct ttgaatttac acttttttaaa ttgttattgt   1020 taatatggat tttgaataaa taatttcagg gaaaggtgaa atgttgacat gctcgcgaca   1080
gctaaaccca gaattgttct atggagtgtt aggaggtttg ggtcaatttg gaattataac   1140
gagagccaga attgttttgg accatgcacc taaacgggta cgtatcatca tattttacca   1200
tttgttttag tcagcattca tttttcatta gtaattccgt ttcaatttct aaattttttt   1260
agtcaataga aaatgattct tatgtcagag cttgattatt tagtgatttt tattgagata   1320
aaataaaata taacctaacg gaaataatta ttttactaat cggataatgt ctgattaaaa   1380
cattttatga tattcactaa agagagttag agacgtatgg atcacaaaac atgaagcttt   1440
cttagatggt atcctaaaac taaagttagg tacaagtttg gaatttaggt caaatgctta   1500
agttgcatta atttgaacaa aatctatgca ttgaataaaa aaaagatatg gattatttta   1560
taaagtatag tccttgtaat cctaggactt gttgtctaat cttgtcttat gcgtgcaaat   1620 cttttttgatg tcaatatata atccttgttt attagagtca agctctttca ttagtcaact   1680
actcaaatat actccaaagt ttagaatata gtcttctgac taattagaat cttacaaccg   1740
ataaacgtta caatttggtt atcattttaa aaaacagatt tggtcataat atacgatgac   1800
gttctgtttt agtttcatct attcacaaat tttatataat tattttcaag aaaatattga   1860
aatactatac tgtaatatgg tttctttata tatgtgtgta taaattaaat gggattgttt   1920
tctctaaatg aaattgtgta ggccaaatgg tttcggatgc tctacagtga tttcacaact   1980
tttacaaagg accaagaacg tttgatatca atggcaaacg atattggagt cgactattta   2040
gaaggtcaaa tatttctatc aaacggtgtc gttgacacct cttttttccc accttcagat   2100
caatctaaag tcgctgatct agtcaagcaa cacggtatca tctatgttct tgaagtagcc   2160
aagtattatg atgatcccaa tctccccatc atcagcaagg tactacacat ttacattttc   2220
atcatcgttt ttatcatacc ataagatatt taaatgattc atcattgcac cacattaaga   2280
tattcatcat catcatcgtt acattttttt ttgcatctta tgcttctcat aatctactat   2340
tgtgtaggtt attgacacat taacgaaaac attaagttac ttgcccgggt tcatatcaat   2400
gcacgacgtg gcctacttcg atttcttgaa ccgtgtacat gtcgaagaaa ataaactcag   2460
atctttggga ttatgggaac ttcctcatcc ttggcttaac ctctacgttc ctaaatctcg   2520
gattctcgat tttcataacg gtgttgtcaa agacattctt cttaagcaaa atcagcttc   2580 gggactcgct cttctctatc caacaaaccg gaataagtac atacttctct tcattcatat   2640
ttatcttcaa gaaccaaagt aaataaattt ctatgaactg attatgctgt tattgttaga   2700
tgggacaatc gtatgtcggc gatgatacca gagatcgatg aagatgttat atatattatc   2760
ggactactac aatccgctac cccaaaggat cttccagaag tggagagcgt taacgagaag   2820
ataattaggt tttgcaagga ttcaggtatt aagattaagc aatatctaat gcattatact   2880
agtaaagaag attggattga gcattttgga tcaaatgggg atgattttc gaagaggaaa   2940 gatctatttg atcccaagaa actgttatct ccagggcaag acatcttttg a            2991
```

<210> SEQ ID NO 4
<211> LENGTH: 501
<212> TYPE: PRT

<213> ORGANISM: Arabidopsis thaliana

<400> SEQUENCE: 4

```
Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
130                 135                 140

Pro Val Ser Trp Thr Asp Tyr Leu His Ile Thr Val Gly Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255

Ile Gly Val Asp Tyr Leu Glu Gly Gln Ile Phe Leu Ser Asn Gly Val
            260                 265                 270

Val Asp Thr Ser Phe Phe Pro Ser Asp Gln Ser Lys Val Ala Asp
        275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400
```

```
Thr Asn Arg Asn Lys Trp Asp Asn Arg Met Ser Ala Met Ile Pro Glu
            405                 410                 415
Ile Asp Glu Asp Val Ile Tyr Ile Ile Gly Leu Leu Gln Ser Ala Thr
        420                 425                 430
Pro Lys Asp Leu Pro Glu Val Glu Ser Val Asn Glu Lys Ile Ile Arg
        435                 440                 445
Phe Cys Lys Asp Ser Gly Ile Lys Ile Lys Gln Tyr Leu Met His Tyr
450                 455                 460
Thr Ser Lys Glu Asp Trp Ile Glu His Phe Gly Ser Lys Trp Asp Asp
465                 470                 475                 480
Phe Ser Lys Arg Lys Asp Leu Phe Asp Pro Lys Lys Leu Leu Ser Pro
                485                 490                 495
Gly Gln Asp Ile Phe
            500

<210> SEQ ID NO 5
<211> LENGTH: 3302
<212> TYPE: DNA
<213> ORGANISM: Arabidopsis thaliana

<400> SEQUENCE: 5
atggcgagtt ataatcttcg ttcacaagtt cgtcttatag caataacaat agtaatcatc      60
attactctct caactccgat cacaaccaac acatcaccac aaccatggaa tatcctttca     120
cacaacgaat cgccggaaaa actcacctcc tcctcctcct ccgtcgaatc agccgccaca     180
gatttcggcc acgtcaccaa atcttccct tccgccgtct aatcccttc ctccgttgaa      240 gacatcacag atctcataaa actctctttt gactctcaac tgtcttttcc tttagccgct     300
cgtggtcacg acacagcca ccgtggccaa gcctcggcta agacggagt tgtggtcaac      360 atgcggtcca tggtaaaccg ggatcgaggt atcaaggtgt ctaggacctg tttatatgtt     420
gacgtggacg ctgcgtggct atggattgag gtgttgaata aaactttgga gttagggtta     480
acgccggttt cttggacgga ttatttgtat taacagtcg gtgggacgtt atcaaacggc      540
ggaattagtg gacaaacgtt tcggtacggt ccacagatca ctaatgttct agagatggat     600
gttattactg gtacgtacca cgatcttttt cacacagaga ttaaaaaaaa cagtaatagt     660
gattttaact tcgtacgttt ctgatagaca acaaagaact tcgtacgttt ttcgaagttt     720
tttcgtcttt ttcattttag atctgcgcgg ccattttgg ttatgctatt gtttgtttgt     780
attgtttgtc tctgtttatt tatttctcga acttgttgat agcttttctt cttttcacac     840
atcaatctaa tcacctttt tggtcttaag attagaaaga agatacggac taggtaaaaa     900
taggtggttg taaacgtaga cgcattaaaa aaatattggt ttttttattt tttgataagc     960
aaaattggtg gttggtctaa gattataaac ttgatattaa tgcaaaggtc gatctagcaa    1020
tagaagatta tcaatattc ttggtgtttt aacaacagat tatttcatca ttaaaatcgt     1080
gaaacaaaga aattttggta gtatacatta cgtgtagttt tgttagttta ttaaaaaaaa    1140
tagtatatag ttttgttaaa acgcgattta tttagtaaca cattagtata ttacacgttt    1200
aaccaactaa acttttttt tgaataatt atgttctata tttcttactc aaattatgca     1260
aatttcgtgg attcgaagtc aaatttctgc gaaatttaca tggtcatata ttataaaact    1320
gttcatataa cccggtgaac aaacagacaa ttaagggttt gaatggttac ggcggttggg    1380
gcggacacaa ccgtcaatag atcagaccgt ttttattta ccattcatca attatattcc     1440
gcagtggttt ggggtaaaaa aaatagaaga aaaccgcagc ggaccaattc cataccgttt    1500
```

-continued

```
ttacatacaa ataaacatgg tgcgcaacgg tttattgtcc gcctcaaaaa tgaaatggac    1560
taaaccgcag ataaattaga ccgctttgtc cgctgcctcc attcatagac taaaaaaaaa    1620
caaccaaaaa aaaatggtc ccacgcccat gattttacac gaggtttctt gtggcgtaag    1680
gacaaaactc aaaagttcat aacgtttggt cctaaccagg tgtaatggat taagtaacag    1740
tcaattttct tattatagct gtatccatta tgtccacata tgcatccata tacattacac    1800
tgttggtctc aagtgtagtt agattacgaa gactttcaag ttccattttt tggttaggag    1860
ataaacataa tttaatgata ccgactttag cactctaggc tcaaaacaag tacagaagag    1920
aatagtttta tttcaaactc gttgcattgt tgtatcaatt aattgtgtta gtctttgtat    1980
attcttacat aacggtccaa gtttgttgaa atagtttact tactaaactt ttcctaatgg    2040
ggtcaaattt tattttatag gaaaaggaga gattgcaact tgttccaagg acatgaactc    2100
ggatcttttc ttcgcggtgt taggaggttt gggtcaattc ggcattataa caagagccag    2160
aattaaactt gaagtagctc cgaaaagggt atgttaaatt tgtaaattat gcaactacag    2220
aaaattctat gaaatttatg aatgaacata tatgcatttt tggattttg taggccaagt    2280 ggttaaggtt tctatacata gatttctccg aattcacaag agatcaagaa cgagtgatat    2340
cgaaaacgga cggtgtagat ttcttagaag gttccattat ggtggaccat ggcccaccgg    2400
ataactggag atccacgtat tatccaccgt ccgatcactt gaggatcgcc tcaatggtca    2460
aacgacatcg tgtcatctac tgccttgaag tcgtcaagta ttacgacgaa acttctcaat    2520
acacagtcaa cgaggtccgt acatacatac aatcataaat catacatgta taattgggag    2580
atctttatgc attattcaat tatattaatt tactttagtt atttaactta tgcaggaaat    2640
ggaggagtta agcgatagtt taaaccatgt aagagggttt atgtacgaga agatgtgac    2700 gtatatggat ttcctaaacc gagttcgaac cggagagcta aacctgaaat ccaaaggcca    2760
atgggatgtt ccacatccat ggcttaatct cttcgtacca aaaactcaaa tctccaaatt    2820
tgatgatggt gtttttaagg gtattatcct aagaaataac atcactagcg gtcctgttct    2880
tgtttatcct atgaatcgca acaagtaagt ttaactcgat attgcaaaat ttactatcta    2940
cattttcgtt ttggaatccg aaatattctt acaagctaat tttatgcggc gtttttaggt    3000
ggaatgatcg gatgtctgcc gctataccg aggaagatgt atttatgcg gtagggtttt    3060 taagatccgc gggttttgac aattgggagg cttttgatca agaaaacatg gaaatactga    3120
agttttgtga ggatgctaat atgggggtta tacaatatct tccttatcat tcatcacaag    3180
aaggatgggt tagacatttt ggtccgaggt ggaatatttt cgtagagaga aaatataaat    3240
atgatcccaa aatgatatta tcaccgggac aaaatatatt tcaaaaaata aactcgagtt    3300
ag                                                                  3302
```

<210> SEQ ID NO 6
<211> LENGTH: 523
<212> TYPE: PRT
<213> ORGANISM: Arabidopsis thaliana

<400> SEQUENCE: 6

```
Met Ala Ser Tyr Asn Leu Arg Ser Gln Val Arg Leu Ile Ala Ile Thr
 1               5                  10                  15

Ile Val Ile Ile Ile Thr Leu Ser Thr Pro Ile Thr Thr Asn Thr Ser
             20                  25                  30

Pro Gln Pro Trp Asn Ile Leu Ser His Asn Glu Phe Ala Gly Lys Leu
         35                  40                  45
```

-continued

```
Thr Ser Ser Ser Ser Val Glu Ala Ala Thr Asp Phe Gly His
    50              55              60

Val Thr Lys Ile Phe Pro Ser Ala Val Leu Ile Pro Ser Ser Val Glu
65              70              75              80

Asp Ile Thr Asp Leu Ile Lys Leu Ser Phe Asp Ser Gln Leu Ser Phe
                85              90              95

Pro Leu Ala Ala Arg Gly His Gly His Ser His Arg Gly Gln Ala Ser
            100             105             110

Ala Lys Asp Gly Val Val Asn Met Arg Ser Met Val Asn Arg Asp
    115             120             125

Arg Gly Ile Lys Val Ser Arg Thr Cys Leu Tyr Val Asp Val Asp Ala
    130             135             140

Ala Trp Leu Trp Ile Glu Val Leu Asn Lys Thr Leu Glu Leu Gly Leu
145             150             155             160

Thr Pro Val Ser Trp Thr Asp Tyr Leu Tyr Leu Thr Val Gly Gly Thr
                165             170             175

Leu Ser Asn Gly Gly Ile Ser Gly Gln Thr Phe Arg Tyr Gly Pro Gln
            180             185             190

Ile Thr Asn Val Leu Glu Met Asp Val Ile Thr Gly Lys Gly Glu Ile
    195             200             205

Ala Thr Cys Ser Lys Asp Met Asn Ser Asp Leu Phe Phe Ala Val Leu
    210             215             220

Gly Gly Leu Gly Gln Phe Gly Ile Ile Thr Arg Ala Arg Ile Lys Leu
225             230             235             240

Glu Val Ala Pro Lys Arg Ala Lys Trp Leu Arg Phe Leu Tyr Ile Asp
                245             250             255

Phe Ser Glu Phe Thr Arg Asp Gln Glu Arg Val Ile Ser Lys Thr Asp
            260             265             270

Gly Val Asp Phe Leu Glu Gly Ser Ile Met Val Asp His Gly Pro Pro
    275             280             285

Asp Asn Trp Arg Ser Thr Tyr Tyr Pro Pro Ser Asp His Leu Arg Ile
    290             295             300

Ala Ser Met Val Lys Arg His Arg Val Ile Tyr Cys Leu Glu Val Val
305             310             315             320

Lys Tyr Tyr Asp Glu Thr Ser Gln Tyr Thr Val Asn Glu Glu Met Glu
                325             330             335

Glu Leu Ser Asp Ser Leu Asn His Val Arg Gly Phe Met Tyr Glu Lys
            340             345             350

Asp Val Thr Tyr Met Asp Phe Leu Asn Arg Val Arg Thr Gly Glu Leu
    355             360             365

Asn Leu Lys Ser Lys Gly Gln Trp Asp Val Pro His Pro Trp Leu Asn
    370             375             380

Leu Phe Val Pro Lys Thr Gln Ile Ser Lys Phe Asp Asp Gly Val Phe
385             390             395             400

Lys Gly Ile Ile Leu Arg Asn Asn Ile Thr Ser Gly Pro Val Leu Val
                405             410             415

Tyr Pro Met Asn Arg Asn Lys Trp Asn Asp Arg Met Ser Ala Ala Ile
            420             425             430

Pro Glu Glu Asp Val Phe Tyr Ala Val Gly Phe Leu Arg Ser Ala Gly
    435             440             445

Phe Asp Asn Trp Glu Ala Phe Asp Gln Glu Asn Met Glu Ile Leu Lys
    450             455             460

Phe Cys Glu Asp Ala Asn Met Gly Val Ile Gln Tyr Leu Pro Tyr His
```

| | | | | 465 | | | | | 470 | | | | | 475 | | | | | 480 |

Ser Ser Gln Glu Gly Trp Val Arg His Phe Gly Pro Arg Trp Asn Ile
                485                     490                     495

Phe Val Glu Arg Lys Tyr Lys Tyr Asp Pro Lys Met Ile Leu Ser Pro
            500                     505                     510

Gly Gln Asn Ile Phe Gln Lys Ile Asn Ser Ser
        515                 520

<210> SEQ ID NO 7
<211> LENGTH: 2782
<212> TYPE: DNA
<213> ORGANISM: Arabidopsis thaliana

<400> SEQUENCE: 7

| | |
|---|---|
| atgactaata ctctctgttt aagcctcatc accctaataa cgcttttat aagtttaacc | 60 |
| ccaaccttaa tcaaatcaga tgagggcatt gatgttttct tacccatatc actcaacctt | 120 |
| acggtcctaa ccgatcccct tccatctct gccgcttctc acgacttcgg taacataacc | 180 |
| gacgaaaatc ccggcgccgt cctctgccct tcctccacca cggaggtggc tcgtctcctc | 240 |
| cgtttcgcta acggaggatt ctcttacaat aaaggctcaa ccagccccgc gtctactttc | 300 |
| aaagtggctg ctcgaggcca aggccactcc ctccgtggcc aagcctctgc acccggaggt | 360 |
| gtcgtcgtga acatgacgtg tctcgccatg gcggctaaac cagcggcggt tgttatctcg | 420 |
| gcagacggga cttacgctga cgtggctgcc gggacgatgt gggtggatgt tctgaaggcg | 480 |
| gcggtggata gaggcgtctc gccggttaca tggacggatt atttgtatct cagcgtcggc | 540 |
| gggacgttgt cgaacgctgg aatcggtggt cagacgttta gacacggccc tcagattagt | 600 |
| aacgttcatg agcttgacgt tattaccggt acgtaaatac caaaacttca ctaatctcgt | 660 |
| tacaattttt taattttttg gtaatataaa ttttgtacgg ctcaactctt aattaagaat | 720 |
| gaaacagtat ctatgatctt ctagatgctc ttttttttgtc tgcaagcttt aattgtagta | 780 |
| acatcagcga tatatatatc acatgcatgt gtattattga tgataatata taatgtttta | 840 |
| gttacaaatt tgattctcaa ggtaaaactc acacgccata accagtataa aactccaaaa | 900 |
| atcacgtttt ggtcagaaat acatatcctt cattaacagt agttatgcta aatttgtga | 960 |
| ttataaataa ctccggagtt tgttcacaat actaaatttc aggaaaaggt gaatgatga | 1020 |
| cttgctctcc aaagttaaac cctgaattgt tctatggagt tttaggaggt ttgggtcaat | 1080 |
| tcggtattat aacgagggcc aggattgcgt tggatcatgc acccacaagg gtatgtatca | 1140 |
| tgcatctata gtgtaatcaa tttataattt taatgtagtg gtcctaaatc caaaatttga | 1200 |
| tttgatttgg ttgaacgta cgtatatata ataagtcaaa aggctgattt tgaagacgaa | 1260 |
| tttatatact tttgttgaat taaatctgat tttgcttacg ttttattaga ttctgcgtaa | 1320 |
| taaatcctag gacttgctcg agtgtaatct tgtcttatgc ttgcaaatct tgttgatgtc | 1380 |
| aatatctaat cttttttatt atatttccct acgtaagttt tagatatagt tattttaaac | 1440 |
| tgctataaat tgtgtacgta tagactttag ataaaaagtt gtggtcgctt gcacctattt | 1500 |
| gtttatcgct atagtgattc aaaggtctat atatgattct tggtttttct ttttgaaaaa | 1560 |
| aatagaccat acaatccaag gaagatgatc ttaaatggac taatttatgg atataaattg | 1620 |
| atatacaaat ctgcaggtga atggtctcg catactctac agtgacttct cggctttaa | 1680 |
| aagagaccaa gagcgtttaa tatcaatgac caatgatctc ggagttgact ttttggaagg | 1740 |
| tcaacttatg atgtcaaatg gcttcgtaga cacctctttc ttcccactct ccgatcaaac | 1800 |

-continued

```
aagagtcgca tctcttgtga atgaccaccg gatcatctat gttctcgaag tagccaagta  1860
ttatgacaga accacccttc ccattattga ccaggtacta aaatccatta ttcatgatga  1920
ttatcttcac acaatcagta tcatcaccaa ttaccatcat cacttgtcat atatgatcca  1980
aagtaaatat atcacatgat ataaataaat cgttcaaatc ttttttttta aagaataaaa  2040
gaatcatttt caagcattac tcatacacat ctacgaatca ccgtgaccat atataaccat  2100
acgcttatta aataatcatt tttgtttgta ggtgattgac acgttaagta gaactctagg  2160
tttcgctcca gggtttatgt tcgtacaaga tgttccgtat ttcgatttct tgaaccgtgt  2220
ccgaaacgaa gaagataaac tcagatcttt aggactatgg gaagttcctc atccatggct  2280
taacatcttt gtcccggggt ctcgaatcca agattttcat gatggtgtta ttaatggcct  2340
tcttctaaac caaacctcaa cttctggtgt tactctcttc tatcccacaa accgaaacaa  2400
gtaaatattt acttttttgat tttgttttat ttgaaagtat atcccaataa tgtatgttaa  2460
attgttaaca agaatttatt ttattaatag atggaacaac cgcatgtcaa cgatgacacc  2520
ggacgaagat gttttttatg tgatcggatt actgcaatca gctggtggat ctcaaaattg  2580
gcaagaactt gaaaatctca acgacaaggt tattcagttt tgtgaaaact cgggaattaa  2640
gattaaggaa tatttgatgc actatacaag aaaagaagat tgggttaaac attttggacc  2700
aaaatgggat gattttttaa gaagaaaat tatgtttgat cccaaaagac tattgtctcc  2760
aggacaagac atatttaatt aa                                           2782
```

<210> SEQ ID NO 8
<211> LENGTH: 524
<212> TYPE: PRT
<213> ORGANISM: Arabidopsis thaliana

<400> SEQUENCE: 8

```
Met Thr Asn Thr Leu Cys Leu Ser Leu Ile Thr Leu Ile Thr Leu Phe
  1               5                  10                  15

Ile Ser Leu Thr Pro Thr Leu Ile Lys Ser Asp Glu Gly Ile Asp Val
             20                  25                  30

Phe Leu Pro Ile Ser Leu Asn Leu Thr Val Leu Thr Asp Pro Phe Ser
         35                  40                  45

Ile Ser Ala Ala Ser His Asp Phe Gly Asn Ile Thr Asp Glu Asn Pro
     50                  55                  60

Gly Ala Val Leu Cys Pro Ser Ser Thr Thr Glu Val Ala Arg Leu Leu
 65                  70                  75                  80

Arg Phe Ala Asn Gly Gly Phe Ser Tyr Asn Lys Gly Ser Thr Ser Pro
                 85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Asn Met Thr Cys Leu
        115                 120                 125

Ala Met Ala Ala Lys Pro Ala Ala Val Val Ile Ser Ala Asp Gly Thr
    130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gln Thr
            180                 185                 190

Phe Arg His Gly Pro Gln Ile Ser Asn Val His Glu Leu Asp Val Ile
```

```
                195                 200                 205
Thr Gly Lys Gly Glu Met Met Thr Cys Ser Pro Lys Leu Asn Pro Glu
    210                 215                 220

Leu Phe Tyr Gly Val Leu Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
                260                 265                 270

Leu Ile Ser Met Thr Asn Asp Leu Gly Val Asp Phe Leu Glu Gly Gln
            275                 280                 285

Leu Met Met Ser Asn Gly Phe Val Asp Thr Ser Phe Phe Pro Leu Ser
    290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
                340                 345                 350

Phe Met Phe Val Gln Asp Val Pro Tyr Phe Asp Phe Leu Asn Arg Val
            355                 360                 365

Arg Asn Glu Glu Asp Lys Leu Arg Ser Leu Gly Leu Trp Glu Val Pro
        370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
                420                 425                 430

Met Ser Thr Met Thr Pro Asp Glu Asp Val Phe Tyr Val Ile Gly Leu
            435                 440                 445

Leu Gln Ser Ala Gly Gly Ser Gln Asn Trp Gln Glu Leu Glu Asn Leu
    450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
                485                 490                 495

Gly Pro Lys Trp Asp Asp Phe Leu Arg Lys Lys Ile Met Phe Asp Pro
                500                 505                 510

Lys Arg Leu Leu Ser Pro Gly Gln Asp Ile Phe Asn
            515                 520

<210> SEQ ID NO 9
<211> LENGTH: 2805
<212> TYPE: DNA
<213> ORGANISM: Arabidopsis thaliana

<400> SEQUENCE: 9
atgacgtcaa gctttcttct cctgacgttc gccatatgta aactgatcat agccgtgggt      60
ctaaacgtgg gccccagtga gctcctccgc atcggagcca tagatgtcga cggccacttc     120
accgtccacc cttccgactt agcctccgtc tcctcagact tcggtatgct gaagtcacct     180
gaagagccat tggccgtgct tcatccatca tcggccgaag acgtggcacg actcgtcaga     240
acagcttacg gttcagccac ggcgtttccg gtctcagccc gaggccacgg ccattccata     300
```

```
aacggacaag ccgcggcggg gaggaacggt gtggtggttg aaatgaacca cggcgtaacc      360
gggacgccca agccactcgt ccgaccggat gaaatgtatg tggatgtatg gggtggagag      420
ttatgggtcg atgtgttgaa gaaaacgttg gagcatggct tagcaccaaa atcatggacg      480
gattacttgt atctaaccgt tggaggtaca ctctccaatg caggaatcag tggtcaagct      540
tttcaccatg gtcctcaaat tagtaacgtc cttgagctcg acgttgtaac tggttagtat      600
taaaacattc aagttcatat attttaaatg cttttgtctg aagttttact aataacaaga      660
aattgatacc aaaaagtagg gaaggagag gtgatgagat gctcagaaga agagaacaca      720
aggctattcc atggagttct tggtggatta ggtcaatttg ggatcatcac tcgagcacga      780
atctctctcg aaccagctcc ccaaagggta atatttttt aatgactagc tatcaaaaat      840
ccctggcggg tccatacgtt gtaatctttt tagtttttac tgttgatggt atttttata      900
tattttggat aataaaaccc taaaatggta tattgtgatg acaggtgaga tggatacggg      960
tattgtattc gagcttcaaa gtgtttacgg aggaccaaga gtacttaatc tcaatgcatg     1020
gtcaattaaa gtttgattac gtggaaggtt ttgtgattgt ggacgaagga ctcgtcaaca     1080
attggagatc ttctttcttc tctccacgta accccgtcaa gatctcctct gttagttcca     1140
acggctctgt tttgtattgc cttgagatca ccaagaacta ccacgactcc gactccgaaa     1200
tcgttgatca ggtcactttc attattcact tagaaaaaag cgatattttc attttttata     1260
ttgatgaata tctggaagga tttaacgcta tgcgactatt gggaaatcat tatgaaaaaa     1320
tatttagttt atatgattga agtggtctc catagtattt ttgttgtgtc gactttatta     1380
taacttaaat ttggaagagg acatgaagaa gaagccagag aggatctaca gagatctagc     1440
ttttccacct gaacttaata atgcacattt atataattat ttttcttctt ctaaagttta     1500
gtttatcact agcgaattaa tcatggttac taattaagta gtggacaggg tcatggacca     1560
ctcactcacc aaataatgat tcctctttac tcttaagttt aattttaata aaaccaactc     1620
tactggaatc ttaacttatc cttggttttg gtaggctttt atagcaacac ggttttttta     1680
attttcctat tccagatttt gtatattaaa tgtcgatttt ttttcttttt gtttcaggaa     1740
gttgagattc tgatgaagaa attgaatttc ataccgacat cggtctttac aacggattta     1800
caatatgtgg actttctcga ccgggtacac aaggccgaat tgaagctccg gtccaagaat     1860
ttatgggagg ttccacaccc atggctcaac ctcttcgtgc caaaatcaag aatctctgac     1920
ttcgataaag gcgttttcaa gggcatttg ggaaataaaa caagtggccc tattcttatc     1980
taccccatga acaaagacaa gtaagtcttg acattaccat tgattactac ttctaaattt     2040
cttctctaga aaaagaata aaacgagttt tgcattgcat gcatgcaaag ttacacttgt     2100
ggggattaat tagtggtcca agaaaaaaag tttgtcaaaa ttgaaaaaaa ctagacacgt     2160
ggtacatggg attgtccgaa aaacgttgtc cacatgtgca tcgaaccagc taagattgac     2220
aacaacactt cgtcggctcg tatttctctt tttgttttgt gaccaaatcc gatggtccag     2280
attgggttta tttgttttta agttcctaga actcatggtg ggtgggtccc aatcagattc     2340
tcctagacca aaccgatctc aacgaaccct ccgcacatca ttgattatta cattaatata     2400
gatattgtcg ttgctgacgt gtcgtaattt gatgttattg tcagtgggga cgagaggagc     2460
tcagccgtga cgccggatga ggaagttttc tatctggtgg ctctattgag atcagcttta     2520
acggacggtg aagagacaca gaagctagag tatctgaaag atcagaaccg tcggatcttg     2580
gagttctgtg aacaagccaa gatcaatgtg aagcagtatc ttcctcacca cgcaacacag     2640
```

```
gaagagtggg tggctcattt tggggacaag tgggatcggt tcagaagctt aaaggctgag    2700
tttgatccgc gacacatact cgctactggt cagagaatct ttcaaaaccc atctttgtct    2760
ttgtttcctc cgtcgtcgtc ttcttcgtca gcggcttcat ggtga                   2805
```

<210> SEQ ID NO 10
<211> LENGTH: 536
<212> TYPE: PRT
<213> ORGANISM: Arabidopsis thaliana

<400> SEQUENCE: 10

```
Met Thr Ser Ser Phe Leu Leu Thr Phe Ala Ile Cys Lys Leu Ile
 1               5                  10                  15

Ile Ala Val Gly Leu Asn Val Gly Pro Ser Glu Leu Leu Arg Ile Gly
                20                  25                  30

Ala Ile Asp Val Asp Gly His Phe Thr Val His Pro Ser Asp Leu Ala
            35                  40                  45

Ser Val Ser Ser Asp Phe Gly Met Leu Lys Ser Pro Glu Glu Pro Leu
        50                  55                  60

Ala Val Leu His Pro Ser Ser Ala Glu Asp Val Ala Arg Leu Val Arg
65                  70                  75                  80

Thr Ala Tyr Gly Ser Ala Thr Ala Phe Pro Val Ser Ala Arg Gly His
                85                  90                  95

Gly His Ser Ile Asn Gly Gln Ala Ala Ala Gly Arg Asn Gly Val Val
            100                 105                 110

Val Glu Met Asn His Gly Val Thr Gly Thr Pro Lys Pro Leu Val Arg
        115                 120                 125

Pro Asp Glu Met Tyr Val Asp Val Trp Gly Gly Glu Leu Trp Val Asp
    130                 135                 140

Val Leu Lys Lys Thr Leu Glu His Gly Leu Ala Pro Lys Ser Trp Thr
145                 150                 155                 160

Asp Tyr Leu Tyr Leu Thr Val Gly Gly Thr Leu Ser Asn Ala Gly Ile
                165                 170                 175

Ser Gly Gln Ala Phe His His Gly Pro Gln Ile Ser Asn Val Leu Glu
            180                 185                 190

Leu Asp Val Val Thr Gly Lys Gly Glu Val Met Arg Cys Ser Glu Glu
        195                 200                 205

Glu Asn Thr Arg Leu Phe His Gly Val Leu Gly Gly Leu Gly Gln Phe
    210                 215                 220

Gly Ile Ile Thr Arg Ala Arg Ile Ser Leu Glu Pro Ala Pro Gln Arg
225                 230                 235                 240

Val Arg Trp Ile Arg Val Leu Tyr Ser Ser Phe Lys Val Phe Thr Glu
                245                 250                 255

Asp Gln Glu Tyr Leu Ile Ser Met His Gly Gln Leu Lys Phe Asp Tyr
            260                 265                 270

Val Glu Gly Phe Val Ile Val Asp Glu Gly Leu Val Asn Asn Trp Arg
        275                 280                 285

Ser Ser Phe Phe Ser Pro Arg Asn Pro Val Lys Ile Ser Ser Val Ser
    290                 295                 300

Ser Asn Gly Ser Val Leu Tyr Cys Leu Glu Ile Thr Lys Asn Tyr His
305                 310                 315                 320

Asp Ser Asp Ser Glu Ile Val Asp Gln Glu Val Glu Ile Leu Met Lys
                325                 330                 335

Lys Leu Asn Phe Ile Pro Thr Ser Val Phe Thr Thr Asp Leu Gln Tyr
            340                 345                 350
```

-continued

```
Val Asp Phe Leu Asp Arg Val His Lys Ala Glu Leu Lys Leu Arg Ser
            355                 360                 365
Lys Asn Leu Trp Glu Val Pro His Pro Trp Leu Asn Leu Phe Val Pro
        370                 375                 380
Lys Ser Arg Ile Ser Asp Phe Asp Lys Gly Val Phe Lys Gly Ile Leu
385                 390                 395                 400
Gly Asn Lys Thr Ser Gly Pro Ile Leu Ile Tyr Pro Met Asn Lys Asp
                405                 410                 415
Lys Trp Asp Glu Arg Ser Ser Ala Val Thr Pro Asp Glu Val Phe
            420                 425                 430
Tyr Leu Val Ala Leu Leu Arg Ser Ala Leu Thr Asp Gly Glu Glu Thr
        435                 440                 445
Gln Lys Leu Glu Tyr Leu Lys Asp Gln Asn Arg Arg Ile Leu Glu Phe
    450                 455                 460
Cys Glu Gln Ala Lys Ile Asn Val Lys Gln Tyr Leu Pro His His Ala
465                 470                 475                 480
Thr Gln Glu Glu Trp Val Ala His Phe Gly Asp Lys Trp Asp Arg Phe
                485                 490                 495
Arg Ser Leu Lys Ala Glu Phe Asp Pro Arg His Ile Leu Ala Thr Gly
            500                 505                 510
Gln Arg Ile Phe Gln Asn Pro Ser Leu Ser Leu Phe Pro Pro Ser Ser
        515                 520                 525
Ser Ser Ser Ser Ala Ala Ser Trp
    530                 535
```

<210> SEQ ID NO 11
<211> LENGTH: 1936
<212> TYPE: DNA
<213> ORGANISM: Arabidopsis thaliana

<400> SEQUENCE: 11

```
atgcttatag taagaagttt caccatcttg cttctcagct gcatagcctt taagttggct      60
tgctgcttct ctagcagcat ttcttctttg aaggcgcttc ccctagtagg ccatttggag     120
tttgaacatg tccatcacgc ctccaaagat tttggaaatc gataccagtt gatcccttg      180
gcggtcttac atcccaaatc ggtaagcgac atcgcctcaa cgatacgaca catctggatg     240
atgggcactc attcacagct tacagtggca gcgagaggtc gtggacattc actccaaggc     300
caagctcaaa caagacatgg aattgttata cacatggaat cactccatcc ccagaagctg     360
caggtctaca gtgtggattc ccctgctcca tatgttgatg tgtctggtgg tgagctgtgg     420
ataaacattt tgcatgagac cctcaagtac gggcttgcac caaaatcatg gacggattac     480
ctgcatttaa ctgtaggtgg tactctgtcc aatgctggaa taagcggcca ggcattccga     540
catggaccac agatcagcaa tgttcatcaa ctggagattg tcacaggtta gttcagagtt     600
gcagtattcg tgttttgaaa gcatagactc tatatggttg gtgactatta acaacatgaa     660
gagattcccg agaatagcta cccactaatg tcatgcctat ttattgactg caggaaaagg     720
cgagatccta aactgtacaa agaggcagaa cagcgactta tttaatggtg ttcttggtgg     780
tttaggtcag tttggcatca taacgcgggc aagaatagca ttggaaccag caccaaccat     840
ggtaaacaat aaataaataa aaaacttaaa actgaacaca gcgtgtgtcc tcctaactct     900
gtataatgga caggtaaaat ggataagagt gttatacctg gattttgcag cttttgccaa     960
ggaccaagag caactaatat ctgcccaggg ccacaaattc gattacatag aagggtttgt    1020
```

```
gataataaac aggacaggcc tcctgaacag ctggaggttg tctttcaccg cagaagagcc    1080
tttagaagca agccaattca agtttgatgg aaggactctg tattgtctgg agctagccaa    1140
gtatttgaag caagataaca aagacgtaat caaccaggtg agaaaacaga gtagaagcaa    1200
tcggtagaat cttctttggt agatgacatt cattggaact gaaatatat atatatttgt    1260 ccaatccagg aagtgaaaga aacattatca gagctaagct acgtgacgtc gacactgttt    1320
acaacggagg tagcatatga agcattcttg acagggtac atgtgtctga ggtaaaactc    1380
cgatcgaaag ggcagtggga ggtgccacat ccatggctga acctcctggt accaagaagc    1440
aaaatcaatg aatttgcaag aggtgtattt ggaaacatac taacggatac aagcaacggc    1500
ccagtcatcg tctacccagt gaacaaatca agtaagaaa gaaagaaaga aagagctagt    1560
catgattttg tttcttttca cttgttgaca aaacaaaagc atgttggtga gcaggtggga    1620
caatcaaaca tcagcagtaa caccggagga agaggtattc tacctggtgg cgatcctaac    1680
atcggcatct ccagggtcgg caggaaagga tggagtagaa gagatcttga ggcggaacag    1740
aagaatactg gaattcagtg aagaagcagg gatagggttg aagcagtatc tgccacatta    1800
cacgacaaga gaagagtgga gatcccattt cggggacaag tggggagaat ttgtgaggag    1860
gaaatccaga tatgatccat tggcaattct tgcgcctggc accgaatttt tcaaaaggc    1920 agtctcatac tcatga                                                    1936
```

<210> SEQ ID NO 12
<211> LENGTH: 504
<212> TYPE: PRT
<213> ORGANISM: Arabidopsis thaliana

<400> SEQUENCE: 12

```
Met Leu Ile Val Arg Ser Phe Thr Ile Leu Leu Ser Cys Ile Ala
 1               5                  10                  15

Phe Lys Leu Ala Cys Cys Phe Ser Ser Ser Ile Ser Ser Leu Lys Ala
            20                  25                  30

Leu Pro Leu Val Gly His Leu Glu Phe Glu His Val His His Ala Ser
        35                  40                  45

Lys Asp Phe Gly Asn Arg Tyr Gln Leu Ile Pro Leu Ala Val Leu His
    50                  55                  60

Pro Lys Ser Val Ser Asp Ile Ala Ser Thr Ile Arg His Ile Trp Met
65                  70                  75                  80

Met Gly Thr His Ser Gln Leu Thr Val Ala Ala Arg Gly Arg Gly His
                85                  90                  95

Ser Leu Gln Gly Gln Ala Gln Thr Arg His Gly Ile Val Ile His Met
            100                 105                 110

Glu Ser Leu His Pro Gln Lys Leu Gln Val Tyr Ser Val Asp Ser Pro
        115                 120                 125

Ala Pro Tyr Val Asp Val Ser Gly Gly Glu Leu Trp Ile Asn Ile Leu
    130                 135                 140

His Glu Thr Leu Lys Tyr Gly Leu Ala Pro Lys Ser Trp Thr Asp Tyr
145                 150                 155                 160

Leu His Leu Thr Val Gly Gly Thr Leu Ser Asn Ala Gly Ile Ser Gly
                165                 170                 175

Gln Ala Phe Arg His Gly Pro Gln Ile Ser Asn Val His Gln Leu Glu
            180                 185                 190

Ile Val Thr Gly Lys Gly Glu Ile Leu Asn Cys Thr Lys Arg Gln Asn
        195                 200                 205
```

```
Ser Asp Leu Phe Asn Gly Val Leu Gly Gly Leu Gly Gln Phe Gly Ile
210                 215                 220

Ile Thr Arg Ala Arg Ile Ala Leu Glu Pro Ala Pro Thr Met Asp Gln
225                 230                 235                 240

Glu Gln Leu Ile Ser Ala Gln Gly His Lys Phe Asp Tyr Ile Glu Gly
                245                 250                 255

Phe Val Ile Ile Asn Arg Thr Gly Leu Leu Asn Ser Trp Arg Leu Ser
                260                 265                 270

Phe Thr Ala Glu Glu Pro Leu Glu Ala Ser Gln Phe Lys Phe Asp Gly
                275                 280                 285

Arg Thr Leu Tyr Cys Leu Glu Leu Ala Lys Tyr Leu Lys Gln Asp Asn
290                 295                 300

Lys Asp Val Ile Asn Gln Glu Val Lys Glu Thr Leu Ser Glu Leu Ser
305                 310                 315                 320

Tyr Val Thr Ser Thr Leu Phe Thr Thr Glu Val Ala Tyr Glu Ala Phe
                325                 330                 335

Leu Asp Arg Val His Val Ser Glu Val Lys Leu Arg Ser Lys Gly Gln
                340                 345                 350

Trp Glu Val Pro His Pro Trp Leu Asn Leu Leu Val Pro Arg Ser Lys
                355                 360                 365

Ile Asn Glu Phe Ala Arg Gly Val Phe Gly Asn Ile Leu Thr Asp Thr
370                 375                 380

Ser Asn Gly Pro Val Ile Val Tyr Pro Val Asn Lys Ser Lys Trp Asp
385                 390                 395                 400

Asn Gln Thr Ser Ala Val Thr Pro Glu Glu Val Phe Tyr Leu Val
                405                 410                 415

Ala Ile Leu Thr Ser Ala Ser Pro Gly Ser Ala Gly Lys Asp Gly Val
                420                 425                 430

Glu Glu Ile Leu Arg Arg Asn Arg Arg Ile Leu Glu Phe Ser Glu Glu
                435                 440                 445

Ala Gly Ile Gly Leu Lys Gln Tyr Leu Pro His Tyr Thr Thr Arg Glu
                450                 455                 460

Glu Trp Arg Ser His Phe Gly Asp Lys Trp Gly Glu Phe Val Arg Arg
465                 470                 475                 480

Lys Ser Arg Tyr Asp Pro Leu Ala Ile Leu Ala Pro Gly His Arg Ile
                485                 490                 495

Phe Gln Lys Ala Val Ser Tyr Ser
                500

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 13
cggtcgacat gggattgacc tcatccttac g                               31

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide: primer or probe
```

-continued

<400> SEQUENCE: 14
gcgtcgactt atacagttct aggtttcggc agtat                               35

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 15
gcggtaccag agagagaaac ataaacaaat ggc                                 33

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 16
gcggtaccca attttacttc caccaaaatg c                                   31

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 17
gcggtaccct cattgataag aatcaagcta ttca                                34

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 18
gcggtaccca aagtggtgag aacgactaac a                                   31

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 19
gcggtacccc cattaaccta cccgtttg                                       28

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 20
gcggtaccag acgatgaacg tacttgtctg ta                                     32

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 21
ggggtacctt gatgaatcgt gaaatgac                                          28

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 22
ggggtaccct ttcctcttgg ttttgtcctg t                                      31

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 23
gctctagatc aggaaaagaa ccatgcttat ag                                     32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 24
gctctagatc atgagtatga gactgccttt tg                                     32

<210> SEQ ID NO 25
<211> LENGTH: 1728
<212> TYPE: DNA
<213> ORGANISM: Arabidopsis thaliana

<400> SEQUENCE: 25
atgggattga cctcatcctt acggttccat agacaaaaca acaagacttt cctcggaatc       60
ttcatgatct tagttctaag ctgtatacca ggtagaacca atctttgttc caatcattct      120
gttagtaccc caaaagaatt accttcttca aatccttcag atattcgttc ctcattagtt      180
tcactagatt tggagggtta tataagcttc gacgatgtcc acaatgtggc caaggacttt      240
ggcaacagat accagttacc acctttggca attctacatc aaggtcagt tttttgatatt      300 tcatcgatga tgaagcatat agtacatctg ggctccacct caaatcttac agtagcagct      360
agaggccatg gtcactcgct tcaaggacaa gctctagctc atcaaggtgt tgtcatcaaa      420
atggagtcac ttcgaagtcc tgatatcagg atttataagg ggaagcaacc atatgttgat      480

```
gtctcaggtg gtgaaatatg gataaacatt ctacgcgaga ctctaaaata cggtctttca    540
ccaaagtcct ggacagacta ccttcatttg accgttggag gtacactatc taatgctgga    600
atcagcggtc aagcattcaa gcatggaccc caaatcaaca acgtctacca gctagagatt    660
gttacaggga aggagaagt cgtaacctgt tctgagaagc ggaattctga acttttcttc     720
agtgttcttg gcgggcttgg acagtttggc ataatcaccc gggcacggat ctctcttgaa    780
ccagcaccgc atatggttaa atggatcagg gtactctact ctgactttc tgcattttca     840 agggaccaag aatatctgat ttcgaaggag aaaacttttg attacgttga aggatttgtg    900
ataatcaata gaacagacct tctcaataat tggcgatcgt cattcagtcc caacgattcc    960
acacaggcaa gcagattcaa gtcagatggg aaaactcttt attgcctaga gtggtcaaa    1020 tatttcaacc cagaagaagc tagctctatg gatcaggaaa ctggcaagtt actttcagag   1080
ttaaattata ttccatccac tttgttttca tctgaagtgc catatatcga gtttctggat   1140
cgcgtgcata tcgcagagag aaaactaaga gcaaagggtt tatgggaggt tccacatccc   1200
tggctgaatc tcctgattcc taagagcagc atataccaat ttgctacaga gttttcaac   1260 aacattctca caagcaacaa caacggtcct atccttattt atccagtcaa tcaatccaag   1320
tggaagaaac atacatcttt gataactcca atgaagata tattctatct cgtagccttt    1380
ctcccctctg cagtgccaaa ttcctcaggg aaaaacgatc tagagtacct tttgaaacaa   1440
aaccaaagag ttatgaactt ctgcgcagca gcaaacctca acgtgaagca gtatttgccc   1500
cattatgaaa ctcaaaaaga gtggaaatca cactttggca aaagatggga aacatttgca   1560
cagaggaaac aagcctacga ccctctagcg attctagcac ctggccaaag aatattccaa   1620
aagacaacag gaaaattatc tcccatccaa ctcgcaaagt caaaggcaac aggaagtcct   1680
caaaggtacc attacgcatc aatactgccg aaacctagaa ctgtataa                1728

<210> SEQ ID NO 26
<211> LENGTH: 1506
<212> TYPE: DNA
<213> ORGANISM: Arabidopsis thaliana

<400> SEQUENCE: 26
atggctaatc ttcgttaat gatcacttta atcacggttt taatgatcac caaatcatca      60
aacggtatta aaattgattt acctaaatcc cttaacctca ccctctctac cgatccttcc    120
atcatctccg cagcctctca tgacttcgga aacataacca ccgtgacccc cggcggcgta    180
atctgcccct cctccaccgc tgatatctct cgtctcctcc aatacgccgc aaacggaaaa    240
agtacattcc aagtagcggc tcgtggccaa ggccactcct taaacggcca agcctcggtc    300
tccggcggag taatcgtcaa catgacgtgt atcactacg tggtggtttc aaaagacaag    360
aagtacgctg acgtggcggc cgggacgtta tgggtggatg tgcttaagaa gacggcggag    420 aaagggtgt cgccggtttc ttggacggat tatttgcata taaccgtcgg aggaacgttg     480
tcgaatggtg gaattggtgg tcaagtgttt cgaaacggtc tcttgttag taacgtcctt    540 gaattggacg ttattactgg gaaaggtgaa atgttgacat gctcgcgaca gctaaaccca    600
gaattgttct atggagtgtt aggaggtttg ggtcaatttg gaattataac gagagccaga    660
attgttttgg accatgcacc taaacgggcc aatggtttc ggatgctcta cagtgatttc     720
acaactttta caaggaccaa agaacgtttg atatcaatgg caaacgatat tggagtcgac    780
tatttagaag gtcaaatatt tctatcaaac ggtgtcgttg acacctcttt tttcccacct    840
tcagatcaat ctaaagtcgc tgatctagtc aagcaacacg gtatcatcta tgttcttgaa    900
```

-continued

| | |
|---|---|
| gtagccaagt attatgatga tcccaatctc cccatcatca gcaaggttat tgacacatta | 960 |
| acgaaaacat taagttactt gcccgggttc atatcaatgc acgacgtggc ctacttcgat | 1020 |
| ttcttgaacc gtgtacatgt cgaagaaaat aaactcagat cttgggatt atgggaactt | 1080 |
| cctcatcctt ggcttaacct ctacgttcct aaatctcgga ttctcgattt tcataacggt | 1140 |
| gttgtcaaag acattcttct taagcaaaaa tcagcttcgg gactcgctct tctctatcca | 1200 |
| acaaaccgga ataaatggga caatcgtatg tcggcgatga taccagagat cgatgaagat | 1260 |
| gttatatata ttatcggact actacaatcc gctaccccaa aggatcttcc agaagtggag | 1320 |
| agcgttaacg agaagataat taggttttgc aaggattcag gtattaagat taagcaatat | 1380 |
| ctaatgcatt atactagtaa agaagattgg attgagcatt ttggatcaaa atgggatgat | 1440 |
| ttttcgaaga ggaaagatct atttgatccc aagaaactgt tatctccagg gcaagacatc | 1500 |
| ttttga | 1506 |

<210> SEQ ID NO 27
<211> LENGTH: 1572
<212> TYPE: DNA
<213> ORGANISM: Arabidopsis thaliana

<400> SEQUENCE: 27

| | |
|---|---|
| atggcgagtt ataatcttcg ttcacaagtt cgtcttatag caataacaat agtaatcatc | 60 |
| attactctct caactccgat cacaaccaac acatcaccac aaccatggaa tatcctttca | 120 |
| cacaacgaat tcgccggaaa actccacctcc tcctcctcct ccgtcgaatc agccgccaca | 180 |
| gatttcggcc acgtcaccaa aatcttccct tccgccgtct taatcccttc ctccgttgaa | 240 |
| gacatccacg atctccataaa actctctttt gactctcaac tgtctttcc tttagccgct | 300 |
| cgtggtcacg gacacagcca ccgtggccaa gcctcggcta agacggagt tgtggtcaac | 360 |
| atgcggtcca tggtaaaccg ggatcgaggt atcaaggtgt ctaggacctg ttatatatgtt | 420 |
| gacgtggacg ctgcgtggct atggattgag gtgttgaata aaactttgga gttagggtta | 480 |
| acgccggttt cttggacgga ttatttgtat ttaacagtcg gtgggacgtt atcaaacggc | 540 |
| ggaattagtg gacaaacgtt tcggtacggt ccacagatca ctaatgttct agagatggat | 600 |
| gttattactg gaaaaggaga gattgcaact tgttccaagg gcatgaactc ggatcttttc | 660 |
| ttcgcggtgt taggaggttt gggtcaattc ggcattataa caagagccag aattaaactt | 720 |
| gaagtagctc cgaaaagggc caagtggtta aggtttctat acatagattt ctccgaattc | 780 |
| acaagagatc aagaacgagt gatatcgaaa acggacggtg tagatttctt agaaggttcc | 840 |
| attatggtgg accatggccc accggataac tggagatcca cgtattatcc accgtccgat | 900 |
| cacttgagga tcgcctcaat ggtcaaacga catcgtgtca tctactgcct tgaagtcgtc | 960 |
| aagtattacg acgaaacttc tcaatacaca gtcaacgagg aaatggagga gttaagcgat | 1020 |
| agtttaaacc atgtaagagg gtttatgtac gagaaagatg tgacgtatat ggatttccta | 1080 |
| aaccgagttc gaaccggaga gctaaacctg aaatccaaag gccaatggga tgttccacat | 1140 |
| ccatggctta atctcttcgt accaaaaact caaatctcca aatttgatga tggtgttttt | 1200 |
| aagggtatta tcctaagaaa taacatcact agccggtcctg ttcttgttta tcctatgaat | 1260 |
| cgcaacaagt ggaatgatcg gatgtctgcc gctatacccg aggaagatgt atttttatgcg | 1320 |
| gtagggtttt taagatccgc gggttttgac aattgggagg cttttgatca agaaaacatg | 1380 |
| gaaatactga agttttgtga ggatgctaat atgggggtta tacaatatct tccttatcat | 1440 |

-continued

| tcatcacaag aaggatgggt tagacatttt ggtccgaggt ggaatatttt cgtagagaga | 1500 |
| aaatataaat atgatcccaa aatgatatta tcaccgggac aaaatatatt tcaaaaaata | 1560 |
| aactcgagtt ag | 1572 |

<210> SEQ ID NO 28
<211> LENGTH: 1575
<212> TYPE: DNA
<213> ORGANISM: Arabidopsis thaliana

<400> SEQUENCE: 28

| atgactaata ctctctgttt aagcctcatc accctaataa cgcttttat aagtttaacc | 60 |
| ccaaccttaa tcaaatcaga tgagggcatt gatgttttct tacccatatc actcaacctt | 120 |
| acggtcctaa ccgatccctt ctccatctct gccgcttctc acgacttcgg taacataacc | 180 |
| gacgaaaatc ccggcgccgt cctctgccct tcctccacca cggaggtggc tcgtctcctc | 240 |
| cgtttcgcta acgaggatt ctcttacaat aaaggctcaa ccagccccgc gtctactttc | 300 |
| aaagtggctg ctcgaggcca aggccactcc ctccgtggcc aagcctctgc acccggaggt | 360 |
| gtcgtcgtga acatgacgtg tctcgccatg gcggctaaac cagcggcggt tgttatctcg | 420 |
| gcagacggga cttacgctga cgtggctgcc gggacgatgt gggtggatgt tctgaaggcg | 480 |
| gcggtggata gaggcgtctc gccggttaca tggacggatt atttgtatct cagcgtcggc | 540 |
| gggacgttgt cgaacgctgg aatcggtggt cagacgttta gacacggccc tcagattagt | 600 |
| aacgttcatg agcttgacgt tattaccgga aaaggtgaaa tgatgacttg ctctccaaag | 660 |
| ttaaaccctg aattgttcta tggagttta ggaggtttgg gtcaattcgg tattataacg | 720 |
| agggccagga ttgcgttgga tcatgcaccc acaagggtga atggtctcg catactctac | 780 |
| agtgacttct cggcttttaa aagagaccaa gagcgtttaa tatcaatgac caatgatctc | 840 |
| ggagttgact ttttggaagg tcaacttatg atgtcaaatg cttcgtaga caccttctttc | 900 |
| ttcccactct ccgatcaaac aagagtcgca tctcttgtga atgaccaccg gatcatctat | 960 |
| gttctcgaag tagccaagta ttatgacaga accacccttc ccattattga ccaggtgatt | 1020 |
| gacacgttaa gtagaactct aggtttcgct ccagggttta tgttcgtaca agatgttccg | 1080 |
| tatttcgatt tcttgaaccg tgtccgaaac gaagaagata aactcagatc tttaggacta | 1140 |
| tgggaagttc ctcatccatg gcttaacatc tttgtcccgg ggtctcgaat ccaagatttt | 1200 |
| catgatggtg ttattaatgg ccttcttcta aaccaaacct caacttctgg tgttactctc | 1260 |
| ttctatccca caaaccgaaa caaatggaac aaccgcatgt caacgatgac accggacgaa | 1320 |
| gatgtttttt atgtgatcgg attactgcaa tcagctggtg gatctcaaaa ttggcaagaa | 1380 |
| cttgaaaatc tcaacgacaa ggttattcag ttttgtgaaa actcgggaat taagattaag | 1440 |
| gaatatttga tgcactatac aagaaaagaa gattgggtta acatttttgg accaaaatgg | 1500 |
| gatgattttt taagaaagaa aattatgttt gatcccaaaa gactattgtc tccaggacaa | 1560 |
| gacatattta attaa | 1575 |

<210> SEQ ID NO 29
<211> LENGTH: 1611
<212> TYPE: DNA
<213> ORGANISM: Arabidopsis thaliana

<400> SEQUENCE: 29

| atgacgtcaa gctttcttct cctgacgttc gccatatgta aactgatcat agccgtgggt | 60 |
| ctaaacgtgg gccccagtga gctcctccgc atcggagcca tagatgtcga cggccacttc | 120 |

| | |
|---|---:|
| accgtccacc cttccgactt agcctccgtc tcctcagact tcggtatgct gaagtcacct | 180 |
| gaagagccat tggccgtgct tcatccatca tcggccgaag acgtggcacg actcgtcaga | 240 |
| acagcttacg gttcagccac ggcgtttccg gtctcagccc gaggccacgg ccattccata | 300 |
| aacggacaag ccgcggcggg aggaacggt gtggtggttg aaatgaacca cggcgtaacc | 360 |
| gggacgccca agccactcgt ccgaccggat gaaatgtatg tggatgtatg gggtggagag | 420 |
| ttatgggtcg atgtgttgaa gaaaacgttg gagcatggct tagcaccaaa atcatggacg | 480 |
| gattacttgt atctaaccgt tggaggtaca ctctccaatg caggaatcag tggtcaagct | 540 |
| tttcaccatg gtcctcaaat tagtaacgtc cttgagctcg acgttgtaac tgggaaagga | 600 |
| gaggtgatga gatgctcaga agaagagaac acaaggctat tccatggagt tcttggtgga | 660 |
| ttaggtcaat ttgggatcat cactcgagca cgaatctctc tcgaaccagc tccccaaagg | 720 |
| gtgagatgga tacgggtatt gtattcgagc ttcaaagtgt ttacggagga ccaagagtac | 780 |
| ttaatctcaa tgcatggtca attaaagttt gattacgtgg aaggttttgt gattgtggac | 840 |
| gaaggactcg tcaacaattg gagatcttct ttcttctctc cacgtaaccc cgtcaagatc | 900 |
| tcctctgtta gttccaacgg ctctgttttg tattgccttg agatcaccaa gaactaccac | 960 |
| gactccgact ccgaaatcgt tgatcaggaa gttgagattc tgatgaagaa attgaatttc | 1020 |
| ataccgacat cggtctttac aacggattta caatatgtgg actttctcga ccgggtacac | 1080 |
| aaggccgaat tgaagctccg gtccaagaat ttatgggagg ttccacaccc atggctcaac | 1140 |
| ctcttcgtgc caaaatcaag aatctctgac ttcgataaag gcgttttcaa gggcattttg | 1200 |
| ggaaataaaa caagtggccc tattcttatc taccccatga caaagacaa atgggacgag | 1260 |
| aggagctcag ccgtgacgcc ggatgaggaa gttttctatc tggtggctct attgagatca | 1320 |
| gctttaacgg acggtgaaga gacacagaag ctagagtatc tgaaagatca gaaccgtcgg | 1380 |
| atcttggagt tctgtgaaca agccaagatc aatgtgaagc agtatcttcc tcaccacgca | 1440 |
| acacaggaag agtgggtggc tcatttggg gacaagtggg atcggttcag aagcttaaag | 1500 |
| gctgagtttg atccgcgaca catactcgct actggtcaga gaatctttca aaacccatct | 1560 |
| ttgtctttgt ttcctccgtc gtcgtcttct tcgtcagcgg cttcatggtg a | 1611 |

```
<210> SEQ ID NO 30
<211> LENGTH: 1515
<212> TYPE: DNA
<213> ORGANISM: Arabidopsis thaliana

<400> SEQUENCE: 30
```

| | |
|---|---:|
| atgcttatag taagaagttt caccatcttg cttctcagct gcatagcctt taagttggct | 60 |
| tgctgcttct ctagcagcat ttcttctttg aaggcgcttc ccctagtagg ccatttggag | 120 |
| tttgaacatg tccatcacgc ctccaaagat tttggaaatc gataccagtt gatcccttttg | 180 |
| gcggtcttac atcccaaatc ggtaagcgac atcgcctcaa cgatacgaca catctggatg | 240 |
| atgggcactc attcacagct tacagtggca gcgagaggtc gtggacattc actccaaggc | 300 |
| caagctcaaa caagacatgg aattgttata cacatggaat cactccatcc ccagaagctg | 360 |
| caggtctaca gtgtggattc ccctgctcca tatgttgatg tgtctggtgg tgagctgtgg | 420 |
| ataaacattt tgcatgagac cctcaagtac gggcttgcac caaaatcatg gacggattac | 480 |
| ctgcatttaa ctgtaggtgg tactctgtcc aatgctggaa taagcggcca ggcattccga | 540 |
| catgaccac agatcagcaa tgttcatcaa ctggagattg tcacaggaaa aggcgagatc | 600 |

-continued

```
ctaaactgta caaagaggca gaacagcgac ttatttaatg gtgttcttgg tggtttaggt    660
cagtttggca tcataacgcg ggcaagaata gcattggaac cagcaccaac catggaccaa    720
gagcaactaa tatctgccca gggccacaaa ttcgattaca tagaagggtt tgtgataata    780
aacaggacag gcctcctgaa cagctggagg ttgtctttca ccgcagaaga gcctttagaa    840
gcaagccaat tcaagtttga tggaaggact ctgtattgtc tggagctagc caagtatttg    900
aagcaagata acaaagacgt aatcaaccag gaagtgaaag aaacattatc agagctaagc    960
tacgtgacgt cgacactgtt tacaacggag gtagcatatg aagcattctt ggacagggta   1020
catgtgtctg aggtaaaaact ccgatcgaaa gggcagtggg aggtgccaca tccatggctg   1080
aacctcctgg taccaagaag caaaatcaat gaatttgcaa gaggtgtatt tggaaacata   1140
ctaacggata caagcaacgg cccagtcatc gtctacccag tgaacaaatc aaagtgggac   1200
aatcaaacat cagcagtaac accggaggaa gaggtattct acctggtggc gatcctaaca   1260
tcggcatctc cagggtcggc aggaaaggat ggagtagaag agatcttgag gcggaacaga   1320
agaatactgg aattcagtga gaagcaggg ataggttga agcagtatct gccacattac   1380
acgacaagag aagagtggag atcccatttc ggggacaagt ggggagaatt tgtgaggagg   1440
aaatccagat atgatccatt ggcaattctt gcgcctggcc accgaatttt tcaaaaggca   1500
gtctcatact catga                                                    1515

<210> SEQ ID NO 31
<211> LENGTH: 84
<212> TYPE: DNA
<213> ORGANISM: Arabidopsis thaliana

<400> SEQUENCE: 31
tcagcttcgg gactcgctct tctctatcca acaaaccgga ataaatggga caatcgtatg     60
tcggcgatga taccagagat cgat                                            84

<210> SEQ ID NO 32
<211> LENGTH: 28
<212> TYPE: PRT
<213> ORGANISM: Arabidopsis thaliana

<400> SEQUENCE: 32

Ser Ala Ser Gly Leu Ala Leu Leu Tyr Pro Thr Asn Arg Asn Lys Trp
 1               5                  10                  15

Asp Asn Arg Met Ser Ala Met Ile Pro Glu Ile Asp
             20                  25

<210> SEQ ID NO 33
<211> LENGTH: 2814
<212> TYPE: DNA
<213> ORGANISM: Arabidopsis thaliana

<400> SEQUENCE: 33
atgaatcgta tgacgtcaag ctttcttctc ctgacgttcg ccatatgtaa actgatcata     60
gccgtgggtc taaacgtggg ccccagtgag ctcctccgca tcggagccat agatgtcgac    120
ggccacttca ccgtccaccc ttccgactta gcctccgtct cctcagactt cggtatgctg    180
aagtcacctg aagagccatt ggccgtgctt catccatcat cggccgaaga cgtggcacga    240
ctcgtcagaa cagcttacgg ttcagccacg gcgtttccgg tctcagcccg aggccacggc    300
cattccataa acggacaagc cgcggcgggg aggaacggtg tggtggttga aatgaaccac    360
ggcgtaaccg ggacgcccaa gccactcgtc cgaccggatg aaatgtatgt ggatgtatgg    420
```

```
ggtggagagt tatgggtcga tgtgttgaag aaaacgttgg agcatggctt agcaccaaaa    480
tcatggacgg attacttgta tctaaccgtt ggaggtacac tctccaatgc aggaatcagt    540
ggtcaagctt ttcaccatgg tcctcaaatt agtaacgtcc ttgagctcga cgttgtaact    600
ggttagtatt aaaacattca agttcatata ttttaaatgc ttttgtctga agttttacta    660
ataacaagaa attgatacca aaaagtaggg aaaggagagg tgatgagatg ctcagaagaa    720
gagaacacaa ggctattcca tggagttctt ggtggattag gtcaatttgg gatcatcact    780
cgagcacgaa tctctctcga accagctccc caaagggtaa tatttttta atgactagct    840
atcaaaaatc cctggcgggt ccatacgttg taatctttt agttttact gttgatggta    900
ttttttatat attttggata ataaaaccct aaaatggtat attgtgatga caggtgagat    960
ggatacgggt attgtattcg agcttcaaag tgtttacgga ggaccaagag tacttaatct   1020
caatgcatgg tcaattaaag tttgattacg tggaaggttt tgtgattgtg gacgaaggac   1080
tcgtcaacaa ttggagatct tctttcttct ctccacgtaa ccccgtcaag atctcctctg   1140
ttagttccaa cggctctgtt ttgtattgcc ttgagatcac caagaactac cacgactccg   1200
actccgaaat cgttgatcag gtcactttca ttattcactt agaaaaaagc gatattttca   1260
ttttttatat tgatgaatat ctggaaggat ttaacgctat gcgactattg ggaaatcatt   1320
atgaaaaaat atttagttta tatgattgaa agtggtctcc atagtatttt tgttgtgtcg   1380
actttattat aacttaaatt tggaagagga catgaagaag aagccagaga ggatctacag   1440
agatctagct tttccacctg aacttaataa tgcacattta tataattatt tttcttcttc   1500
taaagtttag tttatcacta gcgaattaat catggttact aattaagtag tggacagggt   1560
catggaccac tcactcacca aataatgatt cctctttact cttaagttta attttaataa   1620
aaccaactct actggaatct taacttatcc ttggttttgg taggctttta tagcaacacg   1680
gttttttaa ttttcctatt ccagattttg tatattaaat gtcgattttt tttcttttg    1740
tttcaggaag ttgagattct gatgaagaaa ttgaatttca taccgacatc ggtctttaca   1800
acggatttac aatatgtgga ctttctcgac cgggtacaca aggccgaatt gaagctccgg   1860
tccaagaatt tatgggaggt tccacaccca tggctcaacc tcttcgtgcc aaaatcaaga   1920
atctctgact cgataaagg cgttttcaag ggcattttgg gaaataaaac aagtggccct   1980
attcttatct accccatgaa caaagacaag taagtcttga cattaccatt gattactact   2040
tctaaatttc ttctctagaa aaaagaataa aacgagtttt gcattgcatg catgcaaagt   2100
tacacttgtg gggattaatt agtggtccaa gaaaaaaagt ttgtcaaaat tgaaaaaaac   2160
tagacacgtg gtacatggga ttgtccgaaa acgttgtcc acatgtgcat cgaaccagct   2220
aagattgaca acaacacttc gtcggctcgt atttctcttt ttgttttgtg accaaatccg   2280
atggtccaga ttgggtttat ttgtttttaa gttcctagaa ctcatggtgg gtgggtccca   2340
atcagattct cctagaccaa accgatctca acgaaccctc cgcacatcat tgattattac   2400
attaatatag atattgtcgt tgctgacgtg tcgtaatttg atgttattgt cagatgggac   2460
gagaggagct cagccgtgac gccggatgag gaagttttct atctggtggc tctattgaga   2520
tcagctttaa cggacggtga agagacacag aagctagagt atctgaaaga tcagaaccgt   2580
cggatcttgg agttctgtga acaagccaag atcaatgtga agcagtatct tcctcaccac   2640
gcaacacagg aagagtgggt ggctcatttt ggggacaagt gggatcggtt cagaagctta   2700
aaggctgagt ttgatccgcg acacatactc gctactggtc agagaatctt tcaaaaccca   2760
```

-continued

```
tctttgtctt tgtttcctcc gtcgtcgtct tcttcgtcag cggcttcatg gtga    2814
```

<210> SEQ ID NO 34
<211> LENGTH: 1620
<212> TYPE: DNA
<213> ORGANISM: Arabidopsis thaliana

<400> SEQUENCE: 34

```
atgaatcgta tgacgtcaag ctttcttctc ctgacgttcg ccatatgtaa actgatcata      60
gccgtgggtc taaacgtggg ccccagtgag ctcctccgca tcggagccat agatgtcgac     120
ggccacttca ccgtccaccc ttccgactta gcctccgtct cctcagactt cggtatgctg     180
aagtcacctg aagagccatt ggccgtgctt catccatcat cggccgaaga cgtggcacga     240
ctcgtcagaa cagcttacgg ttcagccacg gcgtttccgg tctcagcccg aggccacggc     300
cattccataa acggacaagc cgcggcgggg aggaacggtg tggtggttga atgaaccac      360
ggcgtaaccg ggacgcccaa gccactcgtc cgaccggatg aaatgtatgt ggatgtatgg     420
ggtggagagt tatgggtcga tgtgttgaag aaaacgttgg agcatggctt agcaccaaaa     480
tcatggacgg attacttgta tctaaccgtt ggaggtacac tctccaatgc aggaatcagt     540
ggtcaagctt ttcaccatgg tcctcaaatt agtaacgtcc ttgagctcga cgttgtaact     600
gggaaaggag aggtgatgag atgctcagaa gaagagaaca caaggctatt ccatggagtt     660
cttggtggat taggtcaatt tgggatcatc actcgagcac gaatctctct cgaaccagct     720
ccccaaaggg tgagatggat acgggtattg tattcgagct tcaaagtgtt tacggaggac     780
caagagtact taatctcaat gcatggtcaa ttaaagtttg attacgtgga aggttttgtg     840
attgtggacg aaggactcgt caacaattgg agatcttctt tcttctctcc acgtaaccc      900
gtcaagatct cctctgttag ttccaacggc tctgttttgt attgccttga gatcaccaag     960
aactaccacg actccgactc cgaaatcgtt gatcaggaag ttgagattct gatgaagaaa    1020
ttgaatttca taccgacatc ggtctttaca acggatttac aatatgtgga ctttctcgac    1080
cgggtacaca aggccgaatt gaagctccgg tccaagaatt tatgggaggt tccacaccca    1140
tggctcaacc tcttcgtgcc aaaatcaaga atctctgact tcgataaagg cgttttcaag    1200
ggcattttgg gaaataaaac aagtggccct attcttatct accccatgaa caaagacaaa    1260
tgggacgaga ggagctcagc cgtgacgccg gatgaggaag ttttctatct ggtggctcta    1320
ttgagatcag ctttaacgga cggtgaagag acacagaagc tagagtatct gaaagatcag    1380
aaccgtcgga tcttggagtt ctgtgaacaa gccaagatca atgtgaagca gtatcttcct    1440
caccacgcaa cacaggaaga gtgggtggct cattttgggg acaagtggga tcggttcaga    1500
agcttaaagg ctgagtttga tccgcgacac atactcgcta ctggtcagag aatctttcaa    1560
aacccatctt tgtctttgtt tcctccgtcg tcgtcttctt cgtcagcggc ttcatggtga    1620
```

<210> SEQ ID NO 35
<211> LENGTH: 539
<212> TYPE: PRT
<213> ORGANISM: Arabidopsis thaliana

<400> SEQUENCE: 35

```
Met Asn Arg Met Thr Ser Ser Phe Leu Leu Leu Thr Phe Ala Ile Cys
  1               5                  10                  15

Lys Leu Ile Ile Ala Val Gly Leu Asn Val Gly Pro Ser Glu Leu Leu
             20                  25                  30

Arg Ile Gly Ala Ile Asp Val Asp Gly His Phe Thr Val His Pro Ser
```

-continued

```
            35                  40                  45
Asp Leu Ala Ser Val Ser Ser Asp Phe Gly Met Leu Lys Ser Pro Glu
 50                  55                  60
Glu Pro Leu Ala Val Leu His Pro Ser Ala Glu Asp Val Ala Arg
 65                  70                  75                  80
Leu Val Arg Thr Ala Tyr Gly Ser Ala Thr Ala Phe Pro Val Ser Ala
                 85                  90                  95
Arg Gly His Gly His Ser Ile Asn Gly Gln Ala Ala Gly Arg Asn
                100                 105                 110
Gly Val Val Glu Met Asn His Gly Val Thr Gly Thr Pro Lys Pro
             115                 120                 125
Leu Val Arg Pro Asp Glu Met Tyr Val Asp Val Trp Gly Gly Glu Leu
130                 135                 140
Trp Val Asp Val Leu Lys Lys Thr Leu Glu His Gly Leu Ala Pro Lys
145                 150                 155                 160
Ser Trp Thr Asp Tyr Leu Tyr Leu Thr Val Gly Gly Thr Leu Ser Asn
                165                 170                 175
Ala Gly Ile Ser Gly Gln Ala Phe His His Gly Pro Gln Ile Ser Asn
             180                 185                 190
Val Leu Glu Leu Asp Val Val Thr Gly Lys Gly Glu Val Met Arg Cys
             195                 200                 205
Ser Glu Glu Asn Thr Arg Leu Phe His Gly Val Leu Gly Gly Leu
210                 215                 220
Gly Gln Phe Gly Ile Ile Thr Arg Ala Arg Ile Ser Leu Glu Pro Ala
225                 230                 235                 240
Pro Gln Arg Val Arg Trp Ile Arg Val Leu Tyr Ser Ser Phe Lys Val
                245                 250                 255
Phe Thr Glu Asp Gln Glu Tyr Leu Ile Ser Met His Gly Gln Leu Lys
             260                 265                 270
Phe Asp Tyr Val Glu Gly Phe Val Ile Val Asp Glu Gly Leu Val Asn
             275                 280                 285
Asn Trp Arg Ser Ser Phe Phe Ser Pro Arg Asn Pro Val Lys Ile Ser
290                 295                 300
Ser Val Ser Ser Asn Gly Ser Val Leu Tyr Cys Leu Glu Ile Thr Lys
305                 310                 315                 320
Asn Tyr His Asp Ser Asp Ser Glu Ile Val Asp Gln Glu Val Glu Ile
                325                 330                 335
Leu Met Lys Lys Leu Asn Phe Ile Pro Thr Ser Val Phe Thr Thr Asp
             340                 345                 350
Leu Gln Tyr Val Asp Phe Leu Asp Arg Val His Lys Ala Glu Leu Lys
             355                 360                 365
Leu Arg Ser Lys Asn Leu Trp Glu Val Pro His Pro Trp Leu Asn Leu
         370                 375                 380
Phe Val Pro Lys Ser Arg Ile Ser Asp Phe Asp Lys Gly Val Phe Lys
385                 390                 395                 400
Gly Ile Leu Gly Asn Lys Thr Ser Gly Pro Ile Leu Ile Tyr Pro Met
                405                 410                 415
Asn Lys Asp Lys Trp Asp Glu Arg Ser Ser Ala Val Thr Pro Asp Glu
             420                 425                 430
Glu Val Phe Tyr Leu Val Ala Leu Leu Arg Ser Ala Leu Thr Asp Gly
             435                 440                 445
Glu Glu Thr Gln Lys Leu Glu Tyr Leu Lys Asp Gln Asn Arg Arg Ile
450                 455                 460
```

```
Leu Glu Phe Cys Glu Gln Ala Lys Ile Asn Val Lys Gln Tyr Leu Pro
465                 470                 475                 480

His His Ala Thr Gln Glu Glu Trp Val Ala His Phe Gly Asp Lys Trp
                485                 490                 495

Asp Arg Phe Arg Ser Leu Lys Ala Glu Phe Asp Pro Arg His Ile Leu
            500                 505                 510

Ala Thr Gly Gln Arg Ile Phe Gln Asn Pro Ser Leu Ser Leu Phe Pro
        515                 520                 525

Pro Ser Ser Ser Ser Ser Ala Ala Ser Trp
    530                 535

<210> SEQ ID NO 36
<211> LENGTH: 842
<212> TYPE: DNA
<213> ORGANISM: Arabidopsis thaliana

<400> SEQUENCE: 36
aagcttaaat gacaatttag taccttgggt tggtcatgat ttagagcgga acaaatatac      60
catacatcaa acgaggatat acagagaaaa ttcatggaag tatggaattt agaggacaat    120
ttctcttctg ggctacaacg gaccggccca ttcgctcatt tacccagagg tatcgagttt    180
gtggactttt gatgccgcta gagactattg catccggatt gaaaaaaatg tttacttcgt    240
tgttaacaat tttctgaatg caatattttc cttgtcatga atatttaaac ttgttattac    300
tttcttttag cttaggtgtg gacaattatg gagtttactt caaacgagga agaatcttaa    360
acgctcggtt caggtctcga aaacaaacca actcacaatc ctgacttaat tgaggaaaac    420
aatgcaaaac cacatgcatg cttccatatt tctatcataa tcttataaga aaaaacacta    480
ctaagtgaaa tgattctgta tatatataac caatgccttt tgttttgtga tattttatgt    540
atatataact attgactttt gtcatctatg gatagtgtct cgggctcttg gcaaacatat    600
ttcaaagaaa agttaatgac tgtaattaat taatctgaag ctagaaacag aaccccgagg    660
taaaagaaaa agacagagca catgaagttt agtacttta tatatttaat atatcattct    720
ttcttattgc ttatctctaa agcaaaaact tccctaaacc ctaagccaaa ggactcagat    780
cgatgcagaa ccaagaaggc ttgttttgga tttgagagcc aaatgcaaag aaaaaaactc    840
tt                                                                    842

<210> SEQ ID NO 37
<211> LENGTH: 92721
<212> TYPE: DNA
<213> ORGANISM: Arabidopsis thaliana

<400> SEQUENCE: 37
aaagggccac aacttgtagt acacaaaatg taatagtaga cttcatttgc ggacatgcat      60
caccagtgtt ccaaaactgt caagttgagg cctgaaacgt gacatagcaa tgttataatt    120
gttctgtcaa tggaaggaca gagcaatgtt ataactgctc aacaacgtga taagtcgggc    180
gaaagtttgg gattttcaat tcaaaaatgt gaaaatatac taaatatgta ctcatatact    240
aaatatacta aaaagtattt ttgtgaattt atttgagttt atgtatgtta acgtgtatgg    300
ccgtttgata tgggaagtgg atgtttattt ttggccaagg gagatagtag tgttgctaat    360
attgtttttt tgaacgactt gatccctcat tgaaggttta gttctatatt aaacttgtct    420
gtaatttgaa gaagtcatcg agcaaagcct tgggtggctt tgtttgtatg tatctttgtt    480
tggtttggtt aaatgatttt taaaggtaat atgttgaatt gatcaatgga tgtgaaagga    540
```

```
tgatcaagaa actatgttca tgaaaatttt gaaatttgtg ttcaacttttt atgcaaaaga    600 tgagcagaat tacgatcctt tcaaagcctt ttttttttcac caccatattt tctctcagct    660
attgtaaagt gattggttta gttacatttc acgtaaactt tagtgataat caaaatattt    720
tatcttaatg acattagacc cttgactttg tattgtatct cacatttttt cttctagtta    780
tttcttaggt tctttaaaaa ataattactg tatttaacta aattagatat gccatatttt    840
atttcttgtt ccaagtacca aagagcctag gcacgacaat gtgtgtattc actctttaat    900
ggttctataa caaatttta gtgaaaatgg tgttgtttgt tttaggctat ttatcaatat    960
cttcgaggtt catgattcta tttgttattt cattttgata ttattctgcc atgccctta   1020 cccatttgc accacctcca tcatgaggtt tgatattgat atccattaga aaatattatg   1080
aaaacatctt tgacacaaaa aattatgaaa ccaaatgtaa tattcaacaa actaaaattt   1140
tcatttttat tggtttacaa acataatcca aaccacgtac gtaactctct ttttggttt   1200 atcacataaa tatcacaatt tacaaaccat acatttacat gcatataatt aaaaatattg   1260
caccttcaaa taaatgtttt tacaaaaatc cccaatgaga aactagccaa ttaaacaacg   1320
acattagaaa accggactct tgatttccaa tcgcgaatcg cagaccggag cgtatggttc   1380
ggtgtgagct tgaagtggtc tagcttttgt cgagtcaccg gtgaaatgtt atgtttctca   1440
agccacgcta agatcgcttt cctctcgtac gtgaatccat cggcagcaat ctctggctcc   1500
tccattatct cctacatcca acaatccaaa taaataaata aaatctaaac cggttcaaat   1560
ttcttgttac tacatttgtg taccgaacca ggtaaccttt tactcacccg taagattgga   1620
cagaagtaat gactcggtgc acgtaaattg cttccttctt tctttacttt cgaattcgcc   1680
gtctccacaa gccgtttcaa aaccggtata acctctgatt taagatccgg tctatctcgg   1740
catcgaaatt cagcacattt taaaccgatc cgagccaatt cctcggtttc tgccaaaggc   1800
caatcggtaa ccgattatc tagcatttcg gttaacgtcc cttctttac cgcgttttcg   1860 accgctggta caatcccgct cgggttacga gccgtcaaca actgaagaat gattatgccg   1920
aacgcatata gatccgactt tggtctaatt gttccggttc tgtggtattc tggatcaata   1980
taatgcaatg taccggcaag aaccgagttt cggtacatcg tgacattatc gggtgcaaca   2040
tccgtaacca gcttggctag gccaacgtca gcgattttgc taacgtagtt ccggtttaac   2100
aagatatttc ccggttttaa gtcacggtga acaattggtt ccggtttaga gctgtgtaag   2160
aaggccaaac cgcaagctac ctcgaaaatt accctaaacc ggataaacca aggcaaaggc   2220
ggtttatttt ttcggtgaaa tatatattcc tcgaggcttc catttttccaa gtactcgtaa   2280 accaaacaac cattctccgg acaagctccg aggaggagaa ccacgtgtgg gtgtcggagt   2340
tggcttagaa cctcaaccta tagagaaata ttaccaaacc gaaataaaat caaccggatc   2400
aaatcaaaag agttaaccga aaccagacat aatttaaccg ataccttctt caagaactct   2460
tgtttcttct ccggtgtatc tagccggaca actttaacag ccgccggagt actatcaagg   2520
ctacattggt aaactttccc gtatcctcct tctccaatca cttttctctgg cgagaatcct   2580 tctgtggctg ttacaatttc ctcaattgtg tattttctgt accggtgatc agtccctaaa   2640
agctgatcga tcactttctt cttctccaag taagtcctta aagcattcac ctccgcgatc   2700
tgtcgctgac aaaactctct tgcgagcaac gctttcgcgg tttcgacctc tttcaccgcc   2760
ttcatgtacc gctcttctc cagcgccgcg tgttcctct gcaactcttc tttctccaca   2820
gcattgttca ctctttttaga ttcattcaaa tattcagtcg aaagcatttt aacctaacag   2880
```

```
aaaccccaaa ataaacactt tacttggaga aaaagcaagc aaaatgattc accagtgagt    2940
ttggaaaact attttataga aacaataaaa tcagatataa ataaacact tctttcacag     3000 ataagttttg atggccatca caaatataca aatttctctt cccaaaatca tctctaatca    3060
ttttcttgca gattttaggg ttcaagatca gaaatctata ccttgttttg tgtggagaag    3120
agctcttcac aagcttgttt atatttaaag actgtacttt gtagctcatt cttcaaacgt    3180
tcgacctctt cttcaatctc aacctgtcaa acaacaccaa atctttcaaa aacctcggtt    3240
acgtcataat agctagtctc atcattgcag caaaagatga tggtaaagta accttcttgg    3300
attttcttga tgtttccggg ggtgaacgat cagagtctcg gtgttcgcta acgatgttct    3360
caacatttga ttgggcttg gtacatgttt tatcaaaatc tgagtaattc agctgaggaa     3420
tatcggatcc tctccgtcgc ctaaaaatct ctggagttgt tgcactagaa gccttactac    3480
tttgaggcgt tttgggttta ttacaagtaa ggcttaatgc ctcaaatctc agctctcttg    3540
ccgatgctga cctccttgtt cctgcctctt caacatccaa agaaagaga aaacttcag      3600 gccttcaaga catcatagtt tatattatat gcattatcat ttatatattt tataatatga    3660
atctatactt gatagatgca tgttcgttgc aaatttcttc gtataacaaa tttatattca    3720
aagttataat gttatgcaac tagtttactt tttgttaact aagattgttg ttatatattt    3780
ttcaaaatta ggttcaattc aaaaaaatga gtcaattgac cattaaaatt ttttttattt    3840
ttgtttgttt aagaatgtca gaattgagaa tgtactatat attaaaacaa cctaaaaccg    3900
ctattcattt cctatgaatt ctgatggata tttgactagc tatatgtata ttttaccagt    3960
tgactgtcga ggatcgggta acgttggaga ccgtagagtg tggaaactag ccgcccagtc    4020
tctcaagaag tcatgggcag tcgcggctgc gtgtggactt gtgcacggct ctggttacca    4080
cgattaaaga gaagttttaa gaaatgagaa atatgtgt tatcaaataa aatgttttgc      4140
ctataaatta ccatgtttaa gaattacat caactatgga tgtagtatta aacaataatt     4200
ttctttaaaa aaaaacgaa acacaaaatc ctaattttta cctcggttga ttaatggatc     4260
catagatttt gtagtgattc tgtctttaca cacaatgtat acttcacatg tttctggtgc    4320
gtatcttaaa acggtcagtg gtactcctgt acctttgtt ctcctagacc gaaaatatcg     4380
ctgttagtgt atataaccga gttaattaag aagaacgtaa accaaaaccg aactatgtaa    4440
atttaccatg tgaatatgtt tgaagtaaat gatcccataa ccaaactgtt aactcctgat    4500
ttggatatca atctgacaag tgcttttgca ggatcgtcgt actctagcaa tagagtctct    4560
accttacact gaaggttaca atatttcagg gagtttaaag tttgtctctt aatttatcta    4620
gatttataaa ccgaaataaa acaaaaccaa ccttggtact cctagtactc ttgcacattt    4680
tcaaaaaggg aacaaagact gtttcatatt cttttttcac gtctcttaca tacatttcca    4740
ccacactctc ctccacttct tccaccggca atctatctcc ggctgtaaca acccacattc    4800
tcgtaaacat taatatcaaa atatctttaa attacaatga taaattaagt atttaaaaag    4860
atgtcaaaca aaaatttga taagtcgaat tagctaattt acttttaac atacaaaaaa      4920 cggaacaatt tcacctcatt aaaatcaaac tacgaaaaag taattactta atcatttgat    4980
tatcatacga acataatttg taagatttgt gaaacttact tttcacattt tcttccttca    5040
tgttctatat atttggtgtg aaaaaaaaaa aaaaaaaaac tcagtaatta ttatttcctt    5100
tctgtctttt ggtttttact tcattttatc tttatatcat ttacattagg tttttaataa    5160
caataacaag aaaaatgtga atgattgaga gagacttact cggagtagga atagaagtaa    5220
tggtagggat gacgtggatc atcacaaatt tatcagcctt cggtaaaaga ttatcgacag    5280
```

-continued

```
cccaccgtac ggcacgacga cttcctgcac cgcctaattt gtctccgatc aaacccttca    5340
cggccaccgc cacaaacagc tgaccctctt ccgcctttgg accaccaccg ccactcattt    5400
cttgcgtcag catcaccacc atctaatcaa ttatacttac gtataccaca agtaaccaaa    5460
gaataacttt tgttgttgt gactgaggaa cccttgtggg ctgatacact tttgtagttt    5520
tgtttctgaa tttgggtggg gaaatgctat tccagagatg gatattactc tgatcacgac    5580
tatattgtat tgatctcttt atatatatat atataagagt cgtttaggac caagtgttta    5640
aaaatgtaaa aaaaaaaaaa tttgattagt agccgaacaa tgattggtcg tctttcggtc    5700
tatttgttgc tttggtttgt ttaatcaata attaaagtcc taagatatgt tttaatataa    5760
acttgaacaa acaaaatata tgagtttgat tgtagaaatg ctttaattaa cactctaagt    5820
ctaaagtata aacaaaataa caacatcaaa aactaagtga ttgtagtgta ggcgtaataa    5880
tattttgata gtccgttcta aaattagttt ataaatgcta ttttttttatg gaccactatt    5940 aattattaaa tctcaaaaga attatttcta aacaatgttg tttacttaag tgatatagtg    6000
cagtacaata taaaatttt cgtattagtt tataaataca tagcttaaaa aatataagag    6060
aatacgaagt agactcatag gattggatta tataaaatca gtctattgac tttaggaaca    6120
aacaaaagat ataatttgat ctgttttgaa ttttgttggt aatcaccgat atggatcttg    6180
cagtcctgga tatataatta atagtaaaat atgtttggcc aacattagga agaaatcgat    6240
gggatggaaa tcgccttcaa aggaatatat attccattta atactttca aattcgaatt    6300 tttttggacg gccaatttgt taattataat tagtgtgcag ctttattatc tgaagttttc    6360
tagttctatc tacatgatat ttgaacggtt tagatagaga ttttatgtc tgtcagttgt    6420 ataatatgta tcatatacta tgaccagttg taccaatgtg ggcaatgtga tcaatataat    6480
gtaacctact aacttataac ctatgtattt gttgcaaaat aattatgtat gaagtaattt    6540
tgaatttatt tgaattttc cctgactttg tccgtgtcaa caaacaattc gaaatgcctc    6600
gactttttta gaacaggttc tagcaaaata acttagctca gtaagctttc agaataaata    6660
aagtagtcat tttctatcag aagatgacat aatttagttt tttcttctgt gcaaacaatg    6720
acataacaaa aaacaaatga cattacttag ttacggtact agattaatct tgaagtggta    6780
tgtggtcgca acaatctgaa tcttttagta aaaggcatga gattgttgtg gccttgtgag    6840
ataagtcaca ttttgttccg gttaaaatat gaaattattc agtattttt gtcgcagacc    6900 aacctatata ttaaaattct ttataatttt tttttaatac attgtcttga atttccacga    6960
tttcttgcac ataatagttg tttaggattt gatcatctga tacggtaacg tacagatcca    7020
aatttccgat caaaccggtt tgatttggct gagtaatgat gtttgcaatt gtttttctaat   7080 atgtaaccaa aagttgacca aaacagtcta aatgattttt cattaatttt ttgctcagca    7140
caaatgagga tatacccgaa taattaagaa ttatatataa aaaaaaaaca ctaataatgc    7200
actgatcgtt tacgagaacg acataattaa actaattaaa gatcttaacg attgtcgact    7260
ctccaatgtt cttatacaca cacaaatata aatatgatta gtccaatcta tatagtcgaa    7320
cagtaattta cagcagactt agatcgatct ttcgtataga agaaagagac gttaccaatg    7380
acattactga aataacttct ttttttttt taactacata gaattattaa cacattctaa    7440
tacagcatac attaatacat atatactctc actacgtgta aatgatagaa gacgatcaat    7500
attggctaga ggtccatctt tggttaattg ttccatatat gtagatctaa gctatatata    7560
cataatactt tcggaatttt tttgtatttc ttaaaacatt aaatatgcaa atgtaaacgg    7620
```

```
aaacaaatca aacaaaactt ttaatttgat gtcaagaaaa cgatatcata ttttttttatt    7680 ttagcccaag ctgtttttgg gtgtttatta gtatacaatt tatatttaat tggagcgaag    7740
cctacatata gaaagtttag agcatcatgt agacgtcatg tgaattctag gtccaaaatt    7800
atgtacacac tacataaaat atcataacat caaacgaaaa acacatatac cacacacgaa    7860
aaaagggaaa aaagaaaaga aataaccacc atcacttagt ttctgattct ggacaagtag    7920
ttcatgaatc atctaatata ttagtcatta ttgatttctt aaagatttat tgatcaattc    7980
atacatatat ttctatttct agccaaatat aaatagagc tagatttta ttttttttgt     8040 tcataaaaag aaaacagctt taattgataa cagttgttca ttgttatttt tgctacttag    8100
acgatggatc atgcatgaaa aggtaccaag taattcaaac agtactgtta ttggtagatt    8160
ttagatatat gcataaatgt gggggacaaa aaaatatag acataaaat ataatgaaaa     8220 tggtaaaaga acaaaaatag ataaaacata gataaaggga gaaagaaaag tacttttta    8280 cttaagaata tatttctgtc cacaacaaga tttgctagga cgaaaaatca gtaactattt    8340
ctcaattctt ctatgtagct ctttaaaata ctaaaggtca tccgatgacc ggcatcaaac    8400
ccttatccgc aacttgatac gcacgctttg ttcctttgcg atcatgcgtg aaatcttctc    8460
attctcatga tgataaacct tccttatgtc ttgctcctta atttttttct ttgttaaagt    8520
gccttgctcc tctttgtaac tcaaagctca tcatttgtac aaaaattaga tcattttgta    8580
gcctttatta tgttatatat attgatgtga ttagtgtttg taatttgata gaaaaaacgt    8640
acgactctga gctttacaac ggctattttgg caatttacaa cggatatggc gacttacgct    8700
attttactgt aaagattgaa aatgatattt gtgtgtcgtt aggtaaaaca ttagtgaaaa    8760
caaaaggtgg atagacaaga tatggtcata tctatctaac catacacaga gacgtttgct    8820
gccatgcatg catgatgcat atatatatat atatgtggat ataaaatata tttaatttat    8880
atacacatag tccatagata gatagataaa tagacgtaga gagggagaga gcaggagaca    8940
agaagagagt aagcacgcag agctttcgag catgagcatg ctagaaaaag agccatgtgt    9000
gctcactctc ttctgtcgcc ttcgttattg ctattcccct acctcctta gttgacttgc     9060 ttcatcttct tgcatgcata tgatttgat gttatattag cctcggtccc taaaattact     9120
atatgatatg atgatatgat atgaaacagt ttgtctgatt ttagggtcta tatataagga    9180
ttgctagggt ctatatatga tgatgcatgc atagatttca tcatcatcat ccactgacca    9240
ctagctacgt ttaatttata gaaagattcc gccggattaa actcttattt cctgtcaatt    9300
tgagcaacaa gattctctct tttcaattat atatacataa cacatgtcta taatatacgt    9360
acaaaccaat aaaattggac tcttaacaaa attttgagag tgagagatcc cacttaaaac    9420
gaaataaact atttgtttgg tcattgcatg cgtaaacgac cacttgaaca attaagtata    9480
cataacatag gtctagatct atgtgaaaga ttcccaaact taagatctct agctagaaca    9540
ttcattgatc ctccaatcaa aaaccaaagg aataaaaagt aatctttgta agggcgaatg    9600
taaaaccgaa acgtaagcta gaggaattga tattaaaatg gaagtaaaag cgaatattac    9660
taaaggtttt ggagttaatt aaataaagac aaaaagatgca aggacaacga attatgaaca    9720
tcttcgaaat acgttttttaa tattgttttg gcatttgatt tgatttgatt ctccttccac    9780
attcccttgt tcatatgtgt ttgtgtctca cgcaagcact acataagcgg tccccctaaa    9840
tacgtttcta gaaacgtcaa cgtttattca atcataccaa aatttacatg tgtattcatc    9900
aatcagccga cctaaaacta catggtccat tagtcattac ctatactgca atttttctag    9960
cttttaacag ccattatgta cttcacagtt tggaatactg gtatgacgaa gaaaagtcga   10020
```

```
ggtaaaaaac gtattagaat aaatgtttat cgtccaaaga tcgcaccagc aaagaataag    10080
aaacctaaac caacaaagga acaattaatg gaccctgaat tttctgatga agacgtactt    10140
accagcttgg gttttgatga tggcggttac ataataccac taccgaaaaa atctctcatg    10200
ttgattaatc taccagattc ttttcgagat gagttgcaaa cgatgcatgt cagtttttat    10260
ctccgagaag ttggcaaact tatgtttggg tgaggacaaa tatgctctag tgaatagtac    10320
taagaagttg atgcttacag atggtctagg acggcttcat ttgttttgga tgaattcaat    10380 ttttttttccg aatcagtatt tgcgaatgag atttatgtag ccctagatgt gagatttatg    10440
aaagctggaa gtgccaaaaa gaaaggtgga gattttaatt gtaacaaaaa cgcacagagt    10500
cttctttatg atttttttctt ggtagatata gatgaggaga tatatgggtc aaaatttgaa    10560
gagacggaag accaaaagaa gtggaacaaa aaattttgaa ttgatttgtc ttcatcatat    10620
tgtgctatta acattaaaca cgaaatagag catctgaatc ttgaattcta tggaatctct    10680
aaaacgaata gacagatctc cgcggaggaa gtgaaattct ctactcatac tgcattcaaa    10740
attaattgag tttttcaatt acattggagg tttatcctttt gatactttcg gtttggtgat    10800
ttgaatgaaa tgttggtttt gacagaaaaa tgaataacac ttgcattaaa atcatcaaaa    10860
attgaataac actagaatct aaggaggtgt attcgatctt atattttaag ttatttgagt    10920
ttttatataa ttttgatttt ttaaagaatt tggatgaatt taaggaggtt gttatgattt    10980
atggtaaaat cctctcaaat tccacctaaa accatgagat ttaaaattat ataattttta    11040
ctaagaaaat ccacttaagt ctcttaaagt cactaaaatc caatctttaa aatgttttca    11100
ataacagaag atttttaagg agattttaaa atcagtaatt caatagcatt agatttcatg    11160 atactttaa aaattcataa ttgaataaca taggatatgt tagtttgaat aagatatcct    11220
aggtgttaat ttactatttt taaaaggta agattttttt tcatgttttt aaaaaatgtg    11280
agagtttttt tacctatttt tctattaaaa tgaaatgtat aaaattaaaa ttttgttttt    11340
aaataaaatt actaaattaa atattacaaa atatgtatat attactattt agaattcaaa    11400
tattatcgat acaaaattaa atttatttct tcaattcgtc tatttaagca agctagtaat    11460
ttgatcgaca aaaaaaaaac aagctagtaa aatataatta acagaattac taaatcggcc    11520
ggtttaggga ttgctttctc tcagtcgtca attgcactaa accactggtg gtaatatcgc    11580
tggcgtttcg caagtatcac cgggaattgc aaagaagcag aggaccatgt acggagacgc    11640
tacaaactgg aatgaagatg agtatagaga atcaattttg aaggagcgag agatagagac    11700
acgcaccgtc ttcagaaccg cctgggctcc tccggcgaga atctctaatc cagacgcatt    11760
tgttgtagcc tccagcgatg gaactttagc ttttccattca ctgaactcgc ttgtgtctca    11820
atcggcgagt tttggctact cgaaaggtca agatgttatg gtggctgaac ctgagagagt    11880
ggttagggca cacgaaggtc ctgcttatga tgttaagttc tatggtgaag acgaagatgc    11940
tttgctactt aggtagagac ttaaatctct ctttgttgat tgatgagtct ttgatgaatt    12000
gtaattgaga gtttgaaatt ttgatctggt tatgtgtagt tgtggtgatg atggtagagt    12060
taggggatgg aaatggagag aatttgctga atcagatgtg tctcttcatt tgaaaggtgt    12120
gtgtgtgcca ttttttgtggt ttttgatatg aatgatgctt tttggagctt agtggttgtt    12180
tttcttatga tctacagaga atcatctgaa gccattgctt gaactgatta atccacaaca    12240
caagtgagta tgagttttgt tcattttta ttctacttga taactctgtt actgaaaatg    12300
ctataattgt gggttcaaat gtcagtgttc gtaatagttg tgtgtataat caccattctt    12360
```

```
tttcttatag aggtccttgg ggtgcgcttt caccgatgcc tgagatcaat gccatgtctg   12420
ttgatcctca ggttggaatt gtatttaaat ttcattgctt ggttagacag tctcacagga   12480
taactgtttc accctctctc acttctttcg ttttgatagt caggaagtgt atttacagca   12540
gctggtgatt cttgcgcata tgttgggac gtggtatgta tttgaccatg atagatgtat    12600
gtcctatgtg aatccagata tcttaacttt ctaaaatcat ttatgtgtat ccaacaattt   12660
caggagagtg gtaagattaa aatgaccttt aaaggtcatt cagactattt gcatactgta   12720
gtttctcgta gttctgcaag tcaggtaatg atgttaccat aaatattaga aatgcaccta   12780
tccaaatctg agttccacat ttggattttt gtctgattgt agtctctttc tccagatatt   12840
gacgggttca gaggatggga ctgcgagaat ctggggtaac atgctcccga ccatatttct   12900
ttatgctgta atttctagta ttaggtcata cgtggttata gaacttttga aatcatttga   12960
gtcttcatgt tggtacttaa gatccaatgc tcctcagttt tgttggctgc ttcttacaac   13020
tctatgatga ttcattttgg tgattacaga actttccact atgttatgtt ttggttcatg   13080
tggtttactt tagttgtcta gactaagctt tgttcgctca agggcttctt tctgttttgt   13140
caaccagatt gcaaaacggg aaaatgtgtt aaagtaattg gttcccagga taaaaagtcc   13200
cgccttcgcg ttagttctat ggcccttgat gggagtgaaa gctggttggt aagaactaag   13260
caactagata atctaacatt ttcgcaacct gctatttgtt tgaagggatt gttgcctcca   13320
gtaacctaag aatatagttc cttttctcctg aagaatcact tagaagttta aatactgaac   13380
atgtatttac tgttattggt atgattttct cctctttcag gtttgtggac agggcaaaaa   13440
tttagcttta tggaatcttc ccgcctcaga atgcgtacaa acaataccca tccctgcaca   13500
tgtacaggat gtgatgtttg atgaaaagca agtaagcaga acaagattag attgaaattt   13560
aagcagtgta atttaaagcc ttgggaggcc gtgggtgtta tttgtttatc aaggcttaat   13620
aggtttatgt agtatctctt tgaatcatcc ctcttcaacg aagtttatta aaaaaattac   13680
tgacttttct aaactagaaa cagaggtcaa cacctagttt taattcctgt gctaaagttt   13740
aaacatcttt ttaaaaatgt tgtctttaac aagtatcgca ctatcagatt ttgactgtag   13800
gagcagaacc acttctaaga cgtttcgact taaatggagc tttgctttct caaattcact   13860
gtgctccttg ttcagtattt tccatttcct tgcatccagc aggagtatgt ttccaatccc   13920
ttctttttctc cccatttcct atatatgtgt ttgcttttct cccatttcct atgttactgc   13980
taatattctg caaatatgtt accccttctg gactagaaac tcaatgttta accgttgatc   14040
caattctttt gtatttgcag gtagttgctg tgggaggtta tggaggtatt gttgatgtca   14100
tctctcaatt tggaagccat ctctgcacat ttcgtagcag ttcattgtaa aactccttac   14160
agtttcttga tttggctcga taccctaaag aggtaccgaa atgtgtcagt cagattattg   14220
cagaggttaa gaaaccttt ctttgttttt cttaggatct tgctcctgac taaagaccaa   14280
ttagttgttt ggttaagtgt aattggtttg tggttccgta gttgctatca aatttgaacc   14340
attaaaatga cattggaccg gtttagtctg atcacgtaca ttaactgccg ttagagtttc   14400
aattttttgc gagtcctgtt ttcttatgac caccattgat caaatatttg gatccataac   14460
taaatgattc tcactcttcc aagtaaaatt ttaccatatt atgcaattta atacatggac   14520
aaaacatata gtttccatat ccacaaaaat aagtcctcaa aaacatcact aatctaaacc   14580
tcaaacatca ctcctgataa gagaaaccaa actccagcga tcaacaaaac caagaagaa    14640
gaaaatgaag aagctgtgga agcaacaatc tgaatagga aattgcattg tccctgagat    14700
atattctttg tggtaatggt ggccaaacct tggaagatac aagcatcctc atcctggttc   14760
```

```
tttacttgaa aatacatgtt aaacgcatat gaagcgttcc catttgcatc aagagtattg    14820
caagaagacc cgtaaccaag cgcagtgcaa tccgaaaaag tgcaggcgta atctatgtta    14880
gcagcgagtt ttgtcaaatc tttggcttct gtattaaaca tacaccactt cttaggttga    14940
tacgtcacgt tctcggcacc aatcaacaac ttgttctgtc cttgacctga tagatctata    15000
ggaaactttg gttgcccgtc gaatttgaat attccccagt ggcgttcaaa ctctcccggt    15060
gctatacttt tcgcatcctc atcaagtaat ccaaacaagt atacctcaat gtaggttggt    15120
ctcagtggag tgcctctgtt ttccccaagc cttggtaaaa gaccgttgta gaatctgtaa    15180
gcactgcctg cgaaaaatac gttttcaaaa catttcattg catctaaaga actggaaaat    15240
gttagatgtc ttaccactat ttgcgtgttt gtcaccctct gttggccaac cgacttctcc    15300
aacgatgatt ggcatatctc catgaccaac agctttcaaa gccgatacca agtgtcgaa    15360 attggcatcg aaaacgtttg tgtaagcaat accattgtca tctactggtt tagcaccatc    15420
aaagaaggcg taattgagtg gaaaatcatc attcccatag aggcttaaga aagggtagat    15480
gttaatggtg atgggtgcac tgttattgcc aagaaagtca acaatctgag tcatttgacc    15540
gatgatatca ggacggaatc ttcctgcaga tggcacaggg ttgcttgatg gtgaatcgta    15600
gacatccgcg tttaaaggga ctgtcgcttt gacggagctt cctagtccag cttcattcaa    15660
agcgttttgg atgttttgaa gtgcaggaa tgtgaggttt ataaatgatc cattgtatga    15720
tttgaggaat ggctcatttc caacagctac aaacctgaaa acacatccac aagagattag    15780
acatataaac attttgacaa tgttcttacc agattaacat tttcagagaa ttgatttcac    15840
aaccgaacac attagaacca atatataaca agcagaggga gaaactcact aacgtgatat    15900
tgacaccacc attgaagtta taacgagtga cattcttatg aacccaatct ttagctcggt    15960
cataacttcc cataacctta agctgatcat taggaatagc aaccataact tcaagaccag    16020
agccagaaag tgcactcata gtggtctcat ccgcatcaaa aagcttaact ttgttaatgt    16080
tattgtcctt aagcatttga accactttct ttggtggaag cttatgtgta gccattgttc    16140
cccagttgac acctagccca tctaccataa caatacccat gattccaaat caacgacga    16200 aggccaacag attcatcgtc ctgagaaaca atgaaatggc ttaccaggtg ttttcaccca    16260
aattcaaacc cttaacttga acactcgtaa aatctcactt aaaccccaga aattgaagat    16320
atttacattt tcctaaatgg aggtcaatca aaacatcata agttcaaag cttttcacgc    16380 aaaatctacg agataaccaa aaataaagcc aagatacga ttttttaacaa aaaaaaatga    16440 gaatggggac tagacctttc cactgagagt aacaatcgtc aagcaaaaag attgattctt    16500
ttttctctct ttaactttc cggaaaaaaa gttttaagct ttgatctttc tctgattgag    16560
cttgacggtg aataatatgc tttgtgattg gttcttggaa cttggaagta tttggtaaaa    16620
gcccaaatta aaagttttaa gtaaacattg cacttttaga attttattgt attgttttta    16680
tggtcagtaa ataatgaccc aatgtgtttt atgtttgaca aatgttttag agtggttatt    16740
ggtagatgaa tttttctaat tttcagattt tattgtcaat aattcatgga ttcttttaaa    16800
gttttagtaa aatacattgt tattgggttg taagctttta aattctattc aaaaaaaaaa    16860
ttattcaaat agtttagtta ttataaattc tctaattcta acaaatatat cttaatatta    16920
agatatgaaa ttctatgttt ttactcatga agcacaactt tcttaatcta tatatacatt    16980
tttgaggggg attttttgaag ataatgttga agatttgaac cataattcaa caattaattc    17040
aaatgggtgg gttttacccg gtttaactct gttcggatcc tggataacat gtttaattct    17100
```

```
gttctgatct tggataacat taattttttgg aaaagttacc taaaacctaa taattaaaaa    17160
cgaaaattaa tgatttactt accaaattta atataaacaa tatctctaaa ctaaccatat    17220
tttttattta ccttaactaa tttcctaaaa tatttctacc taatttaaac ataaatatat    17280
aaatcttctt tcatttttat ttgatcttat actttattta ttttgaattt atataaaata    17340
tatatagtta ataaaatatt atattttttct gaatatgatg taatttaaat tttttaaaac    17400
ggacatatat tattcaacct atgaagaaat aatatatgta caatgtccca catcgcttag    17460
aaaaattgga caatggttca gacccatatt ataaaaggac caaaatgatt ctgattacga    17520
atgagcagaa agcttgattt atcaggcgtc caaaattaaa atagttatcc gattttactc    17580
ggatttttta ttttaaagaa ttgaaacttt aaaatatttc aagaaattat aaatattata    17640
actttatcaa aagttaaata ttataatttt aaaatctttt tataaagttt atctttaaaa    17700
aatgcttgaa atatttataa ttttaaaact tataaagttt taaagtataa gttttttaaaa    17760 ttataaattg aattttacaa gaaatttaaa tattataaat atataaaaaa tatattaata    17820
cgagacgata tattcagga aaaatcttaa atataacaat caaaattcaa tgatgaattt    17880
tgggtcgata ttgtatttttt ttaagtttca aatttttataa tattgaaatt tataagaaaa    17940
tgacaaaatt atgtttaatt ttacgggact gggttatatg gtaggacggg tttgggtgga    18000
taataattac gattttagaa tgttccacat cgcttaaaaa aattggacaa tggtcaagag    18060
ccatactata aaaaggacca aaatgatttc gattacgaat gagcatgaaa cttgatttat    18120
gaggtgtcca aaattaaaat ggtttgttta ctagggttat ttattttaaa aaattgaaac    18180
gttaaaaagt ttaaaaaatt ataaattaaa tattacaaga aatttaaaca atataaaaga    18240
tattaatacg ggacgatata ctgctagaga aatcttagat ataacactca aaattcaatg    18300
atgaaatttg gatcaatatt aatcattttg aaagtttcta attttataaa tatttgaaat    18360
ttataataaa atgacaaatt tgtgtttaat ttcacgggac ggggttatat ggtgtgacgg    18420
atttgagtgg ataataacat gggatagtat gctatggaaa aaacatataa taacaatcat    18480
aatataatta tataatctta aacactaaac aaaattaaca atattaaaaa aaaaacttaa    18540
aactttaatt tttttttaaaa aaattttgat tcttatatta gaaatttaaa cattataaat    18600
atttaaactt tatactacgg gtgaaatttt agaattgact gtttaggttg ataagaattt    18660
acgatagaac taggagttaa atcctagaat gacaattaaa atataattat acaattaaat    18720
actaccacga gtgaaatcct agaattgacg agtttgaatc gatattaata tgggatagtg    18780
tactacgggt gatattttag aattgactgg tttgggttga taataatttg cgatagaatt    18840
aggagtgaaa tcctagaatg acaattaaaa tataattata caactaaata ctatcacggg    18900
tgaaatccta gaattgacgg gcttgatttg atatcaatat gggatggtgt actacgggtg    18960
atattttaga attgactggt ttgggttgat aataatttgc gatagaatta ggagtgaaat    19020
cctagaatga caattaaaat ataattatac aattaaatac taccacgggt gaaatcttag    19080
aattgacggg tttgattcga tattaatatg ggatggtgta ctacgggtga atccgagaa    19140 acaacaatca aaatacaatt ataaaatatt aaacatttaa caaaataaac aaatacaact    19200
taaaacttta aaatttgagt tataaaattt cttctcgcgg tgaattatac atttaaatca    19260
aacaatagca taaatttatt aaatcatcat aaaaaatatt caattatttt ttatttaata    19320
aaaatatagg cccgcgggtt aatatctagt actatgcata tccaaaaaat tttacaaatt    19380
tatgaaacaa caaaaaaaca caaacccaaa cccaacgatc aaaacaacaa caacctttga    19440 ttttttcttttt agcaaatctc atgtgtagca aagattatta tgcaaatcat gtcacaaccc    19500
```

```
aaatttcgtg agacataacc atggataaaa tatacaaaat aggatattag aagggaaatt   19560
gcaaatgcca gtaaaatttc tctcacctat tctcgacaaa aaacattatt ctgaattgaa   19620
ataattgatt gatactctat acaaaatggt catgtagaaa gaatcatcct tataaacaaa   19680
ttaaaacata cctaaaactg gagaatatga tatgttaatt aggacagcta ggaaaaacaa   19740
aatattgtaa tcatttctaa aaaagcataa atatacaata tctcttatac agagaatttg   19800
gtaaaatata tcttatacat agaattttgg taaaataaat tttgatataa atctattaca   19860
attagtgaca accaatcatg atatttggtt aaaacaatcc atgcatattt gttaatccac   19920
aaaaaaagtt taaatatcta actctgaaat ctctaaaatc tttacaccta tgcatctacc   19980
aataatgatt ctgaaagttt cagaaaaatg tctggaaata taactgtg ttgggttttc     20040 atttgaaaat tatgatctct tactagtaat aacgtcatgg aaattgcaac acagaaaaag   20100
acttataaag ttttctgata ttttttctaat ttaggatttt cttttaaa aatacaaaga    20160 aaaaccgact atagaaatgt tggtgtaaat taaacaggag gaagagtttt atccaataat   20220
acagtataca agtaacaaga tgaagaacct cgggaacttg atacgtttga gggttaacag   20280
tgaatcatat tttttatata accaagtcat aaactagaga aaccatataa attgaacaaa   20340 cgaaaaaga caatctcact tccatggtta gtaatctttc atttagaaag atcttaaggg     20400
aaatatataa ttgtatattc tctctctata ccacacaatt ccgatgaaca cacaatctgg   20460
tatattgtac atttgtttat aatgcttggc acgacggctt gtgataaggc tttatcgtct   20520
cataaaagga aaacgtagtc attcgatcat ctcccaaagt ttcaatcttc tctactgtct   20580
tcgtttattt caaatgatta tgagttgatt aattattcaa acacagaag atctctctat    20640 acatatatat atatatatat atagaaacct ttcaaaccat ttcgcaaatt ggttgtttct   20700
cactttctct agcgtaaatc tcgatgagct taagttaaaa cttaccttca gggtcatttg   20760
ttttgttatg tgacaatctt ctagattaat attccactta ctacttcctg cttaaaatat   20820
ttagttacat cacatgacca tgtaattgaa tttatcctct ttataatata aactacgaaa   20880
atctgaagaa gaaaaaaatt atcgaaaaga gaatcatatt ctggtactag caaaataaat   20940
ttggtagaag atatatatat attttctat atgtaaactt caaaattaat gcctaagata    21000
tgctaaaaat ttgcgaagga gtcagggggga aagcttgaga ggaccaatgc atggcattgc   21060
ttttactgac agtaaacagt gtcacgctca cgacccattc ttcccgttcc atttggtttt   21120
atttatttca aagtttaata ttccttttgt ataacattca aatcttcaca tgattgattg   21180
tgtgaaaacc ccacagattt tactacaata gggggagttg acttaaaata gctattgatg   21240
tcgaaaaaat gtattttagt tataaattat actaaagaaa atttttgatt tgtctgttgt   21300
ttaagcatat gtattgttaa acttaaaaaa atatgtattg ttaatcttaa aaatgtagga   21360
gtacacatca aatactcgag cataatcaaa accgtattca tagaccgatg tgagaatcaa   21420
atagaagata atgtgatttt ttaaaatatc gtatctccaa atcaatcact tagaagataa   21480
tgtaattctt tatgtgctac ataaataaat atatatatat atatatatat atatcttgta   21540
tatatgtctt gacaaaaaat tgccagtcaa aaaccatgac tgaatcaaac tataagtcgg   21600
attgaatcaa actataagtc ggatgagtat taatttccat tatgtttcta tactttacaa   21660
accggaaaat agatattata gataccaaaa aagtagattt gtgtatatta ttagaagatt   21720
tggaatttca tcattatcag gatctaaagt acttccctaa ttaaatcatg tcggttgaaa   21780
aagctcaatg aatgtttgaa atttggaaag tttattaaat tcggatcttt ttttttttgtt   21840
```

```
tgtcgtccca aacattttta ttttattaca aataatcaac ttatccttac tactaaatca   21900
tttcatatct ttgataccaa caaatcattt catattctat tttgatgttt aagaaaacac   21960
tatttaccag ttacaaaata ttataaggat tgttgtttag aaaaaaaagt acaagttgaa   22020 ttcttttgt caaatataaa attgactttt taatatataa ttgacttatt gaacatgatt   22080
acagaattaa tcatctacaa aactttccaa gtttataata aatacatttc aaagactatt   22140
agttcttctt aaaatatttc taaaagtgat caaagactac cacatataat tcagaaaaag   22200
tagaagttga tttcttttg tcaaataaat aattgactta aatagtttg gaaagccatt    22260 gaacttgatt atagaattga taatgtacat aaaaaaattc caagtttata ataaatacat   22320
ttttcaaatg ctatatcagt tcttcttaaa atatttcact aaaaaaacac tcaaatatag   22380
aataaattta ttgaataaca taccaactgt aaaacagaat tgacaaaaa aaaaaaaaaa    22440 atgaaatgaa gatgaagaca aaataaaatc accagaggat cttatgcaaa aaaatatatg   22500
aatacacaat aaaccatatt gatttttta aaataaaata aaaacagaaa aatatcccaa    22560
caccgctttt caattaaaaa tcttccgtca ccattgttgt catcttcctc tctcgtgaat   22620
cctttttcct ttcttcttct tcttctcttc agagaaaact ttgcttctct ttctataagg   22680
aaccagacac gaatcccatt cccaccgatt tcttagcttc ttccttcaat ccgctctttc   22740
cctctccatt agattctgtt tcctctttca atttcttctg catgcttctc gattctctct   22800
gacgcctctt ttctcccgac gctgtttcgt caaacgcttt tcgaaatggc gattttggat   22860
tctgctggcg ttactacggt gacggagaac ggtggcggag agttcgtcga tcttgatagg   22920
cttcgtcgac ggaaatcgag atcggattct tctaacggac ttcttctctc tggttccgat   22980
aataattctc cttcggatga tgttggagct cccgccgacg ttagggatcg gattgattcc   23040
gttgttaacg atgacgctca gggaacagcc aatttggccg gagataataa cggtggtggc   23100
gataataacg gtggtggaag aggcggcgga gaaggaagag gaaacgccga tgctacgttt   23160
acgtatcgac cgtcggttcc agctcatcgg agggcgagag agagtccact tagctccgac   23220
gcaatcttca aacaggttta aaatctcaga aatcttcgaa tttggtgttt gcttgttgtt   23280
ttatatggaa ttgagtttgg tgattgtttt gcattgcaga gccatgccgg attattcaac   23340
ctctgtgtag tagttcttat tgctgtaaac agtagactca tcatcgaaaa tcttatgaag   23400
gtttgctgtt acttgtttct ccttttagga attgaattgc ttgaaaattt atcagagacg   23460
aataactttg ttgttgctat cattcatgta gtatggttgg ttgatcagaa cggatttctg   23520
gtttagttca agatcgctgc gagattggcc gcttttcatg tgttggtaaa agaagatgtt   23580
ttttatttcc agcaatgtta cattgttata cgtataatga tgagtttagt gatcaagttc   23640
ctctttgatt cttctttctt gttgcagtat atcccttttcg atctttcctt tggctgcctt   23700
tacggttgag aaattggtac ttcagaaata catatcagaa cctgtgagta attactattc   23760
tccagccatt actgtaattt ttattgaaga caagtttgta tcatgaagaa cttacaagtt   23820
ctgttttgaa aatgctcaag gttgtcatct ttcttcatat tattatcacc atgacagagg   23880
ttttgtatcc agtttacgtc acccctaaggt gatactgttt ttctggtctc agtttgtgat   23940 actgtttta agtttagttg tctgacccgg tgatcttgaa aatggacagg tgtgattctg   24000
cttttttatc aggtgtcact ttgatgctcc tcacttgcat tgtgtggcta aagttggttt   24060
cttatgctca tactagctat gacataagat ccctagccaa tgcagctgat aaggtaaaat   24120
acgaaaaaga agcgtatgta ttagtcactt gcactgtgtt actgttttaa ccaaacactg   24180
ttatgaactt taggccaatc ctgaagtctc ctactacgtt agcttgaaga gcttggcata   24240
```

```
tttcatggtc gctcccacat tgtgttatca ggtaactgca aagtgcatca accattctta   24300
tacttgcaag agtttcttgt ctaaacctcg gatctttgct tttccccagc caagttatcc   24360
acgttctgca tgtatacgga agggttgggt ggctcgtcaa tttgcaaaac tggtcatatt   24420
caccggattc atgggattta taatagaaca agtacgtttt cacatcttgc tttattagtt   24480
ttccttggtg aaaatcatca tccctgcgtt gtcaccactt gacttcatgt tcttttgtta   24540
cattttggca gtatataaat cctattgtca ggaactcaaa gcatcctttg aaaggcgatc   24600
ttctatatgc tattgaaaga gtgttgaagc tttcagttcc aaatttatat gtgtggctct   24660
gcatgttcta ctgcttcttc cacctttggt atgctgtgat cccatctctt tcaaaataat   24720
ttgcaaattc gaaaaaccga aaaggctaa atctcatacg aatttgatat ttttagtttc   24780
ttagagtcgg tgatgtaatt tcagttactg aacgcaaatc tcttgtccaa aggttaaaca   24840
tattggcaga gcttctctgc ttcggggatc gtgaattcta caagattgg tggaatgcaa   24900 aaagtgtggg agatgtgagc tatttactc aaaagaaaac ttatgatttt taatgttgtc   24960 gttgttttg ggtcatctaa ctaaccaaat tcatgtattc actgtcttcc tttatcagta   25020
ctggagaatg tggaatatgg tatggttctc ttcctaaaca tcaccttctt ttgtacacaa   25080
aatagaagaa gagagctaat taagatcttg ttttccttga cagcctgttc ataaatggat   25140
ggttcgacat atatacttcc cgtgcttgcg cagcaagata ccaaggtga gtgagatata   25200 taccgatatg caattgtcga gatttgtttc tgtgatataa atttaaccct ccacacactt   25260 gttttcaga cactcgccat tatcattgct ttcctagtct ctgcagtctt tcatgaggta   25320
tacatacttt ctacattgcc ctgtctctag acgcatgaac acacgctagt gaaagaaatg   25380
ctaatattca aagcattgtt tttacttaac gatcttgtgt tacaaatttc cttttgacag   25440
ctatgcatcg cagttccttg tcgtctcttc aagctatggg cttttcttgg gattatgttt   25500
caggttaaaa aattactaaa ctgctgcagt cgattttac taaactctaa tctcatattc   25560
tgaccaacca atttgtttga gtaggtgcct ttggtcttca tcacaaacta tctacaggaa   25620
aggtttggct caacggtatg ctctcaaaac ccgagaaaat agaacgaata actctttctt   25680
tcatagccta gccatttaaa tcgcaatgct gaaacttaat aataaaggtg atctgttttg   25740
gaatgggatc atattattag gtggggaaca tgatcttctg gttcatcttc tgcatttcg   25800 gacaaccgat gtgtgtgctt ctttattacc acgacctgat gaaccgaaaa ggatcgatgt   25860
catgaaacaa ctgttcaaaa aatgactttc ttcaaacatc tatggcctcg ttggatctcc   25920
gttgatgttg tggtggttct gatgctaaaa cgacaaatag tgttataacc attgaagaag   25980 aaagaaaat tagagttgtt gtatctgcaa aaatttggt agagacacgc gaacccgttt   26040
ggattttgtt atggtgtaaa gaaatttcaa tcaaaaaact gttgtaataa ttgttaccaa   26100
aaagaaatgc ttttctggaa acgaggggaa aaatagtagt tttgttaggt tttactgttt   26160
ggaccaaatc tagtaaaaaa cttttgtaa taaggaaaaa aaagaacaa atgtgataaa   26220 tgcatgggga ttgtatgaaa ccttccaata aagttgattg gtggtcccgt tttggggatg   26280
gccattattt atttatcttt tttttagcgt atttatttat gtcgtatgta tccaagggga   26340
gacaagactc taaattgcaa taagtgttga ggcccgaaca tcatcattga caatatcagt   26400
taatacatta catatggcaa atggtagaga aaatgtcgat gtgcagcaaa cactttacc   26460 cattcgaatt atgttatgaa gctttctttt acctttcaa acacttagct cattagatgc   26520
tatataaagt gataccttaa atgaatttaa tactgaaatc tagatttcga gaagaaaata   26580
```

```
tgcaacataa ctcttaggat atggaatact aataatctaa tatgtattta ataggtggag    26640
caagcaacga aataatcaac cttttctttg tgttatatta aacctcatcg gcaaattatt    26700
tagctttaat agatatatct tatcttttt ttggtgcgaa tatagagata ccttatctaa    26760
aggtccaagt ctttaacaat ttgcataaat taaattaaaa tatttcattg tacaagaaat    26820
tcaaatgaaa ctcatagtgt ataaacattt agtcgagtta caaagaaaca aagttattta    26880
tggttacttc tttccttaaa aggaaaagaa aatggttacg agaggaacca cgtgaagatc    26940
acgtagagag gttggtcaaa catagaaatt cagttggaag taaatttaat ttttaacgct    27000
ccaccgactc tcgagacag ctgcctctga ctcagcgcct catgttgact tggcagtcta    27060
ttattaatat tgtcgacttt ttttttttgt tggactataa aagcgatatt ttgtgtccta    27120 tttttttt ttttgacaa agtgatatac tatttacatt taagattaat tatttttatt    27180
actcaaatta gtagttatat atttcaattt aattcaatct gaaattcatc tcaatttct    27240 atccacgaaa gaaagacatg aaaatcaact gaagtatggt ttctgttttt atatactttt    27300
taagaatttt ttatgctact agaagaaatt tagaatactg tatatatttt tggatgaaaa    27360
tttaaaataa tctttagaat gcgaaattag aaaataacta cacaataaca ttatatctct    27420 aattttttt tttatatagt ttccaaataa acaaacaac aactgtatca cgttttgtta    27480
atttcattta cctaatcaag acattcttaa atttccaaaa tttaaggaaa gtatatgtag    27540
tcaacaaaaa tgattatcta cttaacatgg tatggttctc ttctttaaga aatcagttaa    27600
tataactaaa ttttgcaaaa taatgagatc gcattattgt aaatacatat tgtcttttac    27660 tatttttat ttatattat aaaaatgtta ccagacaaag gtaacataca atttatttaa    27720
aactcgcacg aaaaaactcc attctcttac aatactttta caaaataaaa atgtaacaaa    27780
taacttccat acattggcta tataaactct tttagaaaaa cttcaacata ccttatgtat    27840
ttatttgaag tatcaatata taaaattgaa acaaaagatt cttttccttct cgtaaaagaa    27900 agaaacaaaa aaagaaatca ttcgtcgact ttattacaaa accctctcac aacaccatca    27960
cttcttcttc gtcttctgtc tgagtccaaa atggaagact acagatccag atcgtacggt    28020
gacgggagaa catcagacct tcaacaatac tctgctcacc gaagatccga cggtccagat    28080
tcattcagtg gtaacggtat gcaagatctt aggtcttaca gtacttccta cacagattac    28140
ccgacccgga tacccgaaga ccagaacccg aagaaaggaa gatcatcttc atcgtcttct    28200
tggggatttg tggatccaga tttacaaagg aagaagagag ttgttagtta cagagcttat    28260
actgttgaag gtaagcttaa aggttctttc agaaaaagct tcaaatggat caaagataaa    28320
tgcaacaaat tacttaatta attctgtcaa atgtgtttta cataagataa taaacttttg    28380
tcacttcgat cggttgagtt tcaatctttt tttgtgtatg tgtgtgtgtg tttgtgtgtg    28440
tgttcttagc ttatgagttg tgatcgatag tgattttgta acaacaatac ttaatagatg    28500
agtaagtgat ttcttattca attttgacg tatcaaaaca agttacaatg ttttaaacat    28560
tttaattaaa acggtgatta ttcatttctt tatcattgaa aacatccatg agttattatt    28620
atcatgtttt gtagtagttt cgtttcatat tatgcgtgtc taaaaagata acttgtttta    28680
tgcatgtgat tatcttgtaa aaacgattag ttcaggtatg ttaagtaatt acggcatgaa    28740
tgttaaagtt cttacgtttt taatttgcga tactcttcct tcagttttga tgaataattt    28800
ttcttatgaa ttatgaagtg gttttgtttc attgtgtgtc taaaagtgtt tacacgaaac    28860
tttgttaatt aagtgaatcc aacgttttta gcgttacatg attataataa cgtcttgatt    28920
tgtagcgatt ggtgtgtttg agaaactatt tttatttgta ttgattagta tatacataag    28980
```

```
aagggactaa ttttttgtaa acaatgtatc actttgtaaa gactagatat gatttataaa    29040
atatgttgtt tttttaata atgattggtg agtttgatga aaatggactg tggaggaaaa    29100
caaatagcag tcaaacaccg attagaacac cacttacgta cgtcttctaa tcgatatttt    29160
actgctactt gtgttcctca agagtacttc aaactcacat cattatacaa ataaaattaa    29220
tatatcttaa tcatacttct tgaatttta tgaccaaaac aacatacaaa atcacatatt    29280
ttagaattca atattagca tttctcttaa tattattata catgataaca acaaaacact    29340
tttagaattt tggggctttt ccatacacaa ctctgcaaaa tcacgaaaaa atgcatata    29400 tacgcaaaca aaactcccac aattctacat gatggattaa ggatagtcaa gaaataaacc    29460
tacaagtgtt tgtatttgaa atatattaca acttttttt aacataggtg tacgaaggaa    29520
ttcttaacta aattataaag ttgttttgaa ttatgctatg ttcctacgct tatacgataa    29580
atgatatatt tcttgttgat tactgaattt tggtttgctt atgcgataaa atgaagtcag    29640
acgagtctct ctttccttct gttttttttt tttttaattg tatattacgt gactttgttg    29700
tttgtttgtt gattccaatt tattacatgt tatgttggc tatgccaaaa tcttaaagcc    29760 gaactttga aaatgaagcc ctgcatatat agtaagagat tacgttgtaa ttataggttt    29820
tgaatacgta aaagtctctc cctaccgaca tagtgttcgt cttcatgttt ctagaaagta    29880
caaattgagt aagtaatttt tgtcaaacaa atttgaccaa ttagacaaat aaaagttcat    29940
ataaattttc aagatatgaa acataaaaca agatattaac ttactcttat ccccactgg    30000 attttatatc attccgcaaa tattatcaga gaggaaggat cttaaaattc gaagagtttc    30060
tctatacaaa tggaggagac aaatgaatat ttgaagaatc atagtttaag cactttcgtt    30120
tggtataata aatctatatt atctctctct tatatatcat cagttctcta gctgtgaaaa    30180
tagcctttct tcagaagaat catagacaac gtcactgagt gagtacaggt tttgttttat    30240
agctgctttg tatgaatcag tcagagagct ttgctttggg gttctacatc gtctccattt    30300
gattgtggcg ttgctgctgt ctcatcgcct gcattgttat tgatccgtaa accatcaatg    30360
cctttgagtg cggtttcata gtttgcattg tcactcccgc cactaaatgg ttcacgactg    30420
ctcgtgtcca caactcgtct tgacgatgat ccctctgatc ggcccaagtt caaagatcca    30480
ggtagctgag aaatcaatgg atcacaatga acatcccgac tcaaaagaag gtacccgaga    30540
agaaaaaaaa acagcatgac aagaaactta ccagcttgtc ctttgcaatt gcagaatcat    30600
ttccattctt gtcttctgc ttcagggtaa aatccggatt tgtcctctga tttgggacat    30660
ctatggcaga caaacacgcc cttagtatat aaatcaatgg acaactatgc ggctgcattt    30720
tcataaagaa ggataataag cattcaaaaa tatacctgga cgcttctcag aattgccaac    30780
cgcagggttt aatccagaac tagttccaac accaccatcc tgaaaaaaga acatagaaa    30840 gatcttgcat tattcatctg tgtatgtata tgtatcatga acgggataga aactttaaag    30900
tatcaagagt gtacatgggg acgaggttga gggtttccag attgtgattg ctgatacttg    30960
tatactgtcc agtcaaacac aaaatcaaac tgaaaacctg gacaaacaa aatactcatt    31020 ttgagtcaac agatgcttct gtatgaactt aatagcctga gaggaagaag agagatagag    31080
aaaatgaatg accttcccgg ataaaaaggt tgcggaatag tctcttcaaa tatgcatagt    31140
ctggcttatc atcaaaccta agtgagcggc agtaatggaa gtaagatgca aactctgttg    31200
gatgaccgct gcataacgtc tgcaaagtta cagtactatc tatgatcaac cgtctctacc    31260
tgatcataat cctttgaaac atggattcgt ataagtttct aaatgtaaac catataagaa    31320
```

```
gaacttactt cgatggaagt tgaaaccttc ttttcgctga tcttatcata cttctgtttc   31380
ttgtttccag ctttcagccc ttgccaaggg agactacaag agaataagat attagagatg   31440
gattgggaga caagaatcag aacagaaaga aaagttactt aatgactctc accttccctt   31500
gaggaaatac atgaggatgt aaccaagcga ttctatatca tctctccgac tttgctctac   31560
caagtgaaaa atgtcaaaaa gtaatcagtg aaagaggaga aaaagatccg cgattatcat   31620
gagggtttat agaaagtgat ggagtatacc aatccctagg tgagtgttca agctggcata   31680
cctcggagtc ccaattagac ttttattctc cctgaatcat ttacacgtaa aatccaaaca   31740
ataaagaacc cgttgtcagg aaatctgaag ctgacataca atatgctgaa aatgctgaat   31800
ctgtgacatc caaaatcttg ttacctgtat gggatatgtc tatgagttga gctgtctcta   31860
tatttcttag ccaaaccata gtctatgatg tagacctaga gaaagagacc aaaatcagtc   31920
atacaatagc gagacccaa aaacaaatcc aactgagaga atttgcaaaa gtaagaaaac    31980
ctgatttgcc cgcctcccta agcccatgag aaaattatcc ggctttatat cacgatgaag   32040
atacgactta gaatgaatga actcgagacg atttatctga cacaagataa acccaacagt   32100
gagagagtta cattaagaat gacaagacac caatccaaag cataattacc atttgatcag   32160
caagcataag aacagtcttc aagctaaact gcctcttgca ataactaaac aaatcttcaa   32220
gacttggacc aagcaaatcc atgactaaga cattgtagtc cccctcaaca ccataccatt   32280
tcatatttgg aatcccagct acattaacga acatacacaa gaaatgaata accaaatgag   32340
aattcaataa caatagagat aaacatttca ttgcatactt ccaccctgaa gaactctata   32400
tatcctcgac tcatatgaca attgcggatg cgcagtcttc acactttcct gcacacacac   32460
aaaaaaaact aagttttgat gatccaagtt gggactttga agagatgaaa cactcacaag   32520
cttaatagca acttcttcgt tagtctgaac atcagttcct gcaatcaaaa cagtctcatc   32580
aaacgactat tgaagagatt ttatatgtat agagagggga ggaacgaacc gaggtaaatc   32640
tctccgaaag agccgctccc aattttgcgg ccaaggcgaa acttgttccc aacacgaggt   32700 tccatacccca attgaaaaaa ccctaacttt gtggttttat ctatctacta cgtcgagcgg   32760
atttctcgat ttctcatgcg gaggagagtg aagtgcgatg atcaaaacta gggcttttgc   32820
gaagaagagg ggaagaatcg agcaggttga aattggaagt gagtaggtga ggaaatttag   32880
ggagattcca tggtgttttg gttaagcaac cagaagcaag caagatgaag aagactgcgc   32940
gtgtgtgtgt gtctcgctta gcctgttgct tttggtcttt tctattcctt ttctcaattt   33000
attaaatatc tttattcggt gaaaaaaata tacagtatat ttcttagaaa ctttataata   33060
agaataagga ttttgttttt atattttcct aaattccata aatctcttaa gtttacaaat   33120
tcatatatct tttaacattt aaacaaataa ccagacttct agtaatatat ataaatttat   33180
ttagggagtg ttattggttt gtgatgtatt cgaagtttca gtgacttaaa atgttatgaa   33240
gaatttgttt ttattcaata aagatttttc aattttttgt taaagtttgg tgttattagt   33300
ttaagatttg taaaagtaa tataaaatct tcataaatgt agagttattg gattcatatt    33360
tttataaagt tattaaattt tttgtgtaat tcatttaaaa caaagaatct atgattatta   33420
taatgaatta aattattgtg ttattggttt atgactttct acccttttt ttataaaata    33480 aagttgtgaa aaatatcata ccctttttt ttacaaaata aagttgtgaa aaatatcata    33540
aaaataaaga aattgtttga gaaactttac aaaattatta aaaactaatc aacaagttta   33600
ttaatgacct taaaccaaaa taggtacata taatattaga tagatcatgc aaatgcgttt   33660
ggtggttatg ttacttttgt atcatttgat tggcatgatg ttctacattt ttttaccatt   33720
```

```
tctctattct taagtcgaaa tctttaggac caaataagca ttttccccta aactaacaaa    33780
gcagcatctc actagatgtt ttccaatcag atttgcttac tatagtgtgc taatatgaaa    33840
tttgagtgac tcatgacaat gcatcaatcc agattaagca ttaacatgtg atcagctagc    33900
attcatgaga atatgagaat tgtcttcgag ctaaaagaaa gtagactctt ttttcacttg    33960
agaaactcat gacatacttt ttttttatat acatttgttt tttgatgatt aggttaaact    34020
tttgtaataa ataaatttt agttaaataa ataaacttct atcatcaaaa gactcgtgag     34080
tttcttccta tgttgcaatg aaatggaaac gaaaacgcga atacgaaacg tttcggaaac    34140
gagaaacgat tttttcttaa aattagggat tggaaacgat tttttcttaa aattagggat    34200
tggaaacgta tacacataca tacatatata tatatatata tataacat taacataaaa      34260 ctatattaaa gaaaaaatgg tttaaacaat acaagtccaa aacatcaata ttaaataaat    34320
aaactaaaat tctaaaagat aaaaattaaa aggttcaagt tcaaatagtt aatttagacc    34380
aacattttca ttttcattag tttcatcaaa gataatataa agctcttttc aaatctggtt    34440
tatcaaaaga aatatcttaa aactcaaagt cttccaaaat tagttatatg tattaataat    34500
tttaataatt ttaattttag ttattaaatt ttcaaagttg aaaaaaattt gtcgtatgtc    34560
tatttgggaa acatgagttt ctatctttaa aacgtaagtt tccatcgtgt ttccaaacat    34620 aaattttaa aaaacgcgtt tccgttacgt ttttcatgtt tccggagagt ttctgttttc      34680
gtaacgtttc ggaaatggga aatagacctc ggggcgagtt tccatgcaac ctagatttct    34740
tctaaccaat agaaatgctc ttaaaagcct tttttaaaa aaaatcaaca gaaatgctct      34800
taaatgttaa aaacaaatat tcatgccaaa ttttgatgta aaaatttgtt attttcgctt    34860
tagttgtgtc ttatttcggt ctggtcattt tctcaaagcc ctttagtta tttatatata     34920 tattctctgt ctcgtatttg tccccaaaaa tctagggttt taaggtttct tatccttcct    34980
cttcctccgc cagattcttt tcttgcgaag atgagcaacg acaaggacag catgaacatg    35040
tccgatctct ccaccggtaa gatattataa tcttattgtc ctatagaatg aggcctggat    35100
tctcttttgt tctcttgatt tattgaaaaa agcttctctt gttttgtgtt ttgcttatag    35160
ctcttaacga ggaggatcgt gccgggcttg ttaatgctct taaggtgagt ttttcttca     35220 cgatatgatt tgcgtatgac tatctggaga ttgggctatt catctttgta acttttaggg    35280
attgttttct cttcctgact agttttgaga aattgatttg attcttatgg cttagagaat    35340
ttgactttgg ttttgaggat tgtctatgca tcttaatttg gttgtttgaa agtttgtgac    35400
ttttcctgat ttgatttacg tgtttgctgc agaacaagtt gcagaatttg gctggacaac    35460
actctgatgt ccttgaaaac ttgactccac cagtcaggaa gcgtgtcgag tttctaagag    35520
agattcaggt gagtaaattt tcagctttta gatgatcttg gattttgtat tggttttgaa    35580
ttagctggct gttcaggtct aatgagtttt tggtggagca aatttatctg attccttttg    35640
tattttaacc tttgcagaac caatatgatg agatggaagc aaaattcttt gaggagagag    35700
cagctcttga agctaagtat caaaagttat atcagccttt ataccaag gtttgaatac       35760 ggtctttgat tctgcgagat tcttatggtc tttagtttcc tattattaga atatctttga    35820
aacacatgat gacacctcaa ttgataaagg tttaataaga cttctctctg ttgctactta    35880
cgtgaatgat tagtgcttca tggttttcac ttctttctgc atcattcgtg attgtaactg    35940
atattgatgg tcttctgcct tctgcatcac agcgatatga gattgtgaat ggtgtggtcg    36000
aagttgaagg tgcagctgaa gaagtaaaat ccgaacaagg agaagataaa tcagctgaag    36060
```

```
gtgtgtttat cgattctttt actgaaacat gtttatttt  agtatcttat gatgatgatg   36120
gtgaactcat gattttata  tgatatgaaa ctgtctttct gcagagaaag gagtaccaga   36180
tttctggctt attgcattga agaacaatga aattactgcg gaagaggttc gttattagaa   36240
tattcttctt tttggtttat aaaatggcga ttctctttat cattatgtgg ttttttccac   36300
ggttttagat aactgagcga gatgaagggg ctctcaagta tctcaaagat atcaagtgga   36360
gtagggttga agaaccaaaa gggttcaagc ttgagttttt ctttgatcag aatccttact   36420
tcaagaacac tgtcttgacc aagacatatc acatgattga tgaagatgag cctatccttg   36480
agaaggccct cggtaatgt  tttgctctat caagtattta ctgtttatgt tctgaagaca   36540
ataagtcttt attgactgtc gtttactgct gttcaggacg gagattgagt ggtatcctgg   36600
aaagtgtttg acacagaaga ttctaaaaaa gaagccaaag aaaggatcca aaacacaaa    36660
gccgatcact aagactgagg actgtgagag tttcttcaac ttttcagtc  cacctcaagt   36720
tcctgacgat gatgaggatc ttgatgatga catggtattt ccatctccat aagcagttta   36780
gttttagag  tcagtaatta agattgtgtt ggattttaat ctgatcatct aatattcaca   36840
ggctgatgaa ctccaaggac aaatggagca tgattatgat atcgggtgtg tacctttcta   36900
tttcatattc agttctcttc acttagttca gttctaggat ctgagtctgt ccactgttta   36960
tcctgtagtt caacaatcaa agagaaaatc atctcgcatg ctgtgtcatg gttcactggt   37020
gaagctgttg aggcagatga ccttgatatt gaggacgacg atgatgagat tgatgaagat   37080
gatgatgaag aggacgagga agatgatgag gatgacgagg aggaggatga tgaggatgat   37140
gacgaggagg aagaagcaga tcaaggaaag aagagcaaaa agaaggtaaa ttatgtggtt   37200
ttgttctact taaaaccttc ctacatagga aactaaaacc tctgaaactg atttggtggt   37260
ttatcttttg ttttgttgca gtcatcagct gggcacaagg tttaacaatc aatcaatctc   37320
gatcttttt  ttttgttgat aatgcaatgg ctaacctgag gtatccttt  ttaatgaaca   37380
gaaggctgga agaagtcaac ttgcggaagg tcaagcaggt gagaggccac cggaatgtaa   37440
gcagcagtga agaagtgaag aatcttggct tagttatgat gaagaagaag agtgaagagt   37500
gtctttgagc cgaggttgtg tttctttaat ttgcagagtc atggtccggt ttattatata   37560
tcagttttgg gtgattggtt tgctatttaa aaaaaaaaaa tgggttcttt ggtttggttt   37620
gtgtctcttg attttcctt  ttgtaatgat cttatgaatt tgtttcgagt taatgtcgtt   37680
ctctggtcag atttcgaatt caattctatt tatcctccct cgttaatgag agaatttgtg   37740
agacaatcta gtttacttaa gattgatcga attttataaa ccaacattac caaaccgtca   37800
aataattaaa accaatcaat cttatttatc ggtttgcata acccatcaat gagccggttt   37860
agacatcggt ttgagtttct ctgggaaaga caaaagtcaa aaacatctct gccgacttgt   37920
aaaagaccga tcaacagaaa cccaaaaaaa atagttgaaa cggagggaaa cgaaaaccta   37980
aaaccctaaa aaactcttcc ttttttttt  ccagtgaaat ttctcttctt ctccgttttc   38040
atacaagtct gacttctggg tagttggaat tttccagttt ttggtttgtt tctgtatctg   38100
tggtttaaaa aagtgggagaa gaagcttttt agtgcttttc tatggcgagg attctccgaa  38160
acgtttattc actgagaagc tctctgtttt cgtcagaggt atgtttatcg tgtttctcat   38220
ttgggtatta cgagaaatta aaaaaactct gttactgtcg ttttcattgc ttatttgggt   38280
attcattcat gagaaagaat ccgaaatgtt gtctcttaat ttgaattcat tctttttttc   38340
tgggtaatgt ttattgacaa gggtttcatg gggttttgca gttacttaga agaagtgtgg   38400
ttggaacatc gtttcagctc cgaggctttg ctgccaaagg ttgtcttaag cttttacctt   38460
```

```
ttgtttctat gaatcgattt tactcaaatt ggttttgat tttgatgaat atatgtattt    38520
ccacagatta ctagagctaa atccgtttgc gtttctgatt gcttagctca ctgtggttgt    38580
taaagttgag gttttgcca ttaactctgc aattgttttt gttttgaagc taaaagaaa     38640
tccaagtcag atggaaatgg atcatctgaa gaaggtatgt cgaaaaagga gattgctctt    38700
cagcaagcac ttgatcagat taccagttca tttggcaaag gtccataat gtatctcggt     38760
cgtgctgttt ctcctagaaa tgtcccggtt ttctctaccg gatcttttgc ccttgatgta    38820
gctttgggag ttggtggcct tcctaaggta tatatactta tctcttttgg tgatattatt    38880
cttttcccaa tatgtgtgtt ttagagtttt tataggttgg ttctattagc taagttaatt    38940
gaggtttatg tataagtctg tattctcttt gaagaatcta ataatattgg tctccccatt    39000
gtgaattcca taggggcgtg ttgtggagat atatggtcct gaagcatcgg gaaagacaac    39060
acttgctctt catgttattg cagaagcaca aaaacaagga ggttattcct tgtttctttt    39120
aactcctcgg ctatgttctt tacagagcca tacgtcgtat cctaaagaag tttttttgcat   39180
acaggaacct gtgtctttgt agatgctgag catgctcttg attcgtcact tgctaaggca    39240
atcggtgtaa atacagaaaa tctgcttcta tcacagcctg attgtggcga acaggccctt    39300
agtcttgtgg atactttaat ccgaagtggt tcagttgatg ttattgtagt tgacagtgta    39360
agtaaggtga tttatatggg atggataatg ggttgatgct tttgctattg gatctatatt    39420
tcgctctctc atgttttcat gtgattttgt tttacaggtg gctgctcttg tacctaaagg    39480
agaacttgag ggcgagatgg gtgatgcaca tatggctatg caagccagat tgatgagcca    39540
agctttgcgt aaattgagcc attctttatc gttatcgcaa acacttctga tctttataaa    39600
tcaggtaaga gaacgttact agctgagatt tgtattcgaa atgtaaagtc tcttatgcaa    39660
atgtatcttt acttccccat gtttcatatt caggtgagat caaaactatc tacgtttgga    39720
ggatttgag gtccaacaga agttacttgt ggtggaaatg ctttgaagtt ttatgcttct     39780
atgcgtttga atatcaagcg aattggactt atcaagaaag gcgaagaggt aaacttccga    39840
aacccgctta cacattttgg gttcgaaggt cttatcctac gacctgtctt atgttcgtga    39900
tgtgtgttta actgatcact taacctttct attgtctcct tagttcttca gaatgattaa    39960
atgcttgtgt ttgaaacctg agattgtatg cttgtgcaga caacgggaag tcaagtctcc    40020
gtgaagatag tgaagaacaa actcgctccg ccgtttagaa ctgctcagtt tgagcttgaa    40080
ttcggcaaag gaatctgcaa gatcacggag ataatcgacc tgagcataaa gcacaagttc    40140
atcgcgaaaa acggaacatt ctacaatctc aacggtaaaa actaccatgg aaaagaggct    40200
ttaaagagat tccttaaaca gaacgaatct gatcaagaag agctcatgaa gaagctccaa    40260
gacaagctca tcgccgatga agctgcagat aaggaaactg aatctgaatc tgaggaagaa    40320
gattccctga gagttgtggt ttcacctgac aacacagatg atgaatcacc agctcttgtt    40380
gttggagctg ctgcagtggt tgttgaggca gcatgattag cgacctccgg tttagtataa    40440
tattcttcct ttggcctaga gttttccggt ttaacgcggt ttggattcgg tttccttctc    40500
ctcatgtaat ttatgtgcta gttaaatcac atttacatat aaccgttgtt gtgggtgaga    40560
aaattttgta gttttatgg ggaaatttaa tgttaacgaa aagcagaata tttaaatgtt     40620
attgatcaat tttacttcca ccaaaatgct attattatat agtaactata ttatagtttt    40680
agatattaga cctcacaaat gacatatcac attaagttaa tcaaaagatg tcttgccctg    40740
gagataacag tttcttggga tcaaatagat ctttcctctt cgaaaaatca tcccattttg    40800
```

```
atccaaaatg ctcaatccaa tcttctttac tagtataatg cattagatat tgcttaatct    40860
taatacctga atccttgcaa aacctaatta tcttctcgtt aacgctctcc acttctggaa    40920
gatcctttgg ggtagcggat tgtagtagtc cgataatata tataacatct tcatcgatct    40980
ctggtatcat cgccgacata cgattgtccc atctaacaat aacagcataa tcagttcata    41040
gaaatttatt tactttggtt cttgaagata aatatgaatg aagagaagta tgtacttatt    41100
ccggtttgtt ggatagagaa gagcgagtcc cgaagctgat ttttgcttaa gaagaatgtc    41160
tttgacaaca ccgttatgaa aatcgagaat ccgagattta ggaacgtaga ggttaagcca    41220
aggatgagga agttcccata atcccaaaga tctgagttta ttttcttcga catgtacacg    41280
gttcaagaaa tcgaagtagg ccacgtcgtg cattgatatg aacccgggca agtaacttaa    41340
tgttttcgtt aatgtgtcaa taacctacac aatagtagat tatgagaagc ataagatgca    41400
aaaaaaaatg taacgatgat gatgatgaat atcttaatgt ggtgcaatga tgaatcattt    41460
aaatatctta tggtatgata aaaacgatga tgaaaatgta aatgtgtagt accttgctga    41520
tgatggggag attgggatca tcataatact tggctacttc aagaacatag atgataccgt    41580
gttgcttgac tagatcagcg actttagatt gatctgaagg tgggaaaaaa gaggtgtcaa    41640
cgacaccgtt tgatagaaat atttgacctt ctaaatagtc gactccaata tcgtttgcca    41700
ttgatatcaa acgttcttgg tcctttgtaa aagttgtgaa atcactgtag agcatccgaa    41760
accatttggc ctacacaatt tcatttagag aaaacaatcc catttaattt atacacacat    41820
atataaagaa accatattac agtatagtat ttcaatattt tcttgaaaat aattatataa    41880
aatttgtgaa tagatgaaac taaaacagaa cgtcatcgta tattatgacc aaatctgttt    41940
tttaaaatga taaccaaatt gtaacgttta tcggttgtaa gattctaatt agtcagaaga    42000
ctatattcta aactttggag tatatttgag tagttgacta atgaaagagc ttgactctaa    42060
taaacaagga ttatatattg acatcaaaaa gatttgcacg cataagacaa gattagacaa    42120
caagtcctag gattacaagg actatacttt ataaaataat ccatatcttt ttttttattca    42180 atgcatagat tttgttcaaa ttaatgcaac ttaagcattt gacctaaatt ccaaacttgt    42240
acctaacttt agttttagga taccatctaa gaaagcttca tgttttgtga tccatacgtc    42300
tctaactctc ttagtgtaat atcataaaat gttttaatca gacattatcc gattagtaaa    42360
ataattattt ccgttaggtt atattttatt ttatctcaat aaaaatcact aaataatcaa    42420
gctctgacat aagaatcatt ttctattgac taaaaaaatt tagaaattga aacggaatta    42480
ctaatgaaaa atgaatgctg actaaaacaa atggtaaaat atgatgatac gtacccgttt    42540
aggtgcatgg tccaaaacaa ttctggctct cgttataatt ccaaattgac ccaaacctcc    42600
taacactcca tagaacaatt ctgggtttag ctgtcgcgag catgtcaaca tttcacctttt    42660 ccctgaaatt atttattcaa aatccatatt aacaataaca atttaaaaag tgtaaattca    42720
aagaaaaatt ctgaaatgtt gctatttaa aaatatacca cctctttatt cgaaagaaaa    42780
taaatgatat atttgaaata ctacacaaat ctaagaaaac cgaaaagctc catatgcatg    42840
cgtcatgcat gtacattaca aaaatcccaa attaacacgc taccaattgt gaaaatttgt    42900
ctttaattat ttatatatgt acgacaataa atgtgtgtat atgtaattac tttatttctc    42960
atgaacaaca ttcaatatgt acaaaaaaca tatagatgcg ttacgcattt tgtgtttcga    43020
agacttacgt gtggtgcaag aagtttagca caactataaa acataaaacc tatggtacaa    43080
aaaatgaaaa atactataaa acaaaaacag ttttttgttgt tgtatgtaca tcaaagttta    43140
gaagatgcgt accagtaata acgtccaatt caaggacgtt actaacaaga ggaccgtttc    43200
```

```
gaaacacttg accaccaatt ccaccattcg acaacgttcc tccgacggtt atatgcaaat   43260
aatccgtcca agaaaccggc gacacccctt tctccgccgt cttcttaagc acatccaccc   43320
ataacgtccc ggccgccacg tcagcgtact tcttgtcttt tgaaaccacc acgtcagtga   43380
tacacgtcat gttgacgatt actccgccgg agaccgaggc ttggccgttt aaggagtggc   43440
cttggccacg agccgctact tggaatgtac tttttccgtt tgcggcgtat tggaggagac   43500
gagagatatc agcggtggag gaggggcaga ttacgccgcc ggggtcacg gtggttatgt    43560 ttccgaagtc atgagaggct gcggagatga tggaaggatc ggtagagagg gtgaggttaa   43620
gggatttagg taaatcaatt ttaataccgt ttgatgattt ggtgatcatt aaaaccgtga   43680
ttaaagtgat cattaaacga agattagcca tttgtttatg tttctctctc tctctgattt   43740
gatttttgaa gaagagaatt acaacgaaag aattagatat cgctataatt tgttacttat   43800
atagacaccg taggaatgta tgtataacat aaaatatgga atcctaccaa aaaaaaaaag   43860
acaataaata ttgaagtcaa aatgaaatct caaataattc ctaaaaatga aaaaggaaa    43920 tcttactgtt ttgtcaactt gttgaattaa tacttcaagg cacatcctca tatttagata   43980
tataataaat cttgttgact atagttagcc atatctatcc ataaatatct ttttagaatt   44040
tgaatttagt attaaccaac aaaaaaattt acattaattt tcttggaata aaatcgagta   44100
aagctttcac taaggtttgt tgagaaaaat attaaagagt gaaactgaat taaaaaaaac   44160
ttatgtttat gtatgtgcat ttccatgaac cagcatgtca taacataaaa gcctagaggg   44220
gagggtcgag gggagagtcg ggtagttcaa ggagttgatt tggttgcaaa tgattcggtg   44280
aatatgccgt tgaaagtaaa ctgccgattg gagaggcatg cattacgttc ttgccaactt   44340
gactaaagat catatacgta ggtcgtggtt tattttgcg ggaaccaaaa cttttgggat    44400
tttgattcaa agacatcata acagataaga tgatcgagat gtagtaagac aaggaatgtt   44460
ttacatggat gtaggcgtgt tctgactcat gtaagtactt agaacgagga tttacggaaa   44520 caacccttt atgttatgaa ttttacgttc tcgaaaattg tgaattttt ttagagtagc     44580 ctctctaata ggtttatata tgaaatttag gaggattatt tggaaaattc cttccgctta   44640
atgataaaat tcattcgttt taagttttaa ccttatgttt ctcctctttc acggtcatgc   44700
tctcgactga tcttttcata actatatata tgacatagtt tgagtatcta agtactgtga   44760
agtgaagatt agttttttat aaaatatttt aaagtctat gccaccatttt ctctgacaag   44820 ttatatctat acgatttctc tctctctcaa ttgataaaac aagcaagaaa taaataaaat   44880
tgttttgatt atagtagaac actatagttt gataaacgaa gaacgagaaa aaaatctaca   44940
aaattgtgat tatagtagaa cactatagta gtcgagttat ttatggacac caaaaataac   45000
cactagaact tttaattctg gaacaaagtt gggaatatct tggtagatat ggcaccgata   45060
atcacaatga tatgatgttt cgctaaagtc atgacaggtg gcgaaatggt ctttgtttag   45120
ttatagttga ttacttgatc tttgtttgca tagagataat tgcaattttt ctttgttctt   45180
tactagtata actaccttaa actattgaag agatttgaag aatatcagaa ctgttgtcat   45240
atttgtttgc agtttctgtt ctataacttc tgttaaaata atcactttct gacattgttg   45300
cagatattgg ttgaggaatg ctctgagtgt tcagagaacc gtataggact taatcgcagc   45360
gggtggagct ggatgcgtct ttaagataac gaattagttt ctggttcttg tgatcagttg   45420
tgtttaatgt atattcatgg gtgatagatt taatcactca taatcttatg ttacaatcct   45480
ttgtgctatt ttagttatgt tcattagagt atttatgata agaactcact agctgcgagg   45540
```

```
aggagatgga acttgccaga gaaccactca gattcaagag gaggacaaca aagatgaatg   45600
gacatgggtt tggtacttat ttggaagaat actcctacta ggttactgtt tgagatgatg   45660
gataagcttc tgaatgagag aatgacgaag aggagtggat gtgtcatgta aaccaaatac   45720
tgagctacta agaactgatt tcaagaattt gtttagattt tgatttggaa tcatagcaaa   45780
accatatgtg atacgttttg gatcagaaaa aaaaaacgat ccaaggcagc caattgttgc   45840
gggcaggccc gtctgccatc tttagataat tagatgtaac taaaatatta ttattattat   45900
taaataagaa tggattttgt caatttgttt ttgtctaatt acttatctga ttagaaatag   45960
tttgatttca atgattggat gattagtcca tctgtccata tactatgaaa actatgatat   46020
ataccacatt ttcacattct accacttctt tcatccttt ttttaaatc taccatattt     46080 cccaaaccaa aaaactaatt tacactcaaa tctatctttt tagtttatac tgttactagc   46140
aaaagtccaa cgcgttgcat ggtgtaatta atatacttaa atgtataata aaatgtaact   46200
aaatatatac tgaaacattt tttgttactt ttaaaatata ataattatat ttatatttta   46260
tattgcacta atttgttgtt agtggtagaa gcttttgta cactacaaaa ctaaacattt    46320
gtaatatttg gtttttaaat agatgatgtt ttcaactttc aataaataat tgattaactt   46380
tttagtattg gttttaacta tttatactat gtaaattatt ttattattgg ttgaattgta   46440
ttcaaacatc taataaatga tgatttagtt tagaaaataa aaaaataata attagattaa   46500
tgtgcaatag aaataaagaa ggatcatcat gtctacttaa gtgaaaaaac attagatcca   46560
aaatatcgtt tggttaaagt gcattttatt aaccgtgtga atgaagacca tatgtggcaa   46620
cactacatga agcttgtttt attgaaatat aggatttta taggctttta ctcgacggtg    46680
gccattcaca gaatcctatt agacaaaaaa gaatagtcac aaatcctaaa tatctttagt   46740
ttgatatttt ggaaacattg acaagtgcac aataaaaac ttgcactaaa attctagtga    46800
aagtcggatt agataccaaa tattggaaag aaaaaatgat gcatgctaga gacacacact   46860 taaaattt gtaaagtgaa acggattaaa gaaccaaatt aactaaacca tttatcaagt     46920
taactaattt accaccataa ttaaatttta atattaaaac taaatatac aatgatcatt     46980 ttaaattgaa tttaattatt tatataaata gaaaaccatt ttccaataat atttctataa   47040 tatatttat catttaataa taatatatta gcatcaaatt atattaataa tcgaccacaa    47100
cctaatgacc caaaaacaaa gacgaccata tagaattaa acttatgaaa atcttaaata    47160
tagttatgta gctaaaacta tacacgagat taatatatat tgtggtgtgc ttgtgacaat   47220
gaagacaaca acgacgcatg ctacaaaaat aagtcaaatt ttctattgga atcatgaacc   47280
cactcaacca ctgttttctt acacaattgg tttttagcga taaaaaacac cgtgtaatag   47340
taaaatcttg aaattgagtg tgagaaatac ataacgtcgc taatagatac atgaactgtt   47400
cgactactgt ttttatacac aattagtctt tagcggaaaa tatcgtgtaa tgataaaaat   47460
tttgaaattg agtatgagaa ataatatatc tgaaattata aacttttaa ccaatgaaaa    47520 tcataccgag agtttaaatt tatatctaga aaataagcat ggccattaga caccaaaaaa   47580
actcttaatt tactcactta gaagttaaaa cacattttcc ccattgtttt tgatggtatg   47640
cattcaataa aacgttagta attgaataaa taaaaaatta tggtaatttg gatatattgt    47700
agttatatgc aattatgcat ttaataatag gttttaaaat gaatgagtag tcaacgacgt   47760
cgctatcgat tttttttgt gattagttat tgatttcctt tataatttc ttttttttt      47820 tttattttct ttataattac gatcatatgt ttataaaaat aatatttta atgatttat     47880 gattagacct tcactattgg gtcttcatat acaatcttta caatttcatt tgtcattttt   47940
```

```
actcatctttt gagaaacatc agaatcgtat tttacttcat ctgactctgt ttgttttacc    48000
gcttatgttg aaccgatgaa attattgttt ttgttttcat gttttattt atttatttta     48060 catgactaat tttatgattt aaatccatga ttataaacct taaattgttt tattttagtg    48120
gatatttata atttagggaa aattagtagg atttcctatt atttctagta acgtgaagtc    48180
attgtagaaa acaaatagtc aaagaagtta tgggtccaat ataaatcatt ataaatttag    48240
attttttcta aattttatg ttaaattttt aaattaaata tttataataa aaatgaaatt     48300 ttaaatttt agacaccaat aactaaaatg ttaataaaat tattttttat ccaaaattat     48360
aaaattaata tcataacatc taaaaattaa tagttaattg agatgataag ggtaaaattg    48420
aaattttatt tttgttatga gatcgtgagt atgaaaataa cgacatttaa ttgcttgggt    48480
attaaattgc acagttttat tatttcatgt atttaccttc aaccaaaaa caattaggta     48540 ttaaacgtcc aaacaaagaa tattttaggt ttgttttgg attttttccc ttttattgt      48600 ttatagttga ataattttat tcccgtgtaa agttctcaaa cgatacgttt cttctttatt    48660
atataagata ttatttctttatttattt ttgttttctc tctctttctt cttctctttt      48720
tttcctctct aaatatatta ttcctctctt tcttccttc ccttgaattt taccacaata    48780
ataaattttc aaagtcaaa tagacgatct aaacttgttc tcgatccact attattcatt     48840
cgattgtaat ttgttcccga tcaaattcta ttactcattc aatatgaact tgtccccggt    48900
ataattatat tactcattcg atttgaactt gtccccgata aaggtattag atctggacat    48960
gccatgcaag atgggtaata taattagatc gggacaagtt ctattacttt ttctatagtc    49020 tttttaaaa ttaacactct gttaaattta gggacaactg gctttgatga ttgtccttcg     49080
tcatatgagg tgggtttatc cgctagaaat cttaacttac ttttcgggga tttcattcac    49140
tatatttcat aattattgtc tacggtaaat gttaactaca tttaatgcaa cattttgttc    49200
ttattctccg ccataaagct gttttttctgg cacaagttac cattttttctc taacacaaac   49260 tttcacactt ttaagggaca aaattgtcaa taaaatacta taataccata aatatggtag    49320
ttttagaaag gtcaatacaa ttgtggtaga tttggaaaga atcttttcaa aagttgtaaa    49380
ctagtcaata ttcccaaaat ttagggtaat ataatattag ttttttttcaa gtcaaatgta  49440 atctcaattt acttccaaaa caaaacaaaa taaattaatg tgttgaattt ttaatgcaca    49500
tcatatattt ggatctctaa ttaatttctt tgactgcatt ctgcaaacat tatctataaa    49560
tacttatttg atagtgtaat ttttattcat ccttaaatta ctcaatcaat ttttatttct    49620
aaaagaacaa attattgtta tggaaccact aggagatcgt cgtccttgct gcgtatgtat    49680
caccaaaaat agaaattgtc ctagattctg cgaatatgcg gaatactttc catatgagtt    49740
gtatactttt tttaaaaact ttttttcctt actattatct tctgctaaac attttacttg    49800
atattaatta attttaattt tcaggcgaag tcattatgaa agtactaatg aattgtttgg    49860
cacaccaaag atcattaaga tgatgaggca tgctcctgaa gaaaaaaaac aaatgcttgc    49920
aacttccata atcatggaag gtaatgcttg gacaaatgat cctgtaagtg gtggatttgg    49980
tatggtgcaa aagatcatgt ggaagattat gttacacaaa gcctaccttc atgaactcga    50040
ggagaagatt aaggaagaga aggaaaaaat cgagcttcat ctttaagtga tacattgtag    50100
catatattat ttatgcatca aataatgatt atttaatata aaatcatatt taagatgaat    50160
attaaattac cgtcgagcaa gttaataacct tatatttctt attcatatttt cttgtgatta   50220 aattgtttgt gtatttagat gatcataaat gaaactttga aatctagaga aacatattgt    50280
```

```
acatataata aagtaaaagt ataaaaaatt gataattttta aaaatacgag aacttctcgt   50340
ttcttgttct aagtaaaata acattccaat atagaattag ggtttagttg cctttggaaa   50400
attgctttgt aaaaagctag atattatgtt tcgtttagta tatctttgac tcatgatatt   50460
tgacatttga ttaaaaatca tgtttgcctt acatgcataa tatcttaaat gcttgtatca   50520
catgtctcta actaccacga aaactttgt gtataaaaaa ttcaaatctt taatttttgg    50580
acgacaaatt cattagcgtt actaatttca ttgtacctat cagttttatg acgataataa   50640
tacaatttat ttcgtcccaa aaaaataat atttatttat taagttaata ggaaaatagg    50700
tgtaaatata caaatatgta tatgtaatat gcaattagag aatatatgaa acaccactat   50760
actatcaaca ttaatattag taagatgaga aacataaatt agatgatttg agtcaatatt   50820
tttccctagt aatcttagta atagtttttt ttttctttta tttgcatagt tcatatacat   50880
atttgtatac atatatgttg tgcagatcta aaattttgt ttaatacctta ttttgcacct   50940
ctaccaaata aattgtgtta gaattttaaa aaattcataa tcacaacaaa atttctaaca   51000
ctatttaatt tgttgatcat aaaaaatctg aattttatg cacaaaacgt tcttaatag    51060
tcaaaactag tgatataaga agtgcaatgc caagaattat agagatttga agcgaaattt   51120
taaaatgaca tgattataca taacttttaa gttctaaact ataatcataa taaaaaaaat   51180
taagatatta aatagagcga acagacgttt aggtttttt cggatttacc atattcatca   51240
gattaatcca tgctggattg agaaaaagcc tcaagcttgg aacaactaca tgtaaatcat   51300
aacctcgaga tattttaagg ctttcaatgt cccaaagaaa gttatttggt gtcgaatcca   51360
tgagtgaaaa ttgagctttt cacatagaac aaagagggat atgaaatagt acaattttat   51420
gttttaaata aagaagataa aatgaaaggt aaatttata ggtttagcca gcagagaaca    51480
aatgaaatga atgttttaag tttagacacc aagaacaaac ttagggttca agtctaagct   51540
tagtcatata cttctgaaca atattggact ttattgttca agtattaaac aaacattgaa   51600
atcttcttaa atcacttttc aaaatgcaac gaggatctat tcttttttt tttttcagaa    51660
gaagctacaa gaaagaacaa caagtttgga tatgaattat aaagttagta atccatgtaa   51720
gagacgctta tattaattaa tttatactgt taattatttc atccgtaatt tttattatta   51780
ttcaataaag tatttatttt actgaattaa aaaataataa ttatgggtgt ttggatattc   51840
ggtcgggtat tttgggtttg agttttttcgg gtttagaatt ttaagatccg ttcgagtaat   51900
tcaagattcc gggtcgggtt tggttcggtt tcgggtttag ttatatattg aaatatcaaa   51960
attttgtgtc cgaatctatt aaattatttg aaaatttcaa aaattcccta aacaacccga   52020
gtagttttgc ttgaatatat ttaaaaatac ataaaagtaa ctaaaatatc cgaaaaatca   52080
taatattgtc tatatgtaaa tataaatata aatatttag ttatatttat atttaagata    52140
tgtttgggta ccagttcggg ttcgggtttt tcaggttttg aagtttagat tcagtcggat   52200
atttgaaaat ttcaggttcg aatttagatt gggattttg gattgggatt tttggatcgg    52260
gttcagatcg gttttttcgg attcaggtat tatgtccaaa gtaaaaatgg taaacggtgg   52320
ttgttttgtt tgtatttgta aagcagaaga gagagagata tagagacact gaaagcaaag   52380
accaaaaaag aaaaattaaa aagagagaga ggaaaatgga gagcgacgaa gcagcagcag   52440
tgtctcctca agcaacgaca ccgagcgag gaaccgagc ttctgggccg aagaagagag     52500
gtcggaaacc taaaccaag gaagattctc agacgccgtc gtctcagcaa cagagcgatg    52560
ttaaaatgaa agaagtggg aagaaaacgc agcagtcgcc gagtgttgac gagaagtact    52620
ctcagtggaa aggtctcgtc cccattctct acgactggct cgctaaccat aacctcgtct   52680
```

```
ggccttcact ctcttgcagg tctccccctt tctccttcc  tctccttcta gggtttcgtt    52740
tcgtaatcgt ttcttagctt tgaacattct catgtttgga atgaatttag taaaatctta    52800
cacatacatt ttctcgattt ctgggtttaa gtgagattgt tgcgattgtt ctagttaggg    52860
ttttggatgt ggctctgtct tcataccttg atatatctga tgttctattc atgaattgtt    52920
actattgatt accttgttgg ttactaatga ctaagaggaa ttttcagttt ctctgagtgt    52980
ttatatctga tgaagtcttt agttgttgtg ctaagagttt ccatttggtg aattgttgtt    53040
tgatttttt  atagatgggg tccgcagctt gagcaagcaa cctacaagaa tcgccagcgt    53100
ctgtacctct cagagcaagt aagtttttag ctttctcttg tatcttgttg tctcatcttc    53160
tttatatact tctcatcgta ttatttgtat ttttcttggt tgtgtcacca gactgatgga    53220
agtgtgccca atactttggt catagcaaat tgtgaagttg ttaagccaag ggttgctgca    53280
gcagagcaca tttctcaggt attatgtggt ttaatactaa gcttgtgtcc tttccatatc    53340
ctactccaca ctacaattgg tttcatgttt gacacttata tactatcttc tgaaaatgtg    53400
ttctcagttc aatgaagaag cacgttctcc atttgtgaag aagtacaaga ccatcattca    53460
ccctggagag gtgtgaattc tgcccactct tgagatattt ctgtattgac attgttcttt    53520
ttagttctat ttggtttgtt aattgtatct gcatccctgt ttcatctgtc catgaagtta    53580
ttcgtttggc acgttggtga aagtaaattt tgatgtgtat tcattactaa tttgcaattg    53640
caggttaaca gaatcaggga actcccacag aatagtaaga ttgttgctac tcacaccgac    53700
agtcctgatg tgagtgctgc ttctattttg ttatggtcat agcaacttga aatatgtcgg    53760
tttcatattt ctgtatttgg cagtcaaaga gcatcctttg ttcggacata tgtccagttt    53820
cagagttatc taaatacaat atgttgattt caggttctca tttgggatgt tgaaacccaa    53880
ccaaaccgtc atgctgtgct tggagctgca aattcccgtc cagatttggt atgtccactt    53940
ctgagaatgt tgttttatgc tttattcttg tttgtttctc atcattggaa gtgataaatc    54000
tctttgatat cttcttaaat agtgcttctt gtttgcatca tctgaatgaa ccattttca    54060
tgcagatact aactgggcac caagataatg ctgaatttgc tcttgccatg tgcccaacgg    54120
aacccttgt  gctctccgga ggtttgtgtt tctgtaattt gtagagtcca atcctgtggt    54180
ttgccagttt ctcatacaaa agttcttctc ttaggcaagg acaagtcagt tgttttgtgg    54240
agtatccaag atcacatcac aacgattggg acagattcca aatcatctgg atctatcatc    54300
aaacagactg tgaaggtac  tgataagaat gagagtccta ctgttggccc acgaggtgta    54360
tatcatggcc atgaagatac agttgaagat gtggcattca gcccgacgag gtaacttctt    54420
agaacagact ccttctattg atatcgtgtt tgtttatgca tactgcagat attttcatga    54480
ttttctaata atacttctgg tgaacttta  taccgtgaag tgcacaagaa ttctgcagtg    54540
ttggtgatga ttccttgcctt atactatggg atgcgagaac tggcacaaac cctgtcacga    54600
aggtactcta tcttttgaat cctatcaaaa gtttgaagat ttacctcctt ttgatattat    54660
atcttacttt tttgttttcc aggttgaaaa agcgcatgat gctgatcttc attgtgttga    54720
ttggaatcct catgacgaca atctgatcct gacagggtat ggagaaatac atacaaatag    54780
atgattaata catacttagt atctaattaa gaaattgatg aatatttcag gtcagcagac    54840
aacactgtcc ggttgtttga tcgtaggaag cttaccgcta atggagttgg ttcgcctatt    54900
tacaaatttg agggacacaa agctgctgtt ctttgtgttc aggtataatc aacttttttt    54960
tttttttcc  ttctttgtat gaagtatatc tcttaaccca ctgacactat cttgttattc    55020
```

```
aattcagtgg tctcctgata agtcatccgt cttgggagc tctgcagaag atggtctctt   55080
gaacatctgg gattatgaca gggtgtgtac atagttcact cagatgtcta aaattaatct   55140
ttcttcacta tcatcactga aacatattca ttgtactcat gtttggtttg tttaattaac   55200
catcaggtca gtaagaagtc tgatcgtgca gctaaaagcc ccgctgggct cttcttccag   55260
catgctggtc acaggttctt aaagacttat cttgattttt cttgattgct ttctcatttt   55320
acttgcttct aagttccctt gtttataaac catattaggg acaaagttgt tgatttccac   55380
tggaatgctt cagacccttg gactattgtc agtgtttctg atgactgtga gactactggt   55440
ggaggtggaa cattgcaggt aaccttgaaa tctttcttgg taccttgata agcaatttta   55500
ttgacatacc gttaaatgtt gtttatactt tcttctatgg cagatatggc ggatgagtga   55560
cttgatttac agaccagaag aagaagtcgt ggcagaattg agaagttca agtcgcatgt   55620
tatgacttgt gcctccaagc cttaagagta aagaaaaccc attgtctatc tatctatcgc   55680
ctatggtaaa ctaatgcggg ttttagcgag gagtcttggt ttttgtaagg ctggtttgtc   55740
ttttgagata ttggtggtag cttttaggac cttccatat cagttagggg tacatggttc   55800
tggttcatga tcctgtttca tcagactctt aggtgctgtt ttgttcaact gagatgttaa   55860
tcaaatcgga ccaactttat gtgttttggt ttaaggtttc aatacttggc ctgaacctaa   55920
tgattccttc tctgtaacta gtcgagacca acccggctac aaaaaaaata gttgcattga   55980
tgttcaaatg caaagcagaa ggggtcatta taaaacaata tagtaataag catcgcaaaa   56040
tttgaaaact gggttcttga tgattcgtcg catcttaaat aatgtttgca ttgtcgtttt   56100
cattagaaaa aaactgttaa tcacgcttag cagtaggatt aggtgatttt caattcacag   56160
atttattcgt aggattttga agaaatttta agtattaaca gtcactaaac aatcagacca   56220
ttgcaaatca tacatagatc acctggtcat ttcataaaac taaactatat gataatgttt   56280
tactttattg ggcttaacgt taatggtcct cccgcttaat aggctttatg aagtctcttg   56340
atgagctaga gactttaaaa atccaatcac aaagcctaca tgagaccgtc aagatcagtc   56400
agagaagatc aaacgaagaa gttttttgttc caaaagatac taaagagaga acatgaatc   56460
aatgtattgc ttgaggaata aggtagggaa gctaatcaat cacaagtaga cgaatcggag   56520
tatttcataa aattagggtt tttagaccta cattttcttt tctttttccg acgatactta   56580
aattgctcga gaaactctat tagtgagaaa tcccccatcg gaatctcgat ggaatcatct   56640
ccttctggat ccgaacctcc gcagaaagtc gtttctaaac tgcagaaagt aggctggcga   56700
gctacgatga tcttcaatct cggttttgca ggttagagaa atcttcatta ctttcttagt   56760
aaggtttta gttttacgtc cgtaatgtgt tcgatgtaat gcctagctga gaaagttctt   56820
tccttttct ttattaattt ttgagaatag aaaatacgaa ttcttctagc ggtcgtctga   56880
tatatatgat actacaattt atcccttgaa ctgttgttgt tgtccttgct ttgattctcg   56940
aagaaagctg attgcattac tctgagagtg tttgattctc cactctatta tcagatatta   57000
gaacatgctt attgaaagga catttttgg atctgtatct ctcagtcact gttgatgttt   57060
tcagcgacat tgaattaagc aaatgtagta tctagaaact atctatatct ctgtgtgcgt   57120
gtgtgtatat atcttggcta agcatttttg cgttgaatag aggattcaca caggttcttg   57180
taaattttct ggttcatgga catgattgca catcttatta tcttgtactc aatacttttc   57240
aaatgtttca gcatctcgat ttttagctgg cagaactaca agcttggtct aaatcagaat   57300
tgagaaaagc atgcttgctt gatttcttat gatatagcat tcatgataga caacttcaat   57360
gtttgctgat ttgatcattt ggttctgcag cttatatatt tgcgataaaa cgagaaaagg   57420
```

```
acattgatgc ggacgagaag aagaaagtta aaaagggcag cgaggctaga cataaaggtg   57480
tgaaaaaggg tgctgttaac accgaaatcg agaagaaagg tgcagaagaa actgataagg   57540
ctaaggaagc agaaactgca ataccggaga aggaagaaac caaactgatc cctgaactgg   57600
atccactgtt tgaatttaca gatgcaactg atcaatccat gtttcaaact gtggcaactg   57660
aacatgtaaa ggtagcaagg aaaccaattc cagaagatga gcaaaaggag cttttcaagt   57720
ggatattgga agagaaaagg aagatagaac caaaagacag aaaagaaaag aaacaaatcg   57780
atgaagagaa agctattctg aaacagttca ttcgtgctga gaggattcca aaacttctac   57840
ctgatgattc cgttgattct tcacttcgtg attgggacaa attcttctcc aagtagaacg   57900
aatacagaaa ctagtgtgta cttgtttttt gttagtacac caaatgacca ttgttggctt   57960
tttagtttta ctactctgat tgttactcta atcaacgaat agtttaaatg tgatttcttg   58020
ggggttgaga gtggcacttt tataaaactt tggggtaatg tttctatttc ttataatata   58080
aaggacttaa aatataaatt caataaaaat aagggtgttt ctgagaaaga gggtataaat   58140
agcttaaacc ctagagaaac tgaagaatcc taaattgatc atcgtcgtcc tttgagtaat   58200
ttagaaaatc aaaatgggtc gcaacgtcaa aaccaaggca agaggaaga acaaggtttg   58260 aacttttga atcccagctt tatcttgttt cgattctcca atctgatgtt ctcaaaccaa   58320
aacctaattg tgtgaattgg attattttt gtttggtttt gaattataat agaagaaagc   58380
agaggcgtct tcttccgaga taccatcgat accaactagg gtttggcaac caggtgttga   58440
tacccttgaa gatggagaag aacttcagtg tgacccttct gcttataatt ctctccatgg   58500
cttccatgtt ggttggccct gtctgaggta atatcatttc tactcctata catgtgttca   58560
tgaagctgaa agcgtgagac ttaagggata attcaaatga gaagcttctt ctttgtttgt   58620
caacagtgta aagaaatgtg tttgcaagtt tacgattcat taagtttaaga aaactactgt   58680 ttgtgaatga ttacagtgaa agttttggtg atttgatggc tttcaattat ttttctcagc   58740
tttgacattt taggtgataa gttgggtttg aaccgaactg agtttcctca cacactttat   58800
atggtggctg ggactcaggt aagttttgta ctttttatat cttcatatgt atttgtgctt   58860
ttagaatcct gtgtatacgt tttcttttt tctttaggct gagaaagcag ctcataactc   58920
catagggtta tttaaaatca ccaacgtatc tggtaagaga cgtgatgttg tgcctaagac   58980
atttggcaat ggtgaggatg aggatgagga tgacgaagat gacagtgaca gcgatgatga   59040
tgacggagat gaagcttcta aaactccaaa tattcaggta attcttgatt cgttttaact   59100
cttgtgttat tcattcatat ctcttgtctc ctaaggcggg agagtcctcg tggttgatat   59160
tttctctcaa aattttggta tacaggttcg aagggttgct caccatggat gtgttaaccg   59220
tatacgtgca atgccacaaa actctcatat ctgtgtctct tgggcagatt ctggtcatgt   59280
acaggtaaga ttatttttt gtctactttc acagcttggg tgtctttttt tgtatgtgtc   59340
tttgttaatg tggattagct tttgtgtttc ttgacaggtc tgggacatga gctctcatct   59400 taatgctttta gccgaatcag aaacagaggg taaagatgga acttcaccgg ttcttaacca   59460
agcacccttg gttaactttt ctggtcacaa agatgaaggc tatgctatag actggagtcc   59520
tgcaaccgct ggaagacttc tttccggtat agttatctca gaaatttctg cgatactaaa   59580
taattacatg cttttcggca tggtcaatgt aattttttt tctccactgg ctaggggact   59640
gcaagagtat gattcacctg tgggagccag cttctggttc atgggctgtt gatcctattc   59700
cgttcgctgg acacactgca agtgttgaag atttacaagt aaaactgcca ctttacagct   59760
```

```
aaataatatg tttgcttgta ccatttcctt ttggctgaac aatctgtttc tttattccag   59820
tggagtccag ccgaagaaaa cgtgtttgcc tcatgttctg tggatgggag tgttgcagtc   59880
tgggatattc gacttgggaa gtcccctgca ctatctttca aggcacataa cgcagatgtg   59940
aatgtcatct catggaacag gttcttgtcc cactatgctg tataacttaa ttctgtttgg   60000
ttttgtgctt cccacgaatg ttgtagtctt aattttctt ctttcatgaa ggctggctag    60060
ttgcatgttg gcctcaggaa gtgatgacgg gacattctcc atccgtgatc ttagactgat   60120
caaagtaagt taaaaaccgt agctatatat tttccttagc aatctcttaa caagattctg   60180
atatggtggc atataaatct tgaactaggg tggagatgct gtggtagcac attttgagta   60240
ccataagcat cctattacgt caattgaatg gagcgctcat gaagcttcga cacttgcagt   60300
cacttccggt gataaccagc tcacgtaagc aagaatacaa tacacaccga ttctctccag   60360
aaaaaccaaa actctgtctt aattgttttt ggctatctgt tgtatttaca ggatatggga   60420
tctatcctta gagaaggatg aagaagaaga ggcagagttc aatgcacaga ccaaggaact   60480
agtcaacaca cctcaagact tgcctcctca gcttctcttt gttcaccaag taacattctt   60540
acttcaacta tcattagctt ggtttatttg atctatgtat attttgtctg aaaacctcga   60600 ttatttttt ggggaaaacc agggacaaaa agatctgaag gaacttcact ggcacaacca    60660
gattccgggg atgatcatct caactgctgg tgatggtttc aacatcttaa tgccttacaa   60720
cattcagaac acgcttccgt ctgagctacc agcctgaaag acaaggtctt actctgaaaa   60780
ctcttgaagt attactcata gttttgtgtt gtcctctctc tgttctcttt ccttgtatca   60840
ttgatggcaa gttgcaagaa ttatacactc tttcacaagt ttcaagtttt catcatcagt   60900
ttatttactg atttcagttg tgacaaaatg tcaaattttg atttacattc tcctctccag   60960
taacagaagc cacaagccta ataatagttt aatccttaac aagtaaaaaa aaatcaagta   61020
gattaattgt tgaattctgc tcataacatt ctccaatttg aaaattacaa gtagtggata   61080
aactttgatt aaatgatcga aaacactcat gtagaatgta acaactatca tgacgatgat   61140
gagccatctc ccaaagacaa ctaacaaatt gtgttgttca acaatcgcag tcttggtaaa   61200
ctccaccgct atggaaacca attccttctg atgtttggtg taaccatgat tagctccttc   61260
cacaatctcc agcttatgat tcggtataac ctttgcaaac tccttagcat cttccccagg   61320
taccacggta tcatccgaac catgaactgt caaaactttg cattgtttat caatattgag   61380
acaagcttga tgcatatcag tgtttaacct atccattaaa gactcttgag taacacgaaa   61440
acaagatttg ccctctgtag catcaataaa ccctgttcc ttaatctttt ctatataacc    61500
atctccgaga cgcacatcat tcttaagatc aaaacgtcca gagatattga cgacattgcg   61560
gatataatcg ggaaacttgg aagcatagag aagaacgaca tcaccacctt tactatgacc   61620
aagaatgaca ggaactagac ggttcatgat gttagaggag gacaagtgtt gaataacgta   61680
atgcagatca tcctctgctt cactgttgaa gttaccataa tagaaagttc cttcactatc   61740
tccgttacca gagaaatcga aacgaaaaga gctgattttt tctttctcca aagctgtagc   61800 cacgttttg agaatcttgt tggtcttgtc cgatctaaag ccatggcata agaccacaac    61860
ttcttttgat ccagtttcgt gaagcagacc cacgagcttc tcgttgcggc ggttcggaat   61920
cacgatcttc gttggcttca tcgtcttttt gcttcaggtg gtaatcgtag agaagaaaac   61980
aatgaggccc cctattgatg taaaaagaat aaggtaatgg aagtatggaa ctggaactct   62040
cgccaaagat caaattgcat ttttctgtgg agatacgaat gagactcgta atcactttt    62100 cttttttttg ctaaactaaa actcgtaatc acttattctt ctcatgtcga tattcagtgg   62160
```

```
aaatttggac cttactcgta agtagactcc tcaaccatgg tgaaaactcc acagttttaa   62220
agtcacattt ctattgtaaa aacagttttt gttttttgtt tgaatgaatt ttacacacaa   62280
ttagaaaata aaaagtgttt gttgatacaa caaaaaaaat aacacgtgaa gacttatgag   62340
ctaacaggct tcccgtttag tttagggaaa ggatcttgct tgcttagaac taccactttg   62400
ctcttgtgag ctaaataacc tttcacaagg tttttgtata tcaatatcgt cattatacat   62460
tccacctgca aatacagtat tattttgaca actgtgagtt tatagaagat ttcaatttta   62520
gaagaagtca aaagcaatga atgggatggt attgtagaac aaacctcgtc cagatccatg   62580
tccatatcta gccatcttag tgctttggca atcccttcaa gcttcagctg gtgagctctc   62640
gctggatcac tcagcttctg gtttatataa ctgaaacatt gataataata agagttataa   62700
actcaagaat cttggatggt atcatagctt gtctttgctt acattttctt catgagtctc   62760
tggtagactt ggagctctag cttttccaag acaagataca cacccgacct caagaacctg   62820
tataaagaa gagtattaga tcgagatatt aagttgttcg gtgatagaat caaaatactc   62880
atcatataga gacttgcaca actctactct cgacccaact gcaaatccta accccctagac   62940
aaatccagaa catcccaact ctttctgccc caattttctt ttaacctgtt agctctctac   63000
ctaagaacca ggtgttactg acctgtcagc agagctatat aatccactac aagcagccta   63060
tactaattcc aatactcatg ctctagagta tccacaagga ctctatcatt tggattagat   63120
gagaaaagca agatatcgaa agaaatacat accgatcttc atgttcttga agagcatgcc   63180
ggagaagcct tagatcaccc tttctcagag cttgcacaat ctttgtgtac tggacacgta   63240
gagaaatagg attaagagag atatgatatc actcagcaga tgcgaaataa gttttgacat   63300
agattcgaag aaaattttat agaacaacag aaaagtcgtt acctcatgca gattataatt   63360
tcgcaggagc tcatcttttg gtataattcc taaagaaagc ttcaccggta ccaaatactt   63420
taatatcatc ctgattcaca taaggccaca ttagctgatt aagcaacgca atgcaagagt   63480
aaggtaatca cagagtaaaa ccagaatcag accttatatt tcgttctctt tgggggttgc   63540
aattttgcaa ggcatatgat agctttgtat cagcctgcaa gatccaaaaa aagagattaa   63600
atgttactat caatatttgg attgacacta cgaaatgaac tgtgatggta agaaaaaatc   63660
tcttagtgac tcacagcagg aaaattttcg ttgaagactt ctaatcggcc ggtataaac   63720
atgtatgtaa cctggtgttt gcgaagaata aacagaagat aataagtaac cgaataagga   63780
ggccaaaaac taaaactgtt tgcagagaac tgcgccagac cttatctctt cttggaaact   63840
cctcaaagtc aaatatccga gcagtttcga tacttcttat tacacttcga caaagattga   63900
cggttccaag ctaaaataca aaattgggga tacctgttta gtactccatt taatggttaa   63960
atcataaata tcaaactgtt gccagaaagc atatcacctt aaagtaggtc ttgaacaatt   64020
ggcaagtcac atataatgct ccgactcgtt ttggacccttt cccctatagt ttaaaactac   64080
ataaggagcc ggaaaaaata ttgaacacaa atataaacta atattcctga agatatatag   64140
atagatcaaa gggaaaactt acagcaagaa ctccaaaaac tttcatgaga agagacccag   64200
ctgcttttaa tttctctgga gactttccat tagaagttaa atctttatca gcctgcaatt   64260
ccatgtggaa aaatcatgct ttcagaactg actcctcgac acaatgaaac cagacaaggt   64320
taagattttg aaaaagggat atacaaatga gatactacct tttccgcaag aactcgaatt   64380
tcataacaaa ctacatacag agcttccaat gcccaagcag attcccaatt acgaaactcc   64440
tgaacaaatg cactgcacat atagaatcca tcagatatca gacattgtga acagacaaaa   64500
```

```
aaaaaagctt atcaccctga aatcatatta gacatcaata gaggagcaga gaggaacaag    64560
aagactttac ttggcaaact tatcgaaagc aaggtatgct tcgactagat tcccaactcg    64620
gtaactttgt agagaacgaa acacatgagc cagaatctcg ccatattcag agaatctatc    64680
agactgtcta atcaaactgc tagaatcctg tatcagtcaa agaaaagaaa actcaaagga    64740
ttcagcactt tcacagctct ctacatataa ataaaaaccc taaatctaaa atccatactc    64800
ataaactcaa acatagacat agagtgttca ctacaacaac tcaataggag acactttcac    64860
ggcctaaatt catactcatt ggtgaagcag gaggacccaa ttggaaaatc atactcatta    64920
gtgaagtagg aggatcctag attgacattg attgaaccta aagatacac actttgctaa    64980 cataaagata atgttcctag tgttttgagc cctaaattca gaaattcata ctcattggtg    65040
aagtaggagg acccaattag aaaatcatac tcttaaggat cttacattga atcgatttaa    65100
cctaaaagtt acaaactttg ctaacataaa aaccatgctc ctagtgttca caattcatac    65160
gagaacccaa tcggaacata tcagaagcat cctggatttg aaatcgaacc taactttacc    65220
aatttacaag gatcatgcca ctaatcacag gaacatactc caagctgcta atttgaatca    65280
tgggtctcga tttaacagag aatatatgta cctggaagac gttgagtgcg tcggcgagtg    65340
agagaagagg tggagaattg gaagagaaag agaggagacg gcaaagtgta gaagagtctt    65400
ggtacgaaac ggcgtcgcag aatcggttta ggtattcagt gattctccgg tgagcttcac    65460
ccatactaac gtacgccatt gtcaccttct tcgtctgcgt cttccttatt ctttgagaga    65520
gacacgaaat caaataagtc gccaggaaaa aaaggaaat aacggagttg agaaaaacga    65580
cggcgtttgg taattaacta aattgttact acgtactagt cttttctggt attagactta    65640
ttgacatatg ttagttgggc catttaaggc ccatatgaaa tacaatcatt aaaatgtttg    65700
aaaatttatt tgtaaaggat ttgaaaatat cattagtgtt ggaaggattt taaagttcct    65760
gtaatcggtg gtactgatca tgaatttttt ttagagtttt taagttcata taatcgtttt    65820
atagatcatg attaatttgc tttaaggttt tttaagttca tgtaatcgtc cgtaatgttg    65880
acatctgtat gtaaatatgt cttcttagcc cgatggtgac gtgaggaact ttcttgaagg    65940
gacatgaaat caatttatac catgcatata actcaacaag ttgccaaaaa ctcgaagaaa    66000
tgaatataat caacttgtca aaagtaatta actgatcaaa taaatcactt gtttccaaat    66060
gtgatttata ctttcacact tctatatatt cccattgata ttccccttct ttcatagtta    66120
gcaaaggcct ctactacatg tacatgataa ataaataaat aaaaatcacg ctaatcatat    66180
aattatcaat atattttatt cttgaacaca caattaatag aaattttgag ttgagagaag    66240
tcaatccagg attagtattt atgtgtaatg ctaaaagttg aagataacga gaaacttgag    66300 aggttttaa ggttcctact ttattttgg tatgaaggtt cctactaaaa tatgctctta    66360
tatatcattt tatttaaaaa gcattccatt tgaaactaat ctaaaaatct ttagattcat    66420
tgttcaccac tcatagtaag agttgcatgt ggaccatctt atattctcta ctttctcata    66480
cttcgtattt ggaaccttta ttccaacaaa ttcaatgtgt aaagccatca ttacgttcat    66540 ttattttgc cttttgcgt acataaaaga aacatcataa cttgacatgt aaaaaaaaa    66600 atcattgatt cgatttgaga cttttgaaaa ccttgtcaat tttataaaat ttggccgatt    66660
tgatctaatc cacataatcc atcccttata gacgaaatta aattttcaaa ggggatatta    66720
aaaaaaaata tcaaaaaatg gaaaaattta atatcaacaa ttttttttt aacaatactc    66780 cataaacata ataattgtat taaatttaat ttttaatac aataaacatt tttaacaaat    66840
ttaaaaatat aaacttttct tattctctat gtgttatcca tcacatcaat ttcaacactt    66900
```

```
tttttttttc cgtcaatttc aacactttta agaattaaaa agtctcattt tcttttttatt    66960 cctttttttt taaaattcct ttattttcg gataattaaa tgattctcta agcttcatag     67020
caatgaaaca ctttgaattc gcatttcggc gatatagtct ctaataacaa cctcgccgtg    67080
tgctcttgcc tcaccaccgc atcttctttc tccaccagaa ccgctccgac gatcctctcg    67140
tatcctcctc caccaccatt agccacataa tcaaccaacg ccgcctgtac tggtcccata    67200
ctaggattat acgccgccga ttccatatac caacctctgt acactttccc gtcacaatcc    67260
accagcgaaa ctcccgatgg acataaacta tacggcgcgt acgatctatt cgccgccgct    67320
aaagccgttt gtttcaaatc ggcggatgaa tcggtgtttc cgttacaaat cgaatccaga    67380
tctgagattt tgagatggtt atcgtgagat tcgagaagaa gaggatgatc tttcccgaga    67440
agatcgtcgg gaccgaatct gtgtggcaag aagcttccga gacgtaagaa tccgtctgaa    67500
tcggcggcgg aatcggaatc ggcggagttg tttggatcgg tgataaggat tttgatttca    67560
ggtgcgtcgc gaatttcttg gaggaattga cggcaatggc cacatggtgc ggcggagacg    67620
gcgaagaaat tgagatgacg ttcaccgttg agtgtgagat tggtgacgag gaactgttcg    67680
gcgtggattg agtggtggag agggagattt gggaattcga cattgacgcc taagaagatc    67740
cgacctgatg atccgagtcc gacgactgcg acgttgaatt tcgaaatcgg agttcgagcg    67800
taggattgtg ctggtttgac tagcgacggg aggagctgaa tgacggaaac gccgagttgt    67860
ttcgcggcgg attctgcttc tttggattgg attacgaagc ttggcttatc cattgcgggt    67920
tgatccggtt tgggtcgcgt aaatgggtcg ggttatttt agatgggaga gatccgggaa     67980
atgaggaatt atgaaatgga tgctggacaa acaaactatt tatagataca acaacgtagg    68040
aaactacatt acgcaaatga agttttggtt cggtttcggt tatgtttcgg tttacgtttg    68100
gtacaaaata gaaaaattat atcagaattg aatttacaaa taatatgatt tcggtttgac    68160
taagccgcat ggaatcattg ttatgaaaac taccaaaaat gcaatagagt attagtgtaa    68220
cgtaatgtta aaatcgtggt ctaattaaga aaacacctag tagtttcatc aaccacgtta    68280
cgaaactaca ataatctccg gataatatta ttttagaggt cagaaatgaa ttaaactata    68340
gctaaaagac agcttagttt catataattt tgatagtatt aaacatttta attccggtgt    68400 tgtcaattt aagttcccaa aaaaatagtt aagaacaaag gtgatagtac tattgttgac     68460 aaagaaaac aaagattagg ttttgttctt atcgttggaa tcaacgtcac agaccaaaag     68520
agaagtcttt gttgataatt acgttttaac caacggttaa gttttctta atagaagaaa     68580 ctgagaaaac tctatgacaa caatcagttt tccaattagg gtcagttgtt tgtttacata    68640
gataagtgcc attttgtcga acataaactg ataaacatag aaacaaaatc cataaaaga    68700 aaaaaacctt ttccacacac aaagaaatca taatatgacg agctatttcc gaaaactcca    68760
atctcaacaa actacaaaca aatttataga cacaaacaca ttttagaccc aaccttgttt    68820
gtatttgcgg aagagatcct cagtctgagc attcctaaac gcgctacaag caataacata    68880
aacccatatg agaacaacga ctgtgatgat aagtatgaga tttgctttac gccattcttt    68940
tctaaggttt cccaataaac cagctttgca tgagttgcaa ttgtaacaaa gctggctttg    69000
gtcattgctc cataagtaac agtctgcgtc tgcagccata ttggttggat ttagccacag    69060
tgttgggttc acaaagttgt agccacatgc ggttggtggt ttgcagcagc cggactgtaa    69120
aacaacaaat gttcaagaaa ttgtcataat tagatttgac caaatatatg cttaaccatg    69180
ttttcaaata tgataatcat agtcttaaag atatttacac ttttttttta ttggtaaaaa    69240
```

```
atatttacac attgtaaaca caaacgctac catttgcgtc tgcccttgt gtttacaaca    69300
aaaatttcat tttgcttaac atggttaata ttatgggttc atgtggagaa aaaaaaagta   69360
tatactaaag gcaaacacaa acaatcaaga gttcaagagt caagacctaa aacaatgaaa   69420
cactagtttt agtctgaaag ctataaaaat aaaacgacta caagaaacct aaaaaattgc   69480
ttgcttggta tgaaagtaca taaaaaaaat gaaaaaacat gttgaatctt atcacagaat   69540
aatcttcttt tacttatgag taaattttgg ttctgtctcg aggacgagaa attgtataac   69600
tctttcttag aaataaactt atttttttctt gagtcctaat ttatccaata agaaaaatta  69660
taatgtgagt ggggcaacat gggagggata taattatcta ttatgtttca tgatggagac   69720
aaagacttgt gatcgtaatt attgaatcaa atcattggtc caatatttaa taatgtctaa   69780
tgactaaaag atttaaaatt cagtcgagac ctcagcatct aggcttattt aattattagt   69840
ggttccaatc ttgttacagt gacaatggac taggatgaca acttgctata gaagttttag   69900
gaataaaatt atttaaatca cccttaatct ctccatgttt aaagcttaaa agacataaaa   69960
gacatgacaa tgaatttttaa gagtgatttt aattaataaa attaaataga aaagtagga   70020
aattttgtca agtttgagtt gtgatcacga aaaacactat ctaaagtgaa tgggatcatt   70080
gaattttatg agtgagatag tgacaaagga aaaatataat taatacacag ataaaacata   70140
gtttatcatg taccatattg tgggtgcatg ggtgggtcct tatgatagtg tataattttg   70200
aaatctgact atcttactat ataatcttgt ggacttggtc tccagcaact tctacaccag   70260
tctactagga ataaatatgt gttcaataat ggtgattaca tatgcctaat ctatgagttt   70320
taccacaaaa tggcactaac tgcgaaacgt taagaaagct aatgtaggtt tctctccaac   70380
actagaaaac ataagattaa ttaagtcaga aaatatttt ttagtttttt caaagatgag    70440
gaaatccaaa acgaaataac ttaaagctgc aaaacaaaaa aaagaatat agagaataag    70500
aacaattctc ttttggacat cttcacaaaa gctaaagaga aatttttaa ctttttgatt    70560
taaaaccaca tactttactt tttgaaagaa aaaataacct atctttctat ggcaagaaca   70620
aaccgtaggt ctcacataat ctagagattt tacaaaacat tctctttact tcgtatctta   70680
tctccattaa tcatctaata atatctaatt aaacccacaa tgattcgttg gcatagttgc   70740
ataaccgata tttagtctag atttacctct aaaccaaacc taaaccggaa actagaaatt   70800
tcggggttct ttttataaaa gagaataaaa gaagaaagaa catgcctgga gaggagtgat   70860
cttagaggag gagaagaact gatcggcggt gatgaattct tggttgagtt taggacaaac   70920
attagtatca gccaaacaag cccttagcct tccccagttc ttggaatcca caacgttctc   70980
cttaagccaa ttcgagaacc cttcaagcct atactcttta taacctctac ccggaacccg   71040
atacgatcca tcgggccggg tcacgacgaa tgcaaatata agaaccacca gcaaaagtcc   71100
gatcaatatc gccatacagc acaagtaaac cgccagtaga gtttccttgt acctgaaata   71160
tgagagctca aagtttacat ctttatgatt caatttgtgt ctatgttttc aaagtcttga   71220
agttctttga ttcttacttg taggcgccga tgaagcctgt ggcggagacg acgaggatga   71280
gaacgccgag gacgacaacg ggccaacgga ggagattgac acactcgttg tctggctttg   71340
aagctagcca tatacctgac gccgttattg gtatggaaca gagtaacgct agtaagttga   71400
gtatcgccgt taagttattc gctaacgcca ttaaattttc tctctctctc tctctttgtt   71460
cttgaagatt cgtgcttttt atggaaagaa aatgaaataa tgagagtgag aggagtgtct   71520
ctgttttgt cttaatgact tatgaggtcg gtggttagag atgatgggat gtgtgaaacc    71580
agttactgct atttacagaa aacgatgttc ggtttggtcc ggtccggtta atcactgatt   71640
```

```
ttgctgattt ggattttcg acaacggtgg ttttaagaaa aaagaattag atattggatt    71700
aaagttaaca tgtgaatgtc agaataaaat atgtttagca atgaaaagtt aggttttgaa    71760
caagttttgg gttgtgatgt aataaagaga acttgttaat ctggtcggac cggcttttgg    71820
tttagaattt ggaatcttga acgggacacg tggatacgcg agatgccttt tgtgttaata    71880
ttcttccatt ctgcgagtta ccgaatgcat caaccagtga gaactatcca cgtggcaccg    71940
acgactttgg gtcatttgca ttgaacgtat gttactttcg acagagaatg caaaatggag    72000
taagttccat tgttcggaaa tcggaatttt cttcttttcc aagcattaga ggtttcggag    72060
caggatttgt cgttggctga tgagtgaaat gtcgggtaat ggtcaagaga taagcttttg    72120
ttttggttca gaggattggg attgcacaca agctgctcga tagaatgtgt gaaccaaaac    72180
atatggatga attttctca tctcgatttt attgcgattg gagaagaatt ttgagtcaat    72240
acacacttag ctttcagttt tagatgctga tatagaaatg ctatttgttt gattctagga    72300
attgggaagg aaatgagtca aatcagagag aatatggaaa gagatgatgg cggagttgtg    72360
gattacgtta agagttgaat tacatcttat aaatcatgaa attgactgtc aatcttagag    72420
cttagattac aagctctttg tctaatctca agttcgacac agagcttgat gagactgctt    72480
cagtttggct ttggaacttt tcaagtggaa gtgaagaaag aagagtgaag tagtatagct    72540
gaatcagcaa gattctgaca tggctggtta tttaaattat aaggaaacac aagaagaaga    72600
caaagttttt atgatgtgag tacagaagcg tcaaattcca gatgcatcct aggctgaatc    72660
cgcatttccc attttcttca tggtctcaag tctggggcct ttgtctccaa acttggtagt    72720
tgaataaagc tttaggtagt cttgaaaacg gtagccactt ggatacaaga gctttggagc    72780
tggagatatt atggcatcac cagccggatt gtaaaacgta gcaatcgaca gtctacttcc    72840
atgcttcact gtcattacac ggtgaacaac actcttgtac ctcccattac tcagtatctc    72900
tagttgatca ccggtattga caaaaatggt attgttcttg gatggcggta taggaaccca    72960
cttcccatct ttaaagaact caagaccagg cacttgatca tcctgcagga gtaatatgat    73020 tccccccagca tccgtatgtt ctctcagccc tctcataagc tcaggacgtg ggcattctgg    73080
gtatttagcc acttttgttc caaaagctgg accttttgga ccagaaaagg cattcattat    73140
gtcttcctga tcaagaccaa gattctcaca catgagcttg gagagtctct ctgcaaactt    73200
gtgcagttga caaacatatt catccatcgt cttgctgcaa atatcaattt caccctctca    73260
cattgtttag ttaaataagc aaacaggtaa aaatggtaga gcctttggta ctattcaatt    73320
cttaattact ttacctgagt tcctctgaaa tgtttgggat ctgacagata tttgaagttg    73380
gtttatgtga gatgaagaaa ctgctttccc aatctgcatc tgaggttttg ccttcactca    73440
aagccttgac catctctgac tggtaaaact tctctttcaa atgctcctca tagtgagagt    73500
taatcatctt cttcactttc tccatcaact ctttatcaat tccatgatta tcaacctgaa    73560
aattcactaa ctctttaagg atatacagta gacatatctt agaaacact gccttgtgca    73620 taaagatgtt atacatacca tgaagaatcc ccacttatca catgcatgat caagaagtga    73680
catggtcttg cttctcttct ctccatccaa ctctgcaaaa tcaataactg gaatctccat    73740
ctctctctct ttgatcaaaa ccatctcttt tttatttact ttttctcaca cacagatttg    73800
ttgaatgcaa tctagaaaga gtatttatag gcataagtga aaattaaatc tctgtttctc    73860
ttgtgtgtta ggaggcatag ttgcctactt ggaggcaaaa acaatagttt ctttcaacac    73920
tattctgtta actcattgaa tttgaagcat cattacgttt aatgaataaa aaattgtata    73980
```

```
agaatctgct tggaaatgt aaaatgaaca ataggattga agaaaagtcc aagttcagtc    74040
catacaacca tgtgatcaca agttttgaa tttttcataa tttcttaatg gttttgggtc    74100
actcccattg tgtttccttg taacatcatt tatgtgaagt ttctttcttc ttcacaagga    74160
aagttttttt ttttttttt ttttttcct atccctactc atattcgatg gacctagcca    74220
tcatgtctaa ttgtgtatta tgttttcct ttcactgatt tttttttct ttaaaacttc    74280 actaaactac ccatctaagc gtcattggcg tacttgtaaa atgtgttatt ctggtgtcac    74340
caaatttgga tatgcgtggt gttgtgttta gcaaggagct ctataacact catcaaatga    74400
taatatgacc cttttttggt atgaagaaat ctacttggcc taaagctaca gtatcgaatt    74460
gttacttgag aatagatttg tgaaaggta cagtatcgaa ttgtttattt tgagattacc    74520
ggagtactac acaccatttg caatagaaaa agaaataatg tgggtctaag cggaattaag    74580
cgaaagaatt ggcccctcct atgggcgctc tcggttttga atatatattt ttgtgtgtca    74640 tatttataa caccttgtaa agaatttggg attgtgttta agaatgtta tcattttact    74700 ttttggggtc gaatatttcg gatatcgtta gttagtgtag ctctagtcta tataaatcag    74760
caccgacaaa tatattttt atgtggtgta aaattcaacc atgacggccc cttagagcgt    74820
aaacgggcca agacctaatc tacaaagact tttcagttat atataacttt gtttcgttta    74880
gtttgactgt ttgaggaaga aatggtaatg ttattgaatc ttttgttttg gtcatttggt    74940
gttgtaatat gttacataat tcgaaatgat ggtttatcgt taacacggac tttaaatatc    75000
attaacatgc gtgtatttga gattacaacg aattgattca acatttcaac ttttaacatg    75060
ttggagttaa ttattcaaaa agttaatacc ttgtcaagat atctaaacgt tttcaaattt    75120
catgctattg atattagtta gggtcataag acctctttag agtcttcata tattgtttta    75180
gtaaccccat taaaccttct gcttcaccaa gagcctttct ttccaattta ggtacatttt    75240
cttttaagta tgagaatttg gtaaacttaa actccaaact aaacaagcca aaagagacca    75300
aacattacaa tgaaccctaa acaaaaatta taaaaatgtt aaagtgtaat acgcaatttg    75360
caaattcagc aactatcacc tttactttgt tcactttgtt gtataaatga ttttgttct    75420 cactccctga accacgcgct aacggtggcg cgtgttctta acacactttt tagtttccag    75480
aatcgatgga gactttaatt aacattttgc ccttaagcaa acaataaaca ataataaaaa    75540
aataaaatta atttccctct ctctctcaat cttgtgctt tctcgttctc caaccaccgg    75600
aaagagagag agagagagat ctttgtgtgc ttcttctact tcttcttctt ctctctatcg    75660
ctccgccgcg ccacattcac tgagatgcgg cggtgtaaaa acaacactga caaattctct    75720
gtgataacga tgaggcttct aacgcttctt ctgatctgta ctttcttctt cttcttctcc    75780
tttgcttatt ccgccgagtc agataacgag actgactcag ttgttacacg tgagatcaat    75840
ggaaccgtcg ttgagtccaa tgccacgagt gcgaaaccta gggaagatag tttcgctgat    75900
atgatcgatc gagcacttga gaaagagttt cctgataatg accagaacga aggttcctcc    75960
tctctcacta gatagatctt catttcttct atttgttacc tgagctaggg tttctctagg    76020
gatttcaatt ttgttattat tgatccttct tctctaggga tttatcattg attagctgag    76080
tggtttagac tctctctttg tgcccacatt atagcaatta atgcttttgt gttgtttcga    76140
ttttgcagtt cctgatccag gaagcttcaa taatagtgtt gctgatcagc aggttggttg    76200
ttgcaagttt agatcttttt ttaactactc tatgttttct ttcttttaa ttaaaggcat    76260 gtgttgtgct cattaggcgg ttctagagac tgttgcacga gttaagccaa agaaaaatga    76320
aaccaagacc aaggaggaga agtgagtttt tctgatgctt attttgccct gtttggctgt    76380
```

```
tttttttactt ttgtttcact ggttaaagca aactataaca tatgagtgat tttgttctag    76440
atccttcttt aatttggata acgagaatgg cgtagaggat actccaagac tgatagatag    76500
gaaggtaagc ttcgatcgtc ctaaattatt tgtactatat attgctgaag aatgtataat    76560
ctgttatgta cccatatgta aaggcattct cgtgatgtga atttgctgcg attttgatcc    76620
aggacaacgt ttttataatg tccaatccaa aatccaagta ccctgtactg cagctagatt    76680
taaggtgagt atagcattcg taagagaagt tcttcgttcg attatatttt ggaagtatct    76740
aacttacttt tttttgttgg gggcatctct cttaaatcgg tacatttgta ggctgatatc    76800
agatttggtc gtcgtcattg tttctgctac ttgtggtgga attgcctttg cttgtgcggg    76860
tcaaccggtt agcacacact tcctttgcaa agcttgtgac ttcaatatta ttttattagc    76920
attgagtatc cagctttccg gcattgtaga aatgattttg ctagctctta ctaatcaaac    76980
catgacagcg ttatttaatt tctacactac ttatggcagg tcattactgg gtatctattg    77040
gctggatcta tcattggacc gggcgggtta agctttgtta gtgaaatggt gcaggtagct    77100
tacatcagct ttagtacttc aaagttcatc tttttttttt tcttcatata cgtttgtatg    77160
ttttcatgac taccagattg cctgggacaa gggcttgatt tataattttt ttgtgtagca    77220
caggtcgaaa cagtagctca gtttggtgtt atctttctcc tttttgcttt aggattagaa    77280
ttttctgcag cgaaggtttg catgttttca ctctcttata tttgtctggt ttctttgtca    77340
atgcgattga aacttttgag tcagttattg tactgcgtgg ttgcagcttc gtgtggttcg    77400
tgcagtagct attccaggag gtcttcttca gatattttg ttcatgtgct tgagtggaat    77460
aacagcctcg gtatgttcta aaagtgtagc aatcgagtta agaatgagtt attaggcatt    77520
tgtggtatga catgtatgta gagtgcatta ggttgactta gctgtttctt cattgcagtt    77580
atgtggcggt aaactaacag aaggaatatt cgtaggcgca tttctatcga tgtcatcaac    77640
agcagtggta tattctaatt tcctatgtgt acttcaatta atattttgat cttgttctac    77700
actgtttgaa tatttcccta ctctcactta ttttctcttt tctttactgt gccagttata    77760
ttttcctaaa gtattcttta gacttgattg tcatatgtta tccttacctc cccatgattc    77820
ttgtaccagg ttttgaaatt tttaatggaa agaaatagca taagtgctct acatggccag    77880
ataactgtag gaactcttat tcttcaggta tctctacctg ataactctca aaactatagc    77940
ttctctatta tcattttcac acgtttttt gttttccta ttattctaaa actgcatatc    78000
cttttgatcc gaaatatgat tcaaatccaa ttccaatagg tagtatgttg catgcagcaa    78060
gtacttttgt tagaacttta atttactgtt tcatgaatca ccaggattgt gctgtgggct    78120
tgctgtttgc tctcctgcca gttcttggtg gcacatctgg tgtccttcaa ggagtgttgt    78180
ccatggcgaa atcgtatgta ttttctctt ccacgaattt ctatgaaact atcgacaata    78240
ccctgcttcc attgttcact tgttacaata aaacctagtt tttggttaca ctttctttt    78300 gactgggttt taatatcttt ccaggttggc tattttgatt gcgttttgg gagctttgtt    78360 tgtattatcc cgtacctggg taccttggtt tctaaaactt atgacaagcc tttcttctca    78420
ggtatagaca catttcttac ctgctccagt tttggtcttt aaattgttta tcaactcaag    78480 cgttttcaa tctttgacag actaatgagc tctatcagtt ggccgctgta gcattttgtt    78540
tacttgtcgc ttgggttagt ctgatccctt tgttcttctt agctattggc tgtttgcaca    78600
tttgtgactc tcgaattttc atttcttaaa tccagtatcg ttttggcttc ttcagtgtag    78660
tgacaagctc ggtctaagtc tggagttggg ttcctttgcg gcaggagtga tgatctcaac    78720
```

```
aactgatctc gctcagcata ctcttgaaca ggcaagaagt caagtttgac tgtttcgaac    78780
tagagggtct ctacccatat attttggcca ctctcttatt ttgaaagtgt ctttcttgct    78840
tatatactat cttggtttcc tgatgaaata cgtttccttt ctttggcaca ttctaccaaa    78900
gtttttcata taaacctgtt ctgatcgctt ctgtttcctt gcaggtggaa cccatccgca    78960 attttttgc agcactgttc cttgctagta tcggcatgtt gatacatatg cacttcttgt     79020
ggaaccatgt tgacattctg ctagcagctg tgttactggt gatagtgata aagacggtgg    79080
tagttgctat cgttgttaaa gtctttggat acaataacaa aactgcagta cttgtaagaa    79140
gcgaacccct ttttttttcc ttcttctca tcattcgaaa aagccttaa ggttttcttg      79200 tctgtaggtt ggtatgtccc ttgcacagat tggggaattt gcttttgttc tgctaagtcg    79260
agcatctaat cttcacctaa ttgaggtaag ctctctatga ttattgatgc ttagttatat    79320
tatatgttag catatatctt tgaaaccgtg tgtgaccata atagatttct cataatttgc    79380
ttttggtgga gcgataagta acaatgaagg ggttttgtgt ttatttgcag agcaaattgt    79440
acctcctgct tctgggaaca actgctttaa gcctggtatg gtctatttcc tcatcatatt    79500
tataataagt tcatattcaa aaacgaataa acgaatattg acacggacgt tgctttatca    79560
atgaataaca gtagaattta catactccag tatcaatatt gtataattac taaacaaatt    79620
aaatgatgta acaggtaaca acaccattgc tattcaagtt gataccagca gttgtacatt    79680
taggagtgct cttacggtgg ttctctcccg acagctcaac cgaggtaaat acaaatcatc    79740
gtcgtgtgtg tctctctcaa tgactttggc tcaaactcaa ctatgaacta taatcttcat    79800
ctgtacagat tggtttcaaa ggagagttgt atcactcaga gagtgcaaag cgtatatcac    79860
tgatgatcca aggttctctt cacgactctt gaagtgttga tggtatgttc acagcataac    79920
acgcaacatg aagccacatt tggtctcaag gtaggcaaag gcaatgaatg ggagcttccg    79980
aatgtataga tgctttgaga tatcagaaga gaacccccag aggaacctgt ataaaatctc    80040
tctacacgaa gataattaca gagacttgta acttcacttc aattttttgt tttgggattc    80100 tttttttgagt aaaaaggtag gaagaggtta tattttagtt tgtttacttt cttctcatgt   80160
gctctgaaac aaaataagaa acatctccaa cgtattgtag tgattaccaa ccgataaaaa    80220
gctaaagaat ttttgagtta gtcgattaca aagtataaac acaaatttga attgatacac    80280
caaagatttc tttaacattt cgtgggaggc cgagtattat ttggctttag cttcgaacca    80340
agactctctg gagatagaag ctctggctaa atacatgacg gactgagagg actacggggg    80400
ctatcttaat ttcctttat atgaattttt ctatgttaat ttaactttt agatattgat      80460 ttccattgta attaaaacgc tgtttgtcct aattttattt tatatatata ttgtataggt    80520
tccattaacc ctacgatcaa aacagtttca tacaaactcg cctcatcttg ttctctaaga    80580
tcaacgtgtc tgatcaagct tgatctgctt ctctttttt tttgttttg taattattct     80640 tgcttgattc gatcaacgtg tctgagcttt gattcaagtg ggggtttgga ggtatgtgag    80700
cgtcaaatct tcaagttta attctggaat taggtttctc ttagtgggtt tttttttgt     80760 atcatccgag tgttgttgtt tgaatataaa tataaatcca accactagaa catgttttac    80820
ttactttggt tttgttttac ctccagatat ataccgccat cgccatggat aatcacttgg    80880
aattagcgat aaaggatgca atcaccgcgg atgatcttaa acgtgtggat caagaaactc    80940
aacacccttt gttagctcag gagcttgatc ttgattcctt ggagaatcct cctcgggcca    81000
caactcatac atatcggtta tactccaagg gtttggtgag tgaagagctt attaaggatg    81060
atacgatgct ggtcgttggt ctaggtttgt ccctctgtga ctcgcacgat tacacgaaac    81120
```

```
aggagattaa taaagctctg agaaaccaaa agctggcggc acacccagaa gctgcggaac   81180
tggctgccat cattcacggc ttgaaatggg ccttggaact tggtatcgaa cgtatccaat   81240
tcttctgtga cgactccaat atcttggcct acgtatgttt ctctctcttt cttcttttac   81300
cctgaatcca gtatcctgtt tgtacacctc tcatgttgtt tttacaggtt actcgtaaag   81360
ctgcacctaa cgagtccatt gtagcaaaac ttttgggagca tgtgtctctt cttcagacaa   81420
gattcacgtc atgtcaggca cttgcaactg taagcagaga cgacatcgtt tctgtcatta   81480
agctagcaaa agatgctata gcttcccaaa ctagatggtg tgaaggcgac accgagtatg   81540
agagttgtcc agtctgctac gcttacgttt cacctaatga taagtttgag gtgcaaggct   81600
gcttccaccg catctgcgtt acgtgcatga ggaagcccct tctcatccgaa caaatactac   81660 gagggaacac agcaatctgc ccttacccgg attgcgagaa tgatcttgtg ccagaggatt   81720
gtagagcttt tgctgatgct gatgctatta ctcttatgat ccagcgcaag aaggagaagg   81780
ctatccccgt taaagacaga gtctattgtc ccaacccatc ttgttctttt ctgatgtcgg   81840
acctcgacct cattaggcac ataagcaaaa atcctcggca ctcagaagaa gcacggaagt   81900
gcatggagtg cggcttgtct ttctgcaaaa aatgccatgt tccgtggcac tacaagaaga   81960
catgcgatga gttcaagaag tcggagtctt acctgaaatc tgacgcggcg attttggagt   82020
cttttgtgaa gacacaagga tggaaaaagt gttcccagtg tcagagcatc gttcaacatg   82080
gtggcggctg ccaacaaatg acttgcaggt attggacatt tgttatttat tgagcctact   82140
tttatattat ttgactttaa ctatctgtct ttttgttcct ggcagacatt gcaaacacga   82200
gttctgttac acatgtggcg ctccgtgtaa aaagaagaaa ctgacatgta aatgctcgcg   82260
ttcagggaaa taaacatcca aggtttcact atacagatca ttccaaatag tttcttatat   82320
aacttgtttt gatggtgttg aagatattag tctcttctca tgttttctga acaacatta   82380 gagacatacc aaccgagaaa cgctaaaact atctcttata aataaagagt ttttgagtta   82440
atcgattaca aagtacaaac acgaatttaa taaaagaata tttgaattga taaaccaaat   82500
atgagaggaa gaatacaatg aatcaacgtg tgtggtggct ttaacatttc gtgggaaccc   82560 gagttttat tggctttaac ttcaaaccaa gactctctgg tgatagaagc tctggcgaaa   82620
tacatgacgg acttagtgga ctccggggc tatcgctaac ccgaccaggc cgatacaatc   82680
caaaccccat gaaaagaac tccattggta tcaacattgc atgtggttgc tcttctgtca   82740
ccattgatcc acaagcttgc acctgcaatt ctaaaaacat caaagcatgt tccacgaatc   82800
taaaagcctg aatctttagt ctcggagaga agttaagagc taccagagct gttttttacat   82860 taaaccgcat acctcaacca aggcgctgta ctttctgtcc aatgctgtca ccatgtgaag   82920
agtttcagag tggaaaggag attggtcgcc aacaaagatg agtgtacggc atttcaaact   82980
cttcaatcca tcagttaagt catgtctcct gttaactgct tctagaaacc gcataagact   83040
actaccgtgt ctttcaccta gcagctgtat aaacatgtcg tatcaacaac gtaatcaagg   83100
tggtgaaaag cagtaaaatc atctggaaat aactactagg tttaggcgtt tagcactcac   83160
tcttctgcat tcatgtacca catcccgctc tggaacttca gagctaccac gagcttcctg   83220
tcgtaattta agaacaagat taatcggtaa ctattaagta tatacggatc tcattcagaa   83280
atcacaagaa agattacctt actgaagtac ctctgaagga aaatatcttt taacagtcca   83340
gacatgccat agtagtacaa taagtttgac acaacctgca ggaagtttta acatcggttt   83400
atgcgaaaga acctttttgta cagtcatatg aactactatg ggaaggtgaa aaaagaaac   83460
```

```
cttgtaataa aaccattcag accatgaggg tgctttgcat agaggcgata taagaatcaa    83520
acccaaaact cgttctttat gtttaatctg caacctcaaa acaatcactg ataagtaatg    83580
agttacatta ttgtataatg ttctgagaat gcagctacaa ataaatcctc aagaggcctc    83640
aatgagtaca tacagcaaac aaggaaagga tgtaggcacc agctgtgatt cccatgcaca    83700
ttactgcctc gaggctgcaa gagacataga tagttagagg ataatagcgg aaattactct    83760
tgttatgata gcccaaattt agagtgagag ttagtcgaaa catgattcaa gatttaccta    83820
aagaagttca atacttcaag aatctggtcc gcgaggtctt caacagaagg tgacggatca    83880
ttggaacaaa ctggagcagc tccaaactgc aaaaactctt gtggaaacga tggaacccaa    83940
cacaacgtga gcaaacagca agggagatac aaagaaaata atgaattgtt tcaagacaat    84000
caattctgca aacctcatgt cctggaggac taatatggta gatgcagaaa ttatggagca    84060
gtaaggacac tgcttcaggg catagaaaca atccttggaa acaagacata tctagcagcc    84120
ataaaaacat acaagaatct aaaatcagat taccaaatga tgttaaaatg aaaacaaatc    84180
atgtaccaaa tgtatattcg ccactcttac agtttagtgc tacatctgga taagtgatca    84240
atgctggttt ctcttgatct ccatatacta caactgaaac tgaaccatgg caagttttga    84300
catgatgctc ctgcaagaga taagaaaata agcaagaaac gaatcagtct acatccaaat    84360
taagagaaaa atataaacaa taccacatgc ttcattctca tatcctcacc attagtgttc    84420
atccaaaatc aactcaacat ttttaatttg tgttctttaa atcggataca gctaagaaaa    84480
ggaacattcc aactttgttc cagacaacaa aaaatattaa ggacctcaag agattctccc    84540
atgtgcaatg actcagaaaa atcagtacga agagataact tatggctaaa aaaagtcaga    84600
cattatatat caatcatgga gccaataaaa gataccattt tcaagggaat ctcttggacc    84660
ttttaggcaa gaagaacaaa gaatcaaact aaaagaaaca cccaacttgt aaatttcaga    84720
tgacaaagtg aaacaacttt tcggtatcaa tgaagtagta ttaatctccc aactagtaag    84780
taaattaagc atacaaacta aaatcaagaa cacaatagac aaaattgatt tcaatcacga    84840
aactgaagct agattttaga aatcagggag ctaattagat gctatttcgg gaaagtaata    84900
acccagaagg aagaaaacga aatgtgactg ttcttagtgc ctaagagtga agacaaaagg    84960
agaaaaggaa gaaaatttgg tagctcaaag cgtaaacaaa ccttgccacc attgcagatc    85020
tcttcaatgt cgagtgagac ggcgttgttt aaacccacca tgacccgaga accccccaaa    85080
gactgcgcct tcttgctctt tctatcttg aaactgaaat tgaaagagat agcaacaata    85140
ataaagtctt aagctttatt gtgggtactg ccttagattg tacgcttcaa cggctctttt    85200
gggtttcact ttgtcttctt cttcgatgga atggaccact actacttatc tctctctctc    85260
tctctgtctc gatgtctgag tcttataagc aaagccgcgt tgcgtttaat tgtccagcgg    85320
ttaatcaaat cattcccacc gacgccgatg agtcttcttc aatttgattt gcaccgatct    85380
ttaaacggcg ccgtttctgt aatcattttc tcattttatt catactataa ttcatttat    85440 tttatctcta ctaatttggt agctgaagtt ttgattggtc acttgcggat cttcgtagtt    85500
tttataagtt acagtataac ttctataaat taatacttaa taaattaata attttttaaa    85560
attaatattt gggaccaaac caatataaaa attaacacaa atcgataaat aataagataa    85620 taatttttt gaaagttcta tgtaaatata tggttccatc aatatcatta attaataatt    85680
acataaatgt atcaattata tatatatttt atatgtaaga aatttctttg aaatatattt    85740
ctaatatttt tttccataaa tttgtatta ttttatttta aatttagtt ttaatattat    85800 actgtatcaa aaacatttga tgttgttttc taaatatgat atgatttta cttattattg    85860
```

```
attttagaac aatattttct ataatgaaaa aaaattttata gaaattttttt aaaagttatt   85920
aaattaggaa aatctctcta taaaataatg aatattaatt tatcgataaa ttaaaacctc   85980
tctaaattaa taaattttgc agtcccaata ttattaattt atagagattt tacggtatat   86040
tatatcgttt tgtcaatttt atggctaaga agaaacaaat tgtattgttt ccaagtaaat   86100
tttatgttag attaataact tttaccattt ttatgctttt tgacgatttt tatattatat   86160
cattaatagt taatcaagaa aattttgata tcatactaaa aaaaaataga acatactgtt   86220
ttttattagg atcaatcaat cacattcttt ctttcataca attctcttga acttgaaatc   86280
tttaacgatt taatagtttc tcaatatatt ttttcaaaca aaacaaaaat ctcataaaaa   86340
aactcagtcc aacgaggatg atgaatcatg atccaaactg agtttcttta tgagattcat   86400
catcttctag aacccacatt ttaatactca taagaaactc agtccgacga ggtgatatta   86460
ttttgggact cagttttctt tttttgagtt tctgaaaaca aaaatgtcat aagaaagtca   86520
atccagcatt ataaatattg ttctaagatc agagaggaat agatgagaac caagatccaa   86580
actagttcta ttacaaagag ctaggtgtca acttaaaaag tcctaattaa aagaattgca   86640
ttagcttcac atcctctaca tgatccagaa aggtgtaaac attactctct ttaaatgctt   86700
ccattccttg catttcaacc ttttttgattg tgtttctttc gatattgtag tagaaaacgt   86760
agaaacgcat acctttatc gaccagaaga caaattcctt tgtctgagtc attccaacac   86820
aacgtaaatc tgtggttttc attatatcat gcattgcagg caatatgtat gtatgctcag   86880
accattcttg ccttttggca tcttcaagaa cccacaattt aatacttctt attactccat   86940
taaaacggga ataaactgtt gacggcagat acaaacttag tttcccattg tagtttatga   87000
gagatccatg atgcagtgct ccgataataa atctaaactc ctcagacctg acgtcaaagc   87060
aaactatcac aatatcattg ttgttgaccc cagcataata atatataaga ccatcaatgc   87120
atatccctcc atcgaaagaa cgatgtggta tgcaacattg gatcgttctc catgacatgt   87180
ttccacttcc taaggtcaaa atatgatgca tatgataatt gacgactaca ggagacgact   87240
tcttatgatc atcatcagga ttttgaagct gaggtgacga taaaaataaa taatcgctac   87300
cttttctgta ggcgaacaat agcttcgggc gagccaaaga tctagtcaag aacaactcgg   87360
tgaaatatgg acggctaagt gtggaggccc attgcttcga tacgcaacga catctcgcta   87420
tagaattcac cgacaaccctc aagaatatct cgataatgag atcaattggg atctgcaagg   87480
agttttagt tccatcctct aagcgcagag acgttttcat ggccgaaata aataaaccct   87540
aagagagaga gactccttgt agaagaagaa accaatgcgg taaaacaaag gcaagtaaaa   87600
gccaaaaaaa agttaatcac aatggtaaaa acatggactg agagaaagcc cgtatagccc   87660
aaagtttcca agcttgtata aggcccaacc aaataaccta acgagtttaa agttcaaacg   87720
tgatgaaacg ttaccgtttt agcgtttctc atgtttcttc catataaata gttttagttt   87780
tgtagaaaac cctaatcgac gacggccatt atgataaatg acggcggagc taaaccggag   87840
acgctgctta gggttgcaga aatcggtgga agaggaagga gtttggtggc ggcacagtct   87900
cttcgtgctg gacaagttat cctcagagag tctcctctcc ttctctactc tgcttttcca   87960
tttctctcct cctctgtttc tccttactgc gaccattgtt tccgtttgtt agcttcatcg   88020
gcgcatcaga aatgtcaatc ttgctctctc gtctcctttt gtagcccctaa ttgcttcgcc   88080
tctcatactc cttggctctg cgaatctctt cgccggcttc accaatcatc ctcctctgca   88140
ttctccgatc aaccttctga tcgtcaagtc caagctcgtt tcctcctctc tgcttacaat   88200
```

```
ctcgccgctg cttctccttc tgatttccag attttgctct ctctccaagg tagtggcagc    88260
agcaatggag atccttcttg ttctgcgggt gattctgcag ctgctgggtt tcttcattct    88320
cttttatctt ccgtgtgtcc atctcttccg gtgtctatct cgccggatct cacggcggct    88380
ttactgtcaa aggataaagt taacgccttt ggtctgatga aaccgtgctc tgtttcgaat    88440
gagaaaagat ctgtgcgagc ttatgggatt tatccaaaga cttcgttttt caatcatgat    88500
tgtcttccta atgcttgtag attcgattat gttgactctg cttctgatgg taatactgat    88560
atcatcatta ggatgattca tgatgttcct gaaggtagag aagtttgttt aagctacttc    88620
cctgtgaaca tgaactattc gagtagacaa aagagattgc ttgaggatta cggttttaag    88680
tgtgactgtg atcggtgcaa agtggaattt agttggtctg aaggtgagga agatgagaat    88740
gagattatgg aagagatgga ggatcaagat gaacaagaag agatggaaga ttcagtaggt    88800
gagaatgaag aagaagtttg tggaaatggt gtggatgatg aatctaattt tcctcatgct    88860 tactttttg tgagatatat gtgtgagaag gagaattgtt ttggcactct agctccgctt    88920
cccccgaaga ctcatgatgc ttcgagagtt cttgaatgta atgtttgtgg aagcgttaag    88980
gaggatgaag ttggcgtaaa tcaatgagga aggttagctt aaagaattga tcagccgaaa    89040
atctcaagct tgtttgatgc agccagaccc aaacaacaag agacttgtct tggaccacat    89100
cgttaatcaa tgttgtttgt tgtttgatgt ttactttttt tttttttactc agttttgaaa    89160 attcgataag tattctagct ctagaattcc atatctaggt ttttgtttt ctcctagata    89220 gtctgaagaa tcaattgtaa tggtctgtgg aattacacgg aaacagtttt gttgtaataa    89280
tggagcatca gttttctttg gttgaatgaa aaatcataat tttttgact ttttaagttg    89340 aaaactgcag aattacatgg cttgatgatg tttgcattgt taatctctat tactcttcag    89400
tgtgctcagt gcctgaaacc atagcttcct tgatagggat caatgtattg gtaaaccaaa    89460
ttgtgtaata gttttttccat aaaatagatt caatagaacc agtgtaacaa aaaattatta    89520
gggggctctg ttttaaggtc gcaacatgac ggtgacacaa acattttta gtgattaact    89580 tgttctcatt ctgttccaag ttcaacaaca caaactgagt tttttggctt ctctatcaga    89640
gaactaatgt gattctacaa cacaacctgc tctgactgac ttactctgct atgttctgtt    89700
ttgctctgct ctgttctcac ttccacgtct ctgttttgt cattgacatt tcgacttgta    89760
ggaacttaaa catttagtgg attgactggc aagattgatc caacctttc caatcttaca    89820 tccataaata agttgatatt ttttctggtt tttatttggc aaacactaat gcaccctagg    89880
gttcaatgag atatatatat attacactaa cacaagtaca caaccaaatg ttattgtagg    89940
gacttgtaat aatttaacag acccagattc ctcacaaatt ctaccaaatt tgcgagtcat    90000
tcaagctagc aaacattatc atctataaat aaatagtttt ctaaacatag taagaacat    90060 aattttaaaa ttcgaaacgt tcctgataaa tttcttctc acattctaaa gaacaaagt    90120 atagatcagc tccgtcctcg ggaagcgtac gaacgaaagg gagcttgcat cgagagttgc    90180
acacgcagca aagtggtcta caaatagagt ggttggatac aaatgttcct atccatgtta    90240
acgctcctgg catggaatat gcgtaagtat ctataacgca ggaaatatgc aatgtgatcc    90300
cacactcatt gcatgtatag aaccattttt ctgggttcac agttgtttcg catgcttcac    90360
accaatattt gccagccacg cccatttcgc cataagataa aagagagga tgatcgtcgt    90420 acctatgcct cattaccttt tgcggtaaaa tagcacactt gaagcacaaa ccaaattcac    90480
aatcatcgca actcaatttc ccgtctccat cacactcact acaacgtttg gagtgatctg    90540
tagagtagtg taaaggatgt tgatggcttt tgtgctcaaa tggttctgta actgtagcgc    90600
```

```
accgtacatc tatccttaat tccttagatt cataggagaa accggtgaac agttgacggc    90660
aaatactaca cctatgtaac aagtaggtgc cataatttgg ggatagttcg agtggctggt    90720
tgtggcacac atgacgtttc tttaaaggaa gcttggcaca ttttcgtgg attatgaaat     90780 cgcatctctt tctcgcgcaa gcgtagaacg gttctgaaca aatctggaag acacatgcgg    90840
tacaaactac actttctggt agattccagc cacggtaaat tcgtaagtta tgcttatggc    90900
cgtaatggtc tatcgtgttg tcatcaatca ccttgaatgg cgcagtttcc tcttcttcgg    90960
gtgtcccttc cagttcgatc atgtcccata catcccttct ggttgcgcat cttgaatgaa    91020
caaaataatc aaaacatttg gagcaagaat aagccccgta gaacccatcc acatttttac    91080
gacaaactct gcatttcccg tctccatgtc cgaggcgagg ggtgtaagag atgcggtggt    91140
cgtggcggtt gatgtttatg acgcgaggta gatcgataca ttcccgatga atcatgaaat    91200
tgcactgaag acagaaataa gggctacggt cacctagcgt cccacaagca ttgcaagtga    91260
agtcaatgcg tcttggaaca aggtgaagtt gatgttcatg ggtcctcggg cttttaacaa    91320
gaaccggtgg tgggttttc atacatgatc tgcatatgct aaaattacaa acaccacagt     91380
ggtgaagctg gcgatggatt ccatcaaact cctcgcggca aagaagacat ttcttgtcgg    91440
cgtaaccagg gacttcatat ctaagtgact tgagtgggtg ttgggggtga gaagtgtggt    91500
atgcttctgg actattatga tcgatacaat ccagactgat gaaaaactcg cattgatgac    91560
atgtgtagaa atgtttccag ctattatgtt gatggccaca ccctttgcaa tctctgagtg    91620
tttcgtgcgc ttcatgggag agttggagtg gatgctcgtg taggtaggag ttttcagcaa    91680
gaacaagtag ggctggtctc ctcgcgcaaa tcaaatccaa ctggaaatca catttgttac    91740
agcgataacc gacactgaaa aattctccac agaaactaca attagaaact ctggtatgta    91800
ggaggatcag cttgagagga tggactggat ggtaagggtg gtcgatttct ggtaacggct    91860
tggcgcactc ttcatggaac acaacatcac atcccggctc attgcatcgg tgtcctccgt    91920
aaatgtaact gcaaccggga tgtttggaaa tgaagcttgt attatcttca tcggtcgagt    91980
agcatccttt acacttggtg aactcgaagc gtgtaaaagg tatcaacgga tgctcatgaa    92040
atggtaacaa ttttttcaagg cgggatgctt cttcgtccat gccttcatta aacaaagcta    92100
gaaagttttc catggtgatg ttttcttact tccaccaaaa cacaaagctc ttctcttctg    92160
cactagtttc agacttggtt tcttgttttt ctctctttct tttctttcag atttttttt     92220 caagtggttt atcattttca gactttgcaa atagttaata tgaattcgca ccacagaaat    92280
gattcttttc attactgaga ttgagaccac atgtgttggc ttcatccttg cattatttaa    92340
ttaactcaga ccacatatgt tgactctgca actattgtgt ccggccaaaa cataaataat    92400
tgaatgaata caaaaaaggt ttttcttgc attaaatgga atagaagttt atggatagaa     92460
tagtttagaa tttaaatgga tggaactgta cattttgtgg aaaaaacagt ttgaagtctg    92520
aaccacacaa ctccttggcc aagtagcttt ggaggtagac tttgctgcat tcaagtctct    92580
gaaaccaaag ttttattatt gtattgcatc cactaacttt tatgtaattt cagaccaaaa    92640
gatttgtatt tttgtcttta agaccaggat tgggccaatc tttgttttt aattttata     92700 cagccaaaag taagttctat t                                              92721
```

<210> SEQ ID NO 38
<211> LENGTH: 3
<212> TYPE: PRT
<213> ORGANISM: Artificial Sequence
<220> FEATURE:

```
<223> OTHER INFORMATION: GHS motif of cytokinin oxidase

<400> SEQUENCE: 38

Gly His Ser
 1

<210> SEQ ID NO 39
<211> LENGTH: 7
<212> TYPE: PRT
<213> ORGANISM: Artificial Sequence
<220> FEATURE:
<223> OTHER INFORMATION: FAD binding domain motif of cytokinin oxidase

<400> SEQUENCE: 39

Val Gly Gly Thr Leu Ser Asn
 1               5

<210> SEQ ID NO 40
<211> LENGTH: 9
<212> TYPE: PRT
<213> ORGANISM: Artificial Sequence
<220> FEATURE:
<223> OTHER INFORMATION: FAD binding domain motif of cytokinin oxidase

<400> SEQUENCE: 40

Val Leu Gly Gly Leu Gly Gln Phe Cys
 1               5

<210> SEQ ID NO 41
<211> LENGTH: 6
<212> TYPE: PRT
<213> ORGANISM: Artificial Sequence
<220> FEATURE:
<223> OTHER INFORMATION: FAD binding domain motif of cytokinin oxidase

<400> SEQUENCE: 41

Ile Thr Arg Ala Arg Ile
 1               5

<210> SEQ ID NO 42
<211> LENGTH: 534
<212> TYPE: PRT
<213> ORGANISM: Zea mays

<400> SEQUENCE: 42

Met Ala Val Val Tyr Tyr Leu Leu Ala Gly Leu Ile Ala Cys Ser
 1               5                  10                  15

His Ala Leu Ala Ala Gly Thr Pro Ala Leu Gly Asp Asp Arg Gly Arg
                20                  25                  30

Pro Trp Pro Ala Ser Leu Ala Ala Leu Ala Leu Asp Gly Lys Leu Arg
            35                  40                  45

Thr Asp Ser Asn Ala Thr Ala Ala Ser Thr Asp Phe Gly Asn Ile
         50                  55                  60

Thr Ser Ala Leu Pro Ala Ala Val Leu Tyr Pro Ser Ser Thr Gly Asp
 65                  70                  75                  80

Leu Val Ala Leu Leu Ser Ala Ala Asn Ser Thr Pro Gly Trp Pro Tyr
                 85                  90                  95

Thr Ile Ala Phe Arg Gly Arg Gly His Ser Leu Met Gly Gln Ala Phe
            100                 105                 110

Ala Pro Gly Gly Val Val Val Asn Met Ala Ser Leu Gly Asp Ala Ala
        115                 120                 125

Ala Pro Pro Arg Ile Asn Val Ser Ala Asp Gly Arg Tyr Val Asp Ala
```

-continued

```
            130                 135                 140
Gly Gly Glu Gln Val Trp Ile Asp Val Leu Arg Ala Ser Leu Ala Arg
145                 150                 155                 160

Gly Val Ala Pro Arg Ser Trp Asn Asp Tyr Leu Tyr Leu Thr Val Gly
                165                 170                 175

Gly Thr Leu Ser Asn Ala Gly Ile Ser Gly Gln Ala Phe Arg His Gly
                180                 185                 190

Pro Gln Ile Ser Asn Val Leu Glu Met Asp Val Ile Thr Gly His Gly
                195                 200                 205

Glu Met Val Thr Cys Ser Lys Gln Leu Asn Ala Asp Leu Phe Asp Ala
210                 215                 220

Val Leu Gly Gly Leu Gly Gln Phe Gly Val Ile Thr Arg Ala Arg Ile
225                 230                 235                 240

Ala Val Glu Pro Ala Pro Ala Arg Ala Arg Trp Val Arg Phe Val Tyr
                245                 250                 255

Thr Asp Phe Ala Ala Phe Ser Ala Asp Gln Glu Arg Leu Thr Ala Pro
                260                 265                 270

Arg Pro Gly Gly Gly Gly Ala Ser Phe Gly Pro Met Ser Tyr Val Glu
                275                 280                 285

Gly Ser Val Phe Val Asn Gln Ser Leu Ala Thr Asp Leu Ala Asn Thr
290                 295                 300

Gly Phe Phe Thr Asp Ala Asp Val Ala Arg Ile Val Ala Leu Ala Gly
305                 310                 315                 320

Glu Arg Asn Ala Thr Thr Val Tyr Ser Ile Glu Ala Thr Leu Asn Tyr
                325                 330                 335

Asp Asn Ala Thr Ala Ala Ala Ala Val Asp Gln Glu Leu Ala Ser
                340                 345                 350

Val Leu Gly Thr Leu Ser Tyr Val Glu Gly Phe Ala Phe Gln Arg Asp
                355                 360                 365

Val Ala Tyr Ala Ala Phe Leu Asp Arg Val His Gly Glu Glu Val Ala
                370                 375                 380

Leu Asn Lys Leu Gly Leu Trp Arg Val Pro His Pro Trp Leu Asn Met
385                 390                 395                 400

Phe Val Pro Arg Ser Arg Ile Ala Asp Phe Asp Arg Gly Val Phe Lys
                405                 410                 415

Gly Ile Leu Gln Gly Thr Asp Ile Val Gly Pro Leu Ile Val Tyr Pro
                420                 425                 430

Leu Asn Lys Ser Met Trp Asp Asp Gly Met Ser Ala Ala Thr Pro Ser
                435                 440                 445

Glu Asp Val Phe Tyr Ala Val Ser Leu Leu Phe Ser Ser Val Ala Pro
450                 455                 460

Asn Asp Leu Ala Arg Leu Gln Glu Gln Asn Arg Arg Ile Leu Arg Phe
465                 470                 475                 480

Cys Asp Leu Ala Gly Ile Gln Tyr Lys Thr Tyr Leu Ala Arg His Thr
                485                 490                 495

Asp Arg Ser Asp Trp Val Arg His Phe Gly Ala Ala Lys Trp Asn Arg
                500                 505                 510

Phe Val Glu Met Lys Asn Lys Tyr Asp Pro Lys Arg Leu Leu Ser Pro
                515                 520                 525

Gly Gln Asp Ile Phe Asn
530
```

METHOD FOR MODIFYING PLANT MORPHOLOGY, BIOCHEMISTRY AND PHYSIOLOGY

This application is a divisional of U.S. application Ser. No. 10/014,101, filed Dec. 10, 2001, now U.S. Pat. No. 7,259,296, which is a continuation-in-part application of PCT/EP01/06833, having an international filing date of Jun. 18, 2001, which claims priority of U.S. Provisional application No. 60/258,415, filed Dec. 27, 2000.

FIELD OF THE INVENTION

The present invention generally relates to methods for modifying plant morphological, biochemical and physiological properties or characteristics, such as one or more developmental processes and/or environmental adaptive processes, including but not limited to the modification of initiation or stimulation or enhancement of root growth, and/or adventitious root formation, and/or lateral root formation, and/or root geotropism, and/or shoot growth, and/or apical dominance, and/or branching, and/or timing of senescence, and/or timing of flowering, and/or flower formation, and/or seed development, and/or seed yield. Methods for increasing seed size and/or weight, increasing embryo size and/or weight, and increasing cotyledon size and/or weight are also provided. The methods comprise expressing a cytokinin degradation control protein, in particular cytokinin oxidase, in the plant, operably under the control of a regulatable promoter sequence such as a cell-specific promoter, tissue-specific promoter, or organ-specific promoter sequence. Preferably, the characteristics modified by the present invention are cytokinin-mediated and/or auxin-mediated characteristics. The present invention extends to genetic constructs which are useful for performing the inventive method and to transgenic plants produced therewith having altered morphological and/or biochemical and/or physiological properties compared to their otherwise isogenic counterparts.

BACKGROUND OF THE INVENTION

Roots are an important organ of higher plants. Their main functions are anchoring of the plant in the soil and uptake of water and nutrients (N-nutrition, minerals, etc.). Thus, root growth has a direct or indirect influence on growth and yield of aerial organs, particularly under conditions of nutrient limitation. Roots are also relevant for the production of secondary plant products, such as defense compounds and plant hormones.

Roots are also storage organs in a number of important staple crops. Sugar beet is the most important plant for sugar production in Europe (260 Mill t/year; 38% of world production). Manioc (cassava), yams and sweet potato (batate) are important starch producers (app. 150 Mill t/year each). Their content in starch can be twice as high as that of potato. Roots are also the relevant organ for consumption in a number of vegetables (e.g. carrots, radish), herbs (e.g. ginger, kukuma) and medicinal plants (e.g. ginseng). In addition, some of the secondary plant products found in roots are of economic importance for the chemical and pharmaceutical industry. An example is yams, which contain basic molecules for the synthesis of steroid hormones. Another example is shikonin, which is produced by the roots of *Lithospermum erythrorhizon* in hairy root cultures. Shikonin is used for its anti-inflammatory, anti-tumor and wound-healing properties.

Moreover, improved root growth of crop plants will also enhance competitiveness with weedy plants and will improve growth in arid areas, by increasing water accessibility and uptake.

Improved root growth is also relevant for ecological purposes, such as bioremediation and prevention/arrest of soil erosion.

Root architecture is an area that has remained largely unexplored through classical breeding, because of difficulties with assessing this trait in the field. Thus, biotechnology could have significant impact on the improvement of this trait, because it does not rely on large-scale screenings in the field. Rather, biotechnological approaches require a basic understanding of the molecular components that determine a specific characteristic of the plant. Today, this knowledge is only fragmentary, and as a consequence, biotechnology was so far unable to realize a break-through in this area.

A well-established regulator of root growth is auxin. Application of indole-3-acetic acid (IAA) to growing plants stimulates lateral root development and lateral root elongation (Torrey, Am J Bot 37: 257-264, 1950; Blakely et al., Bot Gaz 143: 341-352, 1982; Muday and Haworth, Plant Physiol Biochem 32: 193-203, 1994). Roots exposed to a range of concentrations of IAA initiated increasing numbers of lateral roots (Kerk et al., Plant Physiol, 122: 925-932, 2000). Furthermore, when roots that had produced laterals in response to a particular concentration of exogenous auxin were subsequently exposed to a higher concentration of IAA, numerous supernumerary lateral roots spaced between existing ones were formed (Kerk et al., Plant Physiol, 122: 925-932, 2000). Conversely, growth of roots on agar containing auxin-transport inhibitors, including NPA, decreases the number of lateral roots (Muday and Haworth, Plant Physiol Biochem 32: 193-203, 1994).

*Arabidopsis* mutants containing increased levels of endogenous IAA have been isolated (Boerjan et al., Plant Cell 7: 1405-141, 1995; Celenza et al., Gene Dev 9: 2131-2142, 1995; King et al., Plant Cell 7: 2023-2037, 1995; Lehman et al., Cell 85: 183-194, 1996). They are now known to be alleles of a single locus located on chromosome 2. These mutant seedlings have excess adventitious and lateral roots, which is in accordance with the above-described effects of external auxin application.

The stimulatory effect of auxins on adventitious and lateral root formation suggests that overproduction of auxins in transgenic plants is a valid strategy for increasing root growth. Yet, it is also questionable whether this would yield a commercial product with improved characteristics. Apart from its stimulatory effect on adventitious and lateral root formation, auxin overproduction triggers other effects, such as reduction in leaf number, abnormal leaf morphology (narrow, curled leaves), aborted inflorescences, increased apical dominance, adventitious root formation on the stem, most of which are undesirable from an agronomic perspective (Klee et al., Genes Devel 1: 86-96, 1987; Kares et al., Plant Mol Biol 15: 225-236, 1990). Therefore, the major problem with approaches that rely on increased auxin synthesis is a problem of containment, namely to confine the effects of auxin to the root. This problem of containment is not likely overcome by using tissue-specific promoters: auxins are transported in the plant and their action is consequently not confined to the site of synthesis. Another issue is whether auxins will always enhance the total root biomass. For agar-grown plants, it has been noticed that increasing concentrations progressively stimulated lateral root formation but concurrently inhibited the outgrowth of these roots (Kerk et al., Plant Physiol, 122: 925-932, 2000).

Seeds are the reproduction unit of higher plants. Plant seeds contain reserve compounds to ensure nutrition of the embryo after germination. These storage organs contribute significantly to human nutrition as well as cattle feeding. Seeds consist of three major parts, namely the embryo, the endosperm and the seed coat. Reserve compounds are deposited in the storage organ which is either the endosperm (resulting form double fertilization; e.g. in all cereals), the so-called perisperm (derived from the nucellus tissue) or the cotyledons (e.g. bean varieties). Storage compounds are lipids (oil seed rape), proteins (e.g. in the aleuron of cereals) or carbohydrates (starch, oligosaccharides like raffinose).

Starch is the storage compound in the seeds of cereals. The most important species are maize (yearly production ca. 570 mio t; according to FAO 1995), rice (540 mio t p.a.) and wheat (530 mio t p.a.). Protein rich seeds are different kinds of beans (*Phaseolus* spec., *Vicia faba*, *Vigna* spec.; ca. 20 mio t p.a.), pea (*Pisum sativum;* 14 mio t p.a.) and soybean (*Glycine max;* 136 mio t p.a.). Soybean seeds are also an important source of lipids. Lipid rich seeds are as well those of different *Brassica* species (app. 30 mio t p.a.), cotton, oriental sesame, flax, poppy, castor bean, sunflower, peanut, coconut, oilpalm and some other plants of less economic importance.

After fertilization, the developing seed becomes a sink organ that attracts nutritional compounds from source organs of the plant and uses them to produce the reserve compounds in the storage organ. Increases in seed size and weight, are desirable for many different crop species. In addition to increased starch, protein and lipid reserves and hence enhanced nutrition upon ingestion, increases in seed size and/or weight and cotyledon size and/or weight are correlated with faster growth upon germination (early vigor) and enhanced stress tolerance. Cytokinins are an important factor in determining sink strength. The common concept predicts that cytokinins are a positive regulator of sink strength.

Numerous reports ascribe a stimulatory or inhibitory function to cytokinins in different developmental processes such as root growth and branching, control of apical dominance in the shoot, chloroplast development, and leaf senescence (Mok M. C. (1994) in *Cytokines: Chemistry, Activity and Function*, eds., Mok, D. W. S. & Mok, M. C. (CRC Boca Raton, Fla.), pp. 155-166). Conclusions about the biological functions of cytokinins have mainly been derived from studies on the consequences of exogenous cytokinin application or endogenously enhanced cytokinin levels (Klee, H. J. & Lanehon, M. B. (1995) in *Plant Hormones: Physiology, Biochemisry and Molecular Biology*, ed. Davies, P. J. (Kluwer, Dordrdrocht, the Netherlands), pp. 340-353, Smulling, T., Rupp, H. M. Frank, M& Schafer, S. (1999) in *Advances in Regulation of Plant Growth and Development*, eds. Surnad, M. Pac P. & Beck, E. (Peres, Prague), pp. 85-96). Up to now, it has not been possible to address the reverse question: what are the consequences for plant growth and development if the endogenous cytokinin concentration is decreased? Plants with a reduced cytokinin content are expected to yield more precise information about processes cytokinins limit and, therefore, might regulate. Unlike other plant hormones such as abscisic acid, gibberellins, and ethylene, no cytokinin biosynthetic mutants have been isolated (Hooykens, P. J. J., Hall, M. A. & Libbeuga, K. R., eds. (1999) *Biochemistry and Molecular Biology of plant Hormones* (Elsevier, Amsterdam).

The catabolic enzyme cytokinin oxidase (CKX) plays a principal role in controlling cytokinin levels in plant tissues. CKX activity has been found in a great number of higher plants and in different plant tissues. The enzyme is a FAD-containing oxidoreductase that catalyzes the degradation of cytokinins bearing unsaturated isoprenoid side chains. The free bases iP and Z, and their respective ribosides are the preferred substrates. The reaction products of iP catabolism are adenine and the unsaturated aldehyde 3-methyl-2-butonal (Armstrong, D. J. (1994) in *Cytokinins: Chemistry, Activity and Functions*, eds. Mok. D. W. S & Mok, M. C. (CRC Boca Raton, Fla.), pp. 139-154). Recently, a cytokinin oxidase gene from *Zea mays* has been isolated (Morris, R. O., Bilyeu, K. D., Laskey, J. G. & Cherich, N. N. (1999) *Biochem. Biophys. Res. Commun.* 255, 328-333, Houba-Heria, N., Pethe, C. d'Alayer, J & Lelouc, M. (1999) *Plant J.* 17:615-626). The manipulation of CKX gene expression could partially overcome the lack of cytokinin biosynthetic mutants and can be used as a powerful tool to study the relevance of iP—and Z-type cytokinins during the whole life cycle of higher plants.

The present invention overcomes problems related to containment of auxin effects, maintenance of root outgrowth, and promotion of increased seed, embryo, and cotyledon size and/or weight through reduction of endogenous cytokinin concentration.

SUMMARY OF THE INVENTION

The present invention provides plant cytokinin oxidase proteins, nucleic acid sequences encoding such proteins, and vectors, host cells and transgenic plant cells, plants, and plant parts comprising the proteins, nucleic acid sequences, and vectors. For example, the present invention relates to a genetic construct comprising a gene encoding a protein with cytokinin oxidase activity from *Arabidopsis thaliana*. This gene may be expressed under control of a regulated promoter. This promoter may be regulated by endogenous tissue-specific or environment-specific factors or, alternatively, it may be induced by application of specific chemicals.

The present invention also relates to a method to modify root architecture and biomass by expression of a cytokinin oxidase gene or expression of a nucleic acid encoding a protein that reduces the level of active cytokinins in plants or plant parts. Preferably, expression is under control of a promoter that is specific to the root or to certain tissues or cell types of the root.

Additionally, the present invention relates to methods of increasing seed size and/or weight, embryo size and/or weight, and cotyledon size and/or weight. The methods involve expression of a cytokinin oxidase gene or expression of a nucleic acid encoding a protein that reduces the level of active cytokinins in plants or plant parts. Preferably, expression is under control of a promoter directs expression preferentially in the seed, embryo, or cotyledon.

Shown are the structures of different cytokinin oxidase genes isolated from maize (ZmCKX1, accession number AF044603, Biochem. Biophys. Res. Com. 255:328-333, 1999) and *Arabidopsis* (AtCKX1 to AtCKX4). Exons are denominated with 'E' and represented by shaded boxes. Introns are represented by white boxes. Further indicated are the gene sizes (in kb, on top of each structure), the gene accession numbers (under the names) and a size bar representing 0.5 kb.

Figure 2:
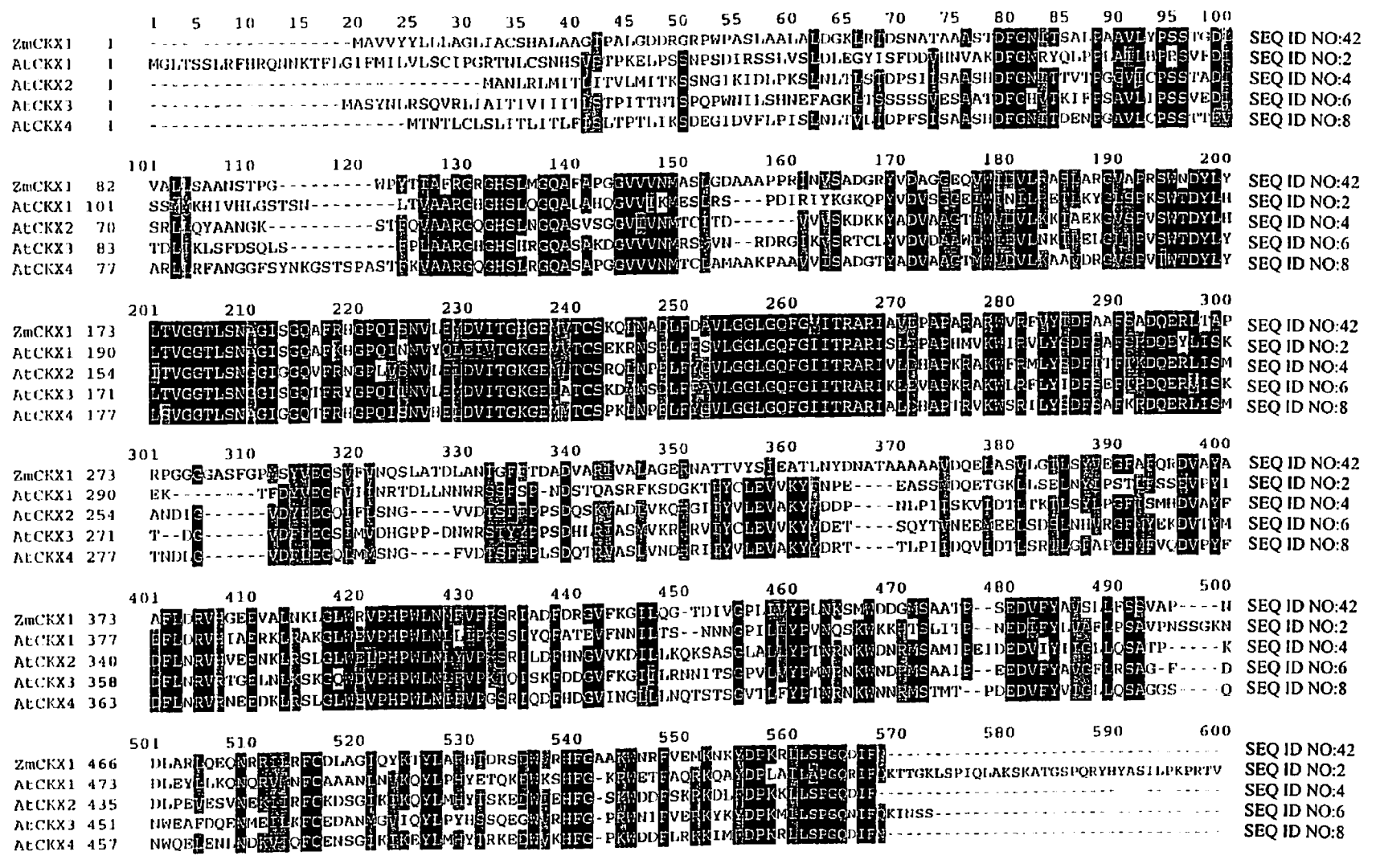

FIG. 2. Alignment of plant cytokinin oxidase amino acid sequences.

The amino acid sequences from cytokinin oxidases from maize (ZmCKX1) and *Arabidopsis* (AtCKX1 to AtCKX4)

are aligned. Identical amino acid residues are marked by a black box, similar amino acid residues are in a grey box. Amino acid similarity groups: (M,I,L,V), (F,W,Y), (G,A), (S,T), (R,K,H), (E,D), (N,Q). ZmCKX1 is SEQ ID NO:42; AtCKX1 is SEQ ID NO:2; AtCKX2 is SEQ ID NO:4; AtCKX3 is SEQ ID NO:6; and AtCKX4 is SEQ ID NO:8.

Figure 3:
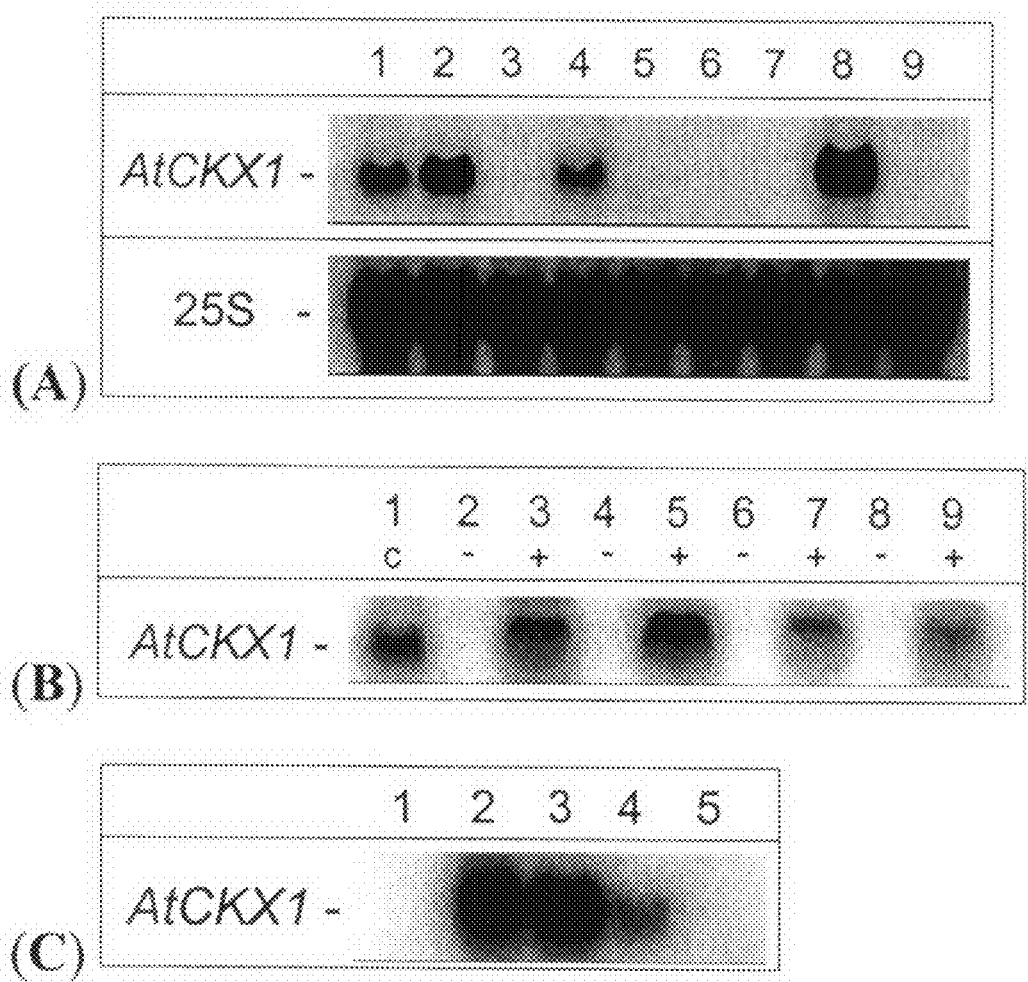

FIG. 3. Northern blot analysis of AtCKX1-expressing tobacco and *Arabidopsis* plants.

(A) Northern blot analysis of constitutively expressing tobacco plants (lanes 1-8) compared to wild type SNN tobacco (lane 9)

(B) Comparison of tetracycline-induced gene expression in leaves after 12 h of induction with a constitutively expressing clone. Lanes 2-9, leaves of four different AtCKX1-W38TetR clones (+,−, with or without tetracycline treatment), lane 1, constitutively expressing 35S::AtCKX1 clone.

(C) Northern blot analysis of *Arabidopsis* plants constitutively expressing AtCKX1 gene. Lanes 24, three different constitutively expressing 35S::AtCKX1 clones compared to wild type *Arabidopsis* plant (lane 1).

Figure 4:
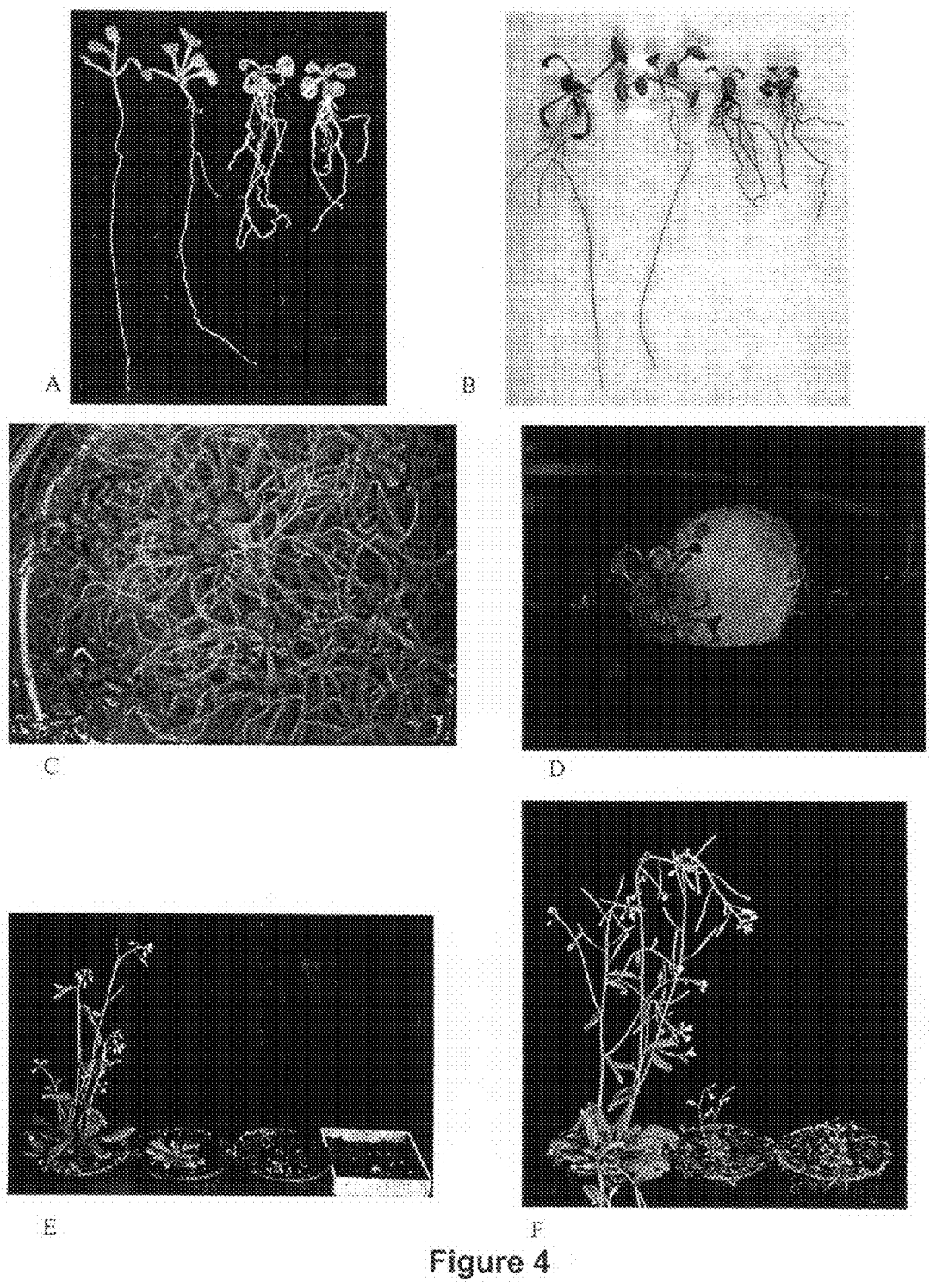

FIG. 4: Growth characteristics of 35S::AtCKX1 transgenic *Arabidopsis* plants.

(A) Two wild type seedlings (left) compared to two 35S::AtCKX1 expressing seedlings (right). Note the increased formation of adventitious roots and increased root branching in the transgenic seedlings. Pictures were taken 14 days after germination. Plants were grown in vitro on MS medium in petri dishes in a vertical position.

(B) Like A, but roots stained with toluidine blue.

(C) Top view of a petri dish with 35S::AtCKX1 transgenic seedlings three weeks after germination.

(D) A 35S::AtCKX1 transgenic plants grown in liquid culture. Roots of wild type seedlings grow poorly under these conditions (not shown).

(E) Transformants (T0) that express the 35S::AtCKX1 gene (three plants on the right), a wild type plant is shown on the left.

(F) Phenotype of T1 plants grown in soil. Wild type plant (left) compared to two 35S::AtCKX1 transgenic plants.

Figure 5:
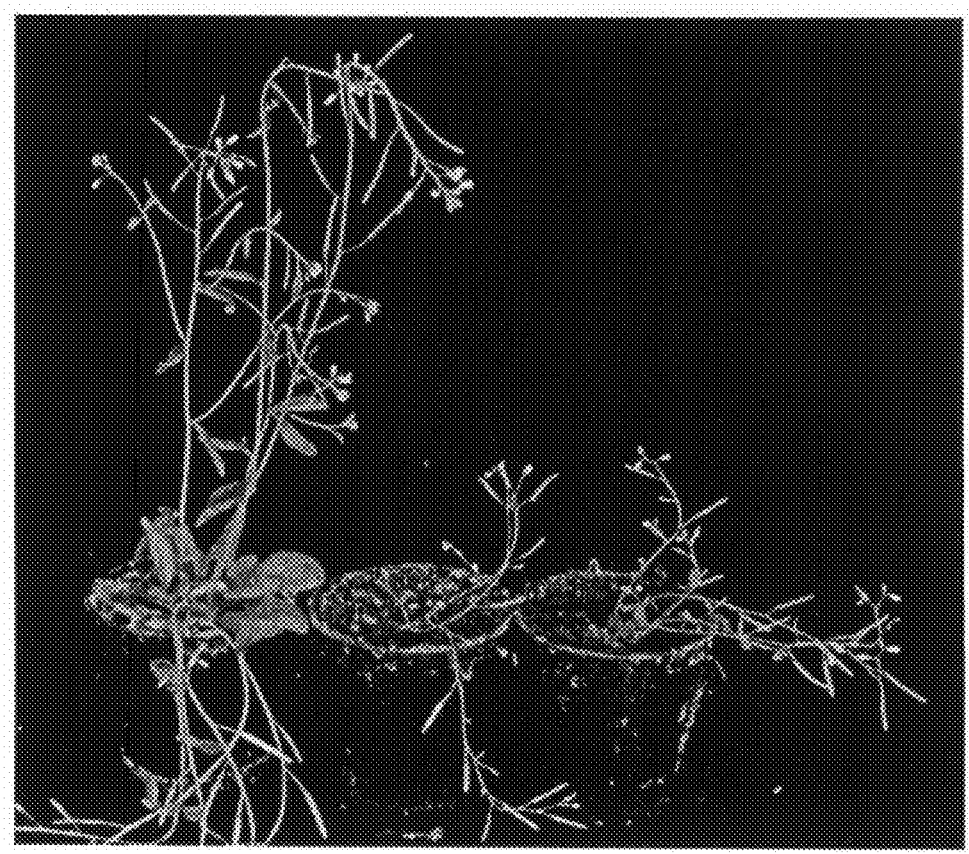

FIG. 5: Phenotype of AtCKX2 overexpressing *Arabidopsis* plants.

T1 generation of 35S::AtCKX2 expressing *Arabidopsis* plants (two plants on the right) compared to wild type (plant on the left).

Figure 6:
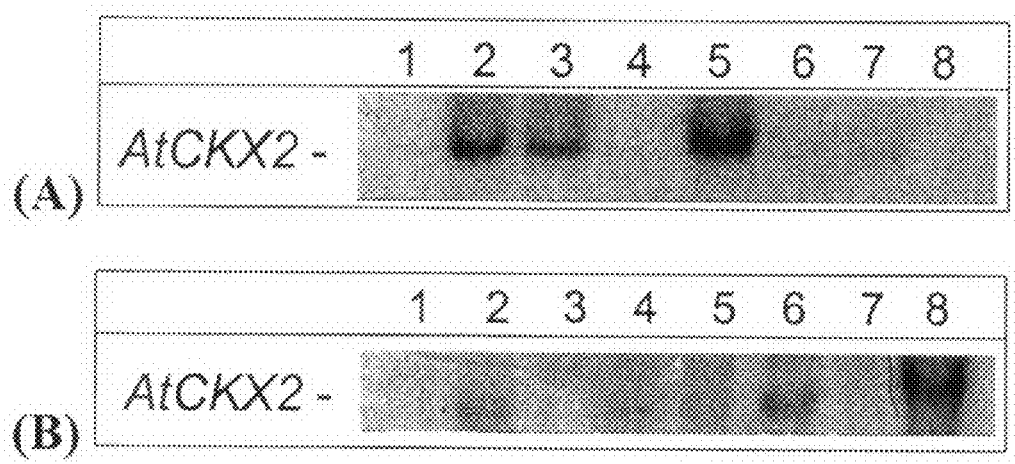

FIG. 6. Northern blot analysis of AtCKX2-expressing tobacco and *Arabidopsis* plants.

(A) Northern blot analysis of constitutively expressing tobacco plants (lanes 1-7) compared to wild type SNN tobacco (lane 8)

(B) Northern blot analysis of *Arabidopsis* plants constitutively expressing AtCKX2 gene. Lanes 2-8, seven different constitutively expressing 35S::AtCKX2 clones compared to wild type *Arabidopsis* plant (lane 1).

Figure 7:
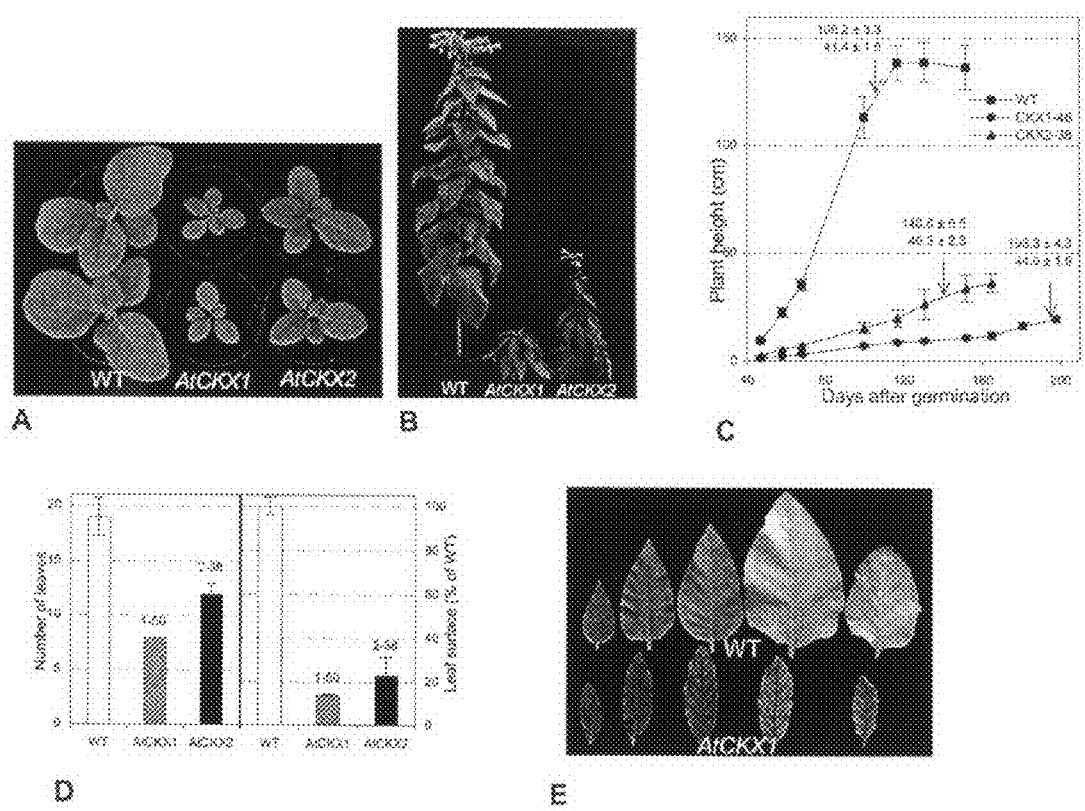

FIG. 7. Shoot phenotype of AtCKX1 and AtCKX2 expressing tobacco plants.

(A) Top view of six week old plants.

(B) Tobacco plants at the flowering stage.

(C) Kinetics of stem elongation. Arrows mark the onset of flowering. Age of plants (days after germination) and leaf number at that stage are indicated above the arrows. Bars indicate SD; n=12.

(D) Number of leaves (n=12) formed between day 68 and day 100 after germination and final surface area of these leaves (100% of wild type is 3646±144 cm$^2$; n=3).

(E) Comparison of leaf size and senescence. Leaves were from nodes number 4, 9, 12, 16 and 20 from the top (from left to right).

Figure 8:
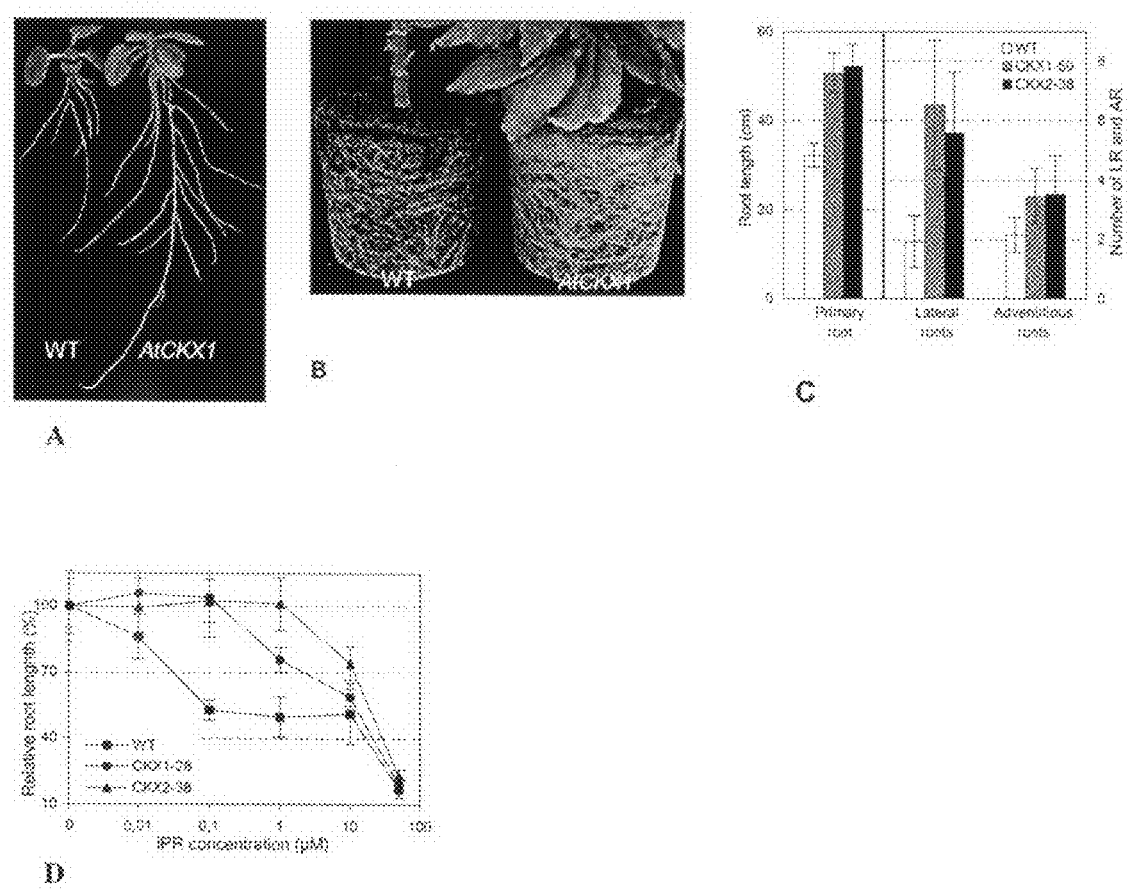

FIG. 8. Root phenotype of AtCKX expressing transgenic tobacco plants.

(A) Seedlings 17 days after germination.

(B) Root system of soil grown plants at the flowering stage.

(C) Root length, number of lateral roots (LR) and adventitious roots (AR) on day 10 after germination.

(D) Dose-response curve of root growth inhibition by exogenous cytokinin. Bars indicate ±SD; n=30.

Figure 9:

FIG. 9: Growth of axillary shoot meristems in 35S::AtCKX1 expressing tobacco plants.

Figure 10:
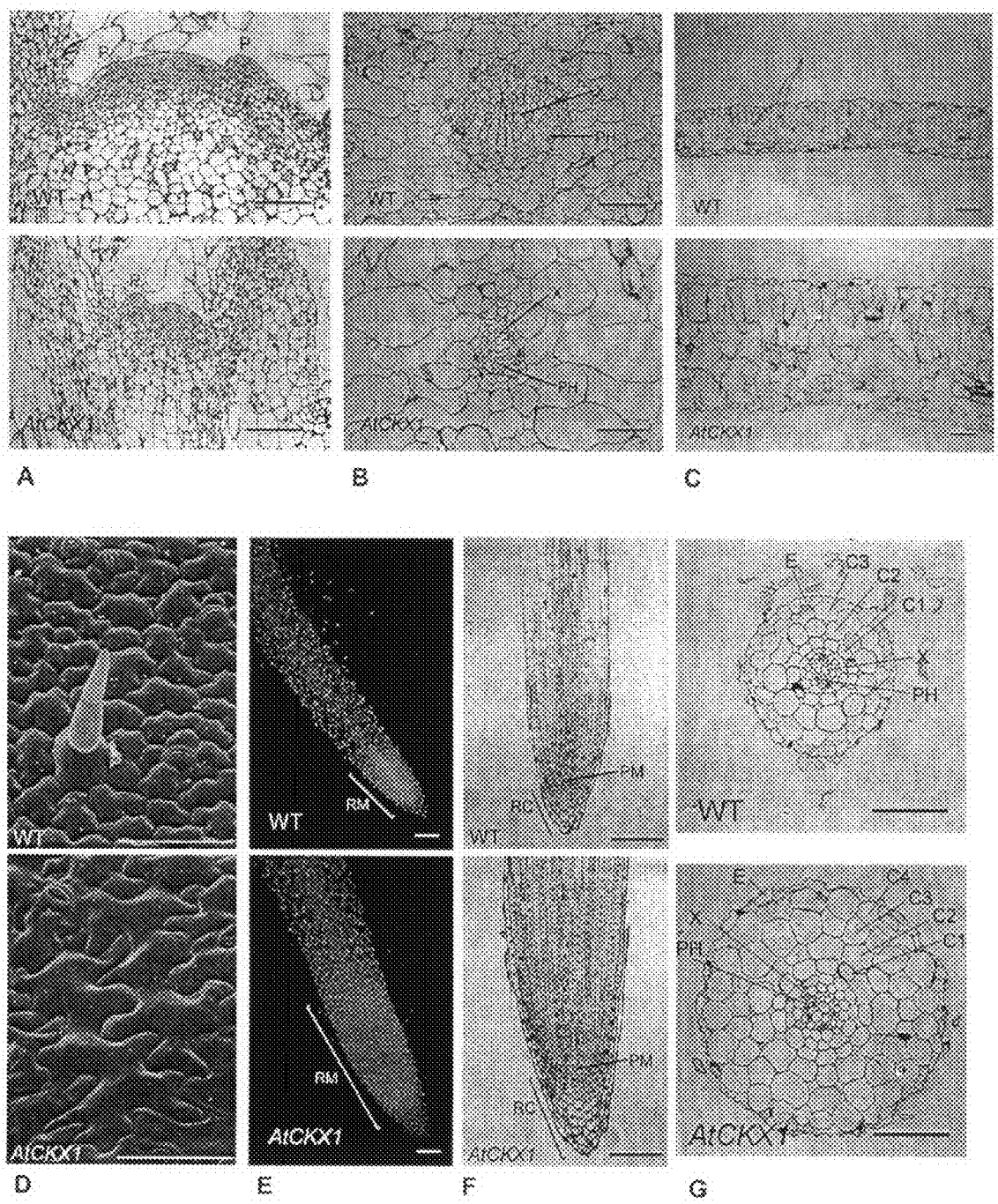

FIG. 10: Histology of shoot meristems, leaves and root meristems of AtCKX1 overexpressing tobacco plants versus wild type (WT) tobacco.

(A) Longitudinal median section through the vegetative shoot apical meristem. P, leaf primordia.

(B) Vascular tissue in second order veins of leaves. X, xylem, PH, a phloem bundle.

(C) Cross sections of fully developed leaves.

(D) Scanning electron microscopy of the upper leaf epidermis.

(E) Root apices stained with DAPI. RM, root meristem.

(F) Longitudinal median sections of root meristems ten days after germination. RC, root cap; PM, promeristem.

(G) Transverse root sections 10 mm from the apex. E, epidermis, C1-C4, cortical cell layer, X, xylem, PH, phloem. Bars are 100 μm.

Figure 11:
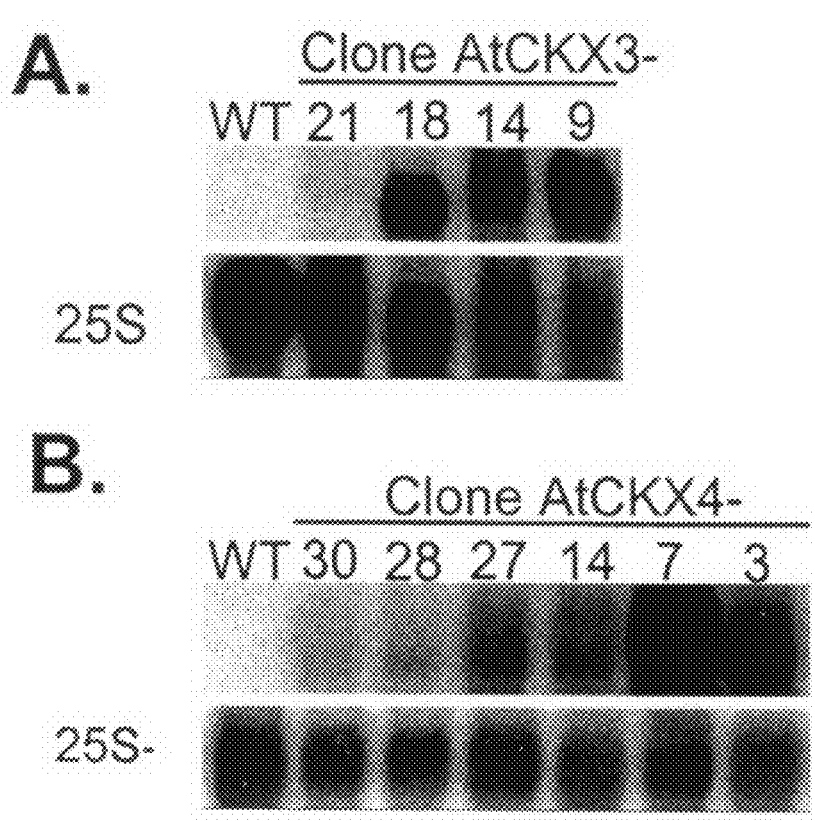

FIG. 11: Northern blot analysis of AtCKX3 and AtCKX4-expressing tobacco plants.

(A) Northern blot analysis of constitutively expressing AtCKX3 tobacco plants. Lane designations indicate individual transgenic plant numbers, WT is wild type SNN tobacco. The blot on top was probed with a AtCKX3 specific probe, the lower blot with a probe specific for the 25S rRNA and serves as a control for RNA loading.

(B) Northern blot analysis of constitutively expressing AtCKX4 tobacco plants. Lane designations indicate individual transgenic plant numbers, WT is wild type SNN tobacco. The blot on top was probed with an AtCKX4 specific probe, the lower blot with a probe specific for the 25S rRNA and serves as a control for RNA loading.

Figure 12:
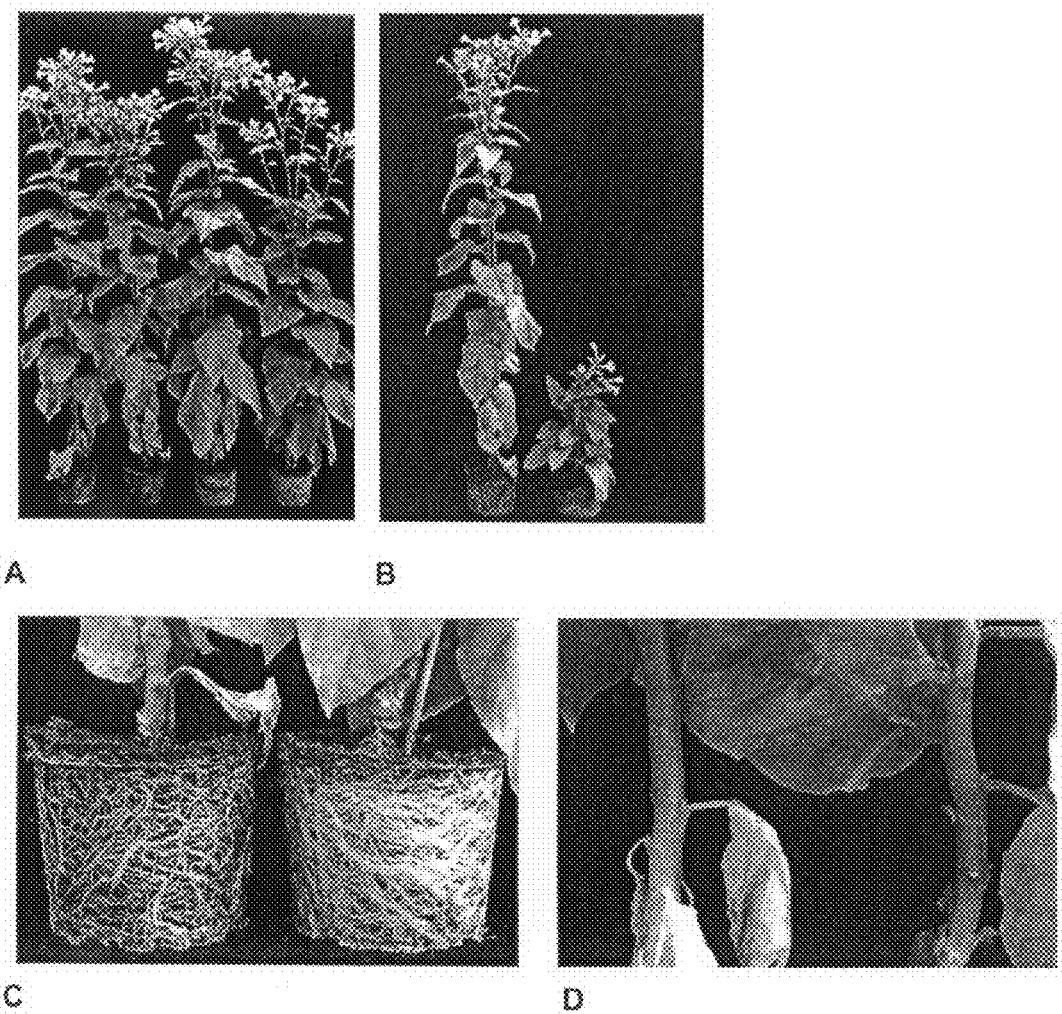
Figure 13A:
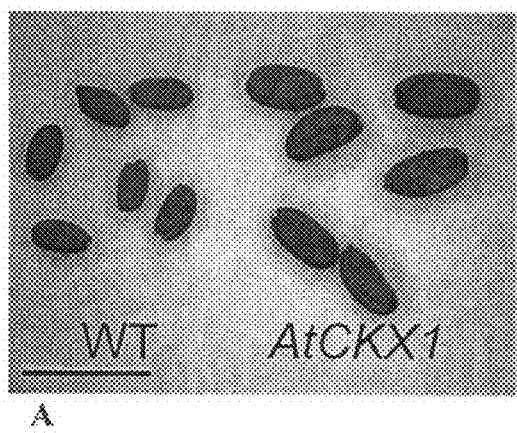
Figure 13B:
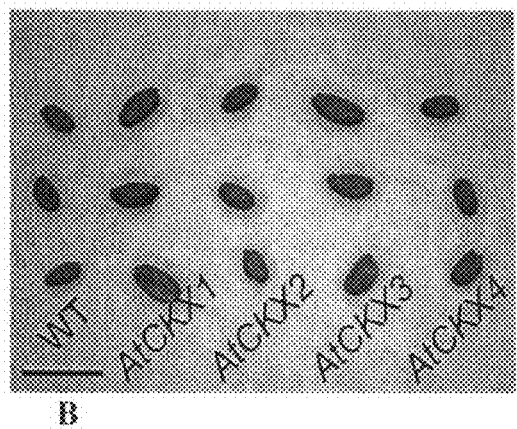
Figure 13C:
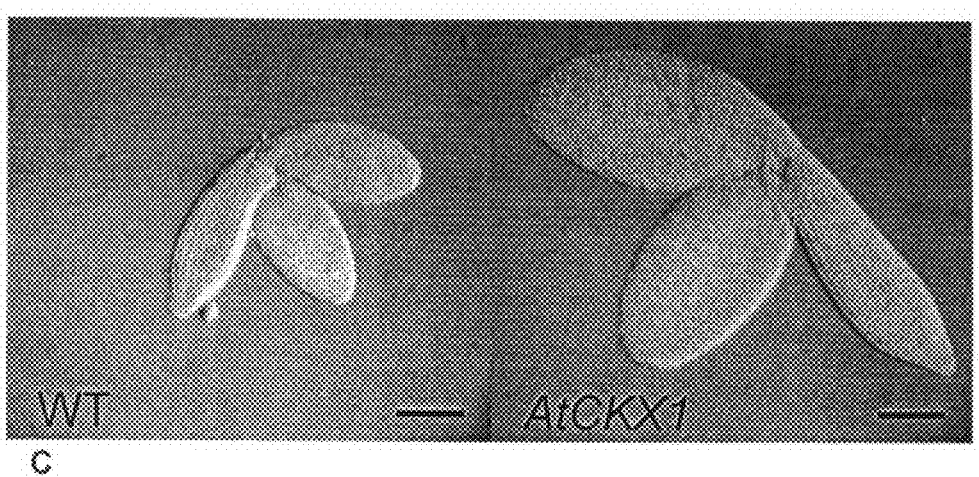
Figure 13D:
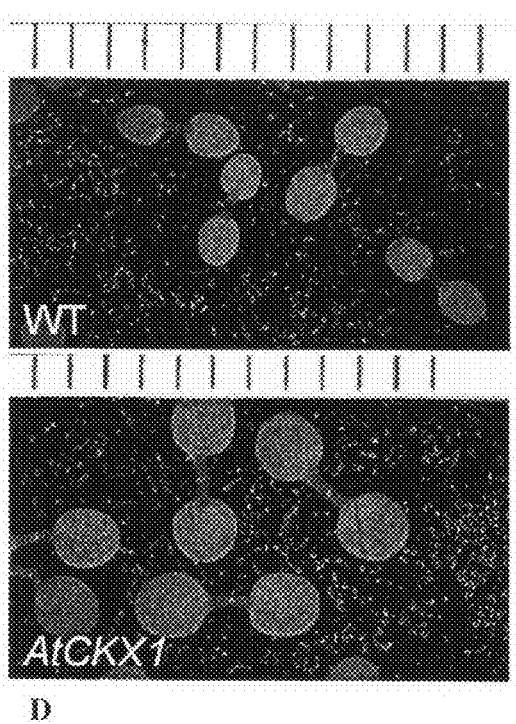
Figure 13E:
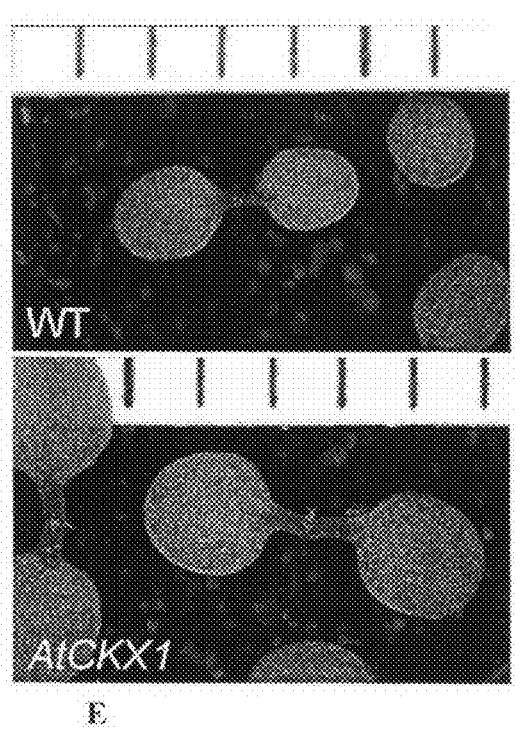

FIG. 12: Reciprocal grafts of AtCKX2 transgenic tobacco plants and wild type plants.

(A) Two plants on the left: Control (WT scion grafted on a WT rootstock).

Two plants on the right: WT scion grafted on a AtCKX2-38 transgenic rootstock.

(B) Left: Control (WT scion grafted on a WT rootstock). Right: Scion of AtCKX2-38 plant grafted on WT rootstock.

(C) Magnification of root area.

Left: Control (WT scion grafted on a WT rootstock).

Right: WT scion grafted on an AtCKX2-38 transgenic rootstock.

(D) Formation of adventitious roots.

Left: Control (WT scion grafted on an WT rootstock).

Right: WT scion grafted on an AtCKX2-38 transgenic rootstock.

FIG. 13: Phenotype of *Arabidopsis* seeds, embryos and seedlings.

(A) Seeds of an AtCKX1 transgenic line and wild type seeds. Bar size 1 mm.

(B) Seeds of AtCKX1, AtCKX2, AtCKX3 and AtCKX4 transgenic lines and wild type seeds. Bar size 1 mm.

(C) Mature embryos of AtCKX1 transgenic *Arabidopsis* and of a wild type plant. Bar size 200 μm. Embryos were obtained from mature seeds that had been imbibed for 12 hours in 20% EtOH, squeezed out from the seed coat, cleared with chloralhydrate and photographed using Nomarski optics.

(D) Wild type (top) and AtCKX1 expressing *Arabidopsis* seedlings 4 days after germination.

(E) Close-up of D.

Figure 14:
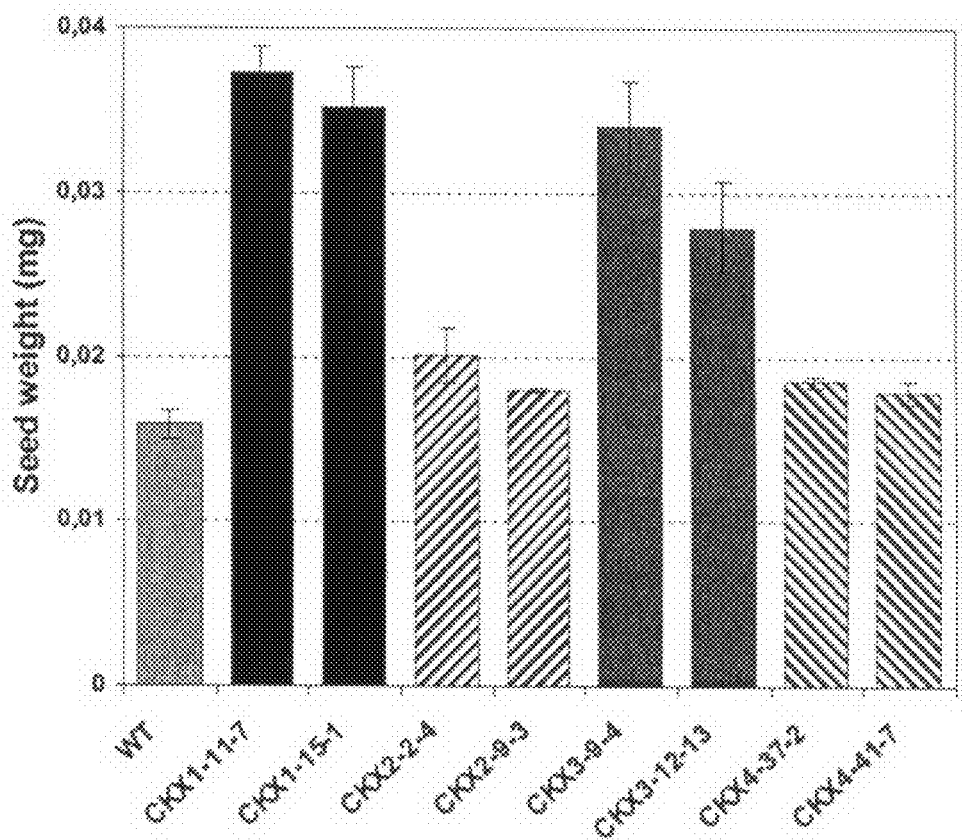

FIG. 14: Seed weight of wild type and two independent clones for each of the four investigated AtCKX genes. Average weight obtained by analysing five different batches of 200 seeds for each clone.

DETAILED DESCRIPTION OF THE INVENTION

To by-pass above-mentioned problems associated with increasing auxin biosynthesis, it was decided to follow an alternative approach. We reasoned that down-regulation of biological antagonists of auxins could evoke similar or even superior effects on root growth as compared to increasing auxin levels. Hormone actions and interactions are extremely complex, but we hypothesized that cytokinins could function as auxin antagonists with respect to root growth. Hormone studies on plant tissue cultures have shown that the ratio of auxin versus cytokinin is more important for organogenesis than the absolute levels of each of these hormones, which indeed indicates that these hormones function as antagonists—at least in certain biological processes. Furthermore, lateral root formation is inhibited by exogenous application of cytokinins. Interestingly, also root elongation is negatively affected by cytokinin treatment, which suggests that cytokinins control both root branching and root outgrowth.

Together, current literature data indicate that increasing cytokinin levels negatively affects root growth, but the mechanisms underlying this process are not understood. The sites of cytokinin synthesis in the plant are root tips and young tissues of the shoot. Endogenous concentrations of cytokinins are in the nM range. However, as their quantification is difficult, rather large tissue amounts need to be extracted and actual local concentrations are not known. Also the subcellular compartmentation of cytokinins is not known. It is generally thought that the free base and ribosides are localized in the cytoplasm and nucleus, while glucosides are localized in the vacuole. There exist also different cytokinins with slightly different chemical structure. As a consequence, it is not known whether the effects of exogenous cytokinins should be ascribed to a raise in total cytokinin concentration or rather to the competing out of other forms of plant-borne cytokinins (which differ either in structure, cellular or subcellular location) for receptors, translocators, transporters, and modifying enzymes.

In order to test the hypothesis that cytokinin levels in the root indeed exceed the level optimal for root growth, novel genes encoding cytokinin oxidases (which are cytokinin metabolizing enzymes) were cloned from *Arabidopsis thaliana* (designated AtCKX) and were subsequently expressed under a strong constitutive promoter in transgenic tobacco and *Arabidopsis*. Transformants showing AtCKX mRNA expression and increased cytokinin oxidase activity also manifested enhanced formation and growth of roots. Negative effects on shoot growth were also observed. The latter is in accordance with the constitutive expression of the cytokinin oxidase gene in these plants, illustrating the importance of confined expression of the cytokinin oxidase gene for general plant growth properties. Containment of cytokinin oxidase activity can be achieved by using cell-, tissue- or organ-specific promoters, since cytokinin degradation is a process limited to the tissues or cells that express the CKX protein, this in contrast to approaches relying on hormone synthesis, as explained above.

The observed negative effects of cytokinin oxidase expression on shoot growth demonstrate that cytokinin oxidases are interesting targets for the design of or screening for growth-promoting chemicals. Such chemicals should inhibit cytokinin oxidase activity, should preferably not be transported to the root and should be rapidly degraded in soil, so that application of these chemicals will not inhibit root growth. Cytokinins also delay leaf senescence, which means that positive effects will include both growth and maintenance of photosynthetic tissues. In addition, the observation that cytokinins delay senescence, enhance greening (chlorophyll content) of leaves and reduce shoot apical dominance shows that strategies based on suppressing CKX activity (such as antisense, ribozyme, and cosuppression technology) in the aerial parts of the plant could result in delayed senescence, enhanced leaf greening and increased branching.

Similarly, the observed positive effects of cytokinin oxidase expression on root growth demonstrate that cytokinin oxidases are interesting targets for the design of or screening for herbicides. Such herbicides should inhibit cytokinin oxidase activity, should preferably not be transported to the shoot, and should be soluble and relatively stable in a solvent that can be administered to the root through the soil.

These effects of cytokinin oxidase overexpression on plant development and architecture were hitherto unknown and, as a consequence, the presented invention and its embodiments could not be envisaged.

The observed negative effects on shoot growth demonstrate that manipulation of cytokinin oxidases can also be used for obtaining dwarfing phenotypes. Dwarfing phenotypes are particularly useful in commercial crops such as cereals and fruit trees for example.

In accordance with the present invention, it has also been surprisingly discovered that transgenic plants overexpressing a cytokinin oxidase gene develop seeds (including embryos) and cotyledons of increased size and/or weight. These results are surprising as a reduced cytokinin content would have been expected to be associated with a reduced organ growth.

Preferable embodiments of the invention relate to the positive effect of cytokinin oxidase expression on plant growth and architecture, and in particular on root growth and architecture, seed size and weight, embryo size and weight, and cotyledon size and weight. The cytokinin oxidase gene family contains at least six members in *Arabidopsis* (see examples below) and the present inventors have shown that there are quantitative differences in the effects achieved with some of these genes in transgenic plants. It is anticipated that functional homologs of the described *Arabidopsis* cytokinin oxidases can be isolated from other organisms, given the evidence for the presence of cytokinin oxidase activity in many green plants (Hare and van Staden, Physiol Plant 91:128-136, 1994; Jones and Schreiber, Plant Growth Reg 23:123-134, 1997), as well as in other organisms (Armstrong, in Cytokinins: Chemistry, Activity and Function. Eds Mok and Mok, CRC Press, pp 139-154, 1994). Therefore, the sequence of the cytokinin oxidase, functional in the invention, need not to be identical to those described herein. This invention is particularly useful for cereal crops and monocot crops in general and cytokinin oxidase genes from for example wheat or maize may be used as well (Morris et al., 1999; Rinaldi and Comandini, 1999). It is envisaged that other genes with cytokinin oxidase activity or with any other cytokinin metabolizing activity (see Za ímalová et al., Biochemistry, and Molecular Biology of Plant Hormones, Hooykaas, Hall and Libbenga (Eds.), Elsevier Science, pp 141-160, 1997) can also be used for the purpose of this invention. Similarly, genes encoding proteins that would increase endogenous cytokinin metabolizing activity can also be used for the purpose of this invention. In principle, similar phenotypes could also be obtained by interfering with genes that function downstream of cytokinin such as receptors or proteins involved in signal transduction pathways of cytokinin.

For the purpose of this invention, it should be understood that the term 'root growth' encompasses all aspects of growth of the different parts that make up the root system at different stages of its development, both in monocotyledonous and dicotyledonous plants. It is to be understood that enhanced growth of the root can result from enhanced growth of one or more of its parts including the primary root, lateral roots, adventitious roots, etc. all of which fall within the scope of this invention.

For purposes of this invention, it should also be understood that increases in seed weight or seed size can include increases in the size of one or more of the embryo, the endosperm, aleurone, and seed coat. Moreover, increases in embryo size and/or weight can include increases in different organs associated therewith such as e.g., cotyledons, hypocotyl, and roots.

According to a first embodiment, the present invention relates to a method for stimulating root growth and/or enhancing the formation of lateral and/or adventitious roots and/or altering root geotropism comprising expression of a plant cytokinin oxidase or comprising expression of another protein that reduces the level of active cytokinins in plants or plant parts.

In another embodiment, the present invention relates to a method for increasing plant seed size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed including different tissues or cell types of the seed.

In another embodiment, the present invention relates to a method for increasing plant embryo size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed. Even more preferably, the increased level or activity of a cytokinin oxidase or expression of another protein that reduces the level of active cytokinins in a plant or plant part is localized in the embryo.

In yet another embodiment, the present invention relates to a method for increasing plant cotyledon size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the cotyledon.

In the context of the present invention it should be understood that the term "expression" and/or 'overexpression' are used interchangeably and both relate to an "enhanced and/or ectopic expression" of a plant cytokinin oxidase or any other protein that reduces the level of active cytokinins in plants. It should be clear that herewith an enhanced expression of the plant cytokinin oxidase as well as "de novo" expression of plant cytokinin oxidases or of said other proteins is meant. Alternatively, said other protein enhances the cytokinin metabolizing activity of a plant cytokinin oxidase.

It further should be understood that in the context of the present invention the expression "lateral and/or adventitious roots" can mean "lateral and adventitious roots" but also "lateral or adventitious roots". The enhancement can exist in the formation of lateral roots or in the formation of adventitious roots as well as in the formation of both types of non-primary roots, but not necessarily.

In addition, as used herein, "increasing seed size and/or weight," can mean increasing seed size and weight, but also size or weight. Thus, the enhancement can exist in an increase in the size of the seed or the weight of the seed or both. Similar interpretations should be applied to "increasing embryo size and/or weight" and "increasing cotyledon size and/or weight."

The terms "plant" and "plant part" are used interchangeably with the terms "plants" and "plant parts."

According to a further embodiment, the present invention relates to a method for stimulating root growth and/or enhancing the formation of lateral or adventitious roots and/or altering root geotropism and/or increasing yield and/or enhancing early vigor and/or modifying root/shoot ratio and/or improving resistance to lodging and/or increasing drought tolerance and/or promoting in vitro propagation of explants, comprising expression of a plant cytokinin oxidase or comprising expression of another protein that reduces the level of active cytokinins in plants or plant parts.

According to a preferred embodiment, the present invention relates to a method for stimulating root growth resulting in an increase of root mass by overexpression of a cytokinin oxidase, preferably a cytokinin oxidase according to the invention, or another protein that reduces the level of active cytokinins in plants or plant parts, preferably in roots.

Higher root biomass production due to overexpression of growth promoting sequences has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

According to a more specific embodiment, the present invention relates to methods for stimulating root growth or for enhancing the formation of lateral and/or adventitious roots or for altering root geotropism or for increasing seed size and/or weight, or for increasing embryo size and/or weight, or for increasing cotyledon size and/or weight. The methods comprise expression of a nucleic acid encoding a plant cytokinin oxidase selected from the group consisting of:

(a) nucleic acids comprising a DNA sequence as given in any of SEQ ID NOs: 27, 1, 3, 5, 7, 9, 11, 25, 26, 28 to 31, 33 or 34, or the complement thereof, (b) nucleic acids comprising the RNA sequences corresponding to any of SEQ ID NOs: 27, 1, 3, 5, 7, 9, 11, 25, 26, 28 to 31, 33 or 34, or the complement thereof, (c) nucleic acids specifically hybridizing to any of SEQ ID NOs: 27, 1, 3, 5, 7, 9, 11, 25, 26, 28 to 31, 33 or 34, or to the complement thereof, (d) nucleic acids encoding a protein comprising the amino acid sequence as given in any of SEQ ID NOs: 2, 4, 6, 8, 10, 12, 32 or 35, or the complement thereof, (e) nucleic acids as defined in any of (a) to (d) characterized in that said nucleic acid is DNA, genomic DNA, cDNA, synthetic DNA or RNA wherein T is replaced by U, (f) nucleic acids which are degenerated to a nucleic acid as given in any of SEQ ID NOs: 27, 1, 3, 5, 7, 9, 11, 25, 26, 28 to 31, 33 or 34, or which are degenerated to a nucleic acid as defined in any of (a) to (e) as a result of the genetic code, (g) nucleic acids which are diverging from a nucleic acid encoding a protein as given in any of SEQ ID NOs: 2, 4, 6, 8, 10, 12 or 35 or which are diverging from a nucleic acid as defined in any of (a) to (e), due to the differences in codon usage between the organisms, (h) nucleic acids encoding a protein as given in SEQ ID NOs: 2, 4, 6, 8, 10, 12 or 35 or nucleic acids as defined in (a) to (e) which are diverging due to the differences between alleles, (i) nucleic acids encoding a protein as given in any of SEQ ID NOs: 2, 4, 6, 8, 10, 12 or 35, (j) functional fragments of nucleic acids as defined in any of (a) to (i) having the biological activity of a cytokinin oxidase, and (k) nucleic acids encoding a plant cytokinin oxidase, or comprise expression, preferably in roots, or in seeds (including parts of seeds such as embryo, endosperm, seed coat or aleurone) or in cotyledons, of a nucleic acid encoding a protein that reduces the level of active cytokinins in plants or plant parts.

In the present invention, nucleic acids encoding novel *Arabidopsis thaliana* cytokinin oxidases have been isolated and for the first time, the present inventors have surprisingly shown that the expression of cytokinin oxidases in transgenic plants or in transgenic plant parts resulted in the above-mentioned root and seed-related features. In order that root-related features be effected, the expression of the cytokinin oxidase(s) should take place in roots, preferably under the control of a root-specific promoter. In order that seed-related features be effected (including the embryo), expression of the cytokinin oxidase(s) should take place in seeds, preferably under the control of a seed-specific promoter. One example of such a root-specific promoter is provided in SEQ ID NO: 36. Examples of seed-specific promoters include but are not limited to those listed in Table 4.

In order that cotyledon-related features be effected, the expression of the cytokinin oxidase(s) should take place in the cotyledons, preferably under the control of a promoter which preferentially expresses in cotyledon.

It should be clear that, although the invention is supported in the examples section by several new AtCKX genes and proteins, the inventive concept also relates to the use of other cytokinin oxidases isolated from and expressed in other plants, preferably in the roots and/or seeds and/or cotyledons of said other plants to obtain similar effects in plants as described in the examples section.

Therefore, the present invention more generally relates to the use of a nucleic acid encoding a plant cytokinin oxidase or encoding a protein that reduces the level of active cytokinins in plants or plant parts for stimulating root growth or for enhancing the formation of lateral or adventitious roots or for altering root geotropism. The present invention also relates to the use of a nucleic acid encoding a plant cytokinin oxidase or encoding a protein that reduces the level of active cytokinins in plants or plant parts for increasing seed size and/or weight, or for increasing embryo size and/or weight, or for increasing plant cotyledon size and/or weight. Preferred cytokinin oxidases to be used are encoded by the nucleic acids encoding the cytokinin oxidases as defined above and are encoded by the novel nucleic acids of the invention as defined hereunder.

The invention relates to an isolated nucleic acid encoding a novel plant protein having cytokinin oxidase activity selected from the group consisting of:

(a) a nucleic acid comprising a DNA sequence as given in any of SEQ ID NOs: 29, 3, 5, 9, 26, 27, 31, 33 or 34, or the complement thereof, (b) a nucleic acid comprising the RNA sequences corresponding to any of SEQ ID NOs: 29, 3, 5, 9, 26, 27, 31, 33 or 34, or the complement thereof, (c) a nucleic acid specifically hybridizing to a nucleic acid as given in any of SEQ ID NOs: 29, 3, 5, 9, 26, 27, 31, 33 or 34, or the complement thereof, (d) a nucleic acid encoding a protein with an amino acid sequence comprising the polypeptide as given in SEQ ID NO: 32 and which is at least 70% similar, preferably at least 75%, 80% or 85%, more preferably at least 90% or 95%, most preferably at least 99% similar to the amino acid sequence as given in SEQ ID NO: 4, (e) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 6, (f) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 10 or 35, (g) a nucleic acid encoding a protein comprising the amino acid sequence as given in any of SEQ ID NOs: 4, 6, 10, 32 or 35, (h) a nucleic acid which is degenerated to a nucleic acid as given in any of SEQ ID NOs: 29, 3, 5, 9, 26, 27, 33 or 34 or which is degenerated to a nucleic acid as defined in any of (a) to (g) as a result of the genetic code, (i) a nucleic acid which is diverging from a nucleic acid encoding a protein as given in any of SEQ ID NOs: 4, 6, 10 or 35 or which is diverging from a nucleic acid as defined in any of (a) to (g) due to the differences in codon usage between the organisms, (j) a nucleic acid encoding a protein as given in SEQ ID NOs: 4, 6, 10 or 35, or a nucleic acid as defined in (a) to (g) which is diverging due to the differences between alleles, (k) a nucleic acid encoding an immunologically active fragment of a cytokinin oxidase encoded by a nucleic acid as given in any of SEQ ID NOs: 29, 3, 5, 9, 26, 27, 31, 33 or 34, or an immunologically active fragment of a nucleic acid as defined in any of (a) to (j), (l) a nucleic acid encoding a functional fragment of a cytokinin oxidase encoded by a nucleic acid as given in any of SEQ ID NOs: 29, 3, 5, 9, 26, 27, 31, 33 or 34, or a functional fragment of a nucleic acid as defined in any of (a) to (j), wherein said fragment has the biological activity of a cytokinin oxidase, and (m) a nucleic acid encoding a protein as defined in SEQ ID NOs: 4, 6, 10 or 35, provided that said nucleic acid is not the nucleic acid as deposited under any of the following Genbank accession numbers: AC005917, AB024035, and AC023754

The invention also relates to an isolated nucleic acid of the invention which is DNA, cDNA, genomic DNA or synthetic DNA, or RNA wherein T is replaced by U.

The invention also relates to a nucleic acid molecule of at least 15 nucleotides in length hybridizing specifically with or specifically amplifying a nucleic acid of the invention.

Different cytokinin forms may have differing roles to play in the various developmental processes. Thus, differential effects of CKX1, CKX2, CKX 3 and CKX4 may relate to distinct effects on the pools of different cytokinins. For example, CKX1 and CKX3 mostly promote root elongation and branching, while CKX2 and CKX4 primarily stimulate the formation of adventitious roots. In addition, CKX1 and CKX3 increase seed size and weight to a greater degree than CKX2 and CKX4. Without being bound to a particular mode of action, this differential effect on cytokine pools may result from some differences in substrate specificity or from differential compartmentation of cytokinin oxidases in the cell (predicted to be mitochondrial for CKX1 and CKX3, while extracellular for CKX 2, CKX4, CKX5, and CKX6).

According to another embodiment, the invention also relates to a vector comprising a nucleic acid of the invention. In a preferred embodiment, said vector is an expression vector wherein the nucleic acid is operably linked to one or more control sequences allowing the expression of said sequence in prokaryotic and/or eukaryotic host cells.

It should be understood that for expression of the cytokinin oxidase genes of the invention in monocots, a nucleic acid sequence corresponding to the cDNA sequence should be used to avoid mis-splicing of introns in monocots. Preferred cDNA sequences to be expressed in monocots have a nucleic acid sequence as represented in any of SEQ ID NOs: 25 to 30 and 34.

The invention also relates to a host cell containing any of the nucleic acid molecules or vectors of the invention. Said host cell is chosen from the group comprising bacterial, insect, fungal, plant or animal cells.

Another embodiment of the invention relates to an isolated polypeptide encodable by a nucleic acid of the invention, or a homologue or a derivative thereof, or an immunologically active or a functional fragment thereof. Preferred polypeptides of the invention comprise the amino acid sequences as represented in any of SEQ ID NOs: 2, 4, 6, 8, 10, 12, 32 and 35, or a homologue or a derivative thereof, or an immunologically active and/or functional fragment thereof. In an even more preferred embodiment, the invention relates to a polypeptide which has an amino acid sequence as given in SEQ ID: NO 2, 4, 6, 8, 10, 12 or 35, or a homologue or a derivative thereof, or an immunologically active and/or functional fragment thereof. Preferred functional fragments thereof are those fragments which are devoid of their signal peptide.

According to yet another embodiment, the invention relates to a method for producing a polypeptide of the invention comprising culturing a host cell of the invention under conditions allowing the expression of the polypeptide and recovering the produced polypeptide from the culture.

The invention also relates to an antibody specifically recognizing a polypeptide of the invention or a specific epitope thereof.

The invention further relates to a method for the production of transgenic plants, plant cells or plant tissues comprising the introduction of a nucleic acid molecule of the invention in an expressible format or a vector of the invention in said plant, plant cell or plant tissue.

The invention also relates to a method for the production of altered plants, plant cells or plant tissues comprising the introduction of a polypeptide of the invention directly into a cell, a tissue or an organ of said plant.

According to another embodiment, the invention relates to a method for effecting the expression of a polypeptide of the invention comprising the introduction of a nucleic acid molecule of the invention operably linked to one or more control sequences or a vector of the invention stably into the genome of a plant cell. The invention further relates to the method as described above further comprising regenerating a plant from said plant cell.

The invention also relates to a transgenic plant cell comprising a nucleic acid sequence of the invention which is operably linked to regulatory elements allowing transcription and/or expression of said nucleic acid in plant cells or obtainable by a method as explained above.

According to another preferred embodiment, the invention relates to a transgenic plant cell as described hereinabove wherein the nucleic acid of the invention is stably integrated into the genome of said plant cell.

The invention further relates to a transgenic plant or plant tissue comprising plant cells as herein described and also to a harvestable part of said transgenic plant, preferably selected from the group consisting of seeds, leaves, fruits, stem cultures, roots, tubers, rhizomes and bulbs. The invention also relates to the progeny derived from any of said transgenic plants or plant parts.

According to another embodiment, the invention relates to a method for stimulating root growth comprising expression of a nucleic acid of the invention or comprising expression of another protein that reduces the level of active cytokinins in plants or plant parts.

In another aspect of the invention, there is provided a method of increasing seed size and/or weight. The method comprises increasing the level or activity of a cytokinin oxidase in a plant or increasing the level or activity of a protein that reduces the level of active cytokinins in a plant or plant part, preferably seeds.

Various parts (organs) of the seed may also be increased in size and/or weight such as e.g., embryo, endosperm, seed coat, or aleurone. For example, in accordance with the present invention, there is provided a method of increasing embryo size and/or weight. The method comprises increasing the level or activity of a cytokinin oxidase in a plant or increasing the level or activity of a protein that reduces the level of active cytokinins in a plant or plant part, preferably embryos.

In still another aspect of the invention, there is provided a method of increasing cotyledon size and/or weight. The method comprises increasing the level or activity of a cytokinin oxidase in a plant or increasing the level or activity of a protein that reduces the level of active cytokinins in a plant or plant part, preferably cotyledons.

In accordance with the methods of increasing seed size and/or weight, there is a resultant increase in the speed of growth of seedlings or an increase in early vigor. Increases in yield are also obtained. Similarly, in accordance with the methods of increasing embryo size and/or weight, or cotyledon size and/or weight, there is a resultant increase in speed of growth of seedlings or an increase in early vigor. In many cases, increases in yield are also obtained. Increases in growth of seedlings or early vigor is often associated with increased stress tolerance. For example, faster development of seedlings, including the root systems of seedlings upon germination is critical for survival particularly under adverse conditions such as drought.

Any nucleotide sequence encoding a polypeptide with cytokinin oxidase activity may be used in the methods of the invention. For example, any of the various sequences provided herein encoding a polypeptide with cytokinin oxidase activity may be used in the methods of increasing seed, embryo, or cotyledon size and/or weight.

Preferably, transgenic plants are produced which express a nucleic acid as set forth in any of SEQ ID NOs: 1, 5, 25, or 27 or an ortholog of said nucleic acid. Preferably, the ortholog is derived from a related species of the transgenic plant. Even more preferably, the ortholog is specific (native or endogenous) to the species of the transgenic plant.

As described above, promoters which control expression specifically, or preferentially may be used in the methods of the invention. Thus, where increases in seed size or weight are desired, a seed-specific promoter may be used. Where increases in embryo size or weight are desired, an embryo-specific promoter may be used. Where increases in cotyledon size or weight is desired, a promoter which controls expression in cotyledons is preferred. Such promoters are well known, widely available and listed herein in e.g., Table 4.

In another embodiment, the invention relates to a method for increasing seed size or seed weight, or both, said method comprising expression of a nucleic acid of the invention or comprising expression of another protein that reduces the level of active cytokinins in plants or plant parts In yet another embodiment, the invention relates to a method for increasing embryo size or weight, or both, said method comprising expression of a nucleic acid of the invention or comprising expression of another protein that reduces the level of active cytokinins in plants or plant parts.

In still another embodiment, the invention relates to a method for increasing cotyledon size comprising expression of a nucleic acid of the invention or comprising expression of another protein that reduces the level of active cytokinins in plants or plant parts. Localized expression of a subject cytokinin oxidase gene or part thereof, or of another protein that reduces the level of active cytokinins in plants or plant parts leads to enhanced growth of cotyledons. In species having cotyledons as storage organs, such enhanced growth of cotyledons leads to enhanced yields and/or to enhanced growth performance of seedlings. Further in this regard, carbohydrates, lipids and proteins are all stored within seeds and are metabolized during germination in order to provide energy and metabolites during early growth of the plant. Seed size is often associated with early vigor, since larger seeds contain more carbohydrates, lipids and proteins and thus confer faster growth. Thus, the methods of the present invention lead to faster growth of seedlings. Such early vigor is associated with enhanced stress tolerance. For example, faster development of a plant's root system is critical for survival, particularly under adverse conditions, such as drought. Early vigor is also related to enhanced yield and shortened time to flowering.

A plant cell or tissue culture is an artificially produced culture of plants cells or plant tissues that is grown in a special medium, either liquid or solid, which provides these plant cells or tissues with all requirements necessary for growth and/or production of certain compounds. Plant cell and/or tissue cultures can be used for the rapid propagation of plants and for the production of transgenic plant to name a few examples. Root formation can be difficult for some explants or under some conditions in said cultures and expression of a cytokinin oxidase gene in said cultured plant cells or tissue(s) can be used to enhance root formation. Plant cell and/or tissue culture can also be used for the industrial production of valuable compounds. Possible production compounds are pharmaceuticals, pesticides, pigments, cosmetics, perfumes, food additives, etc. An example of such a product is shikonin, which is produced by the roots of the plant *Lithospermum erythrorhizon*. An example of a plant tissue culture is a hairy root culture, which is an artificially produced mass of hairy roots. Roots of *L. erythrorhizon* are difficult to collect in large numbers and by preparing hairy root cultures, the end product shikonin could be industrially prepared at a faster rate than would normally occur. As disclosed herein, expression of cytokinin oxidases enhances root growth and development and can therefore be used advantageously in said plant cell and tissue culture procedures. Therefore, according to another embodiment of this invention, a method is provided for stimulating root growth and development comprising expression of a nucleic acid encoding a plant cytokinin oxidase, preferably a cytokinin oxidase of the invention, in a transgenic plant cell or tissue culture comprising said transgenic plant cells.

The invention further relates to a method for enhancing the formation of lateral or adventitious roots comprising expression of a nucleic acid of the invention or comprising expression of another protein that reduces the level of active cytokinins in plants or plant parts.

The invention also relates to method for altering root geotropism comprising altering the expression of a nucleic acid of the invention or comprising expression of another protein that that reduces the level of active cytokinins in plants or plant parts.

The invention also relates to methods for enhancing early vigor and/or for modifying root/shoot ratio and/or for improving resistance to lodging and/or for increasing drought tolerance and/or for promoting in vitro propagation of explants comprising expression of a nucleic acid of the invention comprising expression of another protein that reduces the level of active cytokinins in plants or plant parts.

The invention further relates to methods for increasing the root size or the size of the root meristem comprising expression of a nucleic acid of the invention or comprising expression of another protein that reduces the level of active cytokinins in plants or plant parts, preferably in roots.

According to yet another embodiment, the invention relates to a method for increasing the size of the shoot meristem comprising downregulation of expression of a nucleic acid of the invention, preferably in shoots.

According to a preferred embodiment the invention relates to a method for delaying leaf senescence comprising downregulation of expression of any of the cytokinin oxidases of the invention in leaves, preferably in senescing leaves. Also the invention relates to a method for altering leaf senescence comprising expression of one of the cytokinin oxidases in senescing leaves.

The invention also relates to methods for increasing leaf thickness comprising expression of a nucleic acid of the invention or comprising expression of another protein that reduces the level of active cytokinins in plants or plant parts, preferably in leaves.

The invention also relates to a method for reducing the vessel size comprising expression of a nucleic acid of the invention or comprising expression of another protein that reduces the level of active cytokinins in plants or plant parts, preferably in vessels.

The invention further relates to a method for increasing the vessel size comprising downregulation of expression of a nucleic acid of the invention in plants or plant parts.

According to another embodiment, the invention relates to a method for improving standability of seedlings comprising expression of a nucleic acid of the invention or comprising expression of another protein that reduces the level of active cytokinins in seedlings.

Furthermore, the invention relates to any of the above described methods, said method leading to an increase in yield.

The invention further relates to any of the methods of the invention wherein said expression of said nucleic acid occurs under the control of a strong constitutive promoter. With respect to those aspects of the invention having effects on plant roots such as e.g., methods for stimulating root growth, enhancing the formation of lateral or adventitious roots, or for altering root geotropism, preferably, expression of a subject nucleic acid preferably occurs under the control of a promoter that is preferentially expressed in roots. In Table 5 a nonexhaustive list of root specific promoters is included. A preferred promoter to be used in the methods of the invention is the root clavata homolog promoter, having a sequence as given in SEQ ID NO: 36.

With respect to those aspect of the invention having effects on plant seeds such as e.g., methods for increasing seed size or weight, embryo size or weight, or having effects on plant cotyledons such as methods for increasing cotyledon size of weight, expression of a subject nucleic acid occurs under the control of a promoter that is preferentially expressed in seeds. A seed specific promoter may be one which is expressed in all seed organs or one which shows a preference in expression to one or more organs or tissue such as the embryo, endosperm, or aleurone. Examples of such promoters are set forth herein at Table 4.

According to yet another embodiment, the invention relates to a method for modifying cell fate and/or modifying plant development and/or modifying plant morphology and/or modifying plant biochemistry and/or modifying plant physiology and/or modifying the cell cycle progression rate comprising the modification of expression in particular cells, tissues or organs of a plant, of a nucleic acid of the invention.

The invention also relates to a method for obtaining enhanced growth, and/or increased yield and/or altered senescence of a plant cell, tissue and/or organ and/or increased frequency of formation of lateral organs in a plant, comprising the ectopic expression of a nucleic acid of the invention.

The invention also relates to a method for promoting and extending cell division activity in cells in adverse growth conditions and/or in stress, comprising the ectopic expression of a nucleic acid sequence of the invention.

According to yet another embodiment, the invention relates to a method for identifying and obtaining proteins interacting with a polypeptide of the invention comprising a screening assay wherein a polypeptide of the invention is used.

In a more preferred embodiment, the invention relates to a method for identifying and obtaining proteins interacting with a polypeptide of the invention comprising a two-hybrid screening assay wherein a polypeptide of the invention as a bait and a cDNA library as prey are used.

The invention further relates to a method for modulating the interaction between a polypeptide of the invention and interacting protein partners obtainable by a method as described above.

In a further embodiment, the invention relates to a method for identifying and obtaining compounds interacting with a polypeptide of the invention comprising the steps of:

(a) providing a two-hybrid system wherein a polypeptide of the invention and an interacting protein partner obtainable by a method as described above, (b) interacting said compound with the complex formed by the expressed polypeptides as defined in a), and, (c) performing (real-time) measurement of interaction of said compound with said polypeptide or the complex formed by the expressed polypeptides as defined in a).

The invention further relates to a method for identifying compounds or mixtures of compounds which specifically bind to a polypeptide of the invention, comprising:

(a) combining a polypeptide of the invention with said compound or mixtures of compounds under conditions suitable to allow complex formation, and, (b) detecting complex formation, wherein the presence of a complex identifies a compound or mixture which specifically binds said polypeptide.

The invention also relates to a method as described above wherein said compound or mixture inhibits the activity of said polypeptide of the invention and can be used for the rational design of chemicals.

According to another embodiment, the invention relates to the use of a compound or mixture identified by means of a method as described above as a plant growth regulator or herbicide.

The invention also relates to a method for production of a plant growth regulator or herbicide composition comprising the steps of the compound screening methods described above and formulating the compounds obtained from said steps in a suitable form for the application in agriculture or plant cell or tissue culture.

The invention also relates to a method for increasing branching comprising expression of a nucleic acid of the invention in plants or plant parts, preferably in stems or axillary buds.

The invention also relates to a method for improving lodging resistance comprising expression of a nucleic acid of the invention in plants or plant parts, preferably in stems or axillary buds.

The invention also relates to a method for the design of or screening for growth-promoting chemicals or herbicides comprising the use of a nucleic acid of the invention or a vector of the invention.

According to another embodiment, the invention relates to the use of a nucleic acid molecule of the invention, a vector of the invention or a polypeptide of the invention for increasing yield.

The invention also relates to the use of a nucleic acid molecule of the invention, a vector of the invention or a polypeptide of the invention for stimulating root growth.

The invention also relates to the use of a nucleic acid molecule of the invention, a vector of the invention or a polypeptide of the invention for enhancing the formation of lateral or adventitious roots.

The invention also relates to the use of a nucleic acid molecule of the invention, a vector of the invention or a polypeptide of the invention for altering root geotropism.

The invention also relates to the use of a nucleic acid molecule of the invention, a vector of the invention or a polypeptide of the invention for increasing at least one of seed size, seed weight, embryo size, embryo weight, cotyledon size, and cotyledon weight.

The invention further relates to the use of a nucleic acid molecule of the invention, a vector of the invention or a polypeptide of the invention for enhancing early vigor and/or for modifying root/shoot ratio and/or for improving resistance to lodging and/or for increasing drought tolerance and/or for promoting in vitro propagation of explants.

The invention also relates to the use of a nucleic acid molecule of the invention, a recombinant vector of the invention or a polypeptide of the invention for modifying plant development and/or for modifying plant morphology and/or for modifying plant biochemistry and/or for modifying plant physiology.

According to yet another embodiment, the invention relates to a diagnostic composition comprising at least a nucleic acid molecule of the invention, a vector of the invention, a polypeptide of the invention or an antibody of the invention.

Another embodiment of the current invention relates to the use of a transgenic rootstock that has an enhanced root growth and development due to expression of a cytokinin oxidase in grafting procedures with a scion to produce a plant or tree with improved agricultural or horticultural characteristics.

The scion may be transgenic or non-transgenic. Specific characteristics envisaged by this embodiment are those conferred by root systems and include improved anchoring of the plant/tree in the soil and/or improved uptake of water resulting for example in improved drought tolerance, and/or improved nutrient uptake from the soil and/or improved transport of organic substances throughout the plant and/or enhanced secretion of substances into the soil such as for example phytosiderophores, and/or improved respiration and/or improved disease resistance and/or enhanced yield. An advantage of using AtCKX transformed rootstocks for grafting, in addition to their enhanced root system, is the delayed senescence of leaves on the graft, as disclosed herein (see FIG. 12 A). Preferred plants or trees for this particular embodiment include plants or trees that do not grow well on their own roots and are grafted in cultivated settings such as commercially profitable varieties of grapevines, citrus, apricot, almond, plum, peach, apple, pear, cherry, walnut, fig, hazel and loquat.

As mentioned supra, auxins and cytokinins act as antagonists in certain biological processes. For example, the cytokinin/auxin ratio regulates the production of roots and shoots with a high concentration of auxin resulting in organized roots and a high concentration of cytokinins resulting in shoot production. As disclosed in this invention, expression of cytokinin oxidases in tobacco and *Arabidopsis* results in enhanced root development consistent with enhanced auxin effects. Auxins are also involved in the development of fruit. Treatment of female flower parts with auxin results in the development of parthenocarpic fruit in some plant species. Parthenocarpic fruit development has been genetically engineered in several horticultural crop plants through increased biosynthesis of auxins in the female reproductive organs (WO0105985).

Therefore, according to another embodiment, this invention relates to a method for inducing the parthenocarpic trait in plants, said method consisting of downregulating the expression of one or more cytokinin oxidases or of another protein that reduces the level of active cytokinins in plants or plant parts, preferably in the female reproductive organs such as the placenta, ovules and tissues derived therefrom. The DefH9 promoter region from *Antirrhinum majus* or one of its homologues, which confer high expression specificity in placenta and ovules, can be used for this purpose.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp., *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Buteafrondosa*, *Cadabafarinosa*, *Calliandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthriafleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp.,*Taxodium distichum*, *Themeda triandra*, *Trifolium* spp., *Triticum* spp., *Tsuga heterophylla*, *Vaccinium* spp., *Vicia* spp. *Vitis vinifera*, *Watsonia pyramidata*, *Zantedeschia aethiopica*, *Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to the said protein with respect to which they are a homologue, without altering one or more of its functional properties, in particular without reducing the activity of the resulting. For example, a homologue of said protein will consist of a bioactive amino acid sequence variant of said protein. To produce such homologues, amino acids present in the said protein can be replaced by other amino acids having similar properties, for example hydrophobicity, hydrophilicity, hydrophobic moment, antigenicity, propensity to form or break α-helical structures or β-sheet structures, and so on. An overview of physical and chemical properties of amino acids is given in Table 1.

Substitutional variants of a protein of the invention are those in which at least one residue in said protein amino acid sequence has been removed and a different residue inserted in its place. Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

TABLE 1

Properties of naturally occurring amino acids.

| Charge properties/ hydrophobicity | Side group | Amino Acid |
| --- | --- | --- |
| Nonpolar hydrophobic | Aliphatic | ala, ile, leu, val |
|  | aliphatic, S-containing | met |
|  | aromatic | phe, trp |
|  | imino | pro |
| polar uncharged | Aliphatic | gly |
|  | Amide | asn, gln |
|  | Aromatic | tyr |
|  | Hydroxyl | ser, thr |
|  | Sulfhydryl | cys |
| Positively charged | Basic | arg, his, lys |
| Negatively charged | Acidic | asp, glu |

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in a two-hybrid system, phage coat proteins, (histidine)$_6$-tag, glutathione S-transferase, protein A, maltose-binding protein, dihydrofolate reductase, Tag•100 epitope (EETARFQPGYRS), c-myc epitope (EQKLISEEDL), FLAG®-epitope (DYKDDDK), lacZ, CMP (calmodulin-binding peptide), HA epitope (YPYDVPDYA), protein C epitope (EDQVDPRLIDGK) and VSV epitope (YTDIEMNRLGK).

Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols.

In the current invention "identity" and/or "similarity" percentages between DNA sequences and/or proteins are calculated using computer programs known in the art such as the DNAstar/MegAlign programs in combination with the Clustal method.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as specific epitopes or haptens are recognized by, i.e. bind to antibodies. Specific epitopes may be determined using, for example, peptide scanning techniques as described in Geysen et al. (1996) (Geysen, H. M., Rodda, S. J. and Mason, T. J. (1986). A priori delineation of a peptide which mimics a discontinuous antigenic determinant. *Mol. Immunol.* 23, 709-715.).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to (e.g. "functional fragment"), while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids, up to a maximum of about 20 or 25 amino acids.

Functional fragments can also include those comprising an epitope which is specific for the proteins according to the invention. Preferred functional fragments have a length of at least, for example, 5, 10, 25, 100, 150 or 200 amino acids.

It should thus be understood that functional fragments can also be immunologically active fragments or not.

In the context of the current invention are embodied homologues, derivatives and/or immunologically active and/or functional fragments of the cytokinin oxidases as defined supra. Particularly preferred homologues, derivatives and/or immunologically active and/or functional fragments of the cytokinin oxidase proteins which are contemplated for use in the current invention are derived from plants, more specifically from *Arabidopsis thaliana*, even more specifically said cytokinin oxidases are the *Arabidopsis thaliana* (At)CKX, or are capable of being expressed therein. The present invention clearly contemplates the use of functional homologues or derivatives and/or immunologically active fragments of the AtCKX proteins and is not to be limited in application to the use of a nucleotide sequence encoding one of said AtCKX proteins.

Any of said proteins, polypeptides, peptides and fragments thereof can be produced in a biological system, e.g. a cell culture. Alternatively any of said proteins, polypeptides, peptides and fragments thereof can be chemically manufactured e.g. by solid phase peptide synthesis. Said proteins or fragments thereof can be part of a fusion protein as is the case in e.g. a two-hybrid assay which enables e.g. the identification of proteins interacting with a cytokinin oxidase according to the invention.

The proteins or fragments thereof are furthermore useful e.g. to modulate the interaction between a cytokinin oxidase according to the invention and interacting protein partners obtained by a method of the invention. Chemically synthesized peptides are particularly useful e.g. as a source of antigens for the production of antisera and/or antibodies.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle and Cryer (1991) which comprise the fusion of mouse myeloma cells to spleen cells derived from immunized animals. Furthermore, antibodies or fragments thereof to a molecule or fragments thereof can be obtained by using methods as described in e.g. Harlow and Lane (1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labeled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins (see e.g. Example 6) and immunolocalization. Other uses of antibodies and especially of peptide antibodies include the study of proteolytic processing (Loffler et al. 1994, Woulfe et al. 1994), determination of protein active sites (Lerner 1982), the study of precursor and post-translational processing (Baron and Baltimore 1982, Lerner et al. 1981, Semier et al. 1982), identification of protein domains involved in protein-protein interactions (Murakami et al. 1992) and the study of exon usage in gene expression (Tamura et al. 1991).

Embodied in the current invention are antibodies specifically recognizing a cytokinin oxidase or homologue, derivative or fragment thereof as defined supra. Preferably said cytokinin oxidase is a plant cytokinin oxidase, more specifically one of the *Arabidopsis thaliana* cytokinin oxidases (AtCKX).

The terms "gene(s)", "polynucleotide(s)", "nucleic acid(s)", "nucleic acid sequence(s)", "nucleotide sequence(s)", or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothiorate, RNA, 2'-OMeRNA. Base modifications include 2-amino-dA, 2-aminopurine, 3'-(ddA), 3'dA(cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-1-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$—MedG, S6-DNP-dG, 4-methyl-indole, 5-nitroindole, 2'-OMe-inosine, 2'-dI, $O^6$-phenyl-dI, 4-methyl-indole, 2'-deoxynebularine, 5-nitroindole, 2-aminopurine, dP(purine analogue), dK(pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

The present invention also advantageously provides nucleic acid sequences of at least approximately 15 contiguous nucleotides of a nucleic acid according to the invention and preferably from 15 to 50 nucleotides. These sequences may, advantageously be used as probes to specifically hybridize to sequences of the invention as defined above or primers to initiate specific amplification or replication of sequences of the invention as defined above, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting the presence of any duplex or triplex formation between the probe and any nucleic acid in the sample.

Advantageously, the nucleic acid sequences, according to the invention may be produced using such recombinant or synthetic means, such as for example using PCR cloning mechanisms which generally involve making a pair of primers, which may be from approximately 15 to 50 nucleotides to a region of the gene which is desired to be cloned, bringing the primers into contact with mRNA, cDNA or genomic DNA from a cell, performing a polymerase chain reaction under conditions which bring about amplification of the desired region, isolating the amplified region or fragment and recovering the amplified DNA. Generally, such techniques as defined herein are well known in the art, such as described in Sambrook et al. (Molecular Cloning: a Laboratory Manual, 1989).

A "coding sequence" or "open reading frame" or "ORF" is defined as a nucleotide sequence that can be transcribed into mRNA and/or translated into a polypeptide when placed under the control of appropriate control sequences or regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences.

Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and serine can each be translated from up to six different codons. Differences in preferred codon usage are illustrated in Table 3 for *Agrobacterium tumefaciens* (a bacterium), *A. thaliana*, *M. sativa* (two dicotyledonous plants) and *Oryza sativa* (a monocotyledonous plant). To extract one example, the codon GGC (for glycine) is the most frequently used codon in *A. tumefaciens* (36.2‰), is the second most frequently used codon in *O. sativa* but is used at much lower frequencies in *A. thaliana* and *M. sativa* (9‰ and 8.4‰, respectively). Of the four possible codons encoding glycine (see Table 2), said GGC codon is most preferably used in *A. tumefaciens* and *O. sativa*. However, in *A. thaliana* this is the GGA (and GGU) codon whereas in *M. sativa* this is the GGU (and GGA) codon.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns and mobilizable DNA sequences such as transposons. With "mobilizable DNA sequence" is meant any DNA sequence that can be mobilized as the result of a recombination event.

TABLE 2

Degeneracy of the genetic code.

| Amino Acid | Three-letter code | One-letter code | Possible codons | | | | | |
|---|---|---|---|---|---|---|---|---|
| Alanine | Ala | A | GCA | GCC | GCG | GCU | | |
| Arginine | Arg | R | AGA | AGG | CGA | CGC | CGG | CGU |
| Asparagine | Asn | N | AAC | AAU | | | | |

TABLE 2-continued

Degeneracy of the genetic code.

| Amino Acid | Three-letter code | One-letter code | Possible codons | | | | | |
|---|---|---|---|---|---|---|---|---|
| Aspartic Acid | Asp | D | GAC | GAU | | | | |
| Cysteine | Cys | C | UGC | UGU | | | | |
| Glutamic Acid | Glu | E | GAA | GAG | | | | |
| Glutamine | Gln | Q | CAA | CAG | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Leucine | Leu | L | UUA | UUG | CUA | CUC | CUG | CUU |
| Lysine | Lys | K | AAA | AAG | | | | |
| Methionine | Met | M | AUG | | | | | |
| Phenylalanine | Phe | F | UUC | UUU | | | | |
| Proline | Pro | P | CCA | CCC | CCG | CCU | | |
| Serine | Ser | S | AGC | AGU | UCA | UCC | UCG | UCU |
| Threonine | Thr | T | ACA | ACC | ACG | ACU | | |
| Tryptophan | Trp | W | UGG | | | | | |
| Tyrosine | Tyr | Y | UAC | UAU | | | | |
| Valine | Val | V | GUA | GUC | GUG | GUU | | |

Possible "STOP" codons

UAA UAG UGA

TABLE 3

Usage of the indicated codons in the different organisms given as frequency per thousand codons (http://www.kazusa.or.jp/codon).

| Codon | *Agrobacterium tumefaciens* | *Arabidopsis thaliana* | *Medicago sativa* | *Oryza sativa* |
|---|---|---|---|---|
| UUU | 13.9 | 22.5 | 24.1 | 11.3 |
| UUC | 24.3 | 20.7 | 16.9 | 26.3 |
| UUA | 3.5 | 12.9 | 10.4 | 4.7 |
| UUG | 13.2 | 21.0 | 22.4 | 11.8 |
| UCU | 7.0 | 24.6 | 19.8 | 10.1 |
| UCC | 14.8 | 10.8 | 7.7 | 16.9 |
| UCA | 7.4 | 17.8 | 17.2 | 9.7 |
| UCG | 18.2 | 8.9 | 3.2 | 10.8 |
| UAU | 12.3 | 15.2 | 16.6 | 9.2 |
| UAC | 10.3 | 13.7 | 14.0 | 20.6 |
| UAA | 0.9 | 0.9 | 1.2 | 0.9 |
| UAG | 0.6 | 0.5 | 0.8 | 0.8 |
| UGU | 3.0 | 10.8 | 10.6 | 5.0 |
| UGC | 7.4 | 7.2 | 5.8 | 14.3 |
| UGA | 1.8 | 1.0 | 0.8 | 1.3 |
| UGG | 12.2 | 12.7 | 10.0 | 12.8 |
| CUU | 19.1 | 24.3 | 28.3 | 14.6 |
| CUC | 25.7 | 15.9 | 12.0 | 28.0 |
| CUA | 5.2 | 10.0 | 8.8 | 5.7 |
| CUG | 31.6 | 9.9 | 8.5 | 22.1 |
| CCU | 7.7 | 18.3 | 23.2 | 11.8 |
| CCC | 10.6 | 5.3 | 5.3 | 12.5 |
| CCA | 8.9 | 16.1 | 22.6 | 12.2 |

TABLE 3-continued

Usage of the indicated codons in the different organisms given as frequency per thousand codons (http://www.kazusa.or.jp/codon).

| Codon | Agrobacterium tumefaciens | Arabidopsis thaliana | Medicago sativa | Oryza sativa |
|---|---|---|---|---|
| CCG | 20.7 | 8.3 | 3.6 | 16.7 |
| CAU | 10.6 | 14.0 | 14.6 | 9.2 |
| CAC | 9.1 | 8.7 | 9.1 | 14.6 |
| CAA | 11.2 | 19.7 | 23.2 | 11.9 |
| CAG | 24.9 | 15.2 | 12.3 | 24.6 |
| CGU | 12.2 | 8.9 | 10.1 | 6.8 |
| CGC | 25.5 | 3.7 | 4.2 | 15.9 |
| CGA | 8.2 | 6.2 | 4.2 | 4.2 |
| CGG | 13.2 | 4.8 | 1.8 | 9.7 |
| AUU | 15.4 | 22.0 | 29.4 | 13.8 |
| AUC | 36.9 | 18.5 | 14.7 | 25.5 |
| AUA | 6.2 | 12.9 | 11.7 | 7.2 |
| AUG | 24.7 | 24.5 | 21.7 | 24.4 |
| ACU | 6.4 | 17.8 | 20.8 | 10.3 |
| ACC | 20.9 | 10.3 | 11.7 | 18.6 |
| ACA | 9.1 | 15.9 | 18.9 | 10.0 |
| ACG | 18.8 | 7.6 | 2.8 | 10.8 |
| AAU | 13.5 | 22.7 | 25.0 | 12.9 |
| AAC | 18.7 | 20.9 | 18.7 | 25.1 |
| AAA | 13.6 | 31.0 | 32.2 | 12.0 |
| AAG | 24.4 | 32.6 | 35.1 | 39.4 |
| AGU | 5.7 | 14.0 | 12.6 | 7.3 |
| AGC | 15.8 | 11.1 | 8.8 | 16.9 |
| AGA | 5.3 | 18.7 | 13.6 | 7.7 |
| AGG | 6.5 | 10.9 | 11.7 | 14.9 |
| GUU | 16.6 | 27.3 | 34.7 | 15.0 |
| GUC | 29.3 | 12.7 | 9.9 | 22.8 |
| GUA | 6.1 | 10.1 | 10.0 | 5.7 |
| GUG | 19.7 | 17.5 | 16.5 | 25.0 |
| GCU | 17.4 | 28.0 | 34.6 | 19.8 |
| GCC | 35.8 | 10.3 | 11.4 | 33.2 |
| GCA | 19.5 | 17.6 | 25.9 | 15.6 |
| GCG | 31.7 | 8.8 | 3.4 | 25.3 |
| GAU | 25.8 | 36.8 | 40.0 | 21.5 |
| GAC | 28.0 | 17.3 | 15.5 | 31.6 |
| GAA | 29.9 | 34.4 | 35.9 | 17.1 |
| GAG | 26.3 | 32.2 | 27.4 | 41.1 |
| GGU | 16.5 | 22.2 | 28.7 | 16.3 |
| GGC | 36.2 | 9.0 | 8.4 | 34.7 |
| GGA | 12.5 | 23.9 | 27.3 | 15.0 |
| GGG | 11.3 | 10.2 | 7.4 | 16.6 |

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin. Tools in molecular biology relying on such a process include the isolation of poly (A+) mRNA. The hybridization process can furthermore occur with one of the complementary nucleic acids immobilized to a solid support such as a nitrocellulose or nylon membrane or immobilized by e.g. photolithography to e.g. a silicious glass support (the latter known as nucleic acid arrays or microarrays or as nucleic acid chips). Tools in molecular biology relying on such a process include RNA and DNA gel blot analysis, colony hybridization, plaque hybridization and microarray hybridization. In order to allow hybridization to occur, the nucleic acid molecules are generally thermally or chemically (e.g. by NaOH) denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and Na3-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (1989) but the skilled craftsman will appreciate that numerous different hybridization conditions can be designed in function of the known or the expected homology and/or length of the nucleic acid sequence. Sufficiently low stringency hybridization conditions are particularly preferred to isolate nucleic acids heterologous to the DNA sequences of the invention defined supra. Elements contributing to said heterology include allelism, degeneration of the genetic code and differences in preferred codon usage as discussed supra.

The term "specifically hybridizing" or "hybridizing specifically" refers to the binding, duplexing, or hybridizing of a molecule to a particular nucleotide sequence under medium to stringent conditions when that sequence is presented in a complex mixture e.g., total cellular DNA or RNA.

"Stringent hybridization conditions" and "stringent hybridization wash conditions" in the context of nucleic acid hybridization experiments such as Southern and Northern hybridizations are sequence dependent and are different under different environmental parameters. For example, longer sequences hybridize specifically at higher temperatures. The $T_m$ is the temperature under defined ionic strength and pH, at which 50% of the target sequence hybridizes to a perfectly matched probe. Specificity is typically the function of post-hybridization washes. Critical factors of such washes include the ionic strength and temperature of the final wash solution.

Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° \text{ C.} + (18.5 \times \text{Log}[Na+]) + (58.4° \text{ C.} \times \%[G+C]) - (820/\#bp \text{ in duplex}) - (0.5 \times \% \text{ formamide})$$

More preferred stringent conditions are when the temperature is 20° C. below $T_m$, and the most preferred stringent conditions are when the temperature is 10° C. below $T_m$. Nonspecific binding may also be controlled using any one of a number of known techniques such as, for example, blocking the membrane with protein-containing solutions, addition of heterologous RNA, DNA, and SDS to the hybridization buffer, and treatment with RNase.

Wash conditions are typically performed at or below stringency. Generally, suitable stringent conditions for nucleic acid hybridization assays or gene amplification detection procedures are as set forth above. More or less stringent conditions may also be selected.

For the purposes of defining the level of stringency, reference can conveniently be made to Sambrook, J., E. F. Fritsch, et al. 1989 "Molecular Cloning: a Laboratory Manual, 2$^{nd}$ Edition, Cold Spring Harbor, N.Y., Cold Spring Harbor Laboratory Press, at 11.45. An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at $\geqq$45° C. for 2-3 hours. An example of high stringency conditions includes 0.1-1× SSC/0.1% w/v SDS at 60 C for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05×BLOTTO, and washing at 2×SSC, 0.1% SDS at 62° C.

Clearly, the current invention embodies the use of the inventive DNA sequences encoding a cytokinin oxidase, homologue, derivative or immunologically active and/or functional fragment thereof as defined higher in any method of hybridization. The current invention furthermore also relates to DNA sequences hybridizing to said inventive DNA sequences. Preferably said cytokinin oxidase is a plant cytokinin oxidase, more specifically the *Arabidopsis thaliana* (At)CKX.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a cytokinin oxidase protein or a homologue or derivative thereof or an immunologically active and/or functional fragment thereof as defined supra. The preferred protein of the invention comprises the amino acid sequence of said cytokinin oxidase. Preferably said cytokinin oxidase is a plant cytokinin oxidase and more specifically a *Arabidopsis thaliana* (At)CKX.

With "vector" or "vector sequence" is meant a DNA sequence which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognized by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory or control sequences enable the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors).

The current invention clearly includes any cytokinin oxidase, homologue, derivative and/or immunologically active and/or functional fragment thereof as defined supra. Preferably said cytokinin oxidase is a plant cytokinin oxidase, more specifically a *Arabidopsis thaliana* (At)CKX.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilization of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids. Amino acid side chain protecting groups include methyl (Me), formyl (CHO), ethyl (Et), acetyl (Ac), t-butyl (t-Bu), anisyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z),2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl-Z), 2,4,5-trichlorophenyl, 2-bromobenzyloxycarbonyl (Br-Z), tripheylmethyl (Trityl, Trt), and 2,5,7,8-pentamethyl-chroman-6-sulphonyl (Pmc). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidized and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-β-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (indoleacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory or control sequences including a promoter, preferably a plant-expressible promoter, and a terminator sequence.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory or control elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

Regulatable promoters as part of a binary viral plant expression system are also known to the skilled artisan (Yadav 1999—WO9922003; Yadav 2000—WO0017365).

In the present context, a "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon).

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ.

Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin.

Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Those skilled in the art will readily be capable of selecting appropriate promoter sequences for use in regulating appropriate expression of the cytokinin oxidase protein from publicly-available or readily-available sources, without undue experimentation.

Placing a nucleic acid molecule under the regulatory control of a promoter sequence, or in operable connection with a promoter sequence, means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include those listed in Table 4, amongst others. The promoters listed in Table 4 are provided for the purposes of exemplification only and the present invention is not to be limited by the list provided therein. Those skilled in the art will readily be in a position to provide additional promoters that are useful in performing the present invention.

In the case of constitutive promoters or promoters that induce expression throughout the entire plant, it is preferred that such sequences are modified by the addition of nucleotide sequences derived from one or more of the tissue-specific promoters listed in Table 4, or alternatively, nucleotide sequences derived from one or more of the above-mentioned tissue-specific inducible promoters, to confer tissue-specificity thereon. For example, the CaMV 35S promoter may be modified by the addition of maize Adhl promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000—WO00 15662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, molds, bacteria, insects, birds, mammals and plants are known and described in the literature. They may be isolated from bacteria, fungi, viruses, animals and/or plants.

TABLE 4

Exemplary plant-expressible promoters for use in the performance of the present invention

| GENE SOURCE | EXPRESSION PATTERN | REFERENCE |
|---|---|---|
| I: CELL-SPECIFIC, TISSUE-SPECIFIC, AND ORGAN-SPECIFIC PROMOTERS | | |
| α-amylase (Amy32b) | aleurone | Lanahan, M. B., et al., Plant Cell 4: 203-211, 1992; Skriver, K., et al. Proc. Natl. Acad. Sci. (USA) 88: 7266-7270, 1991 |
| cathepsin β-like gene | aleurone | Cejudo, F. J., et al. Plant Molecular Biology 20: 849-856, 1992. |
| *Agrobacterium rhizogenes* rolB | cambium | Nilsson et al., Physiol. Plant. 100: 456-462, 1997 |
| AtPRP4 | flowers | http://salus.medium.edu/mmg/tierney/html |
| chalcone synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |
| Chitinase | fruit (berries, grapes, etc) | Thomas et al. CSIRO Plant Industry, Urrbrae, South Australia, Australia; http://winetitles.com.au/gwrdc/csh95-1.html |
| rbcs-3A | green tissue (eg leaf) | Lam, E. et al., The Plant Cell 2: 857-866, 1990.; Tucker et al., Plant Physiol. 113: 1303-1308, 1992. |
| leaf-specific genes | leaf | Baszczynski, et al., Nucl. Acid Res. 16: 4732, 1988. |
| AtPRP4 | leaf | http://salus.medium.edu/mmg/tierney/html |
| chlorella virus adenine methyltransferase gene promoter | leaf | Mitra and Higgins, 1994, Plant Molecular Biology 26: 85-93 |
| aldP gene promoter from rice | leaf | Kagaya et al., 1995, Molecular and General Genetics 248: 668-674 |
| rbcs promoter from rice or tomato | leaf | Kyozuka et al., 1993, Plant Physiology 102: 991-1000 |
| Pinus cab-6 | leaf | Yamamoto et al., Plant Cell Physiol. 35: 773-778, 1994. |
| rubisco promoter | leaf | |
| cab (chlorophyll a/b/binding protein | leaf | |
| SAM22 | senescent leaf | Crowell, et al., Plant Mol. Biol. 18: 459-466, 1992. |
| ltp gene (lipid transfer gene) | | Fleming, et al, Plant J. 2, 855-862. |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang, et al., The Plant J. 3: 573-585. |
| PEP carboxylase (PEPC) | Nodule | Pathirana et al., Plant Mol. Biol. 20: 437-450, 1992. |
| Leghaemoglobin (Lb) | Nodule | Gordon, et al., J. Exp. Bot. 44: 1453-1465, 1993. |
| *Tungro bacilliform* virus gene | phloem | Bhattacharyya-Pakrasi, et al, The Plant J. 4: 71-79, 1992. |

TABLE 4-continued

Exemplary plant-expressible promoters for use
in the performance of the present invention

| | | |
|---|---|---|
| pollen-specific genes | pollen; microspore | Albani, et al., Plant Mol. Biol. 15: 605, 1990; Albani, et al., Plant Mol. Biol. 16: 501, 1991) |
| Zm13 | pollen | Guerrero et al Mol. Gen. Genet. 224: 161-168 (1993) |
| apg gene | microspore | Twell et al Sex. Plant Reprod. 6: 217-224 (1993) |
| maize pollen-specific gene | pollen | Hamilton, et al., Plant Mol. Biol. 18: 211-218, 1992. |
| sunflower pollen-expressed gene | pollen | Baltz, et al., The Plant J. 2: 713-721, 1992. |
| *B. napus* pollen-specific gene | pollen; anther; tapetum | Arnoldo, et al., J. Cell. Biochem., Abstract No. Y101, 204, 1992. |
| root-expressible genes | roots | Tingey, et al., EMBO J. 6: 1, 1987. |
| tobacco auxin-inducible gene | root tip | Van der Zaal, et al., Plant Mol. Biol. 16, 983, 1991. |
| β-tubulin | root | Oppenheimer, et al., Gene 63: 87, 1988. |
| tobacco root-specific genes | root | Conkling, et al., Plant Physiol. 93: 1203, 1990. |
| *B. napus* G1-3b gene | root | U.S. Pat. No. 5,401,836 |
| SbPRP1 | roots | Suzuki et al., Plant Mol. Biol. 21: 109-119, 1993. |
| AtPRP1; AtPRP3 | roots; root hairs | http://salus.medium.edu/mmg/tierney/html |
| RD2 gene | root cortex | http://2.cnsu.edu/ncsu/research |
| TobRB7 gene | root vasculature | http://2.cnsu.edu/ncsu/research |
| AtPRP4 | leaves; flowers; lateral root primordia | http://salus.medium.edu/mmg/tierney/html |
| seed-specific genes | seed | Simon, et al., Plant Mol. Biol. 5: 191, 1985; Scofield, et al., J. Biol. Chem. 262: 12202, 1987.; Baszczynski, et al., Plant Mol. Biol. 14: 633, 1990. |
| Brazil Nut albumin | seed | Pearson, et al., Plant Mol. Biol. 18: 235-245, 1992. |
| Legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| Zein | seed | Matzke et al Plant Mol Biol, 14(3): 323-32 1990 |
| NapA | seed | Stalberg, et al, Planta 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley Itr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu at, J. Biochem., 123: 386, 1998 |
| sunflower oleosin | seed (embryo and dry seed) | Cummins, et al., Plant Mol. Biol. 19: 873-876, 1992 |
| LEAFY | shoot meristem | Weigel et al., Cell 69: 843-859, 1992. |

TABLE 4-continued

Exemplary plant-expressible promoters for use
in the performance of the present invention

| | | |
|---|---|---|
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85: 5551, 1988; Trick, et al., Plant Mol. Biol. 15: 203, 1990. |
| class I patatin gene | tuber | Liu et al., Plant Mol. Biol. 153: 386-395, 1991. |
| PCNA rice | meristem | Kosugi et al, Nucleic Acids Research 19: 1571-1576, 1991; Kosugi S. and Ohashi Y, Plant Cell 9: 1607-1619, 1997. |
| Pea TubA1 tubulin | Dividing cells | Stotz and Long, Plant Mol. Biol. 41, 601-614. 1999 |
| *Arabidopsis* cdc2a | cycling cells | Chung and Parish, FEBS Lett, 3; 362(2): 215-9, 1995 |
| *Arabidopsis* Rop1A | Anthers; mature pollen + pollen tubes | Li et al. 1998 Plant Physiol 118, 407-417. |
| *Arabidopsis* AtDMC1 | Meiosis-associated | Klimyuk and Jones 1997 Plant J. 11, 1-14. |
| Pea PS-IAA4/5 and PS-IAA6 | Auxin-inducible | Wong et al. 1996 Plant J. 9, 587-599. |
| Pea farnesyltransferase | Meristematic tissues; phloem near growing tissues; light- and sugar-repressed | Zhou et al. 1997 Plant J. 12, 921-930 |
| Tobacco (*N. sylvestris*) cyclin B1; 1 | Dividing cells/ meristematic tissue | Trehin et al. 1997 Plant Mol. Biol. 35, 667-672. |
| Mitotic cyclins CYS (A-type) and CYM (B-type) | Dividing cells/ meristematic tissue | Ito et al. 1997 Plant J. 11, 983-992 |
| *Arabidopsis* cyc1At (=cyc B1; 1) and cyc3aAt (A-type) | Dividing cells/ meristematic tissue | Shaul et al. 1996 Proc. Natl. Acad. Sci. U.S.A 93, 4868-4872. |
| *Arabidopsis* tef1 promoter box | Dividing cells/ meristematic tissue | Regad et al. 1995 Mol. Gen. Genet. 248, 703-711. |
| *Catharanthus roseus* cyc07 | Dividing cells/ meristematic tissue | Ito et al. 1994 Plant Mol. Biol. 24, 863-878. |

II: EXEMPLARY CONSTITUTIVE PROMOTERS

| | | |
|---|---|---|
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J. 2: 837-844, 1992 |
| Ubiquitin | constitutive | Christensen et al, Plant Mol. Biol. 18: 675-689, 1992 |
| rice cyclophilin | constitutive | Buchholz et al, Plant Mol Biol. 25: 837-843, 1994 |
| maize histone H3 | constitutive | Lepetit et al, Mol. Gen. Genet. 231: 276-285, 1992 |
| alfalfa histone H3 | constitutive | Wu et al., Nucleic Acids Res. 17: 3057-3063, 1989; Wu et al., Plant Mol. Biol. 11: 641-649, 1988 |
| actin 2 | constitutive | An et al, Plant J. 10(1); 107-121, 1996 |

III: EXEMPLARY STRESS-INDUCIBLE PROMOTERS

| NAME | STRESS | REFERENCE |
|---|---|---|
| P5CS (delta(1)-pyrroline-5-carboxylate syntase) | salt, water | Zhang et al. Plant Science. 129: 81-89, 1997 |
| cor15a | cold | Hajela et al., Plant Physiol. 93: 1246-1252, 1990 |
| cor15b | cold | Wlihelm et al., Plant Mol Biol. 23: 1073-1077, 1993 |
| cor15a (−305 to +78 nt) | cold, drought | Baker et al., Plant Mol Biol. 24: 701-713, 1994 |

TABLE 4-continued

Exemplary plant-expressible promoters for use
in the performance of the present invention

| | | |
|---|---|---|
| rd29 | salt, drought, cold | Kasuga et al., Nature Biotechnology 18: 287-291, 1999 |
| heat shock proteins, including artificial promoters containing the heat shock element (HSE) | heat | Barros et al., Plant Mol Biol 19: 665-75, 1992. Marrs et al., Dev Genet.14: 27-41, 1993. Schoffl et al., Mol Gen Gent, 217: 246-53, 1989. |
| smHSP (small heat shock proteins) | heat | Waters et al, J Experimental Botany 47: 325-338, 1996 |
| wcs120 | cold | Ouellet et al., FEBS Lett. 423: 324-328, 1998 |
| ci7 | cold | Kirch et al., Plant Mol Biol 33: 897-909, 1997 |
| Adh | cold, drought, hypoxia | Dolferus et al., Plant Physiol 105: 1075-87, 1994 |
| pwsi18 | water: salt and drought | Joshee et al., Plant Cell Physiol 39: 64-72, 1998 |
| ci21A | cold | Schneider et al., Plant Physiol 113: 335-45, 1997 |
| Trg-31 | drought | Chaudhary et al., Plant Mol Biol 30: 1247-57, 1996 |
| Osmotin | osmotic | Raghothama et al., Plant Mol Biol 23: 1117-28, 1993 |
| Rab17 | osmotic, ABA | Vilardell et al., Plant Mol Biol 17: 985-93, 1991 |
| LapA | wounding, enviromental | WO99/03977 University of California/INRA |

IV: EXEMPLARY PATHOGEN-INDUCIBLE PROMOTERS

| NAME | PATHOGEN | REFERENCE |
|---|---|---|
| RB7 | Root-knot nematodes (*Meloidogyne* spp.) | U.S. Pat. No. 5760386 - North Carolina State University; Opperman et al (1994) Science 263: 221-23. |
| PR-1, 2, 3, 4, 5, 8, 11 | fungal, viral, bacterial | Ward et al (1991) Plant Cell 3: 1085-1094; Reiss et al 1996; Lebel et al (1998), Plant J, 16(2): 223-33; Melchers et al (1994), Plant J, 5(4): 469-80; Lawton et al (1992), Plant Mol Biol, 19(5): 735-43. |
| HMG2 | nematodes | WO9503690 - Virginia Tech Intellectual Properties Inc. |
| Abi3 | Cyst nematodes (*Heterodera* spp.) | Unpublished |
| ARM1 | nematodes | Barthels et al., (1997) The Plant Cell 9, 2119-2134. WO 98/31822 - Plant Genetic Systems |
| Att0728 | nematodes | Barthels et al., (1997) The Plant Cell 9, 2119-2134. PCT/EP98/07761 |
| Att1712 | nematodes | Barthels et al., (1997) The Plant Cell 9, 2119-2134. PCT/EP98/07761 |
| Gst1 | Different types of pathogens | Strittmatter et al (1996) Mol. Plant-Microbe Interact. 9, 68-73. |
| LEMMI | nematodes | WO 92/21757 - Plant Genetic Systems |
| CLE | geminivirus | PCT/EP99/03445 - CINESTAV |
| PDF1.2 | Fungal including *Alternaria brassicicola* and *Botrytis cinerea* | Manners et al (1998), Plant Mol Biol, 38(6): 1071-80. |
| Thi2.1 | Fungal - *Fusarium oxysporum* f sp. matthiolae | Vignutelli et al (1998) Plant J; 14(3): 285-95 |
| DB#226 | nematodes | Bird and Wilson (1994) Mol. Plant-Microbe Interact., 7, 419-42 WO 95.322888 |
| DB#280 | nematodes | Bird and Wilson (1994) Mol. Plant-Microbe Interact., 7,419-42 WO 95.322888 |
| Cat2 | nematodes | Niebel et al (1995) Mol Plant Microbe Interact 1995 May-Jun; 8(3): 371-8 |

TABLE 4-continued

Exemplary plant-expressible promoters for use
in the performance of the present invention

| | | |
|---|---|---|
| ☐Tub | nematodes | Aristizabal et al (1996), 8$^{th}$ International Congress on Plant-Microbe Interaction, Knoxville US B-29 |
| SHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S. A. Ohl (Eds.) |
| Hs1(pro1) | nematodes | WO 98/122335 - Jung |
| NsLTP | viral, fungal, bacterial | Molina & García-Olmedo (1993) FEBS Lett, 316(2): 119-22 |
| RIP | viral, fungal | Turner et al (1997) Proc Natl Acad Sci USA, 94(8): 3866-71 |

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Preferred promoter sequences of the invention include root specific promoters and seed-specific promoters such as but not limited to the ones listed in Table 5, Table 4, and as outlined in the Examples.

TABLE 5

Exemplary root specific promoters for use in the performance of
the present invention

| NAME | ORIGIN | REFERENCE |
|---|---|---|
| SbPRP1 | Soybean | Suzuki et al., Plant Mol Biol, 21: 109-119, 1993 |
| 636 bp fragment of TobRB7 | Tobacco | Yamamoto et al., Plant Cell 3: 371-382, 1991 |
| GGPS3 | *Arabidopsis* | Okada et al., Plant Physiol 122: 1045-1056, 2000 |
| 580 bp fragment of prxEa | *Arabidopsis* | Wanapu and Shinmyo, Ann N Y Acad Sci 782: 107-114, 1996 |
| Ids2 promoter | Barley | Okumura et al., Plant Mol Biol 25: 705-719, 1994 |
| AtPRP3 | *Arabidopsis* | Fowler et al., Plant Physiol 121: 1081-1092, 1999 |

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions, more specifically is meant increased expression and/or increased expression levels. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect. With "ectopic co-expression" is meant the ectopic expression or ectopic overexpression of two or more genes or proteins. The same or, more preferably, different promoters are used to confer ectopic expression of said genes or proteins.

Preferably, the promoter sequence used in the context of the present invention is operably linked to a coding sequence or open reading frame (ORF) encoding a cytokinin oxidase protein or a homologue, derivative or an immunologically active and/or functional fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9853083), Lederer et al. (1999—WO9915682) or Wang et al. (1999—WO9953050). Genetic constructs aimed at silencing gene expression may have the nucleotide sequence of said gene (or one or more parts thereof) contained therein in a sense and/or antisense orientation relative to the promoter sequence. Another method to down-regulate gene expression comprises the use of ribozymes.

Modulating, including lowering, the level of active gene products or of gene product activity can be achieved by administering or exposing cells, tissues, organs or organisms to said gene product, a homologue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an agonist of said gene product or the activity thereof. Such agonists include proteins (comprising e.g. kinases and proteinases) and chemical compounds identified according to the current invention as described supra.

In the context of the current invention is envisaged the downregulation of the expression of a cytokinin oxidase gene as defined earlier. Preferably said cytokinin oxidase gene is a plant cytokinin oxidase gene, more specifically an AtCKX. The invention further comprises downregulation of levels of a cytokinin oxidase protein or of a cytokinin oxidase activity whereby said cytokinin oxidase protein has been defined supra. Preferably said cytokinin oxidase protein is a plant cytokinin oxidase, more specifically an AtCKX.

By "modifying cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogenesis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fiber, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibers, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, daylength, flooding, salt, heavy metals, amongst others), including adaptive responses of plants to said externally-applied factors.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Dodds et al., (1985), Herrera-Estrella et al. (1983a, 1983b, 1985). Methods for transformation of monocotyledonous plants are well known in the art and include *Agrobacterium*-mediated transformation (Cheng et al., 1997—WO9748814; Hansen 1998—WO9854961; Hiei et al., 1994—WO9400977; Hiei et al., 1998—WO9817813; Rikiishi et al., 1999—WO9904618; Saito et al., 1995—WO9506722), microprojectile bombardment (Adams et al., 1999—U.S. Pat. No. 5,969,213; Bowen et al., 1998—U.S. Pat. No. 5,736,369; Chang et al., 1994—WO9413822; Lundquist et al., 1999—U.S. Pat. No. 5,874,265/U.S. Pat. No. 5,990,390; Vasil and Vasil, 1995—U.S. Pat. No. 5,405,765. Walker et al., 1999—U.S. Pat. No. 5,955,362), DNA uptake (Eyal et al., 1993—WO9318168), microinjection of *Agrobacterium* cells (von Holt, 1994—DE4309203) and sonication (Finer et al., 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including in planta transformation), protoplast fusion, or electroporation, amongst others. Most preferably said plant is produced by *Agrobacterium*-mediated transformation.

*Agrobacterium*-mediated transformation or agrolistic transformation of plants, yeast, molds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and by Stuiver et al. (1999—WO9901563).

The current invention clearly considers the inclusion of a DNA sequence encoding a cytokinin oxidase, homologue, derivative or immunologically active and/or functional fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation. Preferably, said cytokinin oxidase is a plant cytokinin oxidase, more specifically an *Arabidopsis thaliana* (At)CKX.

With "binary transformation vector" is meant a T-DNA transformation vector comprising:

(a) a T-DNA region comprising at least one gene of interest and/or at least one selectable marker active in the eukaryotic cell to be transformed; and (b) a vector backbone region comprising at least origins of replication active in *E. coli* and *Agrobacterium* and markers for selection in *E. coli* and *Agrobacterium*.

The T-DNA borders of a binary transformation vector can be derived from octopine-type or nopaline-type Ti plasmids or from both. The T-DNA of a binary vector is only transferred to a eukaryotic cell in conjunction with a helper plasmid.

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

With "co-integrate transformation vector" is meant a T-DNA vector at least comprising:

(a) a T-DNA region comprising at least one gene of interest and/or at least one selectable marker active in plants; and (b) a vector backbone region comprising at least origins of replication active in *Escherichia coli* and *Agrobacterium*, and markers for selection in *E. coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance (Amp$^r$), tetracycline resistance gene (Tc$^r$), bacterial kanamycin resistance gene (Kan$^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997—WO9712046).

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore include intervening DNA sequences as defined supra.

With "recombination event" is meant either a site-specific recombination event or a recombination event effected by transposon 'jumping'.

With "recombinase" is meant either a site-specific recombinase or a transposase.

With "recombination site" is meant either site-specific recombination sites or transposon border sequences.

With "site specific recombination event" is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of the pSR1 plasmid. Recombinases generally are integrases, resolvases or flippases. Also dual-specific recombinases can be used in conjunction with direct or indirect repeats of two different site-specific recombination sites corresponding to the dual-specific recombinase (WO99/25840). The two preferred site-specific recombinase systems are the bacteriophage P1 Cre/lox and the yeast FLP/FRT systems. In these systems a recombinase (Cre or FLP) interact specifically with its respective site-specific recombination sequence (lox or FRT respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990) and *Arabidopsis* (Osborne et al. 1995). Site-specific recombination systems have many applications in plant molecular biology including methods for control of homologous recombination (e.g. U.S. Pat. No. 5,527,695), for targeted insertion, gene stacking, etc. (WO99/25821) and for resolution of complex T-DNA integration patterns or for excision of a selectable marker (WO99/23202).

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987). Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilize, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has been excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site or frt site.

The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

The term "cell cycle progression" refers to the process of passing through the different cell cycle phases. The term "cell cycle progression rate" accordingly refers to the speed at which said cell cycle phases are run through or the time spans required to complete said cell cycle phases.

With "two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel and Fields 1997). Alternatively, a mammalian two-hybrid system can be used which includes e.g. a chimeric green fluorescent protein encoding reporter gene (Shioda et al., 2000).

Furthermore, folding simulations and computer redesign of structural motifs of the protein of the invention can be performed using appropriate computer programs (Olszewski, Proteins 25 (1996), 286-299; Hoffman, Comput. Appl. Biosci. 1 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the cytokinin oxidases, its ligands or other interacting proteins by computer assistant searches for complementary peptide sequences (Fassina, Immunomethods 5 (1994), 114-120). Further appropriate computer systems for the design of protein and peptides are described in the prior art, for example in Berry, Biochem. Soc. Trans. 22 (1994), 1033-1036; Wodak, Ann, N.Y. Acac. Sci. 501 (1987), 1-13; Pabo, Biochemistry 25 (1986), 5987-5991. The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral Ω-amino acid residues into a protein of the invention or a fragment thereof results in the substitution of amino bonds by polymethylene units of an aliphatic chain, thereby providing a convenient strategy for constructing a peptidomimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Ruterber, Bioorg. Med. Chem. 4 (1996), 1545-1558).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of said compound. Alternatively the compound can exert his action by enhancing or decreasing the activity of any of the proteins of the invention. Herein, preferred proteins are novel cytokinin oxidases.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cytokinin oxidase interacting proteins. The reaction mixture may be a cell free extract of may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

The term "early vigor" refers to the ability of a plant to grow rapidly during early development, and relates to the successful establishment, after germination, of a well-developed root system and a well-developed photosynthetic apparatus.

The term "resistance to lodging" or "standability" refers to the ability of a plant to fix itself to the soil. For plants with an erect or semi-erect growth habit this term also refers to the ability to maintain an upright position under adverse (environmental) conditions. This trait relates to the size, depth and morphology of the root system.

The term 'grafting' as used herein, refers to the joining together of the parts of two different plants so that they bind together and the sap can flow, thus forming a single new plant that can grow and develop. A graft therefore consists of two parts: (i) the lower part is the rootstock as referred to herein and essentially consists of the root system and a portion of the stem, and (ii) the upper part, the scion or graft, which gives rise to the aerial parts of the plant.

As used herein, tblastn refers to an alignment tool that is part of the BLAST (Basic Local Alignment Search Tool) family of programs (http://www.ncbi.nlm.nih.gov/BLAST/). BLAST aims to identify regions of optimal local alignment, i.e. the alignment of some portion of two nucleic acid or protein sequences, to detect relationships among sequences which share only isolated regions of similarity (Altschul et al., 1990). In the present invention, tblastn of the BLAST 2.0 suite of programs was used to compare the maize cytokinin oxidase protein sequence against a nucleotide sequence database dynamically translated in all reading frames (Altschul et al., Nucleic Acids Res. 25: 3389-3402 (1997)).

The following examples are given by means of illustration of the present invention and are in no way limiting. The contents of all references included in this application are incorporated by reference herein as if fully set forth.

EXAMPLES

Example 1

Brief Description of the Sequences of the Invention

| SEQ ID NO: | DESCRIPTION |
|---|---|
| 1 | AtCKX1 genomic |
| 2 | AtCKX1 protein |
| 3 | AtCKX2 genomic |
| 4 | AtCKX2 protein |
| 5 | AtCKX3 genomic |
| 6 | AtCKX3 protein |
| 7 | AtCKX4 genomic |
| 8 | AtCKX4 protein |
| 9 | AtCKX5 genomic (short version) |
| 10 | AtCKX5 protein (short version) |
| 11 | AtCKX6 genomic |
| 12 | AtCKX6 protein |
| 13 | 5'primer AtCKX1 |
| 14 | 3'primer AtCKX1 |

-continued

| SEQ ID NO: | DESCRIPTION |
|---|---|
| 15 | 5'primer AtCKX2 |
| 16 | 3'primer AtCKX2 |
| 17 | 5'primer AtCKX3 |
| 18 | 3'primer AtCKX3 |
| 19 | 5'primer AtCKX4 |
| 20 | 3'primer AtCKX4 |
| 21 | 5'primer AtCKX5 |
| 22 | 3'primer AtCKX5 |
| 23 | 5'primer AtCKX6 |
| 24 | 3'primer AtCKX6 |
| 25 | AtCKX1 cDNA |
| 26 | AtCKX2 cDNA |
| 27 | AtCKX3 cDNA |
| 28 | AtCKX4 cDNA |
| 29 | AtCKX5 cDNA (short version) |
| 30 | AtCKX6 cDNA |
| 31 | AtCKX2 cDNA fragment |
| 32 | AtCKX2 peptide fragment |
| 33 | AtCKX5 genomic (long version) |
| 34 | AtCKX5 cDNA (long version) |
| 35 | AtCKX5 protein (long version) |
| 36 | root clavata homolog promoter |

Example 2

Identification of Candidate Cytokinin Oxidase Encoding Genes from *Arabidopsis thaliana*

Six different genes were identified from *Arabidopsis thaliana* that bear sequence similarity to a cytokinin oxidase gene from maize (Morris et al., Biochem Biophys Res Comm 255:328-333, 1999; Houda-Herin et al. Plant J 17:615-626; WO 99/06571). These genes were found by screening 6-frame translations of nucleotide sequences from public genomic databases with the maize protein sequence, employing tblastn program. These sequences were designated as *Arabidopsis thaliana* cytokinin oxidase-like genes or AtCKX. They were arbitrarily numbered as AtCKX1 to AtCKX6. The below list summarizes the information on these genes. The predicted ORF borders and protein sequences are indicative, in order to illustrate by approximation the protein sequence divergence between the *Arabidopsis* and maize cytokinin oxidases, as well as amongst the different *Arabidopsis* cytokinin oxidases. The ORF borders and protein sequences shown should not be taken as conclusive evidence for the mode of action of these AtCKX genes. For DNA and protein sequence comparisons the program MegAlign from DNAstar was used. This program uses the Clustal method for alignments. For multiple alignments of protein and cDNA sequences the gap penalty and gap length penalty was set at 10 each. For pairwise alignments of proteins the parameters were as follows: Ktuple at 1; Gap penalty at 3; window at 5; diagonals saved at 5. For pairwise alignments of cDNA's the parameters were as follows: Ktuple at 2; Gap penalty at 5; window at 4; diagonals saved at 4. The similarity groups for protein alignments was: (M,I,L,V), (F,W,Y), (G,A), (S,T), (R,K,H), (E,D), (N,Q). The values that are indicated amongst the *Arabidopsis* cDNA and protein sequences represent the lowest and highest values found with all combinations.

A. Gene name: AtCKX1 (*Arabidopsis thaliana* cytokinin oxidase-like protein 1, SEQ ID NO: 1)

Location in database (accession number, location on bac): AC002510, *Arabidopsis thaliana* chromosome II section 225 of 255 of the complete sequence. Sequence from clones T32G6.

ORF Predicted in the Database:
15517 . . . 16183, 16415 . . . 16542, 16631 . . . 16891, 16995 . . . 17257, 17344 . . . 17752

The AtCKX1 cDNA sequence is listed as SEQ ID NO: 25

Predicted protein sequence: SEQ ID NO: 2:

Homologies
% identity with *Z. mays* cDNA:
    31.5% (Dnastar/MegAlign-Clustal method)
% similarity with *Z. mays* protein:
    32.2% (Dnastar/MegAlign-Clustal method)
% identity with other *Arabidopsis* cDNA's (range):
    38.2% (AtCKX2)-54.1% (AtCKX6) (Dnastar/MegAlign-Clustal method)
% similarity with other *Arabidopsis* proteins (range):
    37.1% (AtCKX2)-58.1% (AtCKX6) (Dnastar/MegAlign-Clustal method)

B. Gene name: AtCKX2 (*Arabidopsis thaliana* cytokinin oxidase-like protein 2, SEQ ID NO: 3)

Location in database (accession number, location on bac): AC005917, *Arabidopsis thaliana* chromosome II section 113 of 255 of the complete sequence. Sequence from clones F27F23, F3 P11.

ORF Predicted in the Database:
complement, 40721 . . . 41012, 41054 . . . 41364, 41513 . . . 41770, 42535 . . . 42662, 43153 . . . 43711

Please note: The cDNA sequence identified by the inventor using the gene prediction program NetPlantGene (http://www.cbs.dtu.dk/services/NetGene2/) was different than the one annotated in the database. Based on the new cDNA sequence the ORF predicted in the database was revised:
complement, 40721 . . . 41012, 41095 . . . 41364, 41513 . . . 41770, 42535 . . . 42662, 43153 . . . 43711

The protein sequence encoded by this cDNA is listed as SEQ ID NO: 4. The cDNA of AtCKX2 was cloned by RT-PCR from total RNA of AtCKX2 transgenic plant tissue with the one-step RT-PCR kit (Qiagen, Hilden, Germany) and sequenced using an ABI PRISM Big Dye Terminator cycle sequencing reaction kit (Perkin Elmer Applied Biosystems Division). This confirmed that the cDNA sequence identified and predicted by the inventor was correct. The new AtCKX2 cDNA sequence is listed as SEQ ID NO: 26. An 84-bp fragment corresponding to nucleotides 1171 through 1254 of the AtCKX2 cDNA is listed as SEQ ID NO: 31. The corresponding peptide sequence of this 84-bp cDNA sequence is listed as SEQ ID NO: 32.

Homologies
% identity with *Z. mays* cDNA:
    38.4% (Dnastar/MegAlign-Clustal method)
% similarity with *Z. mays* protein:
    37.5% (Dnastar/MegAlign-Clustal method)
% identity with other *Arabidopsis* cDNA's (range):
    34.9% (AtCKX6)-64.5% (AtCKX4) (Dnastar/MegAlign-Clustal method)
% similarity with other *Arabidopsis* proteins (range):
    36.5% (AtCKX6)-66.1% (AtCKX4) (Dnastar/MegAlign-Clustal method)

C. Gene name: AtCKX3 (*Arabidopsis thaliana* cytokinin oxidase-like protein 3, SEQ ID NO: 5)

Location in database (accession number, location on bac): AB024035, *Arabidopsis thaliana* genomic DNA, chromosome 5, P1 clone: MHM17, complete sequence.

No Prediction of the ORF in the Database.
The gene was identified by the inventor using several gene prediction programs including GRAIL (ftp://arthur.epm.ornl.gov/pub/xgrail), Genscan (http://CCR-081.mit.edu/GENSCAN html) and NetPlantGene (http://www.cbs.dtu.dk/services/NetGene2/):
complement, 29415 . . . 29718, 29813 . . . 30081, 30183 . . . 30443, 30529 . . . 30656, 32107 . . . 32716

The new AtCKX3 cDNA sequence identified by the inventor is listed as SEQ ID NO: 27

Predicted protein sequence, based on own ORF prediction: SEQ ID NO: 6

Homologies
% identity with *Z. mays* cDNA:
    38.7% (Dnastar/MegAlign-Clustal method)
% similarity with *Z. mays* protein:
    39.2% (Dnastar/MegAlign-Clustal method)
% identity with other *Arabidopsis* cDNA's (range):
    38.8% (AtCKX6)-51.0% (AtCKX2) (Dnastar/MegAlign-Clustal method)
% similarity with other *Arabidopsis* proteins (range):
    39.9% (AtCKX6)-46.7% (AtCKX2) (Dnastar/MegAlign-Clustal method)

D. Gene name: AtCKX4 (*Arabidopsis thaliana* cytokinin oxidase-like protein 4, SEQ ID NO: 7)

Location in database (accession number, location on bac):
1) AL079344, *Arabidopsis thaliana* DNA chromosome 4, BAC clone T16LA (Essa Project)
2) AL161575, *Arabidopsis thaliana* DNA chromosome 4, contig fragment No. 71.

ORF Predicted in the Database:
1) 76187 . . . 76814, 77189 . . . 77316, 77823 . . . 78080, 78318 . . . 78586, 78677 . . . 78968
2) 101002 . . . 101629, 102004 . . . 102131, 102638 . . . 102895, 103133 . . . 103401, 103492 . . . 103783

The AtCKX4 cDNA sequence is listed as SEQ ID NO: 28

Predicted protein sequence: SEQ ID NO: 8

Homologies
% identity with *Z. mays* cDNA:
    41.0% (Dnastar/MegAlign-Clustal method)
% similarity with *Z. mays* protein:
    41.0% (Dnastar/MegAlign-Clustal method)
% identity with other *Arabidopsis* cDNA's (range):
    35.2% (AtCKX6)-64.5% (AtCKX2) (Dnastar/MegAlign-Clustal method)
% similarity with other *Arabidopsis* proteins (range):
    35.1% (AtCKX6)-66.1% (AtCKX2) (Dnastar/MegAlign-Clustal method)

E. Gene name: AtCKX5 (*Arabidopsis thaliana* cytokinin oxidase-like protein 5, SEQ ID NO: 9)

Location in database (accession number, location on bac): AC023754, F1B16, complete sequence, chromosome 1

No Prediction of the ORF in the Database.
The gene was identified by the inventors using several gene prediction programs including GRAIL (ftp://arthur.epm.ornl.gov/pub/xgrail), Genscan (http://CCR-081.mit.edu/GENSCAN.html) and NetPlantGene (http://www.cbs.dtu.dk/services/NetGene2/).

43756 . . . 44347, 44435 . . . 44562, 44700 . . . 44966, 45493 . . . 45755, 46200 . . . 46560

The new AtCKX5 cDNA sequence identified and predicted by the inventor is listed as SEQ ID NO: 29. The predicted protein sequence for this cDNA is listed as SEQ ID NO: 10. A second potential ATG start codon is present 9 nucleotides more upstream in the genomic sequence. It is unclear which of these 2 start codons encodes the first amino acid of the protein. Therefore, a second potential AtCKX5 cDNA starting at this upstream start codon is also listed in this invention as SEQ ID NO: 34. The corresponding genomic sequence is listed as SEQ ID NO: 33 and the encoded protein as SEQ ID NO: 35.

Homologies
% identity with *Z. mays* cDNA:
  39.1% (Dnastar/MegAlign-Clustal method)
% similarity with *Z. mays* protein:
  36.6% (Dnastar/MegAlign-Clustal method)
% identity with other *Arabidopsis* cDNA's (range):
  40.1% (AtCKX2)-44.0% (AtCKX3) (Dnastar/MegAlign-Clustal method)
% similarity with other *Arabidopsis* proteins (range):
  41.6% (AtCKX4)-46.4% (AtCKX6) (Dnastar/MegAlign-Clustal method)

F. Gene name: AtCKX6 (*Arabidopsis thaliana* cytokinin oxidase-like protein 6, SEQ ID NO: 11)

Location in database (accession number, location on bac): AL163818, *Arabidopsis thaliana* DNA chromosome 3, P1 clone MAA21 (ESSA project).

ORF Predicted in the Database:
46630 . . . 47215, 47343 . . . 47470, 47591 . . . 47806, 47899 . . . 48161, 48244 . . . 48565

The AtCKX6 cDNA sequence is listed as SEQ ID NO: 30

Predicted protein sequence: SEQ ID NO: 12

Homologies
% identity with *Z. mays* cDNA:
  37.3% (Dnastar/MegAlign-Clustal method)
% similarity with *Z. mays* protein:
  36.1% (Dnastar/MegAlign-Clustal method)
% identity with other *Arabidopsis* cDNA's (range):
  34.9% (AtCKX2)-54.1% (AtCKX1) (Dnastar/MegAlign-Clustal method)
% similarity with other *Arabidopsis* proteins (range):
  35.1% (AtCKX4)-58.1% (AtCKX1) (Dnastar/MegAlign-Clustal method)

Genes AtCKX3 and AtCKX5 were not annotated as putative cytokinin oxidases in the database and ORFs for these genes were not given. Furthermore, the ORF (and consequently the protein structures) predicted for AtCKX2 was different from our own prediction and our prediction was confirmed by sequencing the AtCKX2 cDNA.

Figure 1:
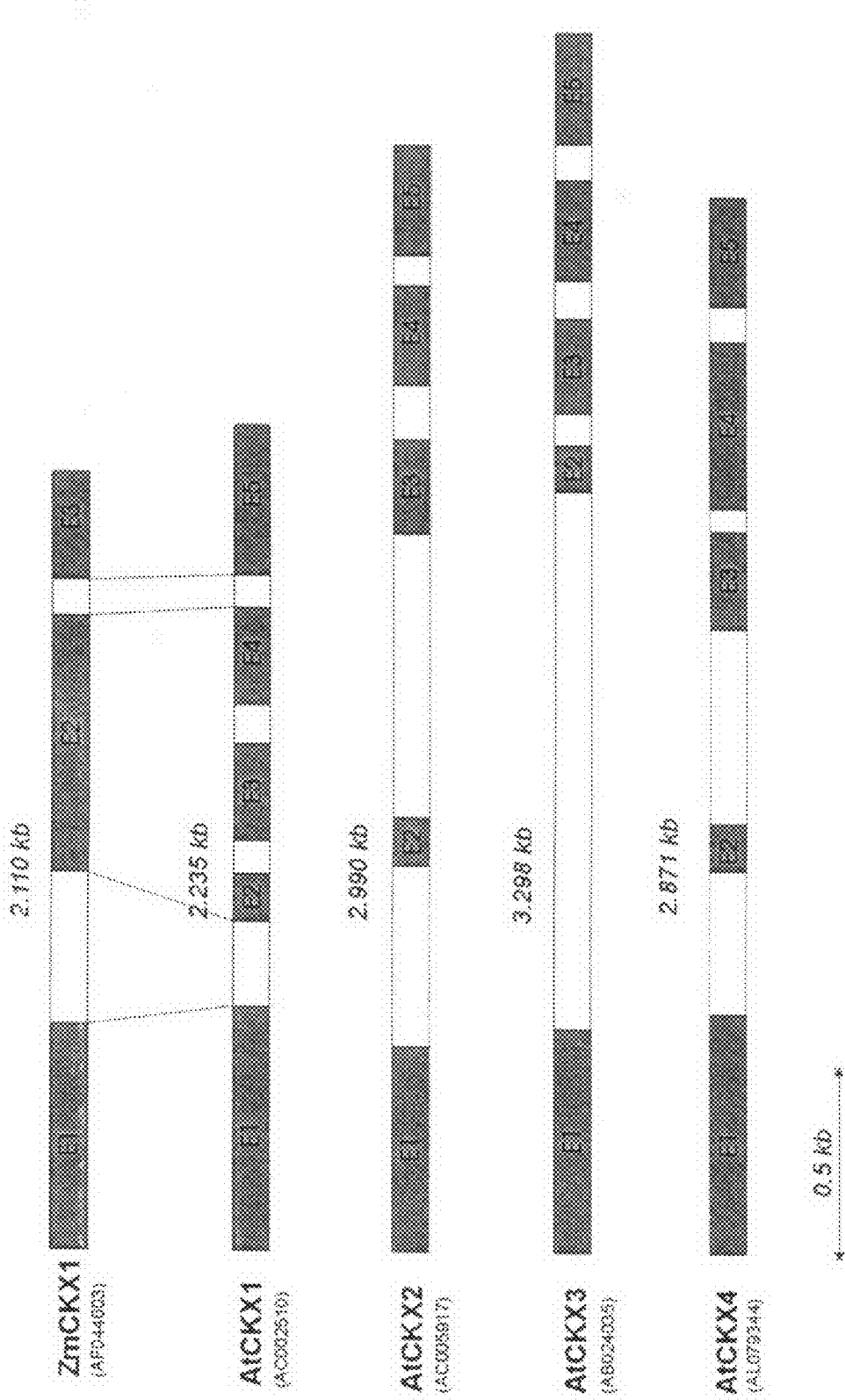
FIG. 1. Schematic representation of plant cytokinin oxidase genes.

A comparison of the gene structure of the *Arabidopsis* AtCKX genes 1 to 4 and the maize CKX gene is shown in FIG. 1.

The predicted proteins encoded by the *Arabidopsis* AtCKX genes show between 32% and 41% sequence similarity with the maize protein, while they show between 35% and 66% sequence similarity to each other. Because of this reduced sequence conservation, it is not clear a priori whether the *Arabidopsis* AtCKX genes encode proteins with cytokinin oxidase activity. An alignment of the *Arabidopsis* AtCKX predicted proteins 1 to 4 and the maize CKX gene is shown in FIG. 2.

Example 3

Transgenic Plants Overexpressing AtCKX1 Showed Increased Cytokinin Oxidase Activity and Altered Plant Morphology 1. Description of the Cloning Process The following primers were used to PCR amplify the AtCKX1 gene from *Arabidopsis thaliana*, accession Columbia (non-homologous sequences used for cloning are in lower case):

```
Sequence of 5' primer:
                                        (SEQ ID NO: 13)
cggtcgacATGGGATTGACCTCATCCTTACG Sequence of 3' primer:
                                        (SEQ ID NO: 14)
gcgtcgacTTATACAGTTCTAGGTTTCGGCAGTAT
```

A 2236 PCR fragment, amplified by these primers, was inserted in the Sal I site of pUC19. The insert was sequenced and confirmed that the PCR amplification product did not contain any mutations. The SalI/SalI fragment of this vector was subcloned in the SalI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX1 transcript at high levels (FIG. 3). Transgenic lines expressing AtCKX1 transcript also showed increased cytokinin oxidase activity as determined by a standard assay for cytokinin oxidase activity based on conversion of [2-$^3$H]iP to adenine as described (Motyka et al., 1996). This is exemplified for 2 tobacco and 2 *Arabidopsis* lines in Table 6. This result proves that the AtCKX1 gene encodes a protein with cytokinin oxidase activity.

TABLE 6

Cytokinin oxidase activity in AtCKX1 transgenic plant tissues

| Leaf sample | | Cytokinin oxidase activity |
| --- | --- | --- |
| Plant species | Plant line | (nmol Ade/mg protein.h) |
| *Arabidopsis* | Col-0 wild-type | 0.009 |
|  | CKX1-11 | 0.024 |
|  | CKX1-22 | 0.026 |
|  | CKX1-22 | 0.027 |
| Tobacco | SNN wild-type | 0.004 |
|  | CKX1-SNN-8 | 0.016 |
|  | CKX1-SNN-28 | 0.021 |

3. Phenotypic Description of the Transgenic Lines 3.1 In Tobacco:

The plants had a dwarfed phenotype with reduced apical dominance (FIG. 7 A, B and C) and increased root production (FIG. 8).

Five Categories of Phenotype:
1) strong—2 clones
2) intermediate—3 clones
3) weak—4 clones
4) tall plants (as WT) with large inflorescence—5 clones
5) similar to WT, 9 clones
Height (see FIG. 7 B and C)
WT: between 100-150 cm
weak: approximately 75 cm
intermediate: appr. 40-45 cm (main stem app. 25 cm but overgrown by side branches.
strong: appr. 10 cm The transgenics AtCKX1-48 and AtCKX1-50 displayed a strong phenotype. Below are measurements for stem elongation as compared to WT plants:

|  | Line | | |
| --- | --- | --- | --- |
| Days after germination | Wild-type Height (cm) | AtCKX1-48 Height (cm) | AtCKX1-50 Height (cm) |
| 47 | 9.5 ± 0.5 | 1.3 ± 0.3 | 1.2 ± 0.2 |
| 58 | 22.4 ± 2.3 | 2.2 ± 0.3 | 2.3 ± 0.3 |
| 68 | 35.3 ± 2.6 | 3.1 ± 0.5 | 2.6 ± 0.5 |
| 100 | 113.3 ± 9.8 | 7.1 ± 0.8 | 4.8 ± 0.9 |
| 117 | 138.6 ± 8.1 | 8.7 ± 0.7 | 6.6 ± 0.9 |
| 131 | 139.0 ± 9.3 | 9.3 ± 0.7 | 8.6 ± 1.0 |
| 152 | 136.6 ± 10.4 | 10.9 ± 1.1 | 10.0 ± 1.0 |
| 165 |  | 11.8 ± 1.9 | 11.4 ± 1.4 |
| 181 |  | 16.5 ± 1.7 | 14.9 ± 1.2 |
| 198 |  | 19.5 ± 1.5 | 18.1 ± 1.3 |

Experimental: Plants were grown in soil in a greenhouse. Data were collected from at least ten plants per line.

Leaves (See FIGS. 7 D and E)

The shape of leaves of AtCKX1 transgenic expressors was lanceolate (longer and narrow): the width-to-length ratio of mature leaves was reduced from 1:2 in wild type plants to 1:3 in AtCKX1 transgenics (FIG. 7 E). The number of leaves and leaf surface was reduced compared to WT (see FIG. 7 D). A prominent difference was also noted for progression of leaf senescence. In WT tobacco, leaf senescence starts in the most basal leaves and leads to a uniform reduction of leaf pigment (FIG. 7 E). By contrast, ageing leaves of strongly expressing AtCKX1 plants stayed green along the leaf veins and turned yellow in the intercostal regions, indicating altered leaf senescence. The texture of older leaves was more rigid.

Roots

In vitro grown plants highly expressing the gene were easily distinguishable from the WT by their ability to form more roots which are thicker (stronger) (FIG. 8 A), as well as by forming aerial roots along the stem.

The primary root was longer and the number of lateral and adventitious roots was higher as illustrated in FIG. 8 C for AtCKX1-50 overexpressing seedlings (see also Example 9).

The dose-response curve of root growth inhibition by exogenous cytokinin showed that roots of transgenic seedlings are more cytokinin resistant than WT roots (FIG. 8 D). The resistance of AtCKX1 transgenics to iPR was less marked than for AtCKX2, which is consistent with the smaller changes in iP-type cytokinins in the latter (see Table 10).

A large increase in root biomass was observed for adult plants grown in soil (see FIG. 8 B for a plant grown in soil for 4 to 5 months) despite the fact that growth of the aerial plant parts was highly reduced.

Internode Distance
intermediate phenotype: the $5^{th}$ internode below inflorescence is about 2.5 cm long and $9^{th}$ internode was about 0.5 cm long compared to 5 cm and 2 cm for the length of the $5^{th}$ and $9^{th}$ internode respectively, in WT plants.

strong phenotype: plant AtCKX1-50 The length of the $20^{th}$ internode from the bottom measured at day 131 after germination was 1.3±0.4 mm compared to 39.2±3.8 mm for WT Apical Dominance and Branching More side branches were formed indicating reduced apical dominance compared to WT plants during vegetative growth (see FIG. 9). The side branches overgrew the main stem, reaching a height of 40-45 cm for intermediate AtCKX1 expressors. Even secondary branches appeared. However, the buds were not completely released from apical dominance, i.e. lateral shoots did not really continue to develop. The reduced apical dominance might be due to reduced auxin production by the smaller shoot apical meristem (see Example 10).

Reproductive Development

The onset of flowering in AtCKX1 transgenics was delayed, the number of flowers and the seed yield per capsule was reduced. The size of flowers was not altered in transgenic plants and the weight of the individual seeds was comparable to the weight of seeds from wild type plants. Data for two representative AtCKX1 transgenics is summarized below:

| A. Onset of flowering | | | |
| --- | --- | --- | --- |
|  | Line | | |
|  | Wild-type | AtCKX1-48 | AtCKX1-50 |
| Flowering time (DAG) | 106.2 ± 3.3 | 193.3 ± 4.3 | 191.8 ± 3.8 |

Experimental: Data collected for at least ten plants per line. The full elongation of the first flower was defined as onset of flowering. DAG=days after germination.

| B. Number of seed capsules per plant | | | |
| --- | --- | --- | --- |
|  | Line | | |
|  | Wild-type | AtCKX1-48 | AtCKX1-50 |
| Number of capsules | 83.33 ± 5.13 | 2.00 ± 1.00 | 2.60 ± 1.67 |

Experimental: Number of seed capsules was determined at least from 5 different plants. Please note that these plants were grown under greenhouse conditions during winter time. This affects negatively the number of flowers that are formed, in particular in the transgenic clones. However, the general picture that they form a reduced number of flowers is correct. n.d., not determined

C. Seed yield/capsule (mg)

| | Line | | |
|---|---|---|---|
| | Wild-type | AtCKX1-48 | AtCKX1-50 |
| Seed/capsule (mg) | 87.41 ± 28.75 | 23.83 ± 13.36 | 61.8 ± 40.66 |

Experimental: Seed yield was determined for at least 12 seed capsules. The size of seed capsules was very variable, hence the large standard deviations. n.d., not determined

D. Weight of 100 seeds (mg)

| | Line | | |
|---|---|---|---|
| | Wild-type | AtCKX1-48 | AtCKX1-50 |
| Seeds weight (mg) | 9.73 ± 0.44 | 10.70 ± 1.60 | 9.54 ± 0.94 |

Experimental: The seed biomass was determined as the weight of 100 seed from at least 5 different seed capsules. n.d., not determined 3.2 In *Arabidopsis* onset of germination was same as for WT the total root system was enlarged and the number of side roots and adventitious roots was enhanced (see FIG. 4 A through D)

the growth of aerial organs was reduced resulting in a dwarfed phenotype (see FIGS. 4 E and F) and the leaf biomass was reduced. Leaf and flower formation is delayed.

the life cycle was longer compared to WT and the seed yield was lower compared to WT The following morphometric data illustrate these phenotypes:

Root Development

A. Total length of the root system

| | Line | | |
|---|---|---|---|
| | Wild-type | AtCKX1-11 | AtCKX1-15 |
| Length (mm) | 32.5 | 76.5 | 68.4 |

B. Primary root length

| | Line | | |
|---|---|---|---|
| | Wild-type | AtCKX1-11 | AtCKX1-15 |
| Length (mm) | 32.3 ± 3.8 | 52.3 ± 4.8 | 39.9 ± 4.2 |

C. Lateral roots (LR) length

| | Line | | |
|---|---|---|---|
| | Wild-type | AtCKX1-11 | AtCKX1-15 |
| Length (mm) | 0.2 ± 0.4 | 15.6 ± 11.0 | 10.4 ± 7.6 |

D. Adventitious roots length

| | Line | | |
|---|---|---|---|
| | Wild-type | AtCKX1-11 | AtCKX1-15 |
| Length (mm) | 0.03 ± 0.18 | 8.6 ± 8.5 | 19.1 ± 11.0 |

E. Number of lateral roots (LR)

| | Line | | |
|---|---|---|---|
| | Wild-type | AtCKX1-11 | AtCKX1-15 |
| Number of LR | 0.3 ± 0.5 | 10.4 ± 5.4 | 2.6 ± 1.1 |

F. Number of adventitious roots (AR)

| | Line | | |
|---|---|---|---|
| | Wild-type | AtCKX1-11 | AtCKX1-15 |
| Number of AR | 0.03 ± 0.18 | 1.6 ± 1.1 | 2.6 ± 1.1 |

Experimental: Measurements were carried out on plants 8 days after germination in vitro on MS medium. At least 17 plants per line were scored.

Shoot Development

A. Leaf surface

| | Line | | | |
|---|---|---|---|---|
| | Wild-type | AtCKX1-11-7 T3 homozygous plants | AtCKX1-11-12 T3 homozygous plants | AtCKX1-15-1 T3 homozygous plants |
| Leaf surface (cm$^2$) | 21.16 ± 1.73 | 2.28 ± 0.58 | 2.62 ± 0.28 | 1.66 ± 0.22 |

Experimental: Leaf surface area of main rosette leaves formed after 30 days after germination was measured. 3 plants per clone were analyzed.

Reproductive Development

| | Onset of flowering | | | |
|---|---|---|---|---|
| | | Line | | |
| | Wild-type | AtCKX1-11 T3 heterozygous plants | AtCKX2-2 T2 heterozygous plants | AtCKX2-5 T2 heterozygous plants |
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG=days after germination Conclusion: The analysis of AtCKX1 transgenic *Arabidopsis* plants confirmed largely the results obtained from tobacco and indicates the general nature of the consequences of a reduced cytokinin content. The total root system was enlarged (the total root length was increased app. 110-140% in AtCKX1 transgenics), the shoot developed more slowly (retarded flowering) and the leaf biomass was reduced. The seed yield was lower in the transgenics as well.

Example 4

Transgenic Plants Overexpressing AtCKX2 Showed Increased Cytokinin Oxidase Activity and Altered Plant Morphology 1. Description of the Cloning Process The following primers were used to PCR amplify the AtCKX2 gene from *Arabidopsis thaliana*, accession Columbia (non-homologous sequences used for cloning are in lower case):

```
Sequence of 5' primer:
gcggtaccAGAGAGAGAAACATAAACAAATGGC     (SEQ ID NO: 15)

Sequence of 3' primer:
gcggtaccCAATTTTACTTCCACCAAAATGC       (SEQ ID NO: 16)
```

A 3104-bp PCR fragment, amplified by these primers, was inserted in the KpnI site of pUC19. The insert was sequenced to check that no differences to the published sequence were introduced by the PCR procedure. The KpnI/KpnI fragment of this vector was subcloned in the KpnI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX2 transcript at high levels (FIG. 6). Transgenic lines expressing AtCKX2 transcript also showed increased cytokinin oxidase activity. This is exemplified for 2 tobacco and 3 *Arabidopsis* lines in Table 7. This result proves that the AtCKX2 gene encodes a protein with cytokinin oxidase activity.

TABLE 7

| Cytokinin oxidase activity in AtCKX2 transgenic plant tissues | | |
|---|---|---|
| Sample | | |
| Plant species and tissue | Plant line | Cytokinin oxidase activity (nmol Ade/mg protein.h) |
| *Arabidopsis* callus | Col-0 wild-type | 0.037 |
| | CKX2-15 | 0.351 |
| | CKX2-17 | 0.380 |
| | CKX2-55 | 0.265 |
| Tobacco leaves | SNN wild-type | 0.009 |
| | CKX2-SNN-18 | 0.091 |
| | CKX2-SNN-19 | 0.091 |

3. Phenotypic Description of the Transgenic Lines 3.1 In tobacco (see FIG. 7 to 10):
Three categories of phenotype:
1) strong—15 clones (similar to intermediate phenotype of AtCKX1)
2) weak—6 clones
3) others—similar to WT plants, 7 clones Aerial Plant Parts The observations concerning plant height, internode distance, branching, leaf form and yellowing were similar as for AtCKX1 transgenics with some generally minor quantitative differences in that the dwarfing characteristics were more severe in AtCKX1 transgenics than in AtCKX2 transgenics (compare AtCKX1 plants with AtCKX2 plants in FIGS. 7 A and B). This is illustrated below for stem elongation and internode distance measurements of clones with a strong phenotype AtCKX2-38 and AtCKX2-40:

| | Stem elongation | | |
|---|---|---|---|
| | | Line | |
| Days after germination | Wild-type Height (cm) | AtCKX2-38 Height (cm) | AtCKX2-40 Height (cm) |
| 47 | 9.5 ± 0.5 | 2.4 ± 0.1 | 2.6 ± 0.2 |
| 58 | 22.4 ± 2.3 | 5.5 ± 0.7 | 5.3 ± 0.5 |
| 68 | 35.3 ± 2.6 | 7.1 ± 0.8 | 7.0 ± 0.7 |
| 100 | 113.3 ± 9.8 | 15.5 ± 2.5 | 20.3 ± 6.4 |
| 117 | 138.6 ± 8.1 | 19.8 ± 3.8 | 29.5 ± 6.0 |
| 131 | 139.0 ± 9.3 | 26.5 ± 7.0 | 33.4 ± 5.8 |
| 152 | 136.6 ± 10.4 | 33.7 ± 6.3 | 33.9 ± 6.4 |
| 165 | | 36.2 ± 4.3 | |

Experimental: Plants were grown in soil in a green house. Data were collected from at least ten plants per line.

| | Internode distance | |
|---|---|---|
| | | Line |
| | Wild-type | AtCKX2-38 |
| Internode distance (mm) | 39.2 ± 3.8 | 7.2 ± 1.6 |

Experimental: The length of the $20^{th}$ internode from the bottom was measured at day 131 after germination.

Roots

In vitro grown plants highly expressing the gene were easily distinguishable from WT plants by their ability to form more roots which are thicker (stronger) as well as by forming aerial roots along the stem.

The primary root was longer and the number of lateral and adventitious roots was higher as illustrated in FIG. 8 C for AtCKX2-38 overexpressing seedlings (see also Example 9).

The dose-response curve of root growth inhibition by exogenous cytokinin showed that roots of transgenic seedlings were more cytokinin resistant than WT roots (FIG. 8 D). The resistance of AtCKX1-28 transgenics to iPR was less marked than for AtCKX2-38, which is consistent with the smaller changes in iP-type cytokinins in the latter (see Table 10).

An increase in fresh and dry weight of the root biomass of TO lines of AtCKX2 transgenic plants compared to WT was observed for plant grown in soil, as illustrated in the following table:

|  | Line | |
|---|---|---|
|  | Wild-type | AtCKX2 (T0) |
| Fresh weight (g) | 45.2 ± 15.4 | 77.1 ± 21.3 |
| Dry weight (g) | 6.3 ± 1.9 | 8.6 ± 2.2 |

Experimental: Six WT plants and six independent TO lines of 35S::AtCKX2 clone were grown on soil. After flowering the root system was washed with water, the soil was removed as far as possible and the fresh weight and dry weight was measured.

An increase in fresh and dry weight of the root biomass was also observed for F1 progeny of AtCKX2 transgenics grown in hydroponics as compared to WT, as illustrated in the following table:

|  | Line | | |
|---|---|---|---|
|  | Wild-type | AtCKX2-38 | AtCKX2-40 |
| Fresh weight ROOT (g) | 19.76 ± 6.79 | 33.38 ± 7.76 | 50.04 ± 15.59 |
| Dry weight ROOT (g) | 2.36 ± 0.43 | 2.61 ± 0.39 | 3.52 ± 1.06 |
| Fresh weight SHOOT (g) | 159.8 ± 44.53 | 33.66 ± 2.67 | 48.84 ± 11.83 |
| Fresh weight SHOOT/ROOT ratio | 8.24 ± 0.63 | 1.04 ± 0.18 | 1.08 ± 0.51 |

Experimental: Soil grown plants were transferred 60 days after germination to a hydroponic system (Hoagland's solution) and grown for additional 60 days. The hydroponic solution was aerated continuously and replaced by fresh solution every third day.

In summary, transgenic plants grown in hydroponic solution formed approximately 65-150% more root biomass (fresh weight) than wild type plants. The increase in dry weight was 10-50%. This difference is possibly in part due to the larger cell volume of the transgenics. This reduces the relative portion of cell walls, which forms the bulk of dry matter material. The shoot biomass was reduced to 20%-70% of wild type shoots. The difference in fresh weight leads to a shift in the shoot/root ratio, which was approximately 8 in wild type but approximately 1 in the transgenic clones.

Conclusion:

An increase in root growth and biomass was observed for AtCKX2 transgenic seedlings and adult plants grown under different conditions compared to WT controls despite the fact that growth of the aerial plant parts is reduced. Quantitative differences were observed between different transgenic plants: higher increases in root biomass were observed for the strongest expressing clones.

Reproductive Development

The onset of flowering in AtCKX2 transgenics was delayed, the number of flowers and the seed yield per capsule was reduced. These effects were very similar to those observed in the AtCKX1 transgenic plants but they were less prominent in the AtCKX2 transgenics, as indicated in the tables below. The size of flowers was not altered in transgenic plants and the weight of the individual seeds was comparable to the weight of seeds from wild type plants.

| A. Onset of flowering | | | | | |
|---|---|---|---|---|---|
| Line | Wild-type | AtCKX1-48 | AtCKX1-50 | AtCKX2-38 | AtCKX2-40 |
| Flowering time (DAG) | 106.2 ± 3.3 | 193.3 ± 4.3 | 191.8 ± 3.8 | 140.6 ± 6.5 | 121.9 ± 9.8 |

Experimental: Data collected for at least ten plants per line. The full elongation of the first flower was defined as onset of flowering. DAG=days after germination.

| B. Number of seed capsules per plant | | | | | |
|---|---|---|---|---|---|
| Line | Wild-type | AtCKX1-48 | AtCKX1-50 | AtCKX2-38 | AtCKX2-40 |
| Number of capsules | 83.33 ± 5.13 | 2.00 ± 1.00 | 2.60 ± 1.67 | 4.30 ± 2.58 | n.d. |

Experimental: Number of seed capsules was determined at least from 5 different plants. Please note that these plants were grown under green house conditions during winter time. This affects negatively the number of flowers that are formed, in particular in the transgenic clones. However, the general picture that they form a reduced number of flowers is correct. n.d., not determined

| C. Seed yield/capsule (mg) | | | | | |
|---|---|---|---|---|---|
| Line | Wild-type | AtCKX1-48 | AtCKX1-50 | AtCKX2-38 | AtCKX2-40 |
| Seed/capsule (mg) | 87.41 ± 28.75 | 23.83 ± 13.36 | 61.8 ± 40.66 | 46.98 ± 29.30 | n.d. |

Experimental: Seed yield was determined for at least 12 seed capsules. The size of seed capsules was very variable, hence the large standard deviations. n.d., not determined

| D. Weight of 100 seeds (mg) | | | | | |
|---|---|---|---|---|---|
| Line | Wild-type | AtCKX1-48 | AtCKX1-50 | AtCKX2-38 | AtCKX2-40 |
| Seeds weight (mg) | 9.73 ± 0.44 | 10.70 ± 1.60 | 9.54 ± 0.94 | 10.16 ± 0.47 | n.d. |

Experimental: The seed biomass was determined as the weight of 100 seed from at least 5 different seed capsules. n.d., not determined 3.2 In *Arabidopsis*:

The following morphometric data were obtained for AtCKX2 transgenics:

Root Development

| A. Total length of the root system | | | |
|---|---|---|---|
| Line | Wild-type | AtCKX2-2 | AtCKX2-5 |
| Length (mm) | 32.5 | 50.6 | 48.5 |

| B. Primary root length | | | |
|---|---|---|---|
| Line | Wild-type | AtCKX2-2 | AtCKX2-5 |
| Length (mm) | 32.3 ± 3.8 | 30.7 ± 4.8 | 31.6 ± 6.8 |

| C. Lateral roots length | | | |
|---|---|---|---|
| Line | Wild-type | AtCKX2-2 | AtCKX2-5 |
| Length (mm) | 0.2 ± 0.4 | 5.5 ± 9.0 | 1.9 ± 2.5 |

| D. Adventitious roots length | | | |
|---|---|---|---|
| Line | Wild-type | AtCKX2-2 | AtCKX2-5 |
| Length (mm) | 0.03 ± 0.18 | 14.4 ± 10.2 | 14.9 ± 9.1 |

| E. Number of lateral roots (LR) | | | |
|---|---|---|---|
| Line | Wild-type | AtCKX2-2 | AtCKX2-5 |
| Number of LR | 0.3 ± 0.5 | 2.9 ± 2.3 | 1.9 ± 1.0 |

| F. Number of adventitious roots (AR) | | | |
|---|---|---|---|
| Line | Wild-type | AtCKX2-2 | AtCKX2-5 |
| Number of AR | 0.03 ± 0.18 | 1.8 ± 0.9 | 1.8 ± 1.0 |

Experimental: Measurements were carried out on plants 8 d.a.g. in vitro on MS medium. At least 17 plants per line were scored.

Shoot Development

| Leaf surface | | | | |
|---|---|---|---|---|
| Line | Wild-type | AtCKX2-2 T2 heterozygous plants | AtCKX2-5 T2 heterozygous plants | AtCKX2-9 T2 heterozygous plants |
| Leaf surface (cm²) | 21.16 ± 1.73 | 8.20 ± 2.35 | 8.22 ± 0.55 | 7.72 ± 0.85 |

Experimental: Leaf surface area of main rosette leaves formed after 30 days after germination was measured. 3 plants per clone were analyzed.

Reproductive Development

| Onset of flowering | | | | |
|---|---|---|---|---|
| Line | Wild-type | AtCKX1-11 T3 heterozygous plants | AtCKX2-2 T2 heterozygous plants | AtCKX2-5 T2 heterozygous plants |
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG=days after germination.

Conclusion: *Arabidopsis* AtCKX2 transgenics had reduced leaf biomass and a dwarfing phenotype similar to AtCKX1 transgenics (compare FIG. 5 with FIG. 4 F). The total root system was also enlarged in AtCKX2 transgenic *Arabidopsis*. The total root length is increased approximately 50% in AtCKX2 transgenics. The AtCKX1 transgenics have longer primary roots, more side roots and form more adventitious roots. AtCKX2 transgenics lack the enhanced growth of the primary root but form more side roots and lateral roots than WT.

Summary:

The phenotypes observed for AtCKX2 transgenics were very similar but not identical to the AtCKX1 transgenics, which in turn were very similar but not identical to the results obtained for the tobacco transgenics. This confirms the general nature of the consequences of a reduced cytokinin content in these two plant species and therefore, similar phenotypes can be expected in other plant species as well. The main difference between tobacco and *Arabidopsis* is the lack of enhanced primary root growth in AtCKX2 overexpressing plants.

Example 5

Transgenic Plants Overexpressing AtCKX3 Showed Increased Cytokinin Oxidase Activity and Altered Plant Morphology

1. Description of the Cloning Process

The following primers were used to PCR amplify the AtCKX3 gene from *Arabidopsis thaliana*, accession Columbia (non-homologous sequences used for cloning are in lower case):

```
Sequence of 5' primer:
gcggtaccTTCATTGATAAGAATCAAGCTATTCA    (SEQ ID NO: 17)

Sequence of 3' primer:
gcggtaccCAAAGTGGTGAGAACGACTAACA       (SEQ ID NO: 18)
```

A 3397-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines were identified that synthesize the AtCKX3 transcript at high levels (FIG. 11 A.). Transgenic tobacco lines expressing AtCKX3 transcript also showed increased cytokinin oxidase activity. This is exemplified for three plants in Table 8. This proves that the AtCKX3 gene encodes a protein with cytokinin oxidase activity.

TABLE 8

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| tobacco leaves | SNN wild-type | 0.011 |
| | CKX3-SNN-3 | 0.049 |
| | CKX3-SNN-6 | 0.053 |
| | CKX3-SNN-21 | 0.05 |

3. Plant Phenotypic Analysis

The phenotypes generated by overexpression of the AtCKX3 gene in tobacco and *Arabidopsis* were basically similar as those of AtCKX1 and AtCKX2 expressing plants, i.e. enhanced rooting and dwarfing. However, overexpression of the AtCKX3 gene in tobacco resulted in a stronger phenotype compared to AtCKX2. In this sense AtCKX3 overexpression was more similar to AtCKX1 overexpression.

Example 6

Transgenic Plants Overexpressing AtCKX4 Showed Increased Cytokinin Oxidase Activity and Altered Plant Morphology

1. Description of the Cloning Process

The following primers were used to PCR amplify the AtCKX4 gene from *Arabidopsis thaliana*, accession Columbia (non-homologous sequences used for cloning are in lower case):

```
Sequence of 5' primer:
gcggtaccCCCATTAACCTACCCGTTTG          (SEQ ID NO: 19)

Sequence of 3' primer:
gcggtaccAGACGATGAACGTACTTGTCTGTA      (SEQ ID NO: 20)
```

A 2890-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBin-Hyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines synthesized the AtCKX4 transcript at high levels (FIG. 11 B.). Transgenic lines expressing AtCKX4 transcript also showed increased cytokinin oxidase activity. This is exemplified for 3 *Arabidopsis* and 3 tobacco lines in Table 9. This result proves that the AtCKX4 gene encodes a protein with cytokinin oxidase activity.

TABLE 9

Cytokinin oxidase activity in AtCKX4 transgenic plant tissues

| Sample | | |
|---|---|---|
| Plant species and tissue | Plant line | Cytokinin oxidase activity (nmol Ade/mg protein.h) |
| *Arabidopsis* callus | Col-0 wild-type | 0.037 |
| | CKX4-37 | 0.244 |
| | CKX4-40 | 0.258 |
| | CKX4-41 | 0.320 |
| tobacco leaves | SNN wild-type | 0.011 |
| | CKX4-SNN-3 | 0.089 |
| | CKX4-SNN-18 | 0.085 |
| | CKX4-SNN-27 | 0.096 |

Overall, the data showed that the apparent $K_m$ values for the four cytokinin oxidases were in the range of 0.2 to 9.5 µM with iP as substrate, which further demonstrates that the proteins encoded by AtCKX1 through 4 are indeed cytokinin oxidase enzymes as disclosed herein.

3. Plant Phenotypic Analysis

The phenotypes generated by overexpression of the AtCKX4 gene in tobacco and *Arabidopsis* were basically similar as those of AtCKX1 and AtCKX2 expressing plants, i.e. enhanced rooting, reduced apical dominance, dwarfing and yellowing of intercostal regions in older leaves of tobacco. An additional phenotype in tobacco was lanceolate leaves (altered length-to-width ratio).

General Observations of AtCKX Overexpressing Tobacco Plants

Overall, the phenotypic analysis demonstrated that AtCKX gene overexpression caused drastic developmental alterations in the plant shoot and root system in tobacco, including enhanced development of the root system and dwarfing of the aerial plant part. Other effects such as altered leaf senescence, formation of adventitious root on stems, and others were also observed as disclosed herein. The alterations were very similar, but not identical, for the different genes. In tobacco, AtCKX1 and AtCKX3 overexpressors were alike as were AtCKX2 and AtCKX4. Generally, the two former showed higher expression of the traits, particularly in the shoot. Therefore, a particular cytokinin oxidase gene may be preferred for achieving the phenotypes that are described in the embodiments of this invention.

Example 7

Cloning of the AtCKX5 Gene

The following primers were used to PCR amplify the AtCKX5 gene from *Arabidopsis thaliana*, accession Columbia (non-homologous sequences used for cloning are in lower case):

```
Sequence of 5' primer:
ggggtaccTTGATGAATCGTGAAATGAC        (SEQ ID NO: 21)

Sequence of 3' primer:
ggggtaccCTTTCCTCTTGGTTTTGTCCTGT     (SEQ ID NO: 22)
```

The sequence of the 5' primer includes the two potential start codons of the AtCKX5 protein, the most 5' start codon is underlined and a second ATG is indicated in italics.

A 2843-bp PCR fragment, produced by this PCR amplification, was inserted as a blunt-end product in pCR-Blunt II-TOPO cloning vector (Invitrogen).

Example 8

Cloning of the AtCKX6 Gene

The following primers were used to PCR amplify the AtCKX6 gene from *Arabidopsis thaliana*, accession Columbia (non-homologous sequences used for cloning are in lower case):

```
Sequence of 5' primer:
gctctagaTCAGGAAAAGAACCATGCTTATAG    (SEQ ID NO: 23)

Sequence of 3' primer:
gctctagaTCATGAGTATGAGACTGCCTTTTG    (SEQ ID NO: 24)
```

A 1949-bp PCR fragment, produced by this PCR amplification, was inserted as a blunt-end product in pCR-Blunt II-TOPO cloning vector (Invitrogen).

Example 9

Tobacco Seedling Growth Test Demonstrated Early Vigor of AtCKX Transgenics

Seeds of AtCKX1-50 and AtCKX2-38 overexpressing transgenics and WT tobacco were sown in vitro on MS medium, brought to culture room 4 days after cold treatment and germinated after 6 days. Observations on seedling growth were made 10 days after germination (see also FIG. 8C) and are summarized below. At least 20 individuals were scored per clone. Similar data have been obtained in two other experiments.

A. Total length of the root system

| Line | Wild-type | AtCKX1-50 | AtCKX2-38 |
|---|---|---|---|
| Length (mm) | 61.1 | 122.0 | 106.5 |

B. Primary root length

| Line | Wild-type | AtCKX1-50 | AtCKX2-38 |
|---|---|---|---|
| Length (mm) | 32.3 ± 2.6 | 50.8 ± 4.5 | 52.4 ± 4.8 |

C. Lateral roots length

| Line | Wild-type | AtCKX1-50 | AtCKX2-38 |
|---|---|---|---|
| Length (mm) | 9.8 ± 5.5 | 18.0 ± 8.1 | 13.0 ± 6.0 |

D. Adventitious roots length

| Line | Wild-type | AtCKX1-50 | AtCKX2-38 |
|---|---|---|---|
| Length (mm) | 19.0 ± 5.0 | 53.0 ± 12.0 | 42.0 ± 9.8 |

E. Number of lateral roots (LR)

| Line | Wild-type | AtCKX1-50 | AtCKX2-38 |
|---|---|---|---|
| Number of LR | 1.9 ± 0.9 | 6.5 ± 2.2 | 5.6 ± 2.0 |

F. Number of adventitious roots (AR)

| Line | Wild-type | AtCKX1-50 | AtCKX2-38 |
|---|---|---|---|
| Number of AR | 2.2 ± 0.6 | 3.5 ± 0.9 | 3.6 ± 1.3 |

AtCKX1 and AtCKX2 Plants, General Observations:

Seedlings of AtCKX1 and AtCKX2 overexpressing tobacco plants had 60% more adventitious roots and three times more lateral roots than untransformed control plants 10 days after germination. The length of the primary root was increased by about 70%. This—together with more and longer side roots and secondary roots—resulted in a 70-100% increase in total root length. These results showed that overexpression of cytokinin oxidase enhances the growth and development of both the main root and the adventitious roots, resulting in early vigor.

Example 10

Histological Analysis of Altered Plant Morphology in AtCKX1 Overexpressing Tobacco Plants Microscopic analysis of different tissues revealed that the morphological changes in AtCKX transgenics are reflected by distinct changes in cell number and rate of cell formation (see FIG. 10). The shoot apical meristem (SAM) of AtCKX1 transgenics was smaller than in wild type and fewer cells occupy the space between the central zone and the peripheral zone of lateral organ formation, but the cells were of the same size (FIG. 10 A). The reduced cell number and size of the SAM as a consequence of a reduced cytokinin content indicates that cytokinins have a role in the control of SAM proliferation. No obvious changes in the differentiation pattern occurred, suggesting that the spatial organization of the differentiation zones in the SAM is largely independent from cell number and from the local cytokinin concentration. The overall tissue pattern of leaves in cytokinin oxidase overexpressors was unchanged. However, the size of the phloem and xylem was significantly reduced (FIG. 10 B). By contrast, the average cell size of leaf parenchyma and epidermal cells was increased four- to fivefold (FIG. 10 C, D). New cells of AtCKX1 transgenics are formed at 3-4% of the rate of wild type leaves and final leaf cell number was estimated to be in the range of 5-6% of wild type. This indicates an absolute requirement for cytokinins in leaves to maintain the cell division cycle. Neither cell size nor cell form of floral organs was altered and seed yield per capsule was similar in wild type and AtCKX transgenic plants. The cell population of root meristems of AtCKX1 transgenic plants was enlarged approximately 4-fold and the cell numbers in both the central and lateral columnella were enhanced (FIG. 10 E, F). The final root diameter was increased by 60% due to an increased diameter of all types of root cells. The radial root patterns was identical in wild type and transgenics, with the exception that frequently a fourth layer of cortex cells was noted in transgenic roots (FIG. 10 G). The increased cell number and the slightly reduced cell length indicates that the enhanced root growth is due to an increased number of cycling cells rather than increased cell growth. In the presence of lowered cytokinin content, root meristem cells must undergo additional rounds of mitosis before they leave the meristem and start to elongate. The exit from the meristem is therefore regulated by a mechanism that is sensitive to cytokinins. Apparently, cytokinins have a negative regulatory role in the root meristem and wild type cytokinin concentrations are inhibitory to the development of a maximal root system. Therefore, reducing the level of active cytokinins by overexpressing cytokinin oxidases stimulates root development, which results in an increase in the size of the root with more lateral and adventitious roots as compared to WT plants.

Example 11

AtCKX1 and AtCKX2-overexpressing Tobacco Plants had a Reduced Cytokinin Content

Among the 16 different cytokinin metabolites that were measured, the greatest change occurred in the iP-type cytokinins in AtCKX2 overexpressers (Table 10): the overall decrease in the content of iP-type cytokinins is more pronounced in AtCKX2 expressing plants than in AtCKX1 transgenics. AtCKX1 transgenics showed a stronger phenotype in the shoot. It is not known which cytokinin metabolite is relevant for the different traits that were analysed. It may be that different cytokinin forms play different roles in the various development processes. Smaller alterations were noted for Z-type cytokinins, which could be due to a different accessibility of the substrate or a lower substrate specificity of the protein. The total content of iP and Z metabolites in individual transgenic clones was between 31% and 63% of wild type. The cytokinin reserve pool of O-glucosides was also lowered in the transgenics (Table 10). The concentration of N-glucosides and DHZ-type cytokinins was very low and was not or only marginally, altered in transgenic seedlings (data not shown).

Table 10. Cytokinin content of AtCKX transgenic plants. Cytokinin extraction, immunopurification, HPLC separation and quantification by ELISA methods was carried out as described by Faiss et al., 1997. Three independently pooled samples of approximately 100 two week old seedlings (2.5 g per sample) were analysed for each clone. Concentrations are in pmol×g fresh weight$^{-1}$. Abbreviations: iP, $N^6$-($\Delta^2$isopentenyl)adenine; iPR, $N^6$-($\Delta^2$ isopentenyl)adenine riboside; iPRP, $N^6$-($\Delta^2$ isopentenyl)adenine riboside 5'-monophosphate; Z, trans-zeatin; ZR, zeatin riboside; ZRP, zeatin riboside 5'-monophosphate; ZOG, zeatin O-glucoside; ZROG, zeatin riboside O-glucoside.

| Line | | AtCKX1-2 | | AtCKX1-28 | | AtCKX2-38 | | AtCKX2-40 | |
|---|---|---|---|---|---|---|---|---|---|
| Cytokinin meta-bolite | WT Concentration | Concentration | % of WT | Concentration | % of WT | Concentration | % of WT | Concentration | % of WT |
| iP | 5.90 ± 1.80 | 4.76 ± 0.82 | 81 | 4.94 ± 2.62 | 84 | 1.82 ± 0.44 | 31 | 2.85 ± 0.62 | 48 |
| iPR | 2.36 ± 0.74 | 1.53 ± 0.14 | 65 | 0.75 ± 0.27 | 32 | 0.55 ± 0.39 | 23 | 0.89 ± 0.07 | 38 |
| iPRP | 3.32 ± 0.73 | 0.87 ± 0.26 | 26 | 1.12 ± 0.13 | 34 | 0.80 ± 0.48 | 24 | 1.68 ± 0.45 | 51 |
| Z | 0.24 ± 0.06 | 0.17 ± 0.02 | 71 | 0.22 ± 0.03 | 92 | 0.21 ± 0.06 | 88 | 0.22 ± 0.02 | 92 |
| ZR | 0.60 ± 0.13 | 0.32 ± 0.12 | 53 | 0.34 ± 0.03 | 57 | 0.34 ± 0.15 | 57 | 0.32 ± 0.05 | 53 |
| ZRP | 0.39 ± 0.17 | 0.42 ± 0.11 | 107 | 0.28 ± 0.15 | 72 | 0.06 ± 0.01 | 15 | 0.17 ± 0.06 | 44 |
| ZOG | 0.46 ± 0.20 | 0.32 ± 0.09 | 70 | 0.26 ± 0.13 | 57 | 0.20 ± 0.07 | 43 | 0.12 ± 0.02 | 26 |
| ZROG | 0.48 ± 0.17 | 0.30 ± 0.06 | 63 | 0.47 ± 0.02 | 98 | 0.23 ± 0.05 | 48 | 0.30 ± 0.13 | 63 |
| Total | 13.75 | 8.69 | 63 | 8.38 | 61 | 4.21 | 31 | 6.55 | 48 |

Example 12

Grafting Experiments Showed that Dwarfing and Enhanced Root Development Due to AtCKX Overexpression is Confined to Transgenic Tissues To investigate which phenotypic effects of cytokinin oxidase overexpression are restricted to expressing tissues, i.e. are cell- or organ-autonomous traits, grafting experiments were performed. Reciprocal grafts were made between an AtCKX2 transgenic tobacco plant and a WT tobacco. The transgenic plant used in this experiment was AtCKX2-38, which displayed a strong phenotype characterized by enhanced root growth and reduced development of the aerial plant parts. As described in Example 3 through 6, these were two important phenotypes that resulted from cytokinin oxidase overexpression in tobacco and *arabidopsis*.

Plants were about 15 cm tall when grafted and the graft junction was about 10 cm above the soil. FIG. 12 shows plants 15 weeks after grafting. The main results were that: (i) the aerial phenotype of a WT scion grafted on a transgenic rootstock was similar to the WT control graft (=WT scion on WT rootstock). Importantly, this showed that overexpression of the AtCKX2 transgene in the rootstock did not induce dwarfing of the non-transgenic aerial parts of the plant (see FIG. 12 A). Improved root growth of the transgenic rootstock was maintained, indicating that improved root growth of AtCKX transgenics is autonomous and does not depend on an AtCKX transgenic shoot (FIG. 12 C). Interestingly, the WT scions grafted on the transgenic rootstocks looked healthier and were better developed. Notably, senescence of the basal leaves was retarded in these plants (see FIG. 12 A); (ii) the transgenic scion grafted on the WT rootstock looked similar to the aerial part of the transgenic plant from which it was derived, i.e. the shoot dwarfing phenotype is also autonomous and not dependent on the improved root growth (see FIG. 12 B).

In addition to the above-mentioned better appearance of WT shoots grafted on a transgenic rootstock, the formation of adventitious roots on the basal part of WT shoots was noted (FIG. 12 D, right plant). Formation of adventitious roots also occurred on the stem of AtCKX transgenics but not on stems of WT control grafts (FIG. 12 D, left plant) and therefore seems to be a non-autonomous trait.

In summary, it is disclosed in this invention that enhanced root formation and dwarfing of the shoot in AtCKX overexpressing tobacco are autonomous traits and can be uncoupled by grafting procedures. Surprisingly, grafting of a WT scion on an AtCKX transgenic rootstock resulted in more vigorously growing plants and retardation of leaf senescence.

As an alternative to grafting, tissue-specific promoters could be used for uncoupling the autonomous phenotypic effects of cytokinin overexpression. Therefore, it is disclosed in this invention that cytokinin oxidase overexpression in a tissue specific manner can be used to alter the morphology of a plant such as the shoot or root system.

Example 13

Expression of an AtCKX Gene Under a Root-specific Promoter in Transgenic Plants Leads to Increased Root Production An AtCKX gene (see example 4) is cloned under control of the root clavata homolog promoter of *Arabidopsis* (SEQ ID NO: 36), which is a promoter that drives root-specific expression. Other root-specific promoters may also be used for the purpose of this invention. See Table 5 for exemplary root-specific promoters.

Transgenic plants expressing the AtCKX gene specifically in the roots show increased root production without negatively affecting growth and development of the aerial parts of the plant. Positive effects on leaf senescence and growth of aerial plant parts are observed.

Example 14

Suppression of an AtCKX Gene Under a Senescence-induced Promoter in Transgenic Plants Leads to Delayed Leaf Senescence and Enhanced Seed Yield A chimeric gene construct derived from an AtCKX gene and designed to suppress expression of endogenous cytokinin oxidase gene(s) is cloned under control of a senescence-induced promoter. For example, promoters derived from senescence-associated genes (SAG) such as the SAG12 promoter can be used (Quirino et al., 2000). Transgenic plants suppressing endogenous cytokinin oxidase gene(s) specifically in senescing leaves show delayed leaf senescence and higher seed yield without negatively affecting the morphology and growth and development of the plant.

Example 15

Overexpression of an AtCKX Gene in the Female Reproductive Organs Leads to Parthenocarpic Fruit Development The open reading frame of an AtCKX gene is cloned under control of a promoter that confers overexpression in the female reproductive organs such as for example the DefH9 promoter from *Antirrhinum majus* or one of its homologues, which have high expression specificity in the placenta and ovules. Transgenic plants with enhanced cytokinin oxidase activity in these tissues show parthenocarpic fruit development.

Example 16

Overexpression of AtCKX Genes Result in Increased Seed and Cotyledon Size

Transgenic *Arabidopsis thaliana* plants that overexpress cytokinin oxidase (AtCKX) genes under control of the 35S promoter as described supra. Transgenic plants, in particular those expressing the AtCKX1 and AtCKX3 genes, developed seeds with increased size which was almost entirely due to an enlarged embryo. Details of the seed, embryo and early postembryonic phenotypes are shown in FIGS. 13 A through 13E. Table 11 shows seed weight of wild type and two independent clones for each of the four investigated AtCKX genes. Average weight was obtained by analysing five different batches of 200 seeds for each clone. A quantitative evaluation showed that the seed weight of AtCKX1 and AtCKX3 expressing clones was app. 1.8-2.3-fold higher than in wild type. Gain of weight for seeds of AtCKX2 and AtCKX4 expressing lines was in the range of 10-25% (Table 11 and FIG. 14).

The increases in size and weight for seeds, embryos, and cotyledons are unexpected as a reduced cytokinin content would have been expected to be associated with a reduced organ growth. One possible reason for the increases in seed, embryo, and cotyledon size is a previously unknown negative regulatory function of cytokinins in these storage organs. A negative regulatory functions of cytokinins in the control of organ growth is so far only known from roots (Werner et al. 2001). We propose, therefore, that localized expression of cytokinin oxidase genes in tissues where growth is negatively regulated by cytokinins leads to enhanced growth of this tissue. For example, localized expression of CKX genes during cotyledon development likely leads to enhanced growth of cotyledons and in species with cotyledons as storage organs, to enhanced yield and to an enhanced growth performance of seedlings. Total number of seeds is lowered in AtCKX1 and AtCKX3 expressers. There have been no previous reports however, of lower seed number in *Arabidopsis* being linked to an increase in size.

TABLE 11

|  | WT | CKX1-11-7 | CKX1-15-1 | CKX2-2-4 | CKX2-9-3 | CKX3-9-4 | CKX3-12-13 | CKX4-37-2 | CKX4-41-7 |
|---|---|---|---|---|---|---|---|---|---|
| Seed Weight | 0.0158 ± 0.0009 | 0.0372 ± 0.0015 | 0.0352 ± 0.0023 | 0.0201 ± 0.0017 | 0.0180 ± 0.0001 | 0.0340 ± 0.0027 | 0.0280 ± 0.0027 | 0.0185 ± 0.0004 | 0.0179 ± 0.0007 |
| % of WT | 100 | 235.5 | 222.6 | 126.7 | 113.7 | 215.0 | 176.7 | 116.8 | 112.7 |

REFERENCES

WO0105985. Method to modulate the expression of genes inducing the parthenocarpic trait in plants.

Alberts, B., Bray, D., Lewis, J., Raff, M., Roberts, K., and Watson, J. D. (1994). "Molecular Biology of the Cell." Garland Publishing Inc.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." *Nucl. Acids Res.* 25, 3389-3402.

Armstrong, D. J. (1994) in *Cytokinins: Chemistry, Activity and Functions*, eds. Mok. D. W. S & Mok, M. C. (CRC Boca Raton, Fla.), pp. 139-154.

An, G., Watson, B. D., Stachel, S., Gordon, M. P., and Nester, E. W. (1985). New cloning vehicles for transformation of higher plants. *EMBO J.* 4, 277-284.

Armstrong, C. L., Petersen, W. P., Buchholz, W. G., Bowen, B. A., and Sulc, S. L. (1990). Factors affecting PEG-mediated stable transformation of maize protoplasts. *Plant Cell Reports* 9, 335-339.

Banerjee, A., Pramanik, A., Bhattachajya, S., and Balaram, P. (1996). Omega amino acids in peptide design: incorporation into helices. *Biopolymers* 39, 769-777.

Baron, M. H. and Baltimore, D. (1982). Antibodies against the chemically synthesized genome-linked protein of poliovirus react with native virus-specific proteins. *Cell* 28, 395404.

Bartel, P. L. and Fields, S. (1997). "The Yeast Two-Hybrid System." Oxford University Press.

Benkirane, N., Guichard, G., Briand, J. P., and Muller, S. (1996). Exploration of requirements for peptidomimetic immune recognition. Antigenic and immunogenic properties of reduced peptide bond pseudopeptide analogues of a histone hexapeptide. *J Biol. Chem.* 271, 33218-33224.

Berry, A. and Brenner, S. E. (1994). A prototype computer system for de novo protein design. *Biochem. Soc. Trans.* 22, 1033-1036.

Christou, P., McCabe, D. E., and Swain, W. F. (1988). Stable transformation of soybean callus by DNA-coated gold particles. *Plant Physiol.* 87, 671-674.

Crossway, A., Oakes, J. V., Irvine, J. M., Ward, B., Knauf, V. C., and Shewmaker, C. K. (1986). Integration of foreign DNA following microinjection of tobacco mesophyll protoplasts. *Mol. Gen. Genet.* 202, 179-185.

Dale, E. C. and Ow, D. W. (1990). Intra- and intermolecular site-specific recombination in plant cells mediated by bacteriophage P1 recombinase. *Gene* 91, 79-85.

Dodds, J. H. (1985). "Plant genetic engineering." Cambridge University Press.

Doerner, P., Jorgensen, J. E., You, R., Steppuhn, J., and Lamb, C. (1996). Control of root growth and development by cyclin expression. *Nature* 380, 520-523.

Dorner, B., Husar, G. M., Ostresh, J. M., and Houghten, R. A. (1996). The synthesis of peptidomimetic combinatorial libraries through successive amide alkylations. *Bioorg. Med. Chem.* 4, 709-715.

Ellis, J. G., Llewellyn, D. J., Dennis, E. S., and Peacock, W. J. (1987). Maize Adh-1 promoter sequences control anaerobic regulation: addition of upstream promoter elements from constitutive genes is necessary for expression in tobacco. *EMBO J.* 6, 11-16.

Faiss, M., Zalubilová, J., Strnad, M., Schmülling, T. (1997). Conditional transgenic expression of the ipt gene indicates a function for cytokinins in paracrine signaling in whole tobacco plants. *Plant J.* 12, 401-415.

Fassina, G. and Melli, M. (1994). Identification of interactive sites of proteins and protein receptors by computer-assisted searches for complementary peptide sequences. *Immunomethods.* 5, 114-120.

Fedoroff, N. V. and Smith, D. L. (1993). A versatile system for detecting transposition in *Arabidopsis. Plant J* 3, 273-289.

Hanahan, D. (1983). Studies on transformation of *Escherichia coli* with plasmids. *J. Mol. Biol.* 166, 557-580.

Hansen, G. and Chilton, M. D. (1996). "Agrolistic" transformation of plant cells: integration of T-strands generated in planta. *Proc. Natl. Acad. Sci. U.S.A* 93, 14978-14983.

Hansen, G., Shillito, R. D., and Chilton, M. D. (1997). T-strand integration in maize protoplasts after codelivery of a T-DNA substrate and virulence genes. *Proc. Natl. Acad. Sci. U.S.A* 94, 11726-11730.

Hanson, B., Engler, D., Moy, Y., Newman, B., Ralston, E., and Gutterson, N. (1999). A simple method to enrich an *Agrobacterium*-transformed population for plants containing only T-DNA sequences. *Plant J* 19, 727-734.

Harlow, E. and Lane, D. (1988). "Antibodies: A Laboratory Manual." Cold Spring Harbor Laboratory Press.

Herrera-Estrella, L., De Block, M., Messens, E. H. J. P., Van Montagu, M., and Schell, J. (1983). Chimeric genes as dominant selectable markers in plant cells. *EMBO J.* 2, 987-995.

P Hoffman, D. L., Laiter, S., Singh, R. K., Vaisman, I. I., and Tropsha, A. (1995). Rapid protein structure classification using one-dimensional structure profiles on the bioSCAN parallel computer. *Comput. Appl. Biosci.* 11, 675-679.

Hooykens, P. J. J., Hall, M. A. & Libbeuga, K. R., eds. (1999) *Biochemistry and Molecular Biology of plant Hormones* (Elsevier, Amsterdam).

Houba-Heria, N., Pethe, C. d'Alayer, J & Lelouc, M. (1999) *Plant J* 17:615-626.

Klee, H. J. & Lanehon, M. B. (1995) in *Plant Hormones: Physiology, Biochemisry and Molecular Biology*, ed. Davies, P. J. (Kluwer, Dordrdrocht, the Netherlands), pp. 340-353.

Krens, F. A., Molendijk, L., Wullems, G. J., and Schilperoort, R. A. (1982). In vitro transformation of plant protoplasts with Ti-plasmid DNA. *Nature* 296, 72-74.

Lerner, R. A. (1982). Tapping the immunological repertoire to produce antibodies of predetermined specificity. *Nature* 299, 593-596.

Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope protein of Dane particles. *Proc. Natl Acad. Sci. U.S.A* 78, 3403-3407.

Liddle, J. E. and Cryer, A. (1991). "A Practical Guide to Monoclonal Antibodies." Wiley New York.

Loffler, J., Langui, D., Probst, A., and Huber, G. (1994). Accumulation of a 50 kDa N-terminal fragment of beta-APP695 in Alzheimer's disease hippocampus and neocortex. *Neurochem. Int.* 24, 281-288.

Mok M. C. (1994) in *Cytokines: Chemistry, Activity and Function*, eds., Mok, D. W. S. & Mok, M. C. (CRC Boca Raton, Fla.), pp. 155-166.

Monge, A., Lathrop, E. J., Gunn, J. R., Shenkin, P. S., and Friesner, R. A. (1995). Computer modeling of protein folding: conformational and energetic analysis of reduced and detailed protein models. *J. Mol. Biol.* 247, 995-1012.

Morris, R. O. et al. (1999). Isolation of a gene encoding a glycosylated cytokinin oxidase from maize. Bioechem. *Biophys. Res. Commun.* 255, 328-333

Motyka, V., Faiss, M., Strnad, M., Kaminek, M. and Schmuelling, T. (1996). Changes in cytokinin content and cytokinin oxidase activity in response to derepression of ipt gene transcription in transgenic tobacco calli and plants. *Plant Physiol.* 112, 1035-1043.

Murakami, T., Simonds, W. F., and Spiegel, A. M. (1992). Site-specific antibodies directed against G protein beta and gamma subunits: effects on alpha and beta gamma subunit interaction. *Biochemistry* 31, 2905-2911.

Olszewski, K. A., Kolinski, A., and Skolnick, J. (1996). Folding simulations and computer redesign of protein A three-helix bundle motifs. *Proteins* 25, 286-299.

Osborne, B. I., Wirtz, U., and Baker, B. (1995). A system for insertional mutagenesis and chromosomal rearrangement using the Ds transposon and Cre-lox. *Plant J* 7, 687-701.

Ostresh, J. M., Blondelle, S. E., Dorner, B., and Houghten, R. A. (1996). Generation and use of nonsupport-bound peptide and peptidomimetic combinatorial libraries. *Methods Enzymol.* 267, 220-234.

Pabo, C. O. and Suchanek, E. G. (1986). Computer-aided model-building strategies for protein design. *Biochemistry* 25, 5987-5991.

Paszkowski, J., Shillito, R. D., Saul, M., Mandak, V., and Hohn, T. H. B. P. I. (1984). Direct gene transfer to plants. *EMBO J.* 3, 2717-2722.

Peralta, E. G., Hellmiss, R., and Ream, W. (1986). Overdrive, a T-DNA transmission enhancer on the *A. tumefaciens* tumour-inducing plasmid. *EMBO J.* 5, 1137-1142.

Quirino, B. F., Noh, Y.-S., Himelbau, E., and Amasino, R. M. (2000). Molecular aspects of leaf senescence. *Trends in Plant Science* 5, 278-282.

Renouf, D. V. and Hounsell, E. F. (1995). Molecular modelling of glycoproteins by homology with non-glycosylated protein domains, computer simulated glycosylation and molecular dynamics. *Adv. Exp. Med. Biol* 376, 37-45.

Rinaldi, A. C. and Comandini, O. (1999). Cytokinin oxidase strikes again. *Trends in Plant Sc.* 4, 300.

Rose, R. B., Craik, C. S., Douglas, N. L., and Stroud, R. M. (1996). Three-dimensional structures of HIV-1 and SIV protease product complexes. *Biochemistry* 35, 12933-12944.

Rutenber, E. E., McPhee, F., Kaplan, A. P., Gallion, S. L., Hogan, J. C., Jr., Craik, C. S., and Stroud, R. M. (1996). A new class of HIV-1 protease inhibitor: the crystallographic structure, inhibition and chemical synthesis of an aminimide peptide isostere. *Bioorg. Med. Chem.* 4, 1545-1558.

Sambrook, J., Fritsch, E. F., and Maniatis, T. (1989). "Molecular Cloning: A Laboratory Manual." Cold Spring Harbor Laboratory Press.

Schlappi, M., Smith, D., and Fedoroff, N. (1993). TnpA trans-activates methylated maize Suppressor-mutator transposable elements in transgenic tobacco. *Genetics* 133, 1009-1021.

Shioda, T., Andriole, S., Yahata, T., and Isselbacher, K. J. (2000). A green fluorescent protein-reporter mammalian two-hybrid system with extrachromosomal maintenance of a prey expression plasmid: Application to interaction screening. *Proc. Natl. Acad. Sci. U.S.A* 97, 5220-5224.

Smulling, T., Rupp, H. M. Frank, M& Schafer, S. (1999) in *Advances in Regulation of plant Growth and Development*, eds. Surnad, M. Pac P. & Beck, E. (Peres, Prague), pp. 85-96.

Tamura, R. N., Cooper, H. M., Collo, G., and Quaranta, V. (1991). Cell type-specific integrin variants with alternative alpha chain cytoplasmic domains. *Proc. Natl. Acad. Sci. U.S.A* 88, 10183-10187.

Werner, T., Vadau Motyka, Miroslav Strnad, and Thomas Schmülling (2001) Regulation of plant growth by cytokinin. *Proc. Nat. Acad. Sci.,* 58 (18) 10487-10492.

Van Haaren, M. J., Sedee, N. J., Schilperoort, R. A., and Hooykaas, P. J. (1987). Overdrive is a T-region transfer enhancer which stimulates T-strand production in *Agrobacterium tumefaciens*. *Nucleic Acids Res.* 15, 8983-8997.

Van Sluys, M. A., Tempe, J., and Fedoroff, N. (1987). Studies on the introduction and mobility of the maize Activator element in *Arabidopsis thaliana* and *Daucus carota*. *EMBO J.* 6, 3881-3889.

Wang, K., Genetello, C., Van Montagu, M., and Zambryski, P. C. (1987). Sequence context of the T-DNA border repeat element determines its relative activity during T-DNA transfer to plant cells. *Mol. Gen. Genet.* 210, 338-346.

Woulfe, J., Lafortune, L., de Nadai, F., Kitabgi, P., and Beaudet, A. (1994). Post-translational processing of the neurotensin/neuromedin N precursor in the central nervous system of the rat-II. Immunohistochemical localization of maturation products. *Neuroscience* 60, 167-181.

Zhang, Y. L., Dawe, A. L., Jiang, Y., Becker, J. M., and Naider, F. (1996). A superactive peptidomimetic analog of a farnesylated dodecapeptide yeast pheromone. *Biochem. Biophys. Res. Commun.* 224, 327-331.

What is claimed is:

1. A method for stimulating root growth or for enhancing the formation of lateral or adventitious roots, said method comprising introducing into a plant a nucleic acid molecule encoding a plant cytokinin oxidase selected from the group consisting of:
   (a) an isolated nucleic acid molecule comprising the DNA sequence as set forth in SEQ ID NOs:1 or 25 or the complement thereof,
   (b) an isolated nucleic acid molecule comprising the RNA sequence encoding the amino acid sequence of SEQ ID NO:2 or the complement thereof,
   (c) an isolated nucleic acid molecule encoding the protein comprising the amino acid sequence as set forth in SEQ ID NO: 2, or the complement thereof, and
   (d) an isolated nucleic acid molecule as defined in any one of (a) to (c) characterized in that said nucleic acid molecule is DNA, genomic DNA, cDNA, synthetic DNA or RNA wherein T is replaced by U,
wherein expression of said nucleic acid molecule is limited to the root or certain tissue or cell type of the root and wherein said expression stimulates root growth or enhances the formation of adventitious roots.

2. A method for increasing the size of the root meristem said method comprising introducing into a plant or plant part a nucleic acid molecule encoding a plant cytokinin oxidase selected from the group consisting of:
   (a) an isolated nucleic acid molecule comprising the DNA sequence as set forth in SEQ ID NOs:1 or 25 or the complement thereof,
   (b) an isolated nucleic acid molecule comprising the RNA sequence encoding the amino acid sequence of SEQ ID NO:2 or the complement thereof,
   (c) an isolated nucleic acid molecule encoding the protein comprising the amino acid sequence as set forth in SEQ ID NO: 2, or the complement thereof, and
   (d) an isolated nucleic acid molecule as defined in any one of (a) to (c) characterized in that said nucleic acid molecule is DNA, genomic DNA, cDNA, synthetic DNA or RNA wherein T is replaced by U,
wherein expression of said nucleic acid molecule is limited to the root or certain tissue or cell type of the root of the plant and wherein said expression of said nucleic acid molecule in roots results in an increase in the size of the root meristem.

3. A method for increasing root size said method comprising introducing into a plant or plant part a nucleic acid molecule encoding a plant cytokinin oxidase selected from the group consisting of:
   (a) an isolated nucleic acid molecule comprising the DNA sequence as set forth in SEQ ID NOs:1 or 25 or the complement thereof,
   (b) an isolated nucleic acid molecule comprising the RNA sequence encoding the amino acid sequence of SEQ ID NO:2 or the complement thereof,
   (c) an isolated nucleic acid molecule encoding the protein comprising the amino acid sequence as set forth in SEQ ID NO: 2, or the complement thereof, and
   (d) an isolated nucleic acid molecule as defined in any one of (a) to (c) characterized in that said nucleic acid molecule is DNA, genomic DNA, cDNA, synthetic DNA or RNA wherein T is replaced by U,
and wherein expression of said nucleic acid molecule is limited to the root or certain tissue or cell type of the root of the plant and wherein expression of said nucleic acid molecule in roots results in an increase in root size.

4. The method of any one of claims 1-3 wherein expression of said nucleic acid molecule is under control of a promoter which preferentially expresses said nucleic acid molecule in the root or certain tissue or cell type of the root.

5. A transgenic plant comprising a transgenic rootstock wherein the transgenic rootstock comprises a nucleic acid molecule selected from the group consisting of:
   (a) an isolated nucleic acid molecule comprising the DNA sequence as set forth in SEQ ID NOs:1 or 25 or the complement thereof,
   (b) an isolated nucleic acid molecule comprising the RNA sequence encoding the amino acid sequence of SEQ ID NO:2 or the complement thereof,
   (c) an isolated nucleic acid molecule encoding the protein comprising the amino acid sequence as set forth in SEQ ID NO: 2, or the complement thereof, and
   (d) an isolated nucleic acid molecule as defined in any one of (a) to (c) characterized in that said nucleic acid molecule is DNA, genomic DNA, cDNA, synthetic DNA or RNA wherein T is replaced by U,
wherein expression of said nucleic acid molecule is limited to the root or certain tissue or cell type of the root.

6. The transgenic plant of claim 5 further comprising a scion.

7. A harvestable part of a plant of claim 5 or 6 wherein the harvestable part comprises the nucleic acid molecule which was introduced into the transgenic plant.

8. A method for improving standability of seedlings said method comprising introducing into a plant a nucleic acid molecule encoding a plant cytokinin oxidase selected from the group consisting of:
   (a) an isolated nucleic acid molecule comprising the DNA sequence as set forth in SEQ ID NOs:1 or 25 or the complement thereof,
   (b) an isolated nucleic acid molecule comprising the RNA sequence encoding the amino acid sequence of SEQ ID NO:2 or the complement thereof,
   (c) an isolated nucleic acid molecule encoding the protein comprising the amino acid sequence as set forth in SEQ ID NO: 2, or the complement thereof, and
   (d) an isolated nucleic acid molecule as defined in any one of (a) to (c) characterized in that said nucleic acid molecule is DNA, genomic DNA, cDNA, synthetic DNA or RNA wherein T is replaced by U,
wherein the isolated nucleic acid molecule is preferentially expressed in the roots of seedlings and wherein said expression improves standability of seedlings.

\* \* \* \* \*